US010858671B2

(12) United States Patent
Clausen et al.

(10) Patent No.: US 10,858,671 B2
(45) Date of Patent: Dec. 8, 2020

(54) N-GLYCOSYLATION

(71) Applicants: University of Copenhagen, København K (DK); DANMARKS TEKNISKE UNIVERSITET, Kgs. Lyngby (DK)

(72) Inventors: Henrik Clausen, Holte (DK); Zhang Yang, Vanløse (DK); Adnan Fevzi Halim, Malmö (SE); Eric Bennett, Kgs. Lyngby (DK); Carsten Behrens, Copenhagen N (DK); Malene Bech Vester-Christensen, Vedbæk (DK); Shamim Herbert Rahman, Valby (DK)

(73) Assignees: University of Copenhagen, København K (DK); Dansmarks Tekniske Universitet, Kgs. Lyngby (DK)

( * ) Notice: Subject to any disclaimer, the term of this patent is extended or adjusted under 35 U.S.C. 154(b) by 194 days.

(21) Appl. No.: 15/534,735

(22) PCT Filed: Dec. 11, 2015

(86) PCT No.: PCT/DK2015/050391
§ 371 (c)(1),
(2) Date: Jun. 9, 2017

(87) PCT Pub. No.: WO2016/091268
PCT Pub. Date: Jun. 16, 2016

(65) Prior Publication Data
US 2017/0369905 A1 Dec. 28, 2017

Related U.S. Application Data

(60) Provisional application No. 62/091,056, filed on Dec. 12, 2014, provisional application No. 62/193,403, filed on Jul. 16, 2015.

(51) Int. Cl.
*C12N 15/90* (2006.01)
*C12P 21/00* (2006.01)
*C07K 14/505* (2006.01)
*C07K 16/46* (2006.01)

(52) U.S. Cl.
CPC .......... *C12N 15/907* (2013.01); *C07K 14/505* (2013.01); *C07K 16/464* (2013.01); *C12P 21/005* (2013.01); *C07K 2317/24* (2013.01); *C07K 2317/56* (2013.01); *C12N 2501/24* (2013.01); *C12N 2501/724* (2013.01); *C12N 2511/00* (2013.01)

(58) Field of Classification Search
CPC .............. C12N 15/907; C12N 2501/24; C12N 2501/724; C12N 2511/00; C12P 21/005; C07K 14/505; C07K 16/464; C07K 2317/24; C07K 2317/56
USPC ............. 435/320.1, 325, 328, 358, 455, 468
See application file for complete search history.

(56) References Cited

U.S. PATENT DOCUMENTS 8,623,611 B2 * 1/2014 Pierce .............. G01N 33/57484
435/7.1
2013/0004992 A1 1/2013 Lin et al.
2014/0349341 A1 11/2014 Lin et al.

FOREIGN PATENT DOCUMENTS

WO WO 2009/009086 1/2009
WO WO 2013/106515 7/2013

OTHER PUBLICATIONS

Johswich et al. (The Journal of Biological Chemistry vol. 289, No. 23, pp. 15927-15941, Apr. 2014). (Year: 2014).*
Bhattacjaryya et al., "Biological Consequences of Inactivating the Mgat3 Gene that encodes GlcNAc-TIII," Glycobiology, vol. 10, No. 10, p. 1081, 2000.
Buffone et al., "Silencing α 1,3-Fucosyltransferases in Human Leukocytes Reveals a Role for FUT9 Enzyme During E-selectin-mediated Cell Adhesion," Journal of Biological Chemistry, vol. 288, No. 3, pp. 1620-1633, 2013.
Kanda et al., "Comparison of Cell Lines for Stable Production of Fucose-Negative Antibodies with Enhanced ADCC," Biotechnology and Bioengineering, vol. 94, No. 4, pp. 680-688, 2006.
Shi et al., "Inactivation of the Mgat1 Gene in Oocytes Impairs Oogenesis, but Embryos Lacking Complex and Hybrid N-Glycans Develop and Implant," Molecular and Cellular Biology, vol. 24, No. 22, pp. 9920-9929, 2004.
Wong et al., Enhancement of DNA Uptake in FUT8-Deleted CHO Cells for Transient Production of Afucosylated Antibodies, Biotechnology and Bioengineering, vol. 106, No. 5, pp. 751-763, 2010.
University of Copenhagen, International Search Report and Written Opinion of the International Searching Authority for PCT/DK2015/050391, 21 pages, Jul. 18, 2016.
Jacobs, et al., Engineering complex-type N-glycosylation in *Pichia pastoris* using GlycoSwitch technology, Nature Protocols, vol. 4, No. 1, pp. 58-70, Feb. 2009.

(Continued)

*Primary Examiner* — Janet L Epps-Smith
(74) *Attorney, Agent, or Firm* — Knobbe, Martens, Olson & Bear LLP

(57) ABSTRACT

The present invention relates to a mammalian cell comprising a gene encoding a polypeptide of interest, wherein the polypeptide of interest is expressed comprising one or more posttranslational modification patterns. These modifications are useful for example in glycoprotein production where the antibodies with the modifications have an enhanced antibody-dependent cell-mediated cytotoxicity (ADCC). The present invention also relates to methods for producing the glycoproteins and compositions comprising the glycoproteins, and their uses.

12 Claims, 56 Drawing Sheets

Specification includes a Sequence Listing.

(56) References Cited

OTHER PUBLICATIONS

Johswich, et al., N-glycan remodeling on glucagon receptor is an effector of nutrient sensing by the hexosamine biosynthesis pathway, J. BioChem, vol. 289, No. 23, pp. 15927-15941, Jun. 6, 2014.
Ohtsubo, et al., Production and characterization of mice lacking the N-glycan GIcNAcT-IV biosynthetic and branching glycosyltransferases encoded by the Mgat4a and Mgat4b genes, Meeting Abstract from FASEB Meeting on Experimental Biology: Translating the Genome; San Diego, Ca, USA; Apr. 11-15, 2003.
Communication pursuant to Rule 164(2)(b) and Article 94(3) EPC issued in corresponding European App. No. 15 822 904.7, dated Nov. 12, 2019.

\* cited by examiner

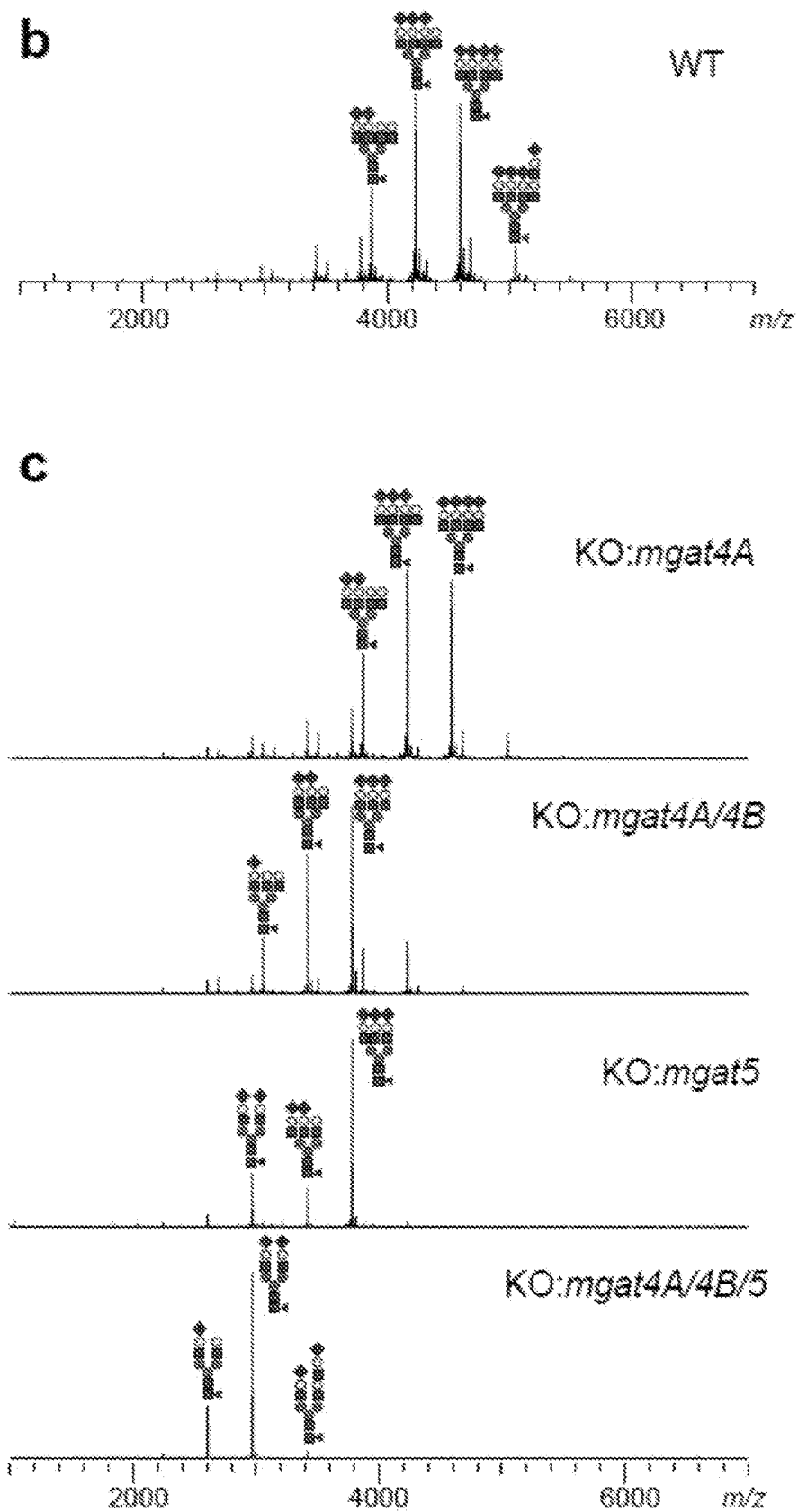
Fig. 1B-C b

KO:B4galt1/mgat4A/4B/5

KO:B4galt2/mgat4A/4B/5

KO:B4galt3/mgat4A/4B/5

KO:B4galt4/mgat4A/4B/5

1B2 mAb b

WT

KO:st3gal4/6

KI:ST6GAL1/KO:st3gal4/6

SNA Lectin

KO:*B3gnt2*
KO:*mgat4A/4B/5*

KI:ST6Gal-I
KO:*st3gal4/6*
KO:*mgat4A/4B/5*

HCD-MS2@1183.9

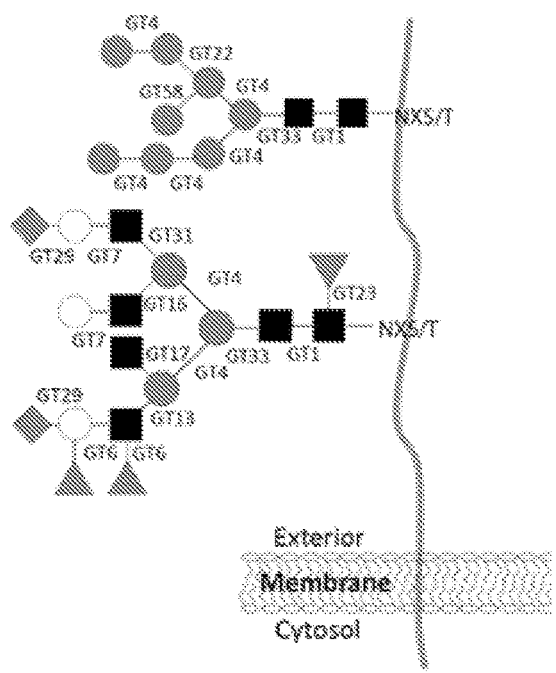
B. N-glycan
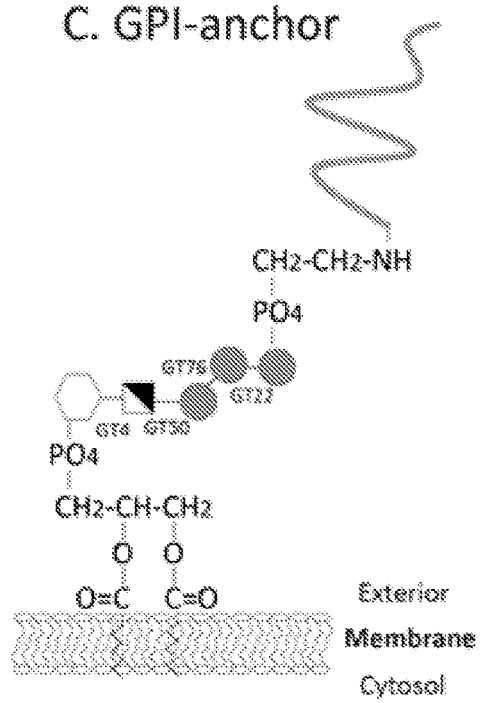
C. GPI-anchor
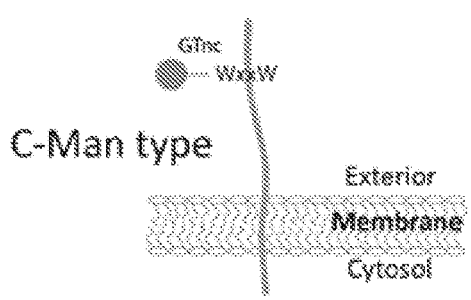
D. C-glycan
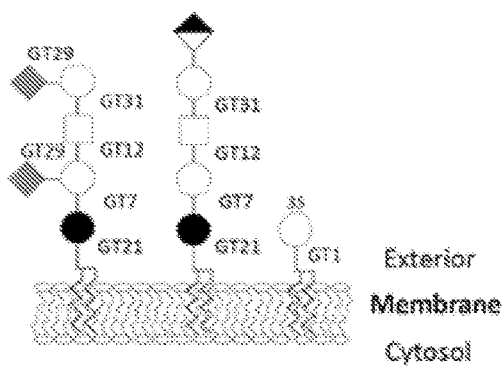
E. Glycosphingolipids
F. Hyaluronan
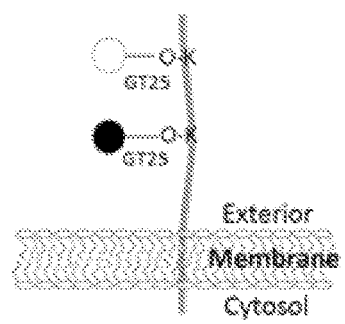
G. HO-Lysine glycan/O-Gal
Fig. 12B-G O-GalNAc
Core 1, only short structures are synthezised
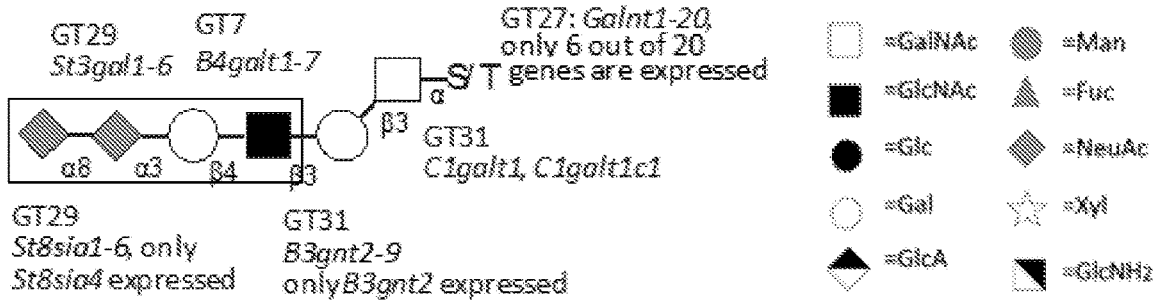
Core 2, missing in CHO-GS/K1
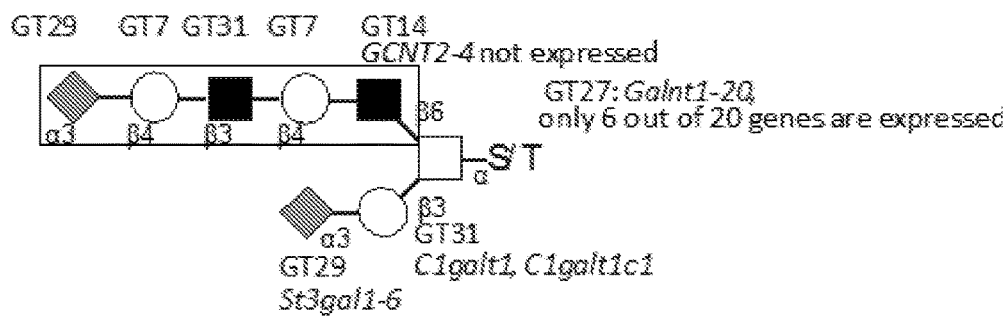
Core 3, missing in CHO-GS/K1
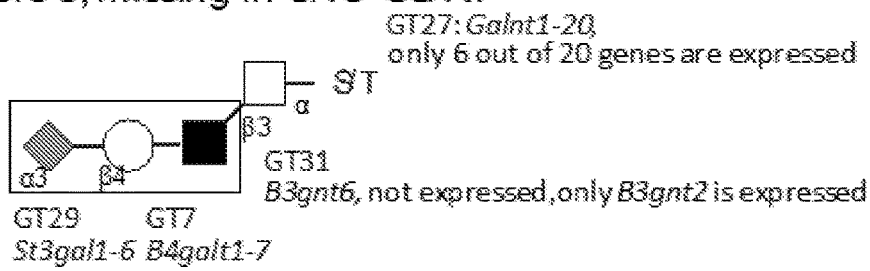
Core 4, missing in CHO-GS/K1
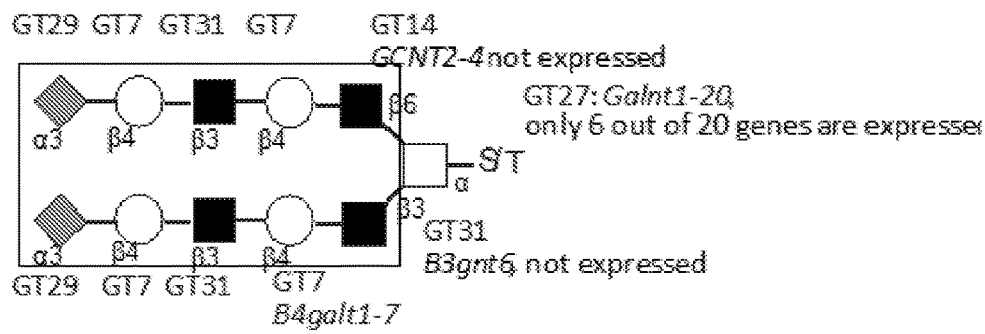
Fig. 13A1

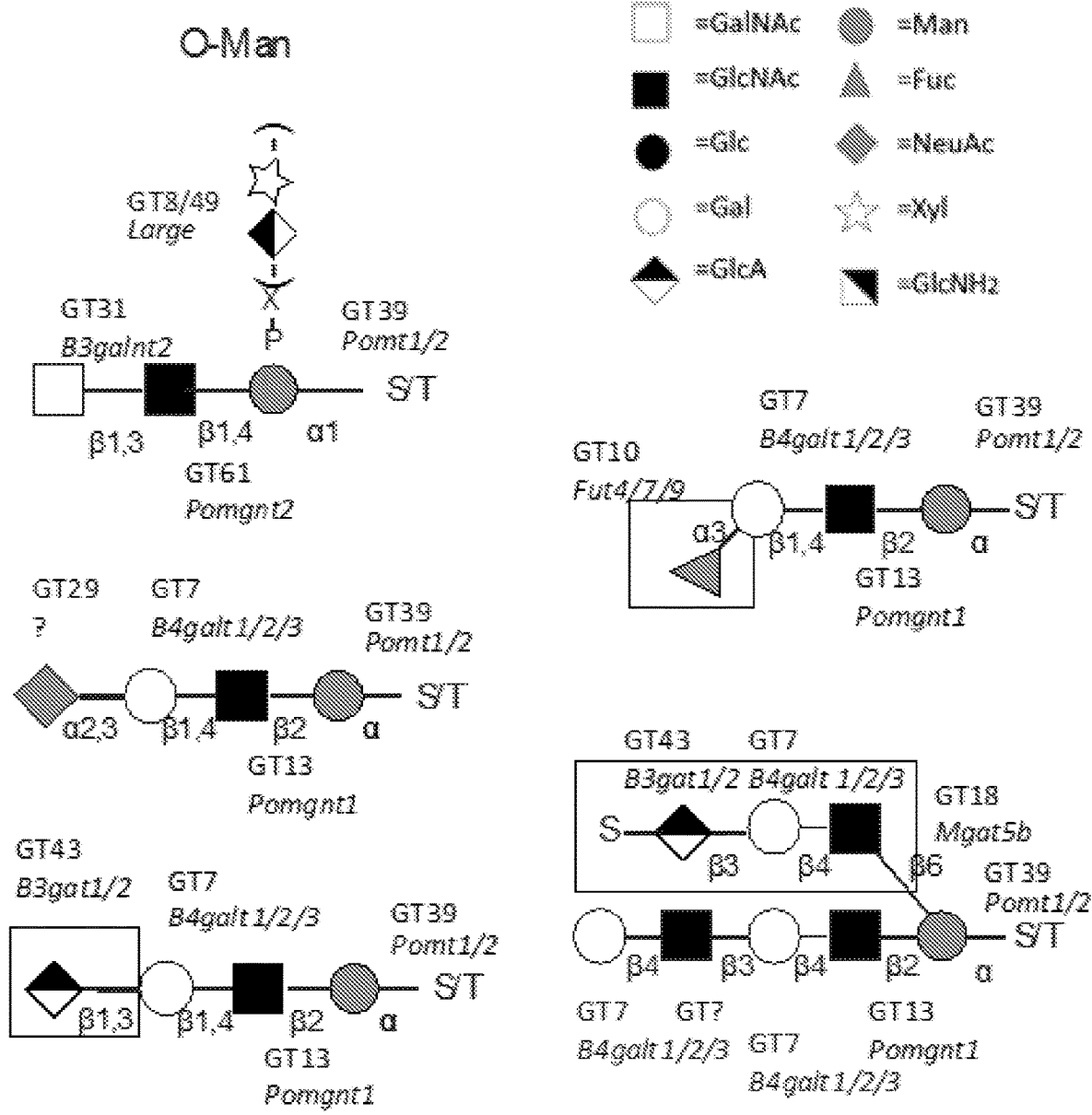
Fig. 13A2

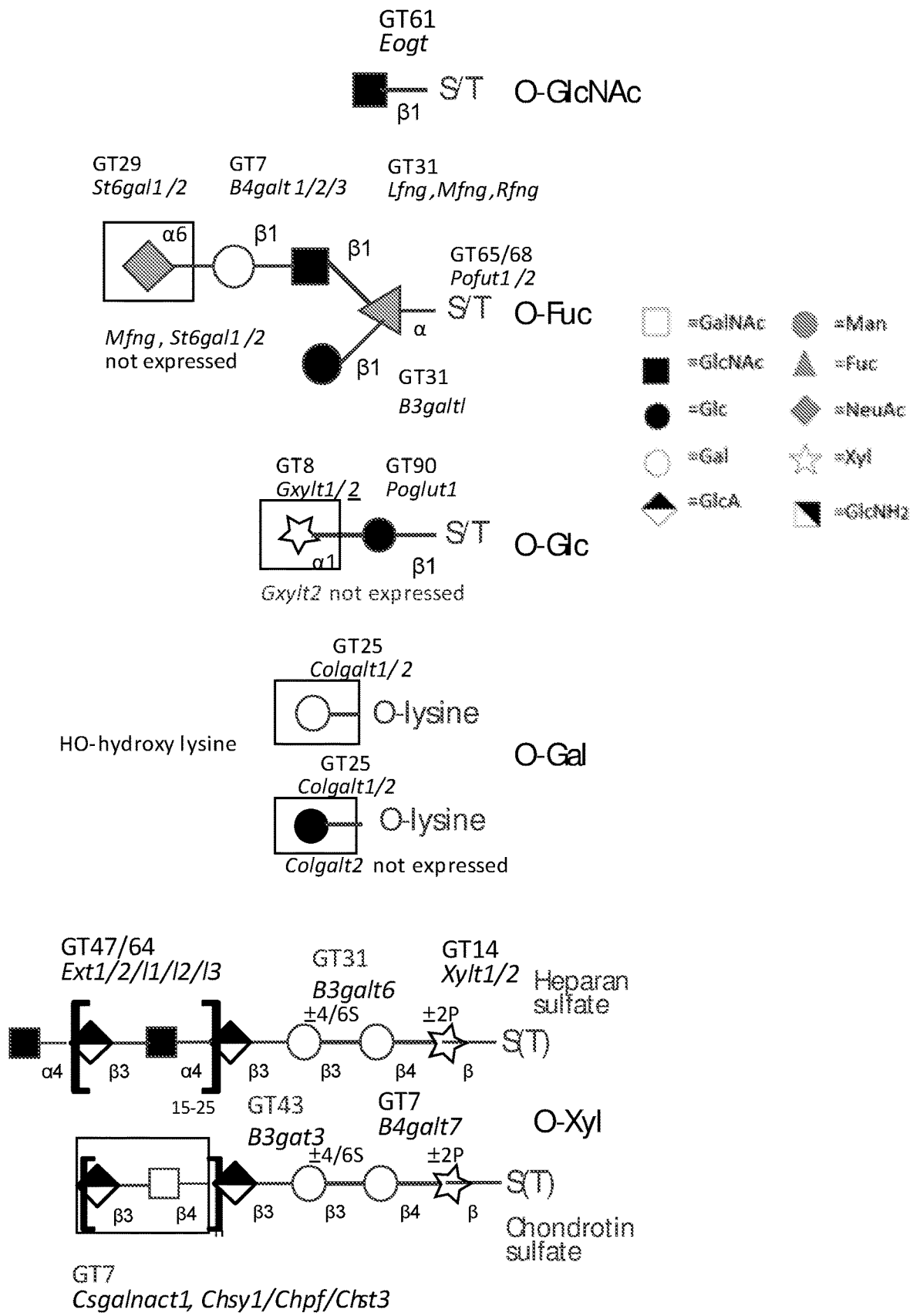
Fig. 13A3

CHO-GS/K1 O-GalNAc structures
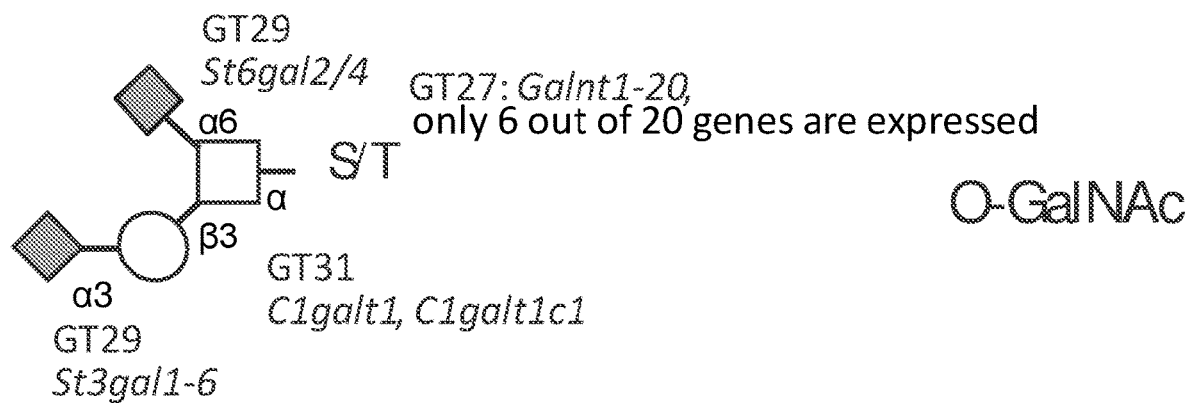
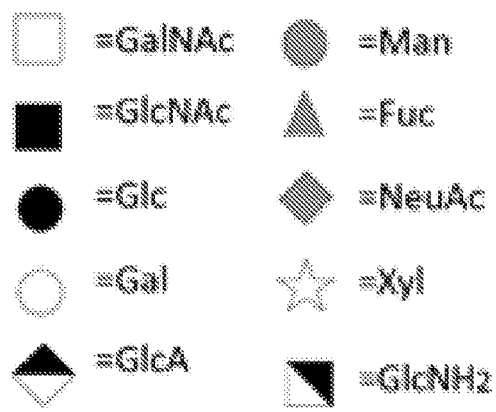
Fig. 13A4

D C-glycan
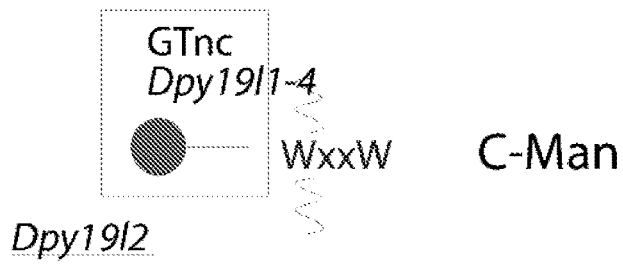
E
GPI-anchor
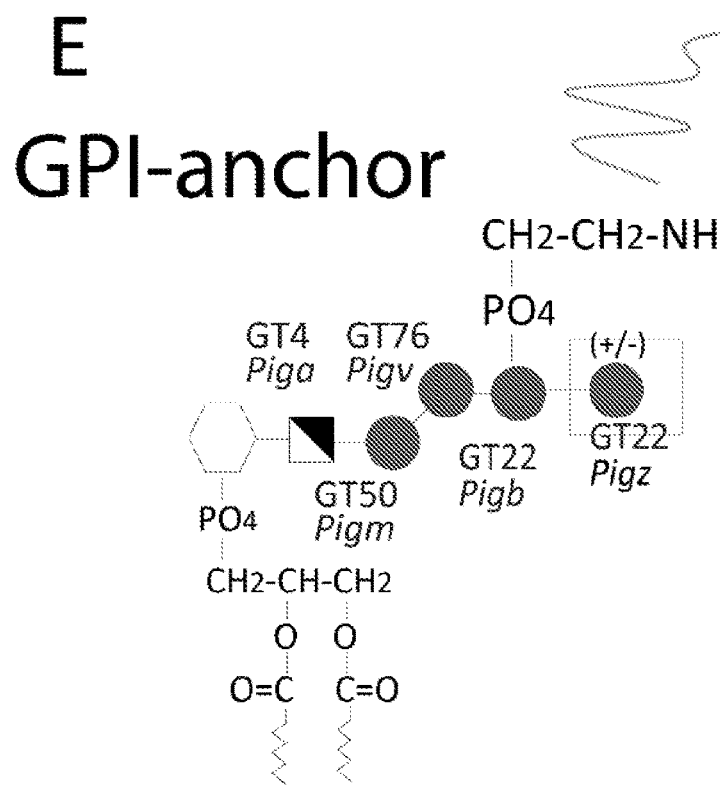
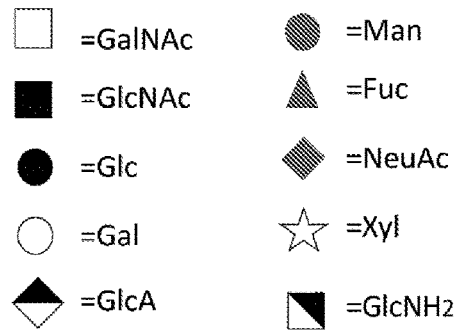
Fig. 13D-E

B

A

B

N-GLYCOSYLATION

CROSS REFERENCE TO RELATED APPLICATIONS

This application is a U.S. National Phase Application of PCT International Application Number PCT/DK2015/050391, filed on Dec. 11, 2015, designating the United States of America and published in the English language, which is an International Application of and claims the benefit of priority to U.S. Provisional Application No. 62/091,056, filed on Dec. 12, 2014, and U.S. Provisional Application No. 62/193,403, filed on Jul. 16, 2015. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG235-001APC.txt, the date of creation of the ASCII text file is Jun. 8, 2017, and the size of the ASCII text file is 17 KB.

TECHNICAL FIELD OF THE INVENTION

The present invention relates to a mammalian cell comprising a gene encoding a polypeptide of interest, wherein the polypeptide of interest is expressed comprising one or more posttranslational modification patterns. These modifications are useful for example in antibody production where the antibodies with the modifications have an enhanced antibody-dependent cell-mediated cytotoxicity (ADCC). These modifications are useful for example in improvement of pharmacokinetic properties, i.e. by attaching PEG or HEP chains to proteins. The present invention also relates to methods for producing the glycoproteins and compositions comprising the glycoproteins, as well as genome engineering, cell culture, protein production, and protein glycosylation. and their uses.

BACKGROUND OF THE INVENTION

Glycoprotein biologics is the fastest growing class of therapeutics, and most of these can only be produced recombinantly in mammalian cells with capacity for human-like glycosylation. The Chinese hamster ovary (CHO) cell has gained a leading role as host cell for recombinant production of glycoprotein therapeutics mainly because it produces rather simple N-glycans with branching and capping similar to what is produced in some human cells.

Notably, CHO produce complex-type heterogenous N-glycans with bi-, tri-, and tetraantennary structures with core α6Fucose (Fuc), a minor amount of poly-N-Acetyllactosamine (poly-LacNAc) mainly on the α1,6 arm of tetraantennary structures, and exclusive capping of LacNAc with α2,3 linked neuraminic acid (NeuAc).

CHO does not generally produce the non-human and in man immunogenic capping structures, such as N-glycolylneuraminic acid (NeuGc) or α3Gal, although the occurrence of these have been reported perhaps as a result of gene induction. N-glycosylation may vary for different proteins as well as for different glycosites in individual proteins, and e.g. IgG antibodies are produced with truncated N-glycan structures at the conserved Asn297 glycosite (biantennary structures with core α6Fuc, limited LacNAc, and NeuAc capping).

A major concern with CHO is the substantial heterogeneity in N-glycan processing, which can be difficult to control during bioprocessing and can pose issues for bioactivity as well as biosafety.

Thus, a major activity in bioprocessing of therapeutics is devoted to glycan analysis and control of fermentation to achieve consistency.

Substantial efforts in the last two decades have been devoted to genetic glycoengineering of CHO cells with the aims to expand the capacity for glycosylation, reduce heterogeneity, and improve or alter especially sialylation.

These studies have essentially all used random integration of cDNAs encoding glycosyltransferases and experienced problems with stability, consistency, and predictability of the introduced glycosylation capacity. The major obstacle has been the need to rely on overexpression of glycosyltransferases and competition with the endogenous expressed enzymes because of lack of simple methods to knock these out in cell lines.

Thus, only very few such glycoengineered CHO cells have reached production of clinical therapeutics. One successful glycoengineering strategy has, however, emerged after the discovery that IgGs without core α6Fuc on the Asn297 N-glycan exhibits markedly higher Antibody-Dependent Cell Cytotoxicity (ADCC).

Thus, through a tour-de-force using two rounds of homologous recombination both alleles of the fut8 gene encoding the α 6fucosyltransferase controlling core fucosylation was knocked out in CHO, and at least one therapeutic IgG produced in CHO without the fut8 gene is now in clinical use.

More recently, the fut8 gene was knocked out using precise gene editing with Zinc finger nuclease (ZFN) gene targeting with a fraction of time and resources spent.

The emergence of precise gene editing technologies for knockout (KO) and knockin (KI) have opened up for an entirely different level of speed and ease with which stable genetic manipulation of host cell lines to remove and introduce glycosyltransferase genes can be achieved, and this will undoubtedly impact engineering of mammalian host cell factories for recombinant production of therapeutics.

Thus, there is a need for mammalian, and especially CHO cells, that have specific glycosylation patterns with or without sialylation.

GTf Genes

Mammalian cells have a large number of glycosyltransferase genes and over 200 distinct genes have been identified and their catalytic properties and functions in glycosylation processes partially determined (Ohtsubo and Marth 2006; Lairson, Henrissat et al. 2008; Bennett, Mandel et al. 2012; Schachter 2014). These genes are classified in homologous gene families with related structural folds in the CAZy database (www.cazy.org). The encoded glycosyltransferases catalyse different steps in the biosynthesis of glycosphingolipids, glycoproteins, GPI-anchors, and proteoglycans (together termed glycoconjugates), as well as oligosaccharides found in mammalian cells. Enormous diversity exists in the structures of glycans on these molecules, and biosynthetic pathways for different types of glycans have been worked out (Kornfeld and Kornfeld 1985; Tarp and Clausen 2008; Bennett, Mandel et al. 2012; Schachter 2014), although our understanding of which glycosyltransferase enzyme(s) that catalyze a particular linkage in the biosynthesis of the diverse set of glycoconjugates produced in a mammalian cell is not complete. Glycosylation in cells is a non-template driven process that relies on a number of factors many of which are unknown for producing the many different glycoconjugates and glycan structures with a high degree of fidelity and differential expression and regulation in cells. These factors may include: expression of the glycosyltransferase proteins; the subcellular topology and retention in the ER-Golgi secretory pathway, the synthesis, transport into, and availability of sugar nucleotide donors in the secretory pathway; availability of acceptor substrates; competing glycosyltransferases; divergence and/or masking of glycosylation pathways that affect availability of acceptor substrates and/or result in different structures; and the general growth conditions and nutritional state of cells.

GTf Isoenzymes

A number of the glycosyltransferase genes have high degree of sequence similarity and these have been classified into subfamilies encoding closely related putative isoenzymes, which have been shown to or predicted to serve related or similar functions in biosynthesis of glycans in cells (Tsuji, Datta et al. 1996; Amado, Almeida et al. 1999; Narimatsu 2006; Bennett, Mandel et al. 2012). Examples of such subfamilies include the polypeptide GalNAc-transferases (GalNAc-T1 to 20), α2,3sialyltransferases (ST3Gal-I to VI), α2,6sialyltransferases (ST6Gal-I and II), α2,6sialyltransferases (ST6GalNAc-I to VI), α2,8sialyltransferases (ST8Sia-I to VI), β4galactosyltransferases (B4Gal-T1 to 7), β3galactosyltransferases (B3Gal-T1 to 6), β3GlcNAc-transferases (B3GnT1 to 5), β6GlcNAc-transferases (C2GnT1-7 and IGnT2A to C), β4GalNAc-transferases (B4GalNAc-T1 to 4), β3glucuronyltransferase (B3GlcUA-1 to 3), α3/4-fucosyltransferases (FUT1 to 11), O-fucosyltransferases (O-POFUT 1 and 2), O-glucosyltransferases (O-GLUT 1 and 2), β4GlcNAc-transferases (MGAT4A to C), β6GlcNAc-transferases (MGAT5 and 5B), and hyaluronan synthases (HAS1 to 3) (Hansen, Lind-Thomsen et al. 2014) (See TABLE 1 for overview of genes and proteins including nomenclature used).

GTf Subfamily Functions

These subfamilies of isoenzymes are generally poorly characterized and the functions of individual isoenzymes unclear. In most cases the function of isoforms are predicted from in vitro enzyme analysis with artificial substrates and these predictions have often turned out to be wrong or partially incorrect (Marcos, Pinho et al. 2004). Isoenzymes may have different or partially overlapping functions or may be able to provide partial or complete backup in biosynthesis of glycan structures in cells in the absence of one or more related glycosyltransferases. It is therefore not possible to reliably predict how deficiency of a particular gene in these subfamilies will affect the glycosylation pathways and glycan structures produced on the different glycoconjugates in a cell and in-vitro state may not reflect in vivo state. Moreover, even more isolated glycosyltransferase genes that are not found to be part of such subfamilies, may have unknown functions in glycosylation or capacities for such unknown functions in the absence of other glycosyltransferase genes.

Knowledge from Knockout Animals—Poor Predictability of Phenotype

This has been particularly evident in studies of knockout mice with deficiency in glycosyltransferase genes that are members of homologous subfamilies, where surprising changes or lack of apparent changes in glycosylation have been observed (Angata, Lee et al. 2006).

For example, mice with targeted elimination of the β4Galt1 gene encoding the β4Gal-T1 isoenzyme (one of 7 members of βGalactosyltransferase family) demonstrated partial loss of protein β4galactosylation, with a shift from type 2 chains (Gal β1-4GlcNAc β3-R) to type 1 chain (Gal β1-3GlcNAc β3-R) (Kotani, Asano et al. 2004). A corresponding sialylation pattern with repression of dominant α2,6 and increased α2,3sialylation characteristic of type 1 chains was observed. Phenotypically, the mice survived to term but exhibited growth retardation and problematic differentiation of epithelia as well as endocrine insufficiencies (Asano, Furukawa et al. 1997).

The same lack of global phenotype is seen when eliminating single members of the large family of sialyltransferases responsible for glycan sialylation (Angata, Lee et al. 2006). For example, mice deficient in sialylation of core 1 O-glycans catalyzed by the ST3Gal-I enzyme are grossly normal, but exhibit a marked decrement in the number of CD8+ T cells in peripheral compartments. ST3Gal-I is one of six other members of the ST3Gal sialyltransferase family, and mice deficient in other of the family members are also mostly without gross phenotypes. One exception is mice lacking ST3Gal-IV that presents with a severe bleeding disorder due to lack of sialylation and exposed galactose residues on von Willebrand Factor and hence its clearance from circulating. In addition these mice present with a leukocyte adhesion defect with diminished P and E-Selectin ligand activation. Similarly, elimination of individual polypeptide GalNAc-Ts from the GALNT gene family that initiates GalNAc-type O-glycosylation only yield very discrete phenotypes that are often difficult to predict (Bennett, Mandel et al. 2012). The same is the case for targeted inactivation of the several GlcNAc-transferases that catalyze the branching of O-linked glycans. For example loss of Core2 GlcNAc-T1 cause only few overt abnormalities, although an effect on E-, P-, and L-selectin functions is seen. Unexpectedly, a compensatory elongation of core 1 glycans was found in Core2 GlcNAc-TI knock out mice rescuing the phenotype in high endothelia venules (Stone, Ismail et al. 2009).

However, in some cases knockout leads to complete loss of a particular glycosylation capacity. In the case of O-glycosylation the core1 synthase, elimination of the C1GALT1, appears to result in complete loss of elongated core1 O-glycans (Wang, Ju et al. 2010), showing that this particular glycosylation function may only be carried out by one enzyme. However, detailed analysis of the function of such isolated genes may often be difficult if the deficiency leads to early embryonic lethality, as is the case for knockout of C1GALT1. Another similar example is the elimination of the GlcCer synthase (UGCG), which cause the elimination of all complex glycosphingolipids based on LacCer and embryonic lethality (Jennemann, Sandhoff et al. 2005). This is also the case in the production of N-linked glycans. In various knockout animals with complete or almost complete lack of N-linked glycans gross phenotypes are seen with no or limited viability (Stone, Ismail et al. 2009). Most pronounced is the effect by loss of the UDP-GlcNAc: dolichol phosphate N-acetylglucosmaine-1-1phosphate transferase (GPT) essential for the initiation of the oligosaccharide precursor in N-linked glycosylation, which causes a complete lack of N-linked glycosylation and lack of viability beyond embryonic stage E5.5 of gestation. Similar severe phenotypes are observed by the loss of Mgat1-/- encoded GnT1 glycosyltransferase that catalyzes the essential step in conversion of high mannose to hybrid and complex structures (Ioffe and Stanley 1994; Schachter 2014). The knockout mice become unviable at midgestation (E9.5-E10.5) with morphogenic abnormalities including defects in neural tube formation ad vascularization.

Elimination of other enzymes functioning in the branching of N-linked glycans demonstrated murine phenotypes of variable severity. Elimination of GlcNAc-TII that catalyzes the formation of complex N-glycans in the subsequent step following GlcNAc-I and αMannosidases, demonstrate limited viability in mice, although differences has been observed dependent on the genetic background (Freeze 2001). Interestingly, an unpredicted increased level of Lewis structures has been observed by a compensatory increase in bisecting GlcNAc structures catalyzed by GlcNAc-TIII encoded by Mgat3 (Wang, Schachter et al. 2002). In contrast to the elimination of Mgat1 and Mgat2 elimination of Mgat3 and Mgat4a encoding GlcNAc-TIVa are both viable without overt phenotypes. The phenotype of Mgat4b KO mice is currently unclear. A number of studies have examined the effect of elimination of Mgat5 encoding the GlcNAc-V transferase. Although no overt phenotype is observed in younger mice, it has become clear that GlcNAc-V catalyzed tetra-antennary glycans are important for the regulation of T-cell activation, leukocyte recruitment in inflammation, as well as other signaling pathways. It is thus clear that complete elimination of core elements of specific glycans causes severe phenotypes, whereas elimination of branching and trimming enzymes often produce unpredictable changes in glycan structures and functional consequences.

Cross-breeding of knockout mice have resulted in mice deficient in up to two glycosyltransferase genes. For example, breeding mice deficient in the sialyltransferases ST8Sia-I (GD3 synthase) and the β4GlcNAcT (GD2 synthase), which are both important for glycosphingolipid biosynthesis, caused a complete lack of all types of complex glycosphingolipids. These double mutant mice were still viable but had a high mortality rate due to extreme sensitivity to audiogenic induced seizures (Kawai, Allende et al. 2001). Other examples of targeted elimination of two glycosyltransferases are the loss of both Fut1 and Fut2. These double knock out animals present without any clear phenotypes. Furthermore, mice have been generated with targeted inactivation of both Fut4 and Fut7. These mice again do not display any obvious phenotypes, except for a complete lack of E-, P- and L-selectin ligand activity on leukocytes.

Knowledge from Knockout Cell Lines

In contrast to our knowledge of the effects of knockout of glycosyltransferase genes in animals and model organisms, very little information exist as to the effects of knockout of glycosyltransferase genes in mammalian cell lines. For human cell lines only a few spontaneous mutants of glycosyltransferase genes have been identified. For example the colon cancer cell line LSC derived from LS174T has a mutation in the COSMC chaperone that leads to misfolded and non-functional core1 synthase C1GalT (Ju, Lanneau et al. 2008). COSMC was originally proposed to encode a core1 synthase glycosyltransferase due to its homology to the C1GALT1 gene, however, it is now believed to be a private chaperone for C1GalT required for folding (Wang, Ju et al. 2010). The COSMC gene is also mutated in the human lymphoblastoid Jurkat cell line (Ju, Lanneau et al. 2008; Steentoft, Vakhrushev et al. 2011). For non-human cell lines there is essentially only information from Chinese hamster ovary (CHO) cell lines, although a similar murine cancer cell line with spontaneous mutation in the COSMC gene has been found. A series of CHO cell lines (Lec cell lines) with deficiency in one glycosyltransferase gene was originally generated by random mutagenesis follow by lectin selection, and the isolated lectin-resistant mutant clones were later shown to have defined mutations in the glycosyltransferase genes MGAT1 (Lec1), MGAT5 (Lec4), and B4GALT1 (Lec20) (Patnaik and Stanley 2006). A number of the mutant CHO lines have also been found to have mutations in non-glycosyltransferase genes affecting glycosylation such as CMP-NANA synthase (Patnaik and Stanley 2006) and C4-Glc/GlcNAc epimerase (Kingsley, Kozarsky et al. 1986). Most of the CHO lines with mutations in glycosyltransferase genes have been found to have partial losses of the relevant glycosylation activity, although loss of the MGAT5 gene was found to completely abrogate synthesis of tetraantennary N-glycans (North, Huang et al. 2010). The latter suggests that only one glycosyltransferase gene encoding β6GlcNAc-transferase activity leading to tetraantennary N-glycan branching exist in CHO and that the homologous gene MGAT5C does not serve as functional backup. The MGAT5C gene has been shown to be involved in branching of O-Man O-glycans instead, although some overlapping function could be predicted or expected based on the sequence similarities of the two MGAT5 genes.

Knockout of Glycosylation Genes in Cell Lines

The limited information of effects of knockout of glycosyltransferase genes in cell lines is partly due to past difficulties with making knockouts in cell lines before the recent advent of precise gene editing technologies (Steentoft, Bennett et al. 2014). Thus, until recently essentially only one glycosyltransferase gene, FUT8, had been knocked out in a directed approach using two rounds of homologous recombination in a tour-de-force effort. The conventional gene disruption by homologous recombination is typically a very laborious process as evidenced by this knockout of FUT8 in CHO, as over 100,000 clonal cell lines were screened to identify a few growing FUT8−/− clones (Yamane-Ohnuki, Kinoshita et al. 2004) (U.S. Pat. No. 7,214,775). With the advent of the Zinc finger nuclease (ZFN) gene targeting strategy it has become less laborious to disrupt genes. This was demonstrated by knockout of the FUT8 gene in a CHO cell line, where additional two other genes unrelated to glycosylation were also effectively targeted (Malphettes, Freyvert et al. 2010).

More recently, the CRISPR/Cas9 editing strategy has emerged and this editing strategy was also used to knockout the FUT8 gene (Ronda, Pedersen et al. 2014). Moreover, knockout of the mgat1 gene was carried out by ZFN targeting in CHO, which rendered the CHO line incapable of making complex type N-glycans, and all N-glycoproteins were produced with only high-mannose type structures (Sealover, Davis et al. 2013) (US20140349341). Finally, ZFNs have been used to knockout the Ggta1 gene (US 20130004992), which encodes an β3Gal-T that forms the xenoantigen Galα1-3Galβ1-4GlcNAc epitope that is highly immunogenic in man because the human GGTA1 gene is a pseudogene and thus this particular glycostructure does not occur in man. In all the cases with directed knockout of glycosyltransferase genes the targeted genes had been shown previously to serve non-redundant unique functions, and it could be expected with reasonable reliability that the knockout would result in CHO cells without the particular glycosylation capacity performed by the encoded enzyme. However, as discussed previously most glycogenes exist in subfamilies of close homologs and the cellular function and role in glycosylation of the encoded isoenzymes of these paralogs are largely unknown and unpredictable. Furthermore, loss of any glycosylation capacity may provide acceptor substrates for unrelated and unpredictable glycosyltransferase producing different glycan structures than predicted (Holmes, Ostrander et al. 1987).

It is thus clear that genetic engineering of the glycosylation genes in mammalian cells and animals are prone to substantial uncertainty, and thus identifying the optimal engineering targets for a given protein will require extensive experimental efforts. Some guide may be found from results of in vitro determined substrate specificities of recombinant expressed enzymes, which are most often performed with truncated secreted forms of the enzymes. While these assays provide general information of the donor sugar and the most simple acceptor substrates, these assays often do not provide intricate acceptor substrate specificities regarding more complex acceptors and the type of glycoconjugate they work on. A number of isoenzymes have been shown to function with small artificial acceptor substrates in in vitro assays or in some cases with large libraries of glycan acceptors. However, predictions of in vivo functions in cells based on these studies have often been erroneous as found for e.g. ST6GalNAc-II (Marcos, Bennett et al. 2011).

It is worth to note in this context that knock down of glycosyltransferase genes using different siRNA silencing strategies largely have produced highly doubtful information. In general knock down of genes in metabolic pathways where the encoded enzymes often are not limiting require highly efficient knock down to produce discernable effects. Furthermore the siRNA technology is not 100% efficient, which inevitably results in some heterogeneity of the glycostructures. For production of biopharmaceuticals even a low % of an undesired glycoform require extensive analysis and control.

Moreover, glycosyltransferases are resident ER and Golgi enzymes with slow turnover, and it is very difficult to sufficiently reduce enzyme levels to affect glycosylation to a detectable extend, and it is essentially impossible to completely abrogate specific glycosylation capacities with siRNA strategies in mammalian cells.

Nevertheless, some studies have reported effects of knock down of glycosylation capacities with resulting biological phenomena in cells despite residual enzyme levels (often confirmed by western blots). While some of these studies may have observed effects related to off-targeting of the silencing strategies used, it is clear that only complete knockout of the relevant glycosylation genes can confirm these results unambiguously and examples of obvious erroneous results have appeared. Knock down of the GALNT6 gene involved in O-glycosylation of proteins in a breast cancer cell line resulted in loss of surface expression of the cancer-associated mucin MUC1 (Bennett, Mandel et al. 2012). However, MUC1 is expressed on the surface of many cells including CHO, which do not express the GALNT6, and it is therefore not likely that partial loss of the encoded GalNAc-T6 enzyme should have such profound effects on MUC1 expression. Thus, it is clear that silencing screening strategies are not reliable to probe cellular in vivo functions of glycosyltransferase genes in order to identify their role in glycosylation and to evaluate potential partial or complete functional redundancies in distinct glycosylation pathways.

Overexpression of Glycosylation Genes in Cell Lines

Further noteworthy in this context is that transient or stable overexpression of a glycosyltransferase gene in a cell most often result in only partial changes in the glycosylation pathways in which the encoded enzyme is involved. A number of studies have attempted to overexpress e.g. the core2 C2GnT1 enzyme in CHO to produce core2 branched O-glycans, the ST6Gal-I sialyltransferase to produce $\alpha$2,6linked sialic acid capping on N-glycoproteins (El Mai, Donadio-Andrei et al. 2013), and the ST6GalNAc-1 sialyltransferase to produce $\alpha$2,6linked sialic acid on O-glycoproteins forming the cancer-associated glycan STn (Sewell, Backstrom et al. 2006). However, in all these studies heterogeneous and often unstable glycosylation characteristics in transfected cell lines have been obtained. This is presumably partly due to competing endogenous glycosyltransferase activities whether acting with the same substrates or diverging pathway substrates. Other factors may also explain the heterogeneous glycosylation characteristics. This includes the availability and competition for donor substrates and possible interference with other mechanisms required for the endogenous glycosylation machinery including e.g. subcellular topology and organization of glycosyltransferases, coordinated functions of glycosyltransferases, as well as availability of co-factors, chaperones, and other unknown factors required for efficient glycosylation.

Function of Glycosylation on Proteins

Glycosylation of proteins is an essential and highly conserved process in all mammalian cells, and the repertoire of glycosyltransferase genes available in mammalian cells is almost identical with well-defined orthologous relationships clarified (Hansen, Lind-Thomsen et al. 2014). Only a few glycosyltransferase genes have been inactivated through evolution in man, such as the xenoantigen $\alpha$3galactosyltransferase gene, GGTA1, and the Forssman $\alpha$3GalNAc-transferase gene, while the human has gained a few new glycosyltransferase activities by introducing polymorphisms, such as for the blood group ABO $\alpha$3Gal/GalNAc-transferase gene. Despite these minor differences in glycosyltransferases acting in the final capping of glycan structures, most of the glycosylation pathways in mammalian cells are identical and can be inferred from one mammalian cell to another with regards to functions of the glycosyltransferases expressed. Proteins entering the ER-Golgi secretory pathway in mammalian cells can undergo N-glycosylation as well as a variety of different types of O-glycosylation (Hansen, Lind-Thomsen et al. 2014). Proteins may also be cleaved and linked by a GPI anchor. Glycosylation affects proteins in a number of ways. Glycosylation can direct folding with quality control for ER exit and transport and secretion, and glycosylation can direct conformation and function of proteins as well as sensitivity for proteolytic processing and/or degradation. Glycosylation is particularly important for recombinant protein therapeutics produced in mammalian cells, and glycans may affect production of proteins, provide solubility and stability to proteins, affect bioactivity, biodistribution and/or circulatory half-life of proteins, and direct proteins to specific carbohydrate-binding receptors. It is therefore important to consider the glycosylation capacity of host cells used for production of recombinant therapeutics for production of effective therapeutics.

Recombinant Production of Therapeutics

Glycoprotein biologics is the fastest growing class of therapeutics (Walsh 2010), and most of these can only be produced recombinantly in mammalian cells with capacity for human-like glycosylation. The Chinese hamster ovary cell has gained a leading role as host cell for recombinant production of glycoprotein therapeutics mainly because it produces rather simple N-glycans with branching and capping similar to what is produced in some human cells (Walsh 2014). Notably, CHO produce heterogeneous complex-type N-glycans with bi-, tri-, and tetraantennary structures with core $\alpha$6Fucose, a minor amount of poly-N-Acetyllactosamine (poly-LacNAc) mainly on the $\alpha$1,6 arm of tetraantennary structures, and exclusive capping of LacNAc with α2,3-linked neuraminic acid (NeuAc) (North, Huang et al. 2010). CHO does not generally produce the non-human and in man immunogenic capping structures, such as N-glycolylneuraminic acid (NeuGc) or α3Gal, although the occurrence of these may be a result of gene induction (Bosques, Collins et al. 2010; North, Huang et al. 2010). N-glycosylation may vary for different proteins as well as for different glycosites in individual proteins, and e.g. IgG antibodies are produced with truncated N-glycan structures. A major concern with CHO is the substantial heterogeneity in N-glycan processing, which can be difficult to control during bioprocessing and can pose issues for bioactivity as well as biosafety. Thus a major activity in bioprocessing of therapeutics is devoted to glycan analysis and control of fermentation to achieve consistency (Walsh 2010).

The generic CHO cell lines produce N-glycans with a variable mixture of bi, tri, and tetraantennary structures with a high degree of α6fucosylation, and a minor degree of poly-LacNAc structures and capping with α2,3NeuAc on most glycoproteins (Sasaki, Bothner et al. 1987). Moreover, some N-glycosylation sites in proteins may have incomplete stoichiometry. For IgG CHO produces only biantennary N-glycans with low galactosylation and sialylation at the conserved Asn297 site.

O-glycans of the GalNAc-type are produced with the core1 structure with α2,3NeuAc and partial α2,6 (to GalNAc) sialylation (Fukuda, Sasaki et al. 1989), and variable stoichiometry are also found. A CHO cell line with inactivated cosmc has been produced and this cell line produce only GalNAc O-glycans structures (Yang, Halim et al. 2014). O-glycans of other types have not been studied and it is only known that O-glycans of the Fuc-type are elongated by LacNAc and capped with α2,3NeuAc.

There are no mammalian cell lines including CHO available that can produce a single homogenous N-glycan antennae species, neither biantennary N-glycans, triantennary N-glycans, or tetraantennary N-glycans. Also lacking are cells that do not produce small amounts of heterogeneous poly-LacNAc structures on antennary branches. Moreover, cells capable of producing N-glycans with homogenous α2,6NeuAc capping are not available, and most plasma proteins in human are capped by α2,6NeuAc and not α2,3NeuAc as produced by CHO and many other mammalian cell lines.

Genetic engineering of CHO cells with respect to knock-out of glycosyltransferase genes are limited to single isolated genes. There are no examples of stacked inactivation of multiple glycosyltransferase genes in mammalian cells including CHO lines. Moreover, there have been no examples of stacked inactivation of multiple glycosyltransferase genes encoding isoenzymes with potential related functions in protein glycosylation. Since many steps in protein glycosylation involve families of isoenzymes and their in vivo functions in cells are largely unknown, it is furthermore not possible to predict which genes to inactivate and/or introduce to obtain many of the glycosylation capacities preferred for recombinant glycoprotein therapeutics.

Substantial efforts in the last two decades have been devoted to genetic glycoengineering of CHO cells with the aims to expand the capacity for glycosylation, reduce heterogeneity, and improve or alter especially sialylation (Sinclair and Elliott 2005; Walsh and Jefferis 2006). These studies build on decades of work deciphering the biosynthetic pathways and genes involved in N-glycosylation (Kornfeld and Kornfeld 1985; Schachter 1991), and have essentially all used random integration of cDNAs encoding glycosyltransferases and experienced problems with stability, consistency, and predictability of the introduced glycosylation capacity (Kramer, Klausing et al. 2010). The major obstacle has been the need to rely on overexpression of glycosyltransferases with resulting competition by endogenous expressed enzymes. It has been difficult to perform directed knockout of genes in cell lines in silencing strategies, but for glycosyltransferase genes success has been achieved with a strategy based on random CHO mutagenesis followed by lectin-resistant selection (Patnaik and Stanley 2006). However, these CHO mutant cells in general do not have glycosylation characteristics preferable for recombinant therapeutics, they may also contain other unknown mutations in the CHO genome and none of them have been used for production of clinical therapeutics.

The discovery of the importance of core α6Fucosylation of the Asn297 N-glycan on IgGs for Antibody-Dependent Cell Cytotoxicity (ADCC) (Shinkawa, Nakamura et al. 2003), motivated the need to produce CHO cells with this glycosylation capacity and CHO lines with inactivated fut8 gene are now available for production of IgG antibodies. Moreover, CHO lines with inactivation of the ggta1 gene or the mgat1 gene have been generated.

However, so far engineering of CHO has not been able to deal with the more common problems of heterogeneity in glycosylation, insufficient sialylation, and introduction of new glycosylation capacities such as more human-like sialylation (α2,6NeuAc). Currently, the bioprocessing industry of recombinant production of glycoprotein therapeutics has only the one generic CHO cell line with its natural glycosylation capacity available for expression with the exception of the above mentioned examples of which only the fut8 knockout line is of value for classical therapeutics.

SUMMARY OF THE INVENTION

The present invention relates to a mammalian cell comprising a gene encoding a polypeptide of interest, wherein the polypeptide of interest is expressed comprising one or more posttranslational modification patterns.

An object of the present invention relates to a cell comprising one or more glycosyltransferase genes that have been inactivated. The cell has new and/or more homogeneous stable glycosylation capacities.

In one embodiment of the present invention the cell comprises two or more glycosyltransferase genes that have been inactivated.

In one embodiment of the present invention comprises these posttranslational modification patterns homogenous biantennary N-glycans with or without α2,3NeuAc capping, or with or without α2,6NeuAc capping.

Another object of the present invention relates to a cell comprising one or more glycosyltransferase genes that have been introduced stably by site-specific gene or non-site-specific knockin and with new and/or more homogeneous glycosylation capacities.

In one embodiment of the present invention the cell comprises two or more glycosyltransferase that have been introduced stably by site-specific or non-site-specific gene knockin.

An embodiment of the present invention relates to a cell comprising one or more glycosyltransferase genes introduced stably by site-specific or non-site-specific gene knockin, and furthermore comprising one or more endogenous glycosyltransferase genes that have been inactivated by knockout, and with improved and/or novel and/or more homogeneous glycosylation capacities.

A further aspect of the present invention relates to a cell comprising two or more glycosyltransferase genes encoding isoenzymes with partial overlapping glycosylation functions in the same biosynthetic pathway and/or same biosynthetic step inactivated, and for which inactivation of two or more of these genes is required for loss of said glycosylation functions in the cell.

In one embodiment of the present invention the cell comprises one or more glycosyltransferase genes inactivated to block and truncate one or more glycosylation pathways.

A further aspect of the present invention relates to a cell comprising two or more glycosyltransferase genes inactivated to block and truncate one or more glycosylation pathways.

In one embodiment of the present invention the cell comprises targeted inactivation of one or more glycosyltransferase genes for which no transcripts are detectable.

A further aspect of the present invention relates to a cell comprising targeted inactivation of one or more glycosyltransferase genes for which no protein products are detectable.

Another aspect of the present invention relates to a cell comprising targeted inactivation of one or more glycosyltransferase genes for which no protein products with intact cytosolic and/or transmembrane region is detectable.

In one embodiment of the present invention the cell is a mammalian cell or an insect cell.

In another embodiment of the present invention the cell is derived from Chinese hamster ovary or from human kidney.

In a further embodiment of the present invention the cell is selected from the group consisting of CHO, NS0, SP2/0, YB2/0, CHO-K1, CHO-DXB11, CHO-DG44, CHO-S, HEK293, HUVEC, HKB, PER-C6, NS0, or derivatives of any of these cells. In one embodiment of the present invention is the cell a CHO cell.

In another embodiment of the present invention the cell furthermore encodes an exogenous protein of interest.

In yet another embodiment of the present invention the protein of interest is an antibody, an antibody fragment, such as a Fab fragment, an Fc domain of an antibody, or a polypeptide.

In yet another embodiment of the present invention the protein of interest is a coagulation factor such as coagulation factor II (FII), coagulation factor V (FV), coagulation factor VII (FVIIa), coagulation factor VIII (FVIII), coagulation factor IX (FIX), coagulation factor X (FX), or coagulation factor XIII (FXIII).

In a further embodiment of the present invention is the antibody is an IgG antibody.

In one embodiment of the present invention is the polypeptide erythropoietin (EPO), a protein involved in hemostasis, including a coagulation factor.

In another embodiment of the present invention is the glycosyltransferase any one or more of the genes listed in Table 1, 2 or 3.

In a further embodiment of the present invention is the glycosyltransferase that is inactivated a glycosyltransferase gene that is not involved in the biosynthesis of the glycans on a particular glycoprotein produced recombinantly in said cell.

In one embodiment of the present invention are the glycosyltransferases that are inactivated working in the same glycosylation pathway.

In another embodiment of the present invention are the glycosyltransferases that are inactivated working in the same glycosylation step.

In yet another embodiment of the present invention are the glycosyltransferases that are inactivated working in consecutive biosynthetic steps.

In one embodiment of the present invention are the glycosyltransferases that are inactivated retained in the same subcellular topology.

In another embodiment of the present invention are the glycosyltransferases that are inactivated having similar amino acid sequence.

In a further embodiment of the present invention are the glycosyltransferases that are inactivated belonging to the CAZy family.

In yet another embodiment of the present invention are the glycosyltransferases that are inactivated belonging to same subfamily of isoenzymes in a CAZy family.

In one embodiment of the present invention are the glycosyltransferases that are inactivated having similar structural retention signals (transmembrane sequence and length).

In another embodiment of the present invention are the glycosyltransferase genes functioning in the same glycosylation pathway inactivated, and wherein they are not involved in the same glycosylation step.

In a further embodiment of the present invention are the glycosyltransferase genes functioning in the same glycosylation pathway inactivated, and wherein they are involved in the same glycosylation step.

In one embodiment of the present invention is the glycosylation made more homogenous.

In another embodiment of the present invention is the glycosylation non-sialylated.

In yet another embodiment of the present invention is the glycosylation non-galactosylated.

In one embodiment of the present invention comprises the glycosylation biantennary N-glycans.

In another embodiment of the present invention does the glycosylation not comprise poly-LacNAc.

In yet another embodiment of the present invention is the glycosylation any combination without fucose.

In a further embodiment of the present invention has FUT8 been knocked out.

In one embodiment of the present invention has B4galt1 been knocked out allowing generation of more homogeneous N-glycans without galactose.

In another embodiment of the present invention has B4galt1 and fut8 been knocked out allowing generation of more homogeneous N-glycans without galactose and fucose.

One aspect of the present invention relates to a method for inactivation of one or more glycosyltransferase genes in a mammalian cell, the method comprising the step of inactivation of one or more glycosyltransferase genes in a mammalian cell, and determining that said gene inactivation can not result in protein product with a transmembrane retention signal, and/or stem region, and/or part of a catalytic domain.

Another aspect of the present invention relates to a method for the production of a cell that can generate recombinant glycoproteins that do not carry specific glycans, the method comprising the step of inactivation of one or more glycosyltransferase genes in a cell, wherein the one or more glycosyltransferase genes are involved in the biosynthesis of the specific glycans, and determining that said gene inactivation can not result in protein product with a transmembrane retention signal, and/or stem region, and/or part of a catalytic domain.

One aspect of the present invention relates to a method for producing a glycoproteins having modified glycan profile wherein the cell producing the glycoprotein has more than one modification of one or more glycosyltransferase genes.

In one embodiment of the present invention has the cells been modified by glycosyltransferase gene knock-out and/or knock-in of an exogeneous DNA sequence coding for a glycosyltransferase.

One aspect of the present invention relates to a method for producing a glycoprotein having a simple glycan profile, the method comprising inactivation of one or more glycosyltransferases, and/or knockin of one or more glycosyltransferases, or a combination hereof in a cell, and expression of a protein in said cell.

Another aspect of the present invention relates to a method for generating glycoproteins with improving glycosylation efficiency, the method comprising the step of inactivation of one or more glycosyltransferase genes to block and truncate one or more glycosylation pathways.

A further aspect of the present invention relates to a method for the production of recombinant glycoproteins that do not have specific types of glycosylation, the method comprising the step of inactivating two or more glycosyltransferase genes to block and truncate one or more glycosylation pathways.

One aspect of the present invention relates to a method for the production of recombinant glycoproteins, comprising the step of generating a mammalian cell with specific glycosylation properties.

A further aspect of the present invention relates to a glycoprotein obtainable from a method according to the present invention.

In one embodiment of the present invention has the glycostructure outcome one or more of the following changes selected from the group consisting of simpler glycan structure, more homogeneous product, more sialic acids per molecule, non-sialylated, non-galactosylated, more homogeneous bi-antennary, more homogeneous monoantennary, more homogeneous triantennary, more homogeneous without poly-LacNAc, higher productivity in cell culture, new stable homogeneous glycosylation capacities, more human glycostructure, more homogeneous glycosylation and improved ADCC targeting of IgG, modified fucose level, no fucose, improved substrate for generating glycoconjugates.

One aspect of the present invention relates to a glycoprotein according to the present invention, which is a homogeneous glycoconjugate produced from a glycoprotein having a simplified glycan profile.

Another aspect of the present invention relates to a glycoprotein according to the present invention, which is a homogeneous glycoprotein conjugate comprising a polymer selected from, PEG, HEP, XTEN, PSA, HES.

A further aspect of the present invention relates to a glycoprotein according to the present invention, which is a homogeneous PEGylated protein conjugate produced from a protein variant according to the invention having a simplified glycan profile.

Another aspect of the present invention relates to a glycoprotein according to the present invention, which is a protein conjugate according to the invention comprising FII, FV, FVIIa, FVIII, FIX, FX, FXIII, a Fab fragment of an antibody, or a Fc domain of an antibody.

A further aspect of the present invention relates to a glycoprotein according to the present invention, which is a protein-protein conjugate produced from a glycoprotein with a simplified glycan profile.

In one embodiment of the present invention is the glycoprotein according to the present invention a protein-protein conjugate produced from a glycoprotein with a simplified glycan profile comprising a Fab fragment and one of either FII, FV, FVIIa, FVIII, FIX, FX or FXIII.

In another embodiment of the present invention is the glycoprotein according to the present invention a protein-protein conjugate produced from a glycoprotein with a simplified glycan profile comprising a Fc Domain and one of either FII, FV, FVIIa, FVIII, FIX, FX or FXIII.

In a further embodiment of the present invention is the glycoprotein according to the present invention a homogeneous PEGylated EPO conjugate produced from an EPO variant having a simplified glycan profile.

One aspect of the present invention relates to the use of recombinant glycoproteins comprising monoantennary N-glycans for enzymatic modification of polypeptides.

Figure 1A:
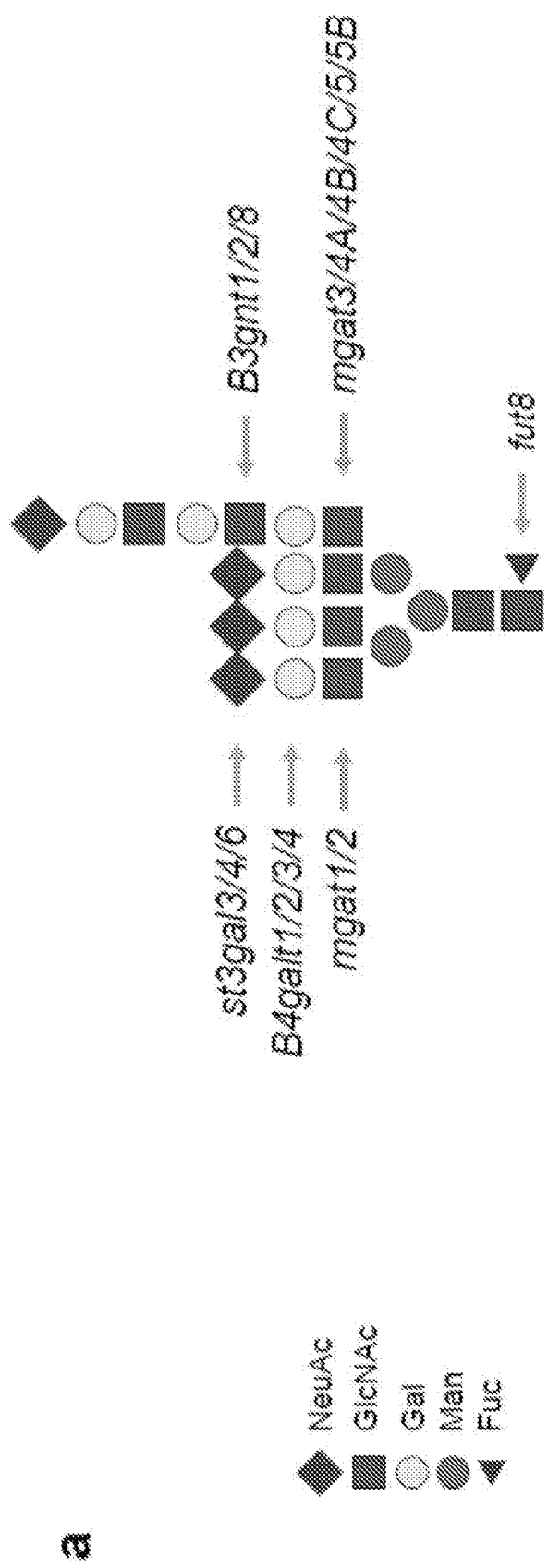
FIG. 1 shows ZFN knockout screen in CHO to define key glycosyltransferase genes involved in N-glycosylation using human EPO as reporter. (a) Graphic depiction of a common tetraantennary N-glycan with poly-LacNAc on the β6-antenna and capping by sialic acids. Arrows indicate glycosyltransferase genes with potential roles in biosynthesis of each step. Designations for monosaccharides according to the Consortium for Functional Glycomics are indicated. (b) Glycoprofiling of EPO expressed in CHO GS WT cells. MALDI-TOF spectra of PNGase F released permethylated N-glycans with labeling of four major species. (c) Glycoprofiling of EPO expressed in CHO GS cells with KO of genes involved in tri- and tetraantennary biosynthesis, showing that triple KO of mgat4A/4B/5 results in homogeneous biantennary N-glycans with a minor amount of poly-LacNAc (lower panel). (d) Glycoprofiling with KO of β4galactosyltransferase genes involved in LacNAc biosynthesis, showing that only B4galt1 KO alone produced substantial albeit partial loss of galactosylation, while only stacked KO of B4galt1/3 resulted in near complete loss of galactosylation. (e) Glycoprofiling with KO of two β3GlcNAc-transferase genes with claimed roles in poly-LacNAc biosynthesis, showing that KO of B3gnt2 results in complete loss of poly-LacNAc. (f) Glycoprofiling with KO of three α2,3sialyltransferase genes with claimed roles in N-glycosylation, showing that only the double KO of st3gal4/6 resulted in complete loss of sialic acid capping.

The present invention will now be described in more detail in the following.

DETAILED DESCRIPTION OF THE INVENTION

Sugar chains of glycoproteins are roughly divided into two types, namely a sugar chain which binds to asparagine (N-glycoside-linked sugar chain) and a sugar chain which binds to other amino acid such as serine, threonine (O-glycoside-linked sugar chain), based on the binding form to the protein moiety.

The sugar chain terminus which binds to asparagine is called a reducing end, and the opposite side is called a non-reducing end. It is known that the N-glycoside-linked sugar chain includes a high mannose type in which mannose alone binds to the non-reducing end of the core structure; a complex type in which the non-reducing end side of the core structure has at least one parallel branches of galactose-N-acetylglucosamine (hereinafter referred to as "Gal-GlcNAc") and the non-reducing end side of Gal-GlcNAc has a structure of sialic acid, bisecting N-acetylglucosamine or the like; a hybrid type in which the non-reducing end side of the core structure has branches of both of the high mannose type and complex type.

In general, most of the humanized antibodies of which application to medicaments is in consideration are prepared using genetic recombination techniques and produced using Chinese hamster ovary tissue-derived CHO cell as the host cell. As described above, the sugar chain structure play important roles for the structure, function, size, circulatory half-life, and pharmacokinetic behaviour of glycoprotein drugs. Moreover, the sugar structure plays a remarkably important role in the effector function of antibodies and differences are observed in the sugar chain structure of glycoproteins expressed by host cells, development of a host cell which can be used for the production of an antibody having higher effector function is desired.

To support production of a growing number of biopharmaceutical glycoproteins there is a need for development of new mammalian cell lines and preferably CHO derived cell lines with different glycosylation capacities and characteristics.

Moreover there is a need to develop design matrices for individual glycosylation pathways involving gene inactivation and/or stable gene introduction that will enable generation of tailored mammalian cell lines with different and more homogenous glycosylation capacities and characteristics.

Further there is a need to develop mammalian cell lines and preferably CHO derived cell lines with inactivation of two or more glycosyltransferase genes that can produce recombinant glycoproteins with different glycosylation than their natural counterpart. More particularly there is a need to develop such cell lines with inactivation of two or more glycosyltransferase genes encoding isoenzymes with related functions in the same glycosylation pathway being for example the N-glycosylation pathway. Further, there is a need to develop such cell lines with inactivation of two or more glycosyltransferase genes encoding enzymes with unrelated functions in the same glycosylation pathway.

Further there is a need to introduce one or more glycosyltransferases into cell lines and preferably CHO derived cell lines to obtain desirable glycosylation capacities including homogeneous and novel capacities. Such introduction of glycosyltransferase(s) may be combined with inactivation of one or more of the endogenous glycosyltransferase genes.

An object of the present invention is to provide a modified cell with genetically engineered stable capacity for production of a therapeutic protein, and that produces said protein with glycan chains with defined structures, and/or more homogenous glycan structures, and/or with improved bioactivity.

This invention discloses an inactivation and deconstruction screen of glycosyltransferase genes in CHO that provides a design matrix for engineering a cell with a multitude of well-defined glycosylation capacities. Moreover the invention provides reconstruction designs for de novo engineering a multitude of desired and/or novel well-defined glycosylation capacities by combining one or more glycosyltransferase gene inactivation and introduction events in a cell to improve production of recombinant glycoprotein therapeutics.

This invention discloses cell lines with inactivation of two or more glycosyltransferase genes and with new glycosylation capacities that enables improvements for recombinant production of protein therapeutics.

In one aspect, ZFN targeting designs for inactivation of glycosyltransferase genes are provided.

In another aspect, TALEN targeting designs for inactivation of glycosyltransferase genes are provided.

In yet another aspect, CRISPR/Cas9 based targeting for inactivation of glycosyltransferase genes are provided.

In certain embodiments, the invention provides cell lines with inactivation of two or more glycosyltransferase genes encoding isoenzymes with partially overlapping glycosylation functions in the same glycosylation pathway, and for which inactivation of two or more of these genes is required for loss of said glycosylation functions in the cell.

In certain embodiments, the invention provides cell lines with inactivation of two or more glycosyltransferase genes encoding isoenzymes with partially overlapping glycosylation functions in the same glycosylation pathway and biosynthetic step, and for which inactivation of two or more of these genes is required for loss of said glycosylation functions in the cell.

In certain embodiments, the invention provides cell lines with inactivation of two or more glycosyltransferase genes encoding isoenzymes with no overlapping glycosylation functions in the same glycosylation pathway, and for which inactivation of two or more of these genes is required for loss of said glycosylation functions in the cell.

In another embodiment, the invention provides cell lines with inactivation of two or more glycosyltransferase genes encoding enzymes with unrelated glycosylation functions in the same glycosylation pathway, and for which inactivation of two or more genes is required for abolishing said glycosylation functions in the cell.

In another embodiment, the invention provides cell lines with inactivation of two or more glycosyltransferase genes encoding enzymes with unrelated glycosylation functions in different glycosylation pathways, and for which inactivation of two or more genes is required for desirable glycosylation functions in the cell.

In another embodiment, the disclosure provides a design matrix to identify which glycosyltransferase gene inactivation(s) that are required for obtaining specific desirable N-glycosylation capacities in a cell line.

In another embodiment, the disclosure provides a design matrix for two or more glycosyltransferase gene inactivation(s) required for obtaining specific desirable N-glycosylation capacities in a cell line.

In yet another embodiment, this invention provides compositions for partial or complete knockout of glycosyltransferase genes, individually and in relevant combinations that encode enzymes involved in biosynthesis of N-glycans on proteins and are members of homologous subfamilies with potential redundant functions in a cell line. The disclosed compositions provide a design matrix for knockout combinations of glycosyltransferase genes that will generate mammalian cell lines with a variety of well-defined and homogeneous N-glycosylation capacities that are useful for production of recombinant glycoproteins such as antibodies, erythropoietin, and other therapeutic glycoproteins with improved and/or more consistent N-glycosylation.

In yet another embodiment, this invention provides a design matrix for one or more glycosyltransferase gene inactivation(s) required for obtaining N-glycosylation capacities in a mammalian cell line that are useful for recombinant production of glycoproteins that can be directly modified enzymatically with galactosyltransferase and/or sialyltransferase enzymes in vitro post production.

In yet another embodiment, the disclosure provides a design matrix for single or multiple glycosyltransferase gene inactivations required to obtain specific desirable N-glycosylation capacities that are advantageous for de novo stable introduction of one or more glycosyltransferases and function of these without direct competition from endogenous glycosyltransferase activities in a cell line.

In yet another embodiment, the disclosure provides a design matrix for single or multiple glycosyltransferase gene inactivations required to obtain specific desirable N-glycosylation capacities that are advantageous for de novo stable introduction of one or more glycosyltransferases and to induce improved and/or more homogenous glycosylation properties in a cell line.

The present inventors have first employed a ZFN-mediated knockout screen in CHO to explore the potential for engineering N-glycosylation of recombinant glycoproteins. Many steps in the N-glycan biosynthetic pathway are potentially catalyzed by multiple isoenzymes, which leave genetic engineering unpredictable (FIG. 1a). Dissection of the in vivo functions of each of these isoenzymes is required to construct a matrix for design options.

Thus, an object of the present invention is to provide a cell capable of expressing a gene encoding a polypeptide of interest, wherein the polypeptide of interest is expressed comprising one or more of the posttranslational modification patterns:

a) eliminated β4-branched tetraantennary N-glycans,
b) eliminated β6-branched tetraantennary structures,
c) elimination of L-PHA lectin labelling,
d) homogenous biantennary N-glycans,
e) abolished galactosylation on N-glycans,
f) elimination of poly-LacNAc,
g) heterogeneous tetraantennary N-glycans without trace of sialylation,
h) biantennary N-glycans without sialylation,
i) lack of sialic acid,
j) uncapped LacNAc termini,
k) homogenous biantennary N-glycans capped by α2,6NeuAc,
l) homogenous α2,6NeuAc capping, or
m) homogenous biantennary N-glycans capped by α2,3NeuAc.

One, two, three, four, five, six, seven, eight, nine, ten, eleven, twelve, or more of these effect can be combined to generate specific posttranslational modification patterns.

The genes involved in this highly complex machinery have been examined by the present inventors (see the examples) and effects have been identified.

Thus, in one aspect of the present invention is one or more of the group selected from mgat4A, mgat4B, mgat4C, mgat5, mgat5B, B4galt1, B4galt2, B4galt3, B4galt4, B3gnt1, B3gnt2, B3gnt8, st3gal3, st3gal4, and st3gal6 involved in the posttranslational modification patterns.

In another aspect of the present invention are one or more of these genes knocked out (KO) or in (KI).

In one aspect of the present invention mgat4A/4B is knocked out in the cell to eliminate β4-branched tetraantennary N-glycans.

In another aspect of the present invention mgat5 is knocked out in the cell to eliminate β6-branched tetraantennary structures.

In yet another aspect of the present invention mgat5 is knocked out in the cell leading to loss of L-PHA lectin labelling.

In a further aspect of the present invention mgat4A, mgat4B and mgat5 are knocked out in the cell leading to homogenous biantennary N-glycans.

In another aspect of the present invention B4galt1/3 is knocked out in the cell leading to abolished galactosylation on N-glycans.

In a further aspect of the present invention B3gnt2 is knocked out in the cell leading to elimination of poly-LacNAc.

In another aspect of the present invention st3gal4 and st4gal6 are knocked out in the cell leading to heterogeneous tetraantennary N-glycans without trace of sialylation.

In another aspect of the present invention st3gal4, st3gal6, mgat4A, mgat4B, and mgat5 are knocked out in the cell leading to biantennary N-glycans without sialylation, but increase in poly-LacNAc.

In another aspect of the present invention st3gal3, st3gal4, and st3gal6 are knocked out in the cell leading to complete lack of sialic acid.

In yet another aspect of the present invention st3gal4 and 6 are knocked out in the cell leading to uncapped LacNAc termini thereby allowing de novo engineering of recombinant glycoproteins with α2,6NeuAc capping.

In a further aspect of the present invention are st3gal4, st3gal6, mgat4A, mgat4B, mgat5 knocked out in the cell leading to homogenous biantennary N-glycans capped by α2,6NeuAc.

In yet another aspect b4galt1 is knocked out in a cell leading to loss of galactosylation and a homogenous N-glycan on the conserved N-glycan site of IgG when expressed recombinantly.

ST6GAL1 introduced (knock in, KI) with KO of st3gal4/6 produces the complete range of N-glycan antennary structures with normal degree of NeuAc capping (FIG. 2a).

ST6GAL1 introduced with additional KO of mgat4A/4B/5 produces glycoproteins with homogenous biantennary N-glycans capped by α2,6NeuAc (FIG. 2b).

De novo introduction of ST6GAL1 abrogates the minor amounts of poly-LacNAc formed on biantennary structures when sialylation is eliminated (FIG. 2b).

Thus, KI of ST6GAL1 can be used in combination with any one or more of the knockouts described herein.

In the present context is NeuAc also known as neuraminic acid.

Thus, an aspect of the present invention relates to a protein expressed in a cell, wherein the posttranslational modification pattern comprises homogenous biantennary N-glycans with or without α2,3NeuAc capping or with and without α2,6NeuAc capping.

Knockout means full or partial impairment of the function of the gene of interest.

In one aspect of the present invention is one or more of the above mentioned genes knocked out using zinc finger nucleases ZFN. ZFNs can be used for inactivation of a FUT8 gene or any of the other genes disclosed herein. ZFNs comprise a zinc finger protein (ZFP) and a nuclease (cleavage) domain.

In yet another embodiment, this invention provides CHO cell lines with different well-defined N-glycosylation capacities that enable recombinant production of glycoprotein therapeutics with N-glycans comprised of biantennary N-glycans with or without poly-LacNAc, and with or without α2,3NeuAc capping.

In yet another embodiment, this invention provides cell lines with different well-defined N-glycosylation capacities that enable recombinant production of glycoprotein therapeutics with N-glycans comprised of either biantennary, triantennary, or tetraantennary N-glycans with or without poly-LacNAc, and with or without α2,6NeuAc capping.

In yet another embodiment, this invention provides cell lines that enable production of glycoproteins with homogeneous N-glycans without sialic acid capping, which enables direct enzymatic modification of N-glycans by sialyltransferases in vitro postproduction.

In yet another embodiment, this invention provides cell lines that enable production of glycoproteins with homogeneous N-glycans without galactose and sialic acid capping, which enables direct enzymatic modification of N-glycans by galactosyltransferases in vitro postproduction.

In yet another embodiment, this invention provides cell lines that enable production of glycoproteins with homogeneous N-glycans of biantennary status without sialic acid capping, which enables direct enzymatic modification of N-glycans by sialyltransferases in vitro postproduction.

In yet another embodiment, this invention provides cell lines that enable production of glycoproteins with homogeneous N-glycans of monoantennary status with or without sialic acid capping, which enables direct enzymatic modification of one N-glycan by sialyltransferases in vitro postproduction.

In yet another aspect, also provided is an isolated cell comprising any of the proteins and/or polynucleotides as described herein. In certain embodiments, one or more glycosyltransferase genes are inactivated (partially or fully) in the cell. Any of the cells described herein may include additional genes that have been inactivated, for example, using zinc finger nucleases, TALENs and/or CRISPR/Cas9 designed to bind to a target site in the selected gene. In certain embodiments, provided herein are cells or cell lines in which two or more glycosyltransferase genes have been inactivated, and cells or cell lines in which one or more glycosyltransferase genes have been inactivated and one or more glycosyltransferases introduced.

In yet another embodiment, this invention provides cell lines with inactivation of undesirable glycosylation pathways for optimized production of glycoproteins with desirable glycosylation features. In certain embodiments inactivation of one or more biosynthetic steps in protein O-glycosylation pathways (O-GalNAc, O-Xyl, O-Man, and glycolipid) are obtained individually or in combination to improve the sugar nucleotide pool available for desirable glycosylation features.

In one embodiment, this invention provides a cell with inactivation of the second step in the O-GalNAc glycosylation pathway, and that produces truncated O-GalNAc O-glycans without sialic acid capping and with improved capacity for sialic acid capping of N-glycans.

In one embodiment, this invention provides a cell with inactivation of the second step in the O-Xyl glycosylation pathway, and that produces truncated O-Xyl O-glycans without proteoglycan chains and with improved capacity for galactosylation, poly-LacNAc, branching and sialic acid capping of N-glycans.

In one embodiment, this invention provides a cell with inactivation of the second step in the O-Man glycosylation pathway, and that produces truncated O-Man O-glycans without sialic acid capping and with improved capacity for galactosylation, poly-LacNAc, branching of N-glycans and sialic acid capping of N-glycans.

In one embodiment, this invention provides a cell with inactivation of the second step in the O-Man, O-Xyl and O-GalNAc glycosylation pathways, and that produces truncated O-Man, O-Xyl, and O-GalNAc O-glycans and with improved capacity for galactosylation, poly-LacNAc, branching of N-glycans and/or sialic acid capping of N-glycans.

In one embodiment, this invention provides a cell with inactivation mgat2, mgat4A, mgat4B, and mgat5, produce erythropoietin with N-glycans having homogenous monoantennary structures, and are suitable for more homogeneous glycomodification.

For example, cell lines as described herein having inactivated mgat2, mgat4A, mgat4B, mgat5, st3gal4 and 6 genes, produce erythropoietin with N-glycans having homogenous monoantennary structures without sialic acid capping, and are suitable for more homogeneous glycomodification.

Inactivation of unnecessary glycosyltransferases to improve desirable glycosylation pathways In yet another embodiment, this invention provides cell lines with inactivation of undesirable glycosylation enzymes to enhance capacity and/or fidelity of desirable glycosylation features. In certain embodiments cell lines with activation of one or more sialyltransferases, and/or galactosyltransferases, and/or GlcNAc-transferases, not functioning in a desirable glycosylation pathway such as for example N-glycosylation are provided.

In one embodiment, this invention provides a cell with inactivation of a β4galactosyltransferase (β4Gal-T7) with little or no function in the N-glycosylation pathway, and improved capacity for galactosylation, polyLacNAc and sialic acid capping of N-glycans.

In one embodiment, this invention provides a cell with inactivation of a sialyltransferase with little or no function in the N-glycosylation pathway, and improved capacity for galactosylation and sialic acid capping of N-glycans.

In one embodiment, this invention provides a cell with inactivation of a β3galactosyltransferase (C1GalT1) with little or no function in the N-glycosylation pathway, and improved capacity for galactosylation and sialic acid capping of N-glycans.

In one embodiment, this invention provides a cell with inactivation of a β4galactosyltransferase with little or no function in the N-glycosylation pathway, and improved capacity for galactosylation and sialic acid capping of N-glycans.

In one embodiment, this invention provides a cell with inactivation of a β2GlcNAc-transferase (POMGnT1) with little or no function in the N-glycosylation pathway, and improved capacity for galactosylation and sialic acid capping of N-glycans.

In one embodiment, this invention provides a cell with inactivation of a β3galactosyltransferase (C1GalT1), and/or a β2GlcNAc-transferase (POMGnT1), and/or a β4galactosyltransferase (β4Gal-T7) with little or no function in the N-glycosylation pathway, and improved capacity for galactosylation and sialic acid capping of N-glycans.

In one embodiment, this invention provides a cell with inactivation of a β4galactosyltransferase (β4Gal-T4) with little or no function in the N-glycosylation pathway, and improved capacity for galactosylation and sialic acid capping of N-glycans.

In addition, methods of using the zinc finger proteins and fusions thereof in methods of inactivating glycosyltransferase genes in a cell or cell line are provided. In certain embodiments, inactivating one or more glycosyltransferase genes results in a cell line, which can produce recombinant proteins at higher levels or in which one or more activities (functions) of the proteins are increased as compared to proteins produced in cells where the gene(s) is not inactivated.

Thus, in another aspect, provided herein are methods for inactivating one or more cellular glycosyltransferase genes (e.g., endogenous mgat1, mgat2, mgat3, mgat4A, mgat4B, mgat4C, mgat5, mgat5B, B4galt1, B4galt2, B4galt3, B4galt4, B3gnt1, B3gnt2, B3gnt8, st3gal3, st3gal4, st3gal6, fut8 genes) in a cell, by use of methods comprising genome perturbation, gene-editing and/or gene disruption capability such as nucleic acid vector systems related to Clustered Regularly Interspaced Short Palindromic Repeats (CRISPR) and components thereof, nucleic acid vector systems encoding fusion proteins comprising zinc finger DNA-binding domains (ZF) and at least one cleavage domain or at least one cleavage half-domain (ZFN) and/or nucleic acid vector systems encoding a first transcription activator-like (TAL) effector endonuclease monomer and a nucleic acid encoding a second cleavage domain or at least one cleavage half-domain (TALEN). Introduction into a cell of either of the above mentioned nucleic acid cleaving agents (CRISPR, TALEN, ZFN) are capable of specifically cleaving a glycosyltransferase gene target site as a result of cellular introduction of: (1) a nucleic acid encoding pair of either ZF or TAL glycosyltransferase gene target binding proteins each fused to said a nucleic acid cleaving moiety, wherein at least one of said ZF or TAL polypeptides is capable of specifically binding to a nucleotide sequence located upstream from said target cleavage site, and the other ZF or TAL protein is capable of specifically binding to a nucleotide sequence located downstream from the target cleavage site, whereby each of the zinc finger proteins are independently bound to and surround the nucleic acid target followed by target nucleic acid disruption by double stranded breakage mediated by the fused endonuclease cleaving moieties, (2) a nucleotide sequence encoding a CRISPR-Cas system guide RNA that hybridizes glycosyltransferase gene target sequence, and b) a second nucleotide sequence encoding a Type-II Cas9 protein, wherein components (a) and (b) are located on same or different vectors of the system, wherein the guide RNA is comprised of a chimeric RNA and includes a guide sequence and a trans-activating cr (tracr) sequence, whereby the guide RNA targets the glycosyltransferase gene target sequence and the Cas9 protein cleaves the glycosyltransferase gene target site.

In yet another embodiment, this invention provides cell lines with inactivation of one or more glycosyltransferase genes and with stable introduction of one or more glycosyltransferases to enhance fidelity of desirable glycosylation features and/or introduce improved glycosylation features and/or novel glycosylation features.

In certain embodiments cell lines with inactivation of one or more sialyltransferases, and/or galactosyltransferases, and/or glucosyltransferases, and/or GlcNAc-transferases, and/or GalNAc-transferases, and/or xylosyl-transferase, and/or glucuronosyltransferases, mannosyltransferases, and/or fucosyltransferases, and in which one or more glycosyltransferases have been stably introduced are provided.

For example, cell lines as described herein having inactivated st3gal4 and 6 genes and in which the human ST6Gal-I sialyltransferase has been introduced, produce erythropoietin with N-glycans homogenous capped by α2,6NeuAc and are more human-like.

For example, cell lines as described herein having inactivated mgat4A, mgat4B, mgat5, st3gal4 and 6 genes and in which the human ST6Gal-I sialyltransferase has been introduced, produce erythropoietin with biantennary N-glycans homogenously capped by α2,6NeuAc and are more human-like.

For example, cell lines as described herein having inactivated mgat4A, mgat4B, mgat5, st3gal4 and 6 genes and in which the human MGAT4A and ST6Gal-I have been introduced, produce erythropoietin with triantennary N-glycans homogenously capped by α2,6NeuAc and are more human-like.

For example, cell lines as described herein having inactivated mgat4A, mgat4B, mgat5, st3gal4 and 6 genes and in which MGAT4A, MGAT5 and ST6Gal-I have been introduced, produce erythropoietin with tetraantennary N-glycans homogenously capped by α2,6NeuAc and are more human-like.

There are a number of methods available for introduction of exogenous genes such as glycosyltransferase genes in mammalian cells and selecting stable clonal cell lines that harbor and express the gene of interest. Typically the gene of interest is co-transfected with a selection marker gene that favors cell lines expressing the selection marker under certain defined media culture conditions. The media could contain an inhibitor of the selection marker protein or the media composition could stress cell metabolism and thus require increased expression of the selection marker. The selection marker gene may be present on same plasmid as gene of interest or on another plasmid.

In one embodiment, introduction of one or more exogenous glycosyltransferase(s) is performed by plasmid transfection with a plasmid encoding constitutive promotor driven expression of both the glycosyltransferase gene and a selectable antibiotic marker, where the selectable marker could also represent an essential gene not present in the host cell such as GS system (Sigma/Lonza), and/or separate plasmids encoding the constitutive promotor driven glycosyltransferase gene or the selectable marker. For example, plasmids encoding ST6GalNAc-I and Zeocin have been transfected into cells and stable ST6Gal-I expressing lines have been selected based on zeocin resistance In another embodiment, introduction of one or more exogenous glycosyltransferase(s) is performed by site-directed nuclease-mediated insertion.

In one embodiment, a method for stably expressing at least one product of an exogenous nucleic acid sequence in a cell by introduction of double stranded breaks at the PPP1R12C or Safe Harbor #1 genomic locus using ZFN nucleic acid cleaving agents and an exogenous nucleic acid sequence that by a homology dependent manner or via compatible flanking ZFN cutting overhangs is inserted into the cleavage site and expressed. Safe Harbor sites are sites in the genome that upon manipulation do not lead to any obvious cellular or phenotypic consequences. In addition to the aforementioned sites, several other sites have been identified such as Safe Harbor #2, CCR5 and Rosa26. Besides ZFN technology, TALEN and CRISPR tools can also provide for integrating exogenous sequences into cell lines or genomes in a precise manner. In doing so it should be should be evaluated; i) to what extend epigenetic silencing and ii) what the desired expression level of the gene of interest should be. In the examples enclosed herein, site-specific integration of human glycosyltransferases e.g. ST6Gal-I, MGAT4A, or MGAT5, using the ObLiGaRe insertion strategy is based on a CMV expression driven insulator flanked vector design.

In yet another aspect, the disclosure provides a method of producing a recombinant protein of interest in a host cell, the method comprising the steps of: (a) providing a host cell comprising two or more endogenous glycosyltransferase genes; (b) inactivating the endogenous glycosyltransferase genes of the host cell by any of the methods described herein; and (c) introducing an expression vector comprising a transgene, the transgene comprising a sequence encoding a protein of interest, into the host cell, thereby producing the recombinant protein. In certain embodiments, the protein of interest comprises e.g. erythropoietin or an antibody, e.g., a monoclonal antibody.

In yet another aspect, the disclosure provides a method of producing a recombinant protein of interest in a cell, the method comprising the steps of: (a) providing a cell comprising one or more endogenous glycosyltransferase gene; (b) inactivating the endogenous glycosyltransferase gene(s) of the host cell; (c) introducing one or more glycosyltransferase gene(s) in the cell by any of the methods described herein;

and (d) introducing an expression vector comprising a transgene, the transgene comprising a sequence encoding a protein of interest, into the cell, thereby producing the recombinant protein. In certain embodiments, the protein of interest comprises e.g. erythropoietin or an antibody, e.g., a monoclonal antibody.

Another aspect of the disclosure encompasses a method for producing a recombinant protein with a more homogeneous and/or human-like and/or novel and/or functionally beneficial glycosylation pattern. The method comprises expressing the protein in a mammalian cell line deficient in two or more glycosyltransferase genes and/or deficient in one or more glycosyltransferase genes combined with one or more gained glycosyltransferase genes. In one specific embodiment, the cell line is a Chinese hamster ovary (CHO) cell line. In one embodiment, the cell line comprises inactivated chromosomal sequences encoding any endogenous glycosyltransferases. In one embodiment, the inactivated chromosomal sequences encoding any endogenous glycosyltransferases is monoallelic and the cell line produces a reduced amount of said glycosyltransferases. In another embodiment, the inactivated chromosomal sequences encoding encoding any endogenous glycosyltransferases are biallelic, and the cell line produces no measurable said glycosyltransferases. In another embodiment, the recombinant protein has more homogeneous and/or human-like and/or novel and/or functionally beneficial glycosylation pattern. In one embodiment, the recombinant protein has at least one property that is improved relative to a similar recombinant protein produced by a comparable cell line not deficient in said endogenous glycosyltransferases, for example, reduced immunogenicity, increased bioavailability, increased efficacy, increased stability, increased solubility, improved half-life, improved clearance, improved pharmacokinetics, and combinations thereof. The recombinant protein can be any protein, including a therapeutic protein. Exemplary proteins include those selected from but not limited to an antibody, an antibody fragment, a growth factor, a cytokine, a hormone, a lysosomal enzyme, a clotting factor, a gonadotropin and functional fragment or variants thereof.

The disclosure may also be used to identify target genes for modification and use this knowledge to glycoengineer an existing mammalian cell line previously transfected with DNA coding for the protein of interest.

In any of the cells and methods described herein, the cell or cell line can be a COS, CHO (e.g., CHO-S, CHO-K1, CHO-DG44, CHO-DUXB11, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and PERC6.

Cell lines as described herein can also be used to produce other N-glycoproteins including without intend for limitation for example α1-antitrypsin, gonadotropins, lysosomal targeted enzyme proteins (e.g. Glycocerebrosidase, alpha-Galactosidase, alpha-glucosidase, sulfatases, glucuronidase, iduronidase). Known human glycosyltransferase genes are assembled in homologous gene families in the CAZy database and these families are further assigned to different glycosylation pathways in Hansen et al. (Hansen, Lind-Thomsen et al. 2014). TABLE 1 lists all human glycosyltransferase genes in CAZy GT families with NCBI Gene IDs and assignment of confirmed or putative functions in biosynthesis of different mammalian glycoconjugates (N-glycans, O-GalNAc, O-GlcNAc, O-Glc, O-Gal, O-Fuc, O-Xyl, O-Man, C-Man, Glycosphingolipids, Hyaluronan, and GPI anchors). FIG. 1 further graphically depicts confirmed and putative roles of the human CAZy GT families in biosynthesis of different glycoconjugates.

TABLE 1

Human GTf genes

| CAZy family[1] | Gene ID[2] | Symbol[3] | Description[4] | Map location[5] |
|---|---|---|---|---|
| GT32 | 53947 | A4GALT | α1,4-galactosyltransferase | 22q13.2 |
| GT32 | 51146 | A4GNT | α1,4-N-acetylglucosaminyltransferase | 3p14.3 |
| GT6 | 28 | ABO | ABO blood group | 9q34.2 |
| GT33 | 56052 | ALG1 | chitobiosyldiphosphodolichol β-mannosyltransferase | 16p13.3 |
| GT59 | 84920 | ALG10 | α1,2-glucosyltransferase | 12p11.1 |
| GT59 | 144245 | ALG10B | α1,2-glucosyltransferase | 12q12 |
| GT4 | 440138 | ALG11 | α1,2-mannosyltransferase | 13q14.2 |
| GT22 | 79087 | ALG12 | α1,6-mannosyltransferase | 22q13.33 |
| GT1 | 79868 | ALG13 | UDP-N-acetylglucosaminyltransferase subunit | Xq23 |
| GT1 | 199857 | ALG14 | UDP-N-acetylglucosaminyltransferase subunit | 1p21.3 |
| GT33 | 200810 | ALG1L | chitobiosyldiphosphodolichol β-mannosyltransferase-like | 3q21.2 |
| GT33 | 644974 | ALG1L2 | chitobiosyldiphosphodolichol β-mannosyltransferase-like 2 | 3q22.1 |
| GT4 | 85365 | ALG2 | α1,3/1,6-mannosyltransferase | 9q22.33 |
| GT58 | 10195 | ALG3 | α1,3-mannosyltransferase | 3q27.1 |
| GT2 | 29880 | ALG5 | dolichyl-phosphate β-glucosyltransferase | 13q13.3 |
| GT57 | 29929 | ALG6 | α1,3-glucosyltransferase | 1p31.3 |
| GT57 | 79053 | ALG8 | α1,3-glucosyltransferase | 11q14.1 |
| GT22 | 79796 | ALG9 | α1,2-mannosyltransferase | 11q23 |
| GT31 | 8706 | B3GALNT1 | β1,3-N-acetylgalactosaminyltransferase 1 | 3q25 |
| GT31 | 148789 | B3GALNT2 | β1,3-N-acetylgalactosaminyltransferase 2 | 1q42.3 |
| GT31 | 8708 | B3GALT1 | UDP-Gal: βGlcNAc β 1,3-galactosyltransferase, polypeptide 1 | 2q24.3 |
| GT31 | 8707 | B3GALT2 | UDP-Gal: βGlcNAc β1,3-galactosyltransferase, polypeptide 2 | 1q31 |
| GT31 | 8705 | B3GALT4 | UDP-Gal: βGlcNAc-β1,3-galactosyltransferase, polypeptide 4 | 6p21.3 |
| GT31 | 10317 | B3GALT5 | UDP-Gal: βGlcNAc-β1,3-galactosyltransferase, polypeptide 5 | 21q22.3 |
| GT31 | 126792 | B3GALT6 | UDP-Gal: βGal-β31,3-galactosyltransferase polypeptide 6 | 1p36.33 |
| GT31 | 145173 | B3GALTL | β1,3-galactosyltransferase-like | 13q12.3 |
| GT43 | 27087 | B3GAT1 | β1,3-glucuronyltransferase 1 | 11q25 |
| GT43 | 135152 | B3GAT2 | β1,3-glucuronyltransferase 2 | 6q13 |
| GT43 | 26229 | B3GAT3 | β1,3-glucuronyltransferase 3 | 11q12.3 |

TABLE 1-continued

Human GTf genes

| CAZy family[1] | Gene ID[2] | Symbol[3] | Description[4] | Map location[5] |
|---|---|---|---|---|
| GT49 | 11041 | B3GNT1 | UDP-GlcNAc: βGal β1,3-N-acetylglucosaminyltransferase 1 | 11q13.2 |
| GT31 | 10678 | B3GNT2 | UDP-GlcNAc: βGal β1,3-N-acetylglucosaminyltransferase 2 | 2p15 |
| GT31 | 10331 | B3GNT3 | UDP-GlcNAc: βGal β1,3-N-acetylglucosaminyltransferase 3 | 19p13.1 |
| GT31 | 79369 | B3GNT4 | UDP-GlcNAc: βGal β1,3-N-acetylglucosaminyltransferase 4 | 12q24 |
| GT31 | 84002 | B3GNT5 | UDP-GlcNAc: βGal β1,3-N-acetylglucosaminyltransferase 5 | 3q28 |
| GT31 | 192134 | B3GNT6 | UDP-GlcNAc: βGal β1,3-N-acetylglucosaminyltransferase 6 | 11q13.4 |
| GT31 | 93010 | B3GNT7 | UDP-GlcNAc: βGal β1,3-N-acetylglucosaminyltransferase 7 | 2q37.1 |
| GT31 | 374907 | B3GNT8 | UDP-GlcNAc: βGal β1,3-N-acetylglucosaminyltransferase 8 | 19q13.2 |
| GT31 | 84752 | B3GNT9 | UDP-GlcNAc: βGal β1,3-N-acetylglucosaminyltransferase 9 | 16q22.1 |
| GT2 | 146712 | B3GNTL1 | UDP-GlcNAc: βGal β1,3-N-acetylglucosaminyltransferase-like 1 | 17q25.3 |
| GT12 | 2583 | B4GALNT1 | β1,4-N-acetyl-galactosaminyl transferase 1 | 12q13.3 |
| GT12 | 124872 | B4GALNT2 | β1,4-N-acetyl-galactosaminyl transferase 2 | 17q21.32 |
| GT7 | 283358 | B4GALNT3 | β1,4-N-acetyl-galactosaminyl transferase 3 | 12p13.33 |
| GT7 | 338707 | B4GALNT4 | β1,4-N-acetyl-galactosaminyl transferase 4 | 11p15.5 |
| GT7 | 2683 | B4GALT1 | UDP-Gal: βGlcNAc β1,4-galactosyltransferase, polypeptide 1 | 9p13 |
| GT7 | 8704 | B4GALT2 | UDP-Gal: βGlcNAc β1,4-galactosyltransferase, polypeptide 2 | 1p34-p33 |
| GT7 | 8703 | B4GALT3 | UDP-Gal: βGlcNAc β1,4-galactosyltransferase, polypeptide 3 | 1q21-q23 |
| GT7 | 8702 | B4GALT4 | UDP-Gal: βGlcNAc β1,4-galactosyltransferase, polypeptide 4 | 3q13.3 |
| GT7 | 9334 | B4GALT5 | UDP-Gal: βGlcNAc β1,4-galactosyltransferase, polypeptide 5 | 20q13.1-q13.2 |
| GT7 | 9331 | B4GALT6 | UDP-Gal: βGlcNAc β1,4-galactosyltransferase, polypeptide 6 | 18q11 |
| GT7 | 11285 | B4GALT7 | xylosylprotein β1,4-galactosyltransferase, polypeptide 7 | 5q35.2-q35.3 |
| GT31 | 56913 | C1GALT1 | core 1 synthase, galactosyltransferase 1 | 7p21.3 |
| GT31 | 29071 | C1GALT1C1 | C1GALT1-specific chaperone 1 | Xq24 |
| GT25 | 51148 | CERCAM | cerebral endothelial cell adhesion molecule | 9q34.11 |
| GT7/31 | 79586 | CHPF | chondroitin polymerizing factor | 2q35 |
| GT7/31 | 54480 | CHPF2 | chondroitin polymerizing factor 2 | 7q36.1 |
| GT7/31 | 22856 | CHSY1 | chondroitin sulfate synthase 1 | 15q26.3 |
| GT7/31 | 337876 | CHSY3 | chondroitin sulfate synthase 3 | 5q23.3 |
| GT25 | 79709 | COLGALT1 | collagen β(1-O)galactosyltransferase 1 | 19p13.11 |
| GT25 | 23127 | COLGALT2 | collagen β(1-O)galactosyltransferase 2 | 1q25 |
| GT7 | 55790 | CSGALNACT1 | chondroitin sulfate N-acetylgalactosaminyltransferase 1 | 8p21.3 |
| GT7 | 55454 | CSGALNACT2 | chondroitin sulfate N-acetylgalactosaminyltransferase 2 | 10q11.21 |
| GT2 | 8813 | DPM1 | dolichyl-phosphate mannosyltransferase polypeptide 1 | 20q13.13 |
| GTnc | 23333 | DPY19L1 | dpy-19-like 1 (*C. elegans*) | 7p14.3-p14.2 |

TABLE 1-continued

Human GTf genes

| CAZy family[1] | Gene ID[2] | Symbol[3] | Description[4] | Map location[5] |
|---|---|---|---|---|
| GTnc | 283417 | DPY19L2 | dpy-19-like 2 (*C. elegans*) | 12q14.2 |
| GTnc | 147991 | DPY19L3 | dpy-19-like 3 (*C. elegans*) | 19q13.11 |
| GTnc | 286148 | DPY19L4 | dpy-19-like 4 (*C. elegans*) | 8q22.1 |
| GT61 | 285203 | EOGT | EGF domain-specific O-linked N-acetylglucosamine transferase | 3p14.1 |
| GT47/64 | 2131 | EXT1 | exostosin glycosyltransferase 1 | 8q24.11 |
| GT47/64 | 2132 | EXT2 | exostosin glycosyltransferase 2 | 11p12-p11 |
| GT47/64 | 2134 | EXTL1 | exostosin-like glycosyltransferase 1 | 1p36.1 |
| GT64 | 2135 | EXTL2 | exostosin-like glycosyltransferase 2 | 1p21 |
| GT47/64 | 2137 | EXTL3 | exostosin-like glycosyltransferase 3 | 8p21 |
| GTnc | 79147 | FKRP | fukutin related protein | 19q13.32 |
| GTnc | 2218 | FKTN | Fukutin | 9q31-q33 |
| GT11 | 2523 | FUT1 | fucosyltransferase 1, H blood group | 19q13.3 |
| GT10 | 84750 | FUT10 | fucosyltransferase 10, α1,3 fucosyltransferase | 8p12 |
| GT10 | 170384 | FUT11 | fucosyltransferase 11, α1,3 fucosyltransferase | 10q22.2 |
| GT11 | 2524 | FUT2 | fucosyltransferase 2 secretor status include | 19q13.3 |
| GT10 | 2525 | FUT3 | fucosyltransferase 3, Lewis blood group | 19p13.3 |
| GT10 | 2526 | FUT4 | fucosyltransferase 4, α1,3 fucosyltransferase, myeloid-specific | 11q21 |
| GT10 | 2527 | FUT5 | fucosyltransferase 5, α1,3 fucosyltransferase | 19p13.3 |
| GT10 | 2528 | FUT6 | fucosyltransferase 6, α1,3 fucosyltransferase | 19p13.3 |
| GT10 | 2529 | FUT7 | fucosyltransferase 7, α1,3 fucosyltransferase | 9q34.3 |
| GT23 | 2530 | FUT8 | fucosyltransferase 8, α1,6 fucosyltransferase | 14q24.3 |
| GT10 | 10690 | FUT9 | fucosyltransferase 9, α1,3 fucosyltransferase | 6q16 |
| GT27 | 2589 | GALNT1 | polypeptide N-acetylgalactosaminyltransferase 1 | 18q12.1 |
| GT27 | 55568 | GALNT10 | polypeptide N-acetylgalactosaminyltransferase 10 | 5q33.2 |
| GT27 | 63917 | GALNT11 | polypeptide N-acetylgalactosaminyltransferase 11 | 7q36.1 |
| GT27 | 79695 | GALNT12 | polypeptide N-acetylgalactosaminyltransferase 12 | 9q22.33 |
| GT27 | 114805 | GALNT13 | polypeptide N-acetylgalactosaminyltransferase 13 | 2q24.1 |
| GT27 | 79623 | GALNT14 | polypeptide N-acetylgalactosaminyltransferase 14 | 2p23.1 |
| GT27 | 117248 | GALNT15 | polypeptide N-acetylgalactosaminyltransferase 15 | 3p25.1 |
| GT27 | 57452 | GALNT16 | polypeptide N-acetylgalactosaminyltransferase 16 | 14q24.1 |
| GT27 | 374378 | GALNT18 | polypeptide N-acetylgalactosaminyltransferase 18 | 11p15.3 |
| GT27 | 2590 | GALNT2 | polypeptide N-acetylgalactosaminyltransferase 2 | 1q41-q42 |
| GT27 | 2591 | GALNT3 | polypeptide N-acetylgalactosaminyltransferase 3 | 2q24-q31 |
| GT27 | 8693 | GALNT4 | polypeptide N-acetylgalactosaminyltransferase 4 | 12q21.33 |

TABLE 1-continued

Human GTf genes

| CAZy family[1] | Gene ID[2] | Symbol[3] | Description[4] | Map location[5] |
|---|---|---|---|---|
| GT27 | 11227 | GALNT5 | polypeptide N-acetylgalactosaminyltransferase 5 | 2q24.1 |
| GT27 | 11226 | GALNT6 | polypeptide N-acetylgalactosaminyltransferase 6 | 12q13 |
| GT27 | 51809 | GALNT7 | polypeptide N-acetylgalactosaminyltransferase 7 | 4q31.1 |
| GT27 | 26290 | GALNT8 | polypeptide N-acetylgalactosaminyltransferase 8 | 12p13.3 |
| GT27 | 50614 | GALNT9 | polypeptide N-acetylgalactosaminyltransferase 9 | 12q24.33 |
| GT27 | 168391 | GALNTL5 | polypeptide N-acetylgalactosaminyltransferase-like 5 | 7q36.1 |
| GT27 | 442117 | GALNTL6 | polypeptide N-acetylgalactosaminyltransferase-like 6 | 4q34.1 |
| GT6 | 26301 | GBGT1 | globoside α1,3-N-acetylgalactosaminyltransferase 1 | 9q34.13-q34.3 |
| GT14 | 2650 | GCNT1 | glucosaminyl (N-acetyl) transferase 1, core 2 | 9q13 |
| GT14 | 2651 | GCNT2 | glucosaminyl (N-acetyl) transferase 2, I-branching enzyme | 6p24.2 |
| GT14 | 9245 | GCNT3 | glucosaminyl (N-acetyl) transferase 3, mucin type | 15q21.3 |
| GT14 | 51301 | GCNT4 | glucosaminyl (N-acetyl) transferase 4, core 2 | 5q12 |
| GT14 | 644378 | GCNT6 | glucosaminyl (N-acetyl) transferase 6 | 6p24.2 |
| GT14 | 140687 | GCNT7 | glucosaminyl (N-acetyl) transferase family member 7 | 20q13.2 |
| GT6 | 2681 | GGTA1P | glycoprotein, α-galactosyltransferase 1 pseudogene | 9q33.2 |
| GT4 | 144423 | GLT1D1 | glycosyltransferase 1 domain containing 1 | 12q24.33 |
| GT6 | 360203 | GLT6D1 | glycosyltransferase 6 domain containing 1 | 9q34.3 |
| GT8 | 55830 | GLT8D1 | glycosyltransferase 8 domain containing 1 | 3p21.1 |
| GT8 | 83468 | GLT8D2 | glycosyltransferase 8 domain containing 2 | 12q |
| GT4 | 79712 | GTDC1 | glycosyltransferase-like domain containing 1 | 2q22.3 |
| GT8 | 283464 | GXYLT1 | glucoside xylosyltransferase 1 | 12q12 |
| GT8 | 727936 | GXYLT2 | glucoside xylosyltransferase 2 | 3p13 |
| GT8 | 2992 | GYG1 | glycogenin 1 | 3q24-q25.1 |
| GT8 | 8908 | GYG2 | glycogenin 2 | Xp22.3 |
| GT8/49 | 120071 | GYLTL1B | glycosyltransferase-like 1B, LARGE2 | 11p11.2 |
| GT3 | 2997 | GYS1 | glycogen synthase 1 (muscle) | 19q13.3 |
| GT3 | 2998 | GYS2 | glycogen synthase 2 (liver) | 12p12.2 |
| GT2 | 3036 | HAS1 | hyaluronan synthase 1 | 19q13.4 |
| GT2 | 3037 | HAS2 | hyaluronan synthase 2 | 8q24.12 |
| GT2 | 3038 | HAS3 | hyaluronan synthase 3 | 16q22.1 |
| GT90 | 79070 | KDELC1 | KDEL (Lys-Asp-Glu-Leu) containing 1 like-glycosyltransferase | 13q33 |
| GT8/49 | 9215 | LARGE | β1,3-xylosyltransferase | 22q12.3 |
| GT31 | 3955 | LFNG | O-fucosylpeptide 3-βN-acetylglucosaminyltransferase | 7p22.2 |
| GT31 | 4242 | MFNG | O-fucosylpeptide 3-βN-acetylglucosaminyltransferase | 22q12 |
| GT13 | 4245 | MGAT1 | mannosyl α1,3glycoprotein β1,2N-acetylglucosaminyltransferase | 5q35 |
| GT16 | 4247 | MGAT2 | mannosyl α1,6glycoprotein β2N-acetylglucosaminyltransferase | 14q21 |

TABLE 1-continued

Human GTf genes

| CAZy family[1] | Gene ID[2] | Symbol[3] | Description[4] | Map location[5] |
|---|---|---|---|---|
| GT17 | 4248 | MGAT3 | mannosyl β1,4glycoprotein β1,4N-acetylglucosaminyltransferase | 22q13.1 |
| GT54 | 11320 | MGAT4A | mannosyl α1,3glycoprotein β1,4N-acetylglucosaminyltransferase | 2q12 |
| GT54 | 11282 | MGAT4B | mannosyl α1,3glycoprotein β1,4N-acetylglucosaminyltransferase | 5q35 |
| GT54 | 25834 | MGAT4C | mannosyl α1,3glycoprotein β1,4N-acetylglucosaminyltransferase | 12q21 |
| GT18 | 4249 | MGAT5 | mannosyl α1,6glycoprotein β1,6N-acetylglucosaminyltransferase | 2q21.3 |
| GT18 | 146664 | MGAT5B | mannosyl α1,6glycoprotein β-1,6-N-acetyl-glucosaminyltransferase, isozyme B | 17q25.2 |
| GT41 | 8473 | OGT | O-linked N-acetylglucosamine (GlcNAc) transferase | Xq13 |
| GT4 | 5277 | PIGA | phosphatidylinositol glycan anchor biosynthesis, class A | Xp22.1 |
| GT22 | 9488 | PIGB | phosphatidylinositol glycan anchor biosynthesis, class B | 15q21.3 |
| GT50 | 93183 | PIGM | phosphatidylinositol glycan anchor biosynthesis, class M | 1q23.2 |
| GT76 | 55650 | PIGV | phosphatidylinositol glycan anchor biosynthesis, class V | 1p36.11 |
| GT22 | 80235 | PIGZ | phosphatidylinositol glycan anchor biosynthesis, class Z | 3q29 |
| GTnc | 8985 | PLOD3 | procollagen-lysine, 2-oxoglutarate 5-dioxygenase 3 | 7q22 |
| GT65 | 23509 | POFUT1 | O-fucosyltransferase 1 | 20q11 |
| GT68 | 23275 | POFUT2 | O-fucosyltransferase 2 | 21q22.3 |
| GT90 | 56983 | POGLUT1 | O-glucosyltransferase 1 | 3q13.33 |
| GT13 | 55624 | POMGNT1 | O-linked mannose N-acetylglucosaminyltransferase 1, β1,2 | 1p34.1 |
| GT61 | 84892 | POMGNT2 | O-linked mannose N-acetylglucosaminyltransferase 2, β1,4 | 3p22.1 |
| GT39 | 10585 | POMT1 | O-mannosyltransferase 1 | 9q34.1 |
| GT39 | 29954 | POMT2 | O-mannosyltransferase 2 | 14q24 |
| GT35 | 5834 | PYGB | phosphorylase, glycogen; brain | 20p11.21 |
| GT35 | 5836 | PYGL | phosphorylase, glycogen, liver | 14q21-q22 |
| GT35 | 5837 | PYGM | phosphorylase, glycogen, muscle | 11q12-q13.2 |
| GT31 | 5986 | RFNG | O-fucosylpeptide 3βN-acetylglucosaminyltransferase | 17q25 |
| GT29 | 6482 | ST3GAL1 | β-galactoside α-2,3-sialyltransferase 1 | 8q24.22 |
| GT29 | 6483 | ST3GAL2 | β-galactoside α-2,3-sialyltransferase 2 | 16q22.1 |
| GT29 | 6487 | ST3GAL3 | β-galactoside α-2,3-sialyltransferase 3 | 1p34.1 |
| GT29 | 6484 | ST3GAL4 | β-galactoside α-2,3-sialyltransferase 4 | 11q24.2 |
| GT29 | 8869 | ST3GAL5 | β-galactoside α-2,3-sialyltransferase 5 | 2p11.2 |
| GT29 | 10402 | ST3GAL6 | β-galactoside α-2,3-sialyltransferase 6 | 3q12.1 |
| GT29 | 6480 | ST6GAL1 | β-galactosamide α-2,6-sialyltranferase 1 | 3q27-q28 |
| GT29 | 84620 | ST6GAL2 | β-galactosamide α-2,6-sialyltranferase 2 | 2q11.2-q12.1 |
| GT29 | 55808 | ST6GALNAC1 | α-N-acetyl-neuraminyl-2,3-β-galactosyl-1,3-N-acetylgalactosaminide α-2,6-sialyltransferase 1 | 17q25.1 |
| GT29 | 10610 | ST6GALNAC2 | α-N-acetyl-neuraminyl-2,3-β-galactosyl-1,3)-N-acetylgalactosaminide α-2,6-sialyltransferase 2 | 17q25.1 |

TABLE 1-continued

Human GTf genes

| CAZy family[1] | Gene ID[2] | Symbol[3] | Description[4] | Map location[5] |
|---|---|---|---|---|
| GT29 | 256435 | ST6GALNAC3 | α-N-acetyl-neuraminyl-2,3-β-galactosyl-1,3)-N-acetylgalactosaminide α-2,6-sialyltransferase 3 | 1p31.1 |
| GT29 | 27090 | ST6GALNAC4 | α-N-acetyl-neuraminyl-2,3-β-galactosyl-1,3-N-acetylgalactosaminide α-2,6-sialyltransferase 4 | 9q34 |
| GT29 | 81849 | ST6GALNAC5 | α-N-acetyl-neuraminyl-2,3-β-galactosyl-1,3-N-acetylgalactosaminide α-2,6-sialyltransferase 5 | 1p31.1 |
| GT29 | 30815 | ST6GALNAC6 | α-N-acetyl-neuraminyl-2,3-β-galactosyl-1,3-N-acetylgalactosaminide α-2,6-sialyltransferase 6 | 9q34.11 |
| GT29 | 6489 | ST8SIA1 | α-N-acetyl-neuraminide α-2,8-sialyltransferase 1 | 12p12.1-p11.2 |
| GT29 | 8128 | ST8SIA2 | α-N-acetyl-neuraminide α-2,8-sialyltransferase 2 | 15q26 |
| GT29 | 51046 | ST8SIA3 | α-N-acetyl-neuraminide α-2,8-sialyltransferase 3 | 18q21.31 |
| GT29 | 7903 | ST8SIA4 | α-N-acetyl-neuraminide α-2,8-sialyltransferase 4 | 5q21 |
| GT29 | 29906 | ST8SIA5 | α-N-acetyl-neuraminide α-2,8-sialyltransferase 5 | 18q21.1 |
| GT29 | 338596 | ST8SIA6 | α-N-acetyl-neuraminide α-2,8-sialyltransferase 6 | 10p12.33 |
| GT66 | 3703 | STT3A | subunit of the oligosaccharyltransferase complex (catalytic) | 11q23.3 |
| GT66 | 201595 | STT3B | subunit of the oligosaccharyltransferase complex (catalytic) | 3p23 |
| GTnc | 10329 | TMEM5 | transmembrane protein 5 | 12q14.2 |
| GT21 | 7357 | ST8SIA | UDP-glucose ceramide glucosyltransferase | 9q31 |
| GT24 | 56886 | UGGT1 | UDP-glucose glycoprotein glucosyltransferase 1 | 2q14.3 |
| GT24 | 55757 | UGGT2 | UDP-glucose glycoprotein glucosyltransferase 2 | 13q32.1 |
| GT1 | 54658 | UGT1A1 | UDP glucuronosyltransferase 1 family, polypeptide A1 | 2q37 |
| GT1 | 54575 | UGT1A10 | UDP glucuronosyltransferase 1 family, polypeptide A10 | 2q37 |
| GT1 | 54659 | UGT1A3 | UDP glucuronosyltransferase 1 family, polypeptide A3 | 2q37 |
| GT1 | 54657 | UGT1A4 | UDP glucuronosyltransferase 1 family, polypeptide A4 | 2q37 |
| GT1 | 54579 | UGT1A5 | UDP glucuronosyltransferase 1 family, polypeptide A5 | 2q37 |
| GT1 | 54578 | UGT1A6 | UDP glucuronosyltransferase 1 family, polypeptide A6 | 2q37 |
| GT1 | 54577 | UGT1A7 | UDP glucuronosyltransferase 1 family, polypeptide A7 | 2q37 |
| GT1 | 54576 | UGT1A8 | UDP glucuronosyltransferase 1 family, polypeptide A8 | 2q37 |
| GT1 | 54600 | UGT1A9 | UDP glucuronosyltransferase 1 family, polypeptide A9 | 2q37 |
| GT1 | 10941 | UGT2A1 | UDP glucuronosyltransferase 2 family, polypeptide A1 | 4q13 |
| GT1 | 79799 | UGT2A3 | UDP glucuronosyltransferase 2 family, polypeptide A3 | 4q13.2 |
| GT1 | 7365 | UGT2B10 | UDP glucuronosyltransferase 2 family, polypeptide B10 | 4q13.2 |
| GT1 | 10720 | UGT2B11 | UDP glucuronosyltransferase 2 family, polypeptide B11 | 4q13.2 |
| GT1 | 7366 | UGT2B15 | UDP glucuronosyltransferase 2 family, polypeptide B15 | 4q13 |
| GT1 | 7367 | UGT2B17 | UDP glucuronosyltransferase 2 family, polypeptide B17 | 4q13 |
| GT1 | 54490 | UGT2B28 | UDP glucuronosyltransferase 2 family, polypeptide B28 | 4q13.2 |
| GT1 | 7363 | UGT2B4 | UDP glucuronosyltransferase 2 family, polypeptide B4 | 4q13 |

TABLE 1-continued

Human GTf genes

| CAZy family[1] | Gene ID[2] | Symbol[3] | Description[4] | Map location[5] |
|---|---|---|---|---|
| GT1 | 7364 | UGT2B7 | UDP glucuronosyltransferase 2 family, polypeptide B7 | 4q13 |
| GT1 | 133688 | UGT3A1 | UDP glycosyltransferase 3 family, polypeptide A1 | 5p13.2 |
| GT1 | 167127 | UGT3A2 | UDP glycosyltransferase 3 family, polypeptide A2 | 5p13.2 |
| GT1 | 7368 | UGT8 | UDP glycosyltransferase 8 | 4q26 |
| GT27 | 64409 | WBSCR17 | Williams-Beuren syndrome chromosome region 17 | 7q11.23 |
| GT8 | 152002 | XXYLT1 | xyloside xylosyltransferase 1 | 3q29 |
| GT14 | 64131 | XYLT1 | xylosyltransferase I | 16p12.3 |
| GT14 | 64132 | XYLT2 | xylosyltransferase II | 17q21.33 |

[1]GT classification system (Lombard et al. (2013). Nucl Acid Res 42: D1P: D490-D495)
[2]gene symbol
[3]Gene ID GenBank
[4]Protein name UniProt
[5]Human chromosomal position (hg19)

Most of the corresponding orthologous CHO glycosyltransferase genes were previously assigned in connection with the recent sequencing of the CHO genome (Xu, Nagarajan et al. 2011), but some genes were wrongly assigned or missed. The current set of orthologous glycosyltransferase genes in human and CHO are listed in TABLE 2.

TABLE 2

Chinese hamster (*Cricetulus griseus*) GTfs genes

| CAZy family[1] | Symbol[2] | Gene ID[3] | Description[4] |
|---|---|---|---|
| GT1 | Alg13 | 100754023 | UDP-N-acetylglucosaminyltransferase subunit |
| GT1 | Alg14 | 100773644 | UDP-N-acetylglucosaminyltransferase subunit |
| GT1 | Ugt1a1 | 100755423 | UDP-glucuronosyltransferase 1-6 |
| GT1 | Ugt2a1 | 100762963 | UDP glucuronosyltransferase 2 family, polypeptide A1, complex locus |
| GT1 | Ugt2a3 | 100762673 | UDP-glucuronosyltransferase 2A3 |
| GT2 | Alg5 | 100769679 | ALG5, dolichyl-phosphate β-glucosyltransferase |
| GT2 | B3gntl1 | 100751193 | UDP-GlcNAc: βGal β-1,3-N-acetylglucosaminyltransferase-like 1 |
| GT2 | Dpm1 | 100689420 | dolichyl-phosphate mannosyltransferase polypeptide 1, catalytic subunit |
| GT2 | Has2 | 100751055 | hyaluronan synthase 2 |
| GT2 | Has2 | 100751055 | hyaluronan synthase 2 |
| GT2 | Has3 | 100757895 | hyaluronan synthase 3 |
| GT3 | Gys1 | 100769788 | glycogen synthase 1 (muscle) |
| GT3 | Gys2 | 100770628 | glycogen synthase 2 (liver) |
| GT4 | Alg11 | 100771009 | α-1,2-mannosyltransferase |
| GT4 | Alg2 | 100768412 | α-1,3/1,6-mannosyltransferase |
| GT4 | Glt1d1 | 100761757 | glycosyltransferase 1 domain containing 1 |
| GT4 | Gtdc1 | 100752161 | glycosyltransferase-like domain containing 1 |
| GT4 | Piga | 100773712 | phosphatidylinositol glycan anchor biosynthesis, class A |
| GT6 | Abo | 100772592 | ABO blood group |
| GT6 | Gbgt1 | 100771256 | globoside α-1,3-N-acetylgalactosaminyltransferase 1 |
| GT7 | B4galnt3 | 100756528 | β-1,4-N-acetyl-galactosaminyl transferase 3 |
| GT7 | B4galnt4 | 100758404 | β-1,4-N-acetyl-galactosaminyl transferase 4 |
| GT7 | B4galt1 | 100689430 | UDP-Gal: βGlcNAc β1,4-galactosyltransferase, polypeptide 1 |
| GT7 | B4galt2 | 100689434 | UDP-Gal: βGlcNAc β1,4-galactosyltransferase, polypeptide 2 |
| GT7 | B4galt3 | 100689346 | UDP-Gal: βGlcNAc β1,4-galactosyltransferase, polypeptide 3 |
| GT7 | B4galt4 | 100689435 | UDP-Gal: βGlcNAc β1,4-galactosyltransferase, polypeptide 4 |

TABLE 2-continued

Chinese hamster (*Cricetulus griseus*) GTfs genes

| CAZy family[1] | Symbol[2] | Gene ID[3] | Description[4] |
|---|---|---|---|
| GT7 | B4galt5 | 100689347 | UDP-Gal: βGlcNAc β1,4-galactosyltransferase, polypeptide 5 |
| GT7 | B4galt6 | 100689438 | UDP-Gal: βGlcNAc β1,4-galactosyltransferase, polypeptide 6 |
| GT7 | B4galt7 | 100769652 | xylosylprotein β1,4-galactosyltransferase, polypeptide 7 |
| GT7/GT31 | Chpf | 100765856 | chondroitin polymerizing factor |
| GT7/GT31 | Chsy1 | 100770803 | chondroitin sulfate synthase 1 |
| GT7/GT31 | Chsy3 | 100767985 | chondroitin sulfate synthase 3 |
| GT7 | Csgalnact1 | 100754969 | chondroitin sulfate N-acetylgalactosaminyltransferase 1 |
| GT7 | Csgalnact2 | 100770830 | chondroitin sulfate N-acetylgalactosaminyltransferase 2 |
| GT8 | Glt8d1 | 100762757 | glycosyltransferase 8 domain containing 1 |
| GT8 | Glt8d2 | 100772458 | glycosyltransferase 8 domain containing 2 |
| GT8 | Gxylt1 | 100760543 | glucoside xylosyltransferase 1 |
| GT8 | Gxylt2 | 100758512 | glucoside xylosyltransferase 2 |
| GT8 | Gyg1 | 100751671 | glycogenin 1 |
| GT8/49 | Gyltl1b | 100750932 | glycosyltransferase-like 1B |
| GT8/49 | Large | 100765249 | like-glycosyltransferase |
| GT8 | Xxylt1 | 100760146 | xyloside xylosyltransferase 1 |
| GT10 | Fut10 | 100760260 | fucosyltransferase 10 (α (1,3) fucosyltransferase) |
| GT10 | Fut11 | 100758336 | fucosyltransferase 11 (α (1,3) fucosyltransferase) |
| GT10 | Fut4 | 100754814 | fucosyltransferase 4 (α (1,3) fucosyltransferase, myeloid-specific) |
| GT10 | Fut6a | 100689084 | α1,3 fucosyltransferase 6A |
| GT10 | Fut6b | 100689083 | α1,3 fucosyltransferase 6B |
| GT10 | Fut7 | 100772214 | α1,3 fucosyltransferase |
| GT10 | Fut9 | 100689036 | α1,3 fucosyltransferase |
| GT11 | Fut1 | 100757047 | galactoside 2α-L-fucosyltransferase, H blood group |
| GT11 | Fut2 | 100751185 | fucosyltransferase 2 |
| GT12 | B4galnt1 | 100764682 | β1,4-N-acetyl-galactosaminyl transferase 1 |
| GT12 | B4galnt2 | 100760696 | β1,4-N-acetyl-galactosaminyl transferase 2 |
| GT13 | Mgat1 | 100682529 | mannosyl (α-1,3-)-glycoprotein β1,2-N-acetylglucosaminyltransferase |
| GT13 | Pomgnt1 | 100772511 | protein O-linked mannose N-acetylglucosaminyltransferase 1 (β1,2-) |
| GT14 | Gcnt1 | 100767124 | glucosaminyl (N-acetyl) transferase 1, core 2 |
| GT14 | Gcnt3 | 100774815 | glucosaminyl (N-acetyl) transferase 3, mucin type |
| GT14 | Gcnt4 | 100757239 | glucosaminyl (N-acetyl) transferase 4, core 2 |
| GT14 | Gcnt7 | 100760777 | glucosaminyl (N-acetyl) transferase family member 7 |
| GT14 | Xylt1 | 100756878 | xylosyltransferase I |
| GT14 | Xylt2 | 100759604 | xylosyltransferase II |
| GT16 | Mgat2 | 100753385 | mannosyl (α-1,6-)-glycoprotein β-1,2-N-acetylglucosaminyltransferase |
| GT17 | Mgat3 | 100689076 | mannosyl (β-1,4-)-glycoprotein β-1,4-N-acetylglucosaminyltransferase |
| GT18 | Mgat5 | 100760162 | mannosyl (α-1,6-)-glycoprotein β-1,6-N-acetyl-glucosaminyltransferase |
| GT18 | Mgat5b | 100771275 | mannosyl (α-1,6-)-glycoprotein β-1,6-N-acetyl-glucosaminyltransferase |
| GT21 | Ugcg | 100689432 | UDP-glucose ceramide glucosyltransferase |
| GT22 | Alg12 | 100770096 | α-1,6-mannosyltransferase |
| GT22 | Alg9 | 100755062 | α-1,2-mannosyltransferase |
| GT22 | Pigb | 100768002 | phosphatidylinositol glycan anchor biosynthesis, class B |
| GT22 | Pigz | 100750622 | phosphatidylinositol glycan anchor biosynthesis, class Z |
| GT23 | Fut8 | 100751648 | α1,6 fucosyltransferase) |
| GT24 | Uggt1 | 100773968 | UDP-glucose glycoprotein glucosyltransferase 1 |
| GT24 | Uggt2 | 100762273 | UDP-glucose glycoprotein glucosyltransferase 2 |

TABLE 2-continued

Chinese hamster (*Cricetulus griseus*) GTfs genes

| CAZy family[1] | Symbol[2] | Gene ID[3] | Description[4] |
|---|---|---|---|
| GT25 | Cercam | 100765284 | cerebral endothelial cell adhesion molecule |
| GT25 | Colgalt1 | 100774081 | collagen β(1-O)galactosyltransferase 1 |
| GT25 | Colgalt2 | 100764465 | collagen β(1-O)galactosyltransferase 2 |
| GT27 | Galnt1 | 100763868 | polypeptide N-acetylgalactosaminyltransferase 1 |
| GT27 | Galnt10 | 100768523 | polypeptide N-acetylgalactosaminyltransferase 10 |
| GT27 | Galnt11 | 100758359 | polypeptide N-acetylgalactosaminyltransferase 11 |
| GT27 | Galnt12 | 100772146 | polypeptide N-acetylgalactosaminyltransferase 12 |
| GT27 | Galnt13 | 100768831 | polypeptide N-acetylgalactosaminyltransferase 13 |
| GT27 | Galnt14 | 100759781 | polypeptide N-acetylgalactosaminyltransferase 14 |
| GT27 | Galnt15 | 100766936 | polypeptide N-acetylgalactosaminyltransferase 15 |
| GT27 | Galnt16 | 100764829 | polypeptide N-acetylgalactosaminyltransferase 16 |
| GT27 | Galnt18 | 100767393 | polypeptide N-acetylgalactosaminyltransferase 18 |
| GT27 | Galnt2 | 100767525 | polypeptide N-acetylgalactosaminyltransferase 2 |
| GT27 | Galnt3 | 100753226 | polypeptide N-acetylgalactosaminyltransferase 3 |
| GT27 | Galnt4 | 100765247 | polypeptide N-acetylgalactosaminyltransferase 4 |
| GT27 | Galnt5 | 100757219 | polypeptide N-acetylgalactosaminyltransferase 5 |
| GT27 | Galnt6 | 100751126 | polypeptide N-acetylgalactosaminyltransferase 6 |
| GT27 | Galnt6 | 100751126 | polypeptide N-acetylgalactosaminyltransferase 6 |
| GT27 | Galnt7 | 100762043 | polypeptide N-acetylgalactosaminyltransferase 7 |
| GT27 | Galnt8 | 100764127 | polypeptide N-acetylgalactosaminyltransferase 8 |
| GT27 | Galnt9 | 100773797 | polypeptide N-acetylgalactosaminyltransferase 9 |
| GT27 | Galntl5 | 100767659 | polypeptide N-acetylgalactosaminyltransferase-like 5 |
| GT27 | Galntl6 | 100761752 | polypeptide N-acetylgalactosaminyltransferase-like 6 |
| GT27 | Wbscr17 | 100750837 | Williams-Beuren syndrome chromosome region 17 |
| GT29 | St3gal1 | 100754088 | β-galactoside α-2,3-sialyltransferase 1 |
| GT29 | St3gal1 | 100754088 | β-galactoside α-2,3-sialyltransferase 1 |
| GT29 | St3gal2 | 100767717 | β-galactoside α-2,3-sialyltransferase 2 |
| GT29 | St3gal2 | 100767717 | β-galactoside α-2,3-sialyltransferase 2 |
| GT29 | St3gal3 | 100689187 | β-galactoside α-2,3-sialyltransferase 3 |
| GT29 | St3gal4 | 100689440 | β-galactoside α-2,3-sialyltransferase 4 |
| GT29 | St3gal5 | 100754838 | β-galactoside α-2,3-sialyltransferase 5 |
| GT29 | St3gal6 | 100771326 | β-galactoside α-2,3-sialyltransferase 6 |
| GT29 | St6gal1 | 100689389 | β-galactosamide α-2,6-sialyltranferase 1 |
| GT29 | St6gal2 | 100763756 | β-galactosamide α-2,6-sialyltranferase 2 |
| GT29 | St6galnac1 | 100763224 | α-N-acetylgalactosaminide α-2,6-sialyltransferase 1 |
| GT29 | St6galnac3 | 100762285 | (α-N-acetyl-neuraminyl-2,3β-galactosyl-1,3)-N-acetylgalactosaminide α-2,6-sialyltransferase 3 |
| GT29 | St6galnac4 | 100759065 | (α-N-acetyl-neuraminyl-2,3β-galactosyl-1,3)-N-acetylgalactosaminide α-2,6-sialyltransferase 4 |
| GT29 | St6galnac5 | 100759381 | (α-N-acetyl-neuraminyl-2,3β-galactosyl-1,3)-N-acetylgalactosaminide α-2,6-sialyltransferase 5 |
| GT29 | St6galnac6 | 100757138 | (α-N-acetyl-neuraminyl-2,3β-galactosyl-1,3)-N-acetylgalactosaminide α-2,6-sialyltransferase 6 |
| GT29 | St8sia1 | 100768920 | α-N-acetyl-neuraminide α-2,8-sialyltransferase 1 |
| GT29 | St8sia2 | 100759559 | α-N-acetyl-neuraminide α-2,8-sialyltransferase 2 |

TABLE 2-continued

Chinese hamster (*Cricetulus griseus*) GTfs genes

| CAZy family[1] | Symbol[2] | Gene ID[3] | Description[4] |
|---|---|---|---|
| GT29 | St8sia3 | 100764454 | α-N-acetyl-neuraminide α-2,8-sialyltransferase 3 |
| GT29 | St8sia4 | 100689217 | α-N-acetyl-neuraminide α-2,8-sialyltransferase 4 |
| GT29 | St8sia5 | 100750766 | α-N-acetyl-neuraminide α-2,8-sialyltransferase 5 |
| GT29 | St8sia6 | 100774188 | α-N-acetyl-neuraminide α-2,8-sialyltransferase 6 |
| GT31 | B3galnt1 | 100756438 | β-1,3-N-acetylgalactosaminyltransferase 1 (globoside blood group) |
| GT31 | B3galnt2 | 100768564 | β-1,3-N-acetylgalactosaminyltransferase 2 |
| GT31 | B3galt1 | 100761765 | UDP-Gal: βGlcNAc β1,3-galactosyltransferase, polypeptide 1 |
| GT31 | B3galt2 | 100766715 | UDP-Gal: βGlcNAc β1,3-galactosyltransferase, polypeptide 2 |
| GT31 | B3galt4 | 100751197 | UDP-Gal: βGlcNAc β1,3-galactosyltransferase, polypeptide 4 |
| GT31 | B3galt5 | 100755714 | UDP-Gal: βGlcNAc β1,3-galactosyltransferase, polypeptide 5 |
| GT31 | B3galt6 | 100767598 | UDP-Gal: βGal β1,3-galactosyltransferase polypeptide 6 |
| GT31 | B3galtl | 100759864 | β1,3-galactosyltransferase-like |
| GT31 | B3gnt2 | 100766691 | UDP-GlcNAc: βGal β-1,3-N-acetylglucosaminyltransferase 2 |
| GT31 | B3gnt3 | 100773213 | UDP-GlcNAc: βGal β-1,3-N-acetylglucosaminyltransferase 3 |
| GT31 | B3gnt4 | 100769077 | UDP-GlcNAc: βGal β-1,3-N-acetylglucosaminyltransferase 4 |
| GT31 | B3gnt5 | 100757919 | UDP-GlcNAc: βGal β-1, 3-N-acetylglucosaminyltransferase 5 |
| GT31 | B3gnt6 | 100768656 | UDP-GlcNAc: βGal β-1,3-N-acetylglucosaminyltransferase 6 |
| GT31 | B3gnt7 | 100760456 | UDP-GlcNAc: βGal β-1,3-N-acetylglucosaminyltransferase 7 |
| GT31 | B3gnt8 | 103160327 | UDP-GlcNAc: βGal β-1,3-N-acetylglucosaminyltransferase 8 |
| GT31 | B3gnt9 | 103159649 | UDP-GlcNAc: βGal β-1,3-N-acetylglucosaminyltransferase 9 |
| GT31 | C1galt1 | 100761169 | glycoprotein-N-acetylgalactosamine 3-β-galactosyltransferase, 1 |
| GT31 | C1galt1c1 | 100751243 | C1GALT1-specific chaperone 1 |
| GT31 | Lfng | 100762397 | O-fucosylpeptide 3-β-N-acetylglucosaminyltransferase |
| GT31 | Mfng | 100762875 | O-fucosylpeptide 3-β-N-acetylglucosaminyltransferase |
| GT31 | Rfng | 100771257 | O-fucosylpeptide 3-β-N-acetylglucosaminyltransferase |
| GT32 | A4galt | 100770462 | α-1,4-galactosyltransferase |
| GT32 | A4gnt | 100771969 | α-1,4-N-acetylglucosaminyltransferase |
| GT33 | Alg1 | 100773731 | chitobiosyldiphosphodolichol β-mannosyltransferase |
| GT35 | Pygb | 100769186 | phosphorylase, glycogen; brain |
| GT35 | Pygm | 100757350 | phosphorylase, glycogen; muscle |
| GT39 | Pomt1 | 100755033 | protein-O-mannosyltransferase 1 |
| GT39 | Pomt2 | 100764752 | protein-O-mannosyltransferase 2 |
| GT41 | Ogt | 100768670 | O-linked N-acetylglucosamine (GlcNAc) transferase |
| GT43 | B3gat1 | 100750701 | β-1,3-glucuronyltransferase 1 (glucuronosyltransferase P) |
| GT43 | B3gat2 | 100756696 | β-1,3-glucuronyltransferase 2 (glucuronosyltransferase S) |
| GT43 | B3gat3 | 100689419 | β-1,3-glucuronyltransferase 3 (glucuronosyltransferase I) |
| GT47/64 | Ext1 | 100689334 | exostosin glycosyltransferase 1 |
| GT47/64 | Ext2 | 100751585 | exostosin glycosyltransferase 2 |
| GT47/64 | Extl1 | 100770000 | exostosin-like glycosyltransferase 1 |
| GT47/64 | Extl3 | 100751999 | exostosin-like glycosyltransferase 3 |
| GT49 | B3gnt1 | 100762253 | UDP-GlcNAc: βGal β-1,3-N-acetylglucosaminyltransferase 1 |
| GT50 | Pigm | 100764842 | phosphatidylinositol glycan anchor biosynthesis, class M |
| GT54 | Mgat4a | 100766200 | mannosyl (α-1,3-)-glycoprotein β-1,4-N-acetylglucosaminyltransferase |

TABLE 2-continued

Chinese hamster (*Cricetulus griseus*) GTfs genes

| CAZy family[1] | Symbol[2] | Gene ID[3] | Description[4] |
|---|---|---|---|
| GT54 | Mgat4b | 100768637 | mannosyl (α-1,3-)-glycoprotein β-1,4-N-acetylglucosaminyltransferase |
| GT54 | Mgat4c | 100760589 | mannosyl (α-1,3-)-glycoprotein β-1,4-N-acetylglucosaminyltransferase |
| GT57 | Alg6 | 100753783 | α-1,3-glucosyltransferase |
| GT57 | Alg8 | 100766150 | α-1,3-glucosyltransferase |
| GT58 | Alg3 | 100772003 | α-1,3-mannosyltransferase |
| GT61 | Eogt | 100757071 | EGF domain-specific O-linked N-acetylglucosamine (GlcNAc) transferase |
| GT61 | Pomgnt2 | 100770708 | protein O-linked mannose N-acetylglucosaminyltransferase 2 (β1,4-) |
| GT64 | Extl2 | 100761218 | exostosin-like glycosyltransferase 2 |
| GT65 | Pofut1 | 100753417 | protein O-fucosyltransferase 1 |
| GT66 | Stt3a | 100751391 | subunit of the oligosaccharyltransferase complex (catalytic) |
| GT66 | Stt3b | 100752084 | subunit of the oligosaccharyltransferase complex (catalytic) |
| GT68 | Pofut2 | 100765129 | protein O-fucosyltransferase 2 |
| GT90 | Kdelc1 | 100763723 | KDEL (Lys-Asp-Glu-Leu) containing 1 |
| GT90 | Poglut1 | 100760325 | protein O-glucosyltransferase 1 |
| GTnc | Dpy19l1 | 100765722 | dpy-19-like 1 (*C. elegans*) |
| GTnc | Dpy19l2 | 100752353 | dpy-19-like 2 (*C. elegans*) |
| GTnc | Dpy19l3 | 100756435 | dpy-19-like 3 (*C. elegans*) |
| GTnc | Dpy19l4 | 100759810 | dpy-19-like 4 (*C. elegans*) |
| GTnc | Fktn | 100761516 | fukutin |
| GTnc | Plod3 | 100768993 | procollagen-lysine, 2-oxoglutarate 5-dioxygenase 3 |
| GTnc | Tmem5 | 100757873 | transmembrane protein 5 |
| — | Dpagt1 | 100689054 | dolichyl-phosphate (UDP-N-acetylglucosamine) N-acetylglucosaminephosphotransferase 1 |

[1]GT classification system (Lombard et al. (2013). Nucl Acid Res 42: D1P: D490-D495)
[2]gene symbol HGNC
[3]Gene ID GenBank
[4]Protein name UniProt Similarly the transcriptome data for a CHO-K1 clone reported in Xu et al. (Xu, Nagarajan et al. 2011) missed several glycosyltransferase genes. We therefore performed RNA sequencing analysis of a panel of CHO lines including ones with ZFN mediated knockout of glycosyltransferase genes to assess the expression of all glycosyltransferase genes in CHO. TABLE 3 provides a list of the expression levels of all assigned CHO glycosyltransferase genes, and a few qualitative differences in expression levels were found compared to those reported previously (Xu, Nagarajan et al. 2011).

TABLE 3

Comparison of GTfs expression levels from RNA_seq data for CHO-GS and CHO-K1

| CAZy family | GTf genes (hGTfs from Table 1)* | CHO-GS_FPKM**[4] | CHO-K1 RNA_seq depth (Xu et al 2011)**[4] |
|---|---|---|---|
| GT1 | Alg13 | 13 | na |
| GT1 | Alg14 | 27 | 55 |
| GT1 | Ugt1a1-10[,21] | 63 | 96 |
| GT1 | Ugt2a1[1] | 0 | 0 |
| GT1 | Ugt2a3[1] | 0 | na |
| GT1 | Ugt2b10[1] | na | 0 |
| GT1 | Ugt2b11[1] | na | na |
| GT1 | Ugt2b15[1] | na | na |
| GT1 | Ugt2b17[1] | na | na |
| GT1 | Ugt2b28[1] | na | 0 |
| GT1 | Ugt2b4[1] | na | na |
| GT1 | Ugt2b7[1] | na | na |
| GT1 | Ugt3a1[1] | na | na |
| GT1 | Ugt3a2[1] | na | na |
| GT1 | Ugt8 | na | 0 |
| GT2 | Alg5 | 53 | 71 |
| GT2 | B3gntl1 | 11 | na |
| GT2 | Dpm1 | 85 | 78 |
| GT2 | Has1 | na | na |
| GT2 | Has2 | 0 | 0 |
| GT2 | Has3 | 0 | 2 |
| GT3 | Gys1 | 47 | na |
| GT3 | Gys2 | 0 | na |
| GT4 | Alg11 | 16 | 20 |
| GT4 | Alg2 | 19 | 52 |
| GT4 | Glt1d1 | 0 | na |
| GT4 | Gtdc1 | 10 | na |
| GT4 | Piga | 8 | 9 |
| GT6 | Abo | 0 | na |
| GT6 | Gbgt1 | 4 | na |
| GT6 | Ggta1p | na | na |
| GT6 | Glt6d1 | na | na |
| GT7 | B4galnt3 | 0 | 0 |
| GT7 | B4galnt4 | 0 | 0 |
| GT7 | B4galt1 | 15 | 36 |
| GT7 | B4galt2 | 38 | 41 |
| GT7 | B4galt3 | 25 | 74 |
| GT7 | B4galt4 | 19 | 28 |

TABLE 3-continued

Comparison of GTfs expression levels from RNA_seq data for CHO-GS and CHO-K1

| CAZy family | GTf genes (hGTfs from Table 1)* | CHO-GS_FPKM**[4] | CHO-K1 RNA_seq depth (Xu et al 2011)**[4] |
|---|---|---|---|
| GT7 | B4galt5 | 14 | 71 |
| GT7 | B4galt6 | 8 | 71 |
| GT7 | B4galt7 | 31 | 169 |
| GT7/31 | Chpf | 53 | 332 |
| GT7/31 | Chpf2 | na | 130 |
| GT7/31 | Chsy1 | 26 | 0 |
| GT7/31 | Chys3 | na | na |
| GT7 | Csgalnact1 | 0 | 0 |
| GT7 | Csgalnact2 | 9 | 0 |
| GT8 | Glt8d1 | 20 | na |
| GT8 | Glt8d2 | 0 | na |
| GT8 | Gxylt1 | 10 | na |
| GT8 | Gxylt2 | 0 | na |
| GT8 | Gyg | 72 | na |
| GT8 | Gyg2 | na | na |
| GT8/49 | Gyltl1b | 0 | 0 |
| GT8/49 | Large | 14 | 22 |
| GT8 | Xxylt1 | 70 | na |
| GT10 | Fut10 | 0 | 0 |
| GT10 | Fut11 | 5 | 0 |
| GT10 | Fut4 | 0 | 0 |
| GT10 | Fut5 | na | 0 |
| GT10 | Fut6a | 0 | 0 |
| GT10 | Fut6b | 0 | 0 |
| GT10 | Fut7 | 0 | 0 |
| GT10 | Fut9 | 0 | 0 |
| GT11 | Fut1 | 0 | 0 |
| GT11 | Fut2 | 0 | 0 |
| GT12 | B4galnt1 | 0 | 0 |
| GT12 | B4galnt2 | 0 | 0 |
| GT13 | Mgat1 | 24 | 61 |
| GT13 | Pomgnt1 | 64 | 101 |
| GT14 | Gcnt1 | 0 | 0 |
| GT14 | Gcnt2 | 0 | na |
| GT14 | Gcnt3 | 0 | 0 |
| GT14 | Gcnt4 | 0 | 0 |
| GT14 | Gcnt6 | na | na |
| GT14 | Gcnt7 | 0 | na |
| GT14 | Xylt1 | 0 | 0 |
| GT14 | Xylt2 | 11 | 6 |
| GT16 | Mgat2 | 29 | 138 |
| GT17 | Mgat3 | 0 | 0 |
| GT18 | Mgat5 | 13 | 20 |
| GT18 | Mgat5b | 0 | 0 |
| GT21 | Ugcg | 40 | na |
| GT22 | Alg12 | 34 | 69 |
| GT22 | Alg9 | 25 | 98 |
| GT22 | Pigb | 24 | 75 |
| GT22 | Pigz | 0 | na |
| GT23 | Fut8 | 18 | 166 |
| GT24 | Uggt1 | 27 | 0 |
| GT24 | Uggt2 | 6 | 95 |
| GT25 | Cercam | 7 | na |
| GT25 | Glt25d1/Colgalt1 | 129 | 0 |
| GT25 | Glt25d2/Colgalt2 | 0 | 0 |
| GT27 | Galnt1 | 39 | 0 |
| GT27 | Galnt10 | 9 | na |
| GT27 | Galnt11 | 32 | 63 |
| GT27 | Galnt12 | 0 | 0 |
| GT27 | Galnt13 | 2 | 0 |
| GT27 | Galnt14 | 0 | 0 |
| GT27 | Galnt15/l2 | 0 | 0 |
| GT27 | Galnt16/l1 | 0 | 0 |
| GT27 | Galnt18 | 0 | 0 |
| GT27 | Galnt19/l3(Wbscr17) | 0 | 63 |
| GT27 | Galnt2 | 60 | 324 |
| GT27 | Galnt3 | 0 | 0 |
| GT27 | Galnt4 | 3 | na |
| GT27 | Galnt5 | 0 | 0 |
| GT27 | Galnt6 | 0 | 0 |
| GT27 | Galnt7 | 30 | 44 |
| GT27 | Galnt8 | 0 | 0 |
| GT27 | Galnt9 | 0 | 0 |
| GT27 | Galnt20/l5 | 0 | 0 |
| GT27 | Galnt17/l6 | 0 | na |
| GT29 | StSgal1 | 54 | 195 |
| GT29 | St3gal2 | 17 | 28 |
| GT29 | St3gal3 | 13 | 75 |
| GT29 | St3gal4 | 44 | 33 |
| GT29 | St3gal5 | 21 | 44 |
| GT29 | St3gal6 | 13 | 29 |
| GT29 | St6gal1 | 0 | 0 |
| GT29 | St6gal2 | 0 | na |
| GT29 | St6galnac1 | 0 | 0 |
| GT29 | St6galnac2 | 0 | 0 |
| GT29 | St6galnac3 | 0 | 0 |
| GT29 | St6galnac4 | 24 | 67 |
| GT29 | St6galnac5 | 0 | 0 |
| GT29 | St6galnac6 | 18 | 25 |
| GT29 | St8sia1 | 0 | 0 |
| GT29 | St8sia2 | 0 | 0 |
| GT29 | St8sia3 | 0 | 0 |
| GT29 | St8sia4 | 3 | 0 |
| GT29 | St8sia5 | 0 | 0 |
| GT29 | St8sia6 | 0 | 0 |
| GT31 | B3galnt1 | 12 | 37 |
| GT31 | B3galnt2 | 30 | 0 |
| GT31 | B3galt1 | 1 | 0 |
| GT31 | B3galt2 | 0 | 0 |
| GT31 | B3galt4 | 2 | 16 |
| GT31 | B3galt5 | 0 | 0 |
| GT31 | B3galt6 | 5 | 42 |
| GT31 | B3galtl | 19 | na |
| GT31 | B3gnt2 | 42 | 189 |
| GT31 | B3gnt3 | 0 | 0 |
| GT31 | B3gnt4 | 0 | 0 |
| GT31 | B3gnt5 | 0 | 0 |
| GT31 | B3gnt6 | 0 | 0 |
| GT31 | B3gnt7 | 0 | 0 |
| GT31 | B3gnt9 | na | na |
| GT31 | B3gntl1 | 11 | 0 |
| GT31 | C1galt1 | 15 | 26 |
| GT31 | C1galt1c1 | 26 | 120 |
| GT31 | Lfng | 5 | 24 |
| GT31 | Mfng | 0 | 0 |
| GT31 | Rfng | 9 | 158 |
| GT32 | A4galt | 0 | 0 |
| GT32 | A4gnt | 0 | 0 |
| GT33 | Alg1 | 13 | 41 |
| GT33 | Alg11 | na | na |
| GT33 | Alg1l2 | na | na |
| GT35 | Pygb | 61 | na |
| GT35 | Pygl | na | na |
| GT35 | Pygm | 1 | na |
| GT39 | Pomt1 | 15 | 0 |
| GT39 | Pomt2 | 9 | 0 |
| GT41 | Ogt | 14 | 39 |
| GT43 | B3gat1 | 0 | 0 |
| GT43 | B3gat2 | 0 | 0 |
| GT43 | B3gat3 | 23 | 31 |
| GT47/64 | Ext1 | 21 | 83 |
| GT47/64 | Ext2 | 43 | 136 |
| GT47/64 | Extl1 | 9 | 2 |
| GT47/64 | Extl3 | 24 | 79 |
| GT49 | B3gnt1 | 32 | 0 |
| GT50 | Pigm | 6 | 54 |
| GT54 | Mgat4a | 0 | 0 |
| GT54 | Mgat4b | 37 | 0 |
| GT54 | Mgat4c | 0 | na |
| GT57 | Alg6 | 19 | 22 |
| GT57 | Alg8 | 18 | 22 |
| GT58 | Alg3 | 15 | 38 |
| GT59 | Alg10 | na | 0 |
| GT59 | Alg10b | na | 0 |

TABLE 3-continued

Comparison of GTfs expression levels from RNA_seq data for CHO-GS and CHO-K1

| CAZy family | GTf genes (hGTfs from Table 1)* | CHO-GS_FPKM**[4] | CHO-K1 RNA_seq depth (Xu et al 2011)**[4] |
|---|---|---|---|
| GT61 | Eogt | 6 | 0 |
| GT61 | Pomgnt2 | 10 | na |
| GT64 | Extl2 | 31 | 179 |
| GT65 | Pofut1 | 44 | 126 |
| GT66 | Stt3a | 71 | 0 |
| GT66 | Stt3b | 85 | 0 |
| GT68 | Pofut2 | 68 | 15 |
| GT76 | Pigv | na | na |
| GT90 | Kdelc1 | 26 | na |
| GT90 | Poglut1 | 22 | na |
| — | Dpagt1[3] | 40 | 59 |
| GTnc | Dpy19l1 | 25 | na |
| GTnc | Dpy19l2 | 0 | na |
| GTnc | Dpy19l3 | 11 | na |
| GTnc | Dpy19l4 | 5 | na |
| GTnc | Fkrp | na | na |
| GTnc | Fktn | 16 | na |
| GTnc | Plod3 | 61 | na |
| GTnc | Tmem5 | 49 | na |

Figure 14A:
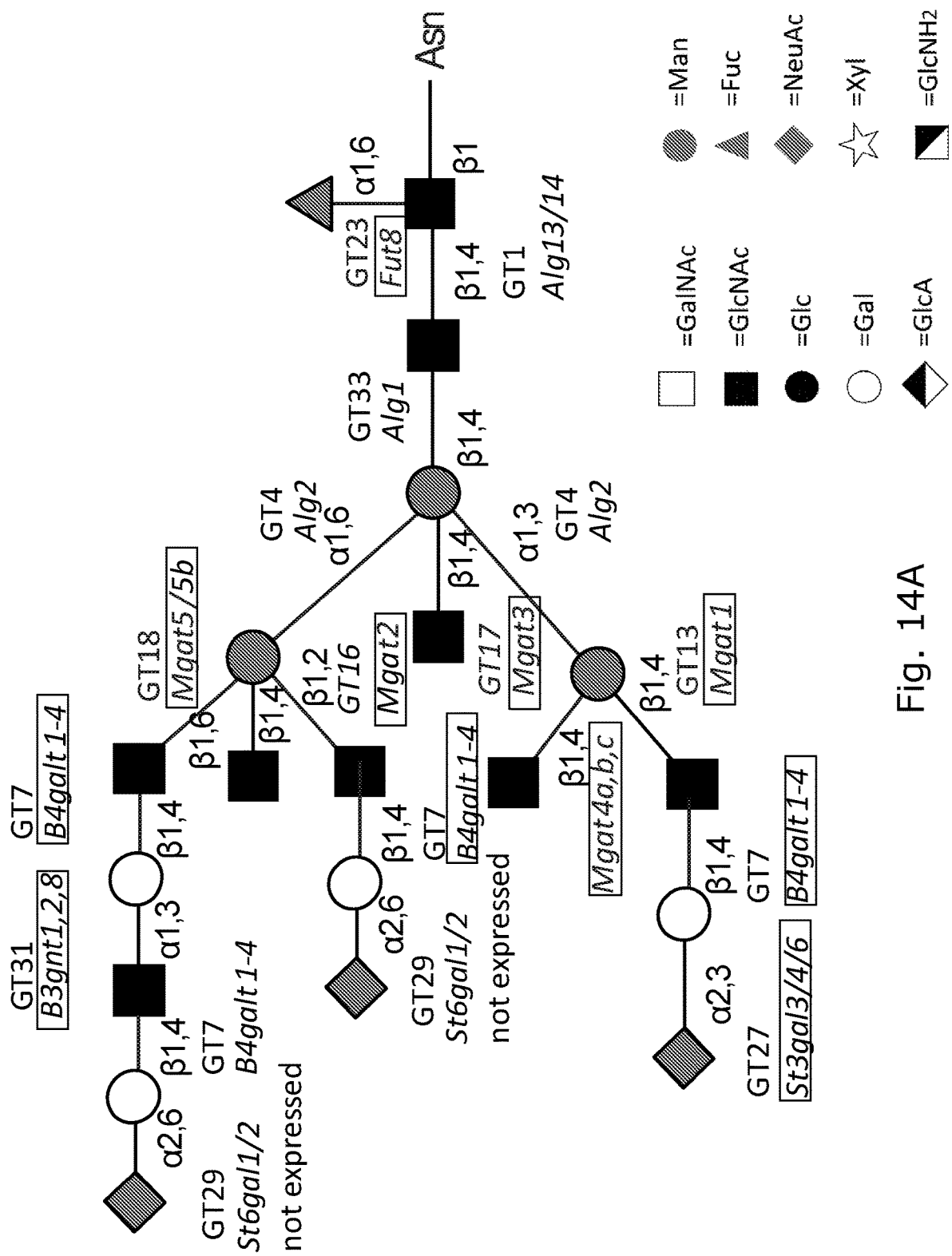
FIG. 14 Graphic depictions of all genes encoding isoenzymes with potential to regulate N-glycosylation branching, elongation, and terminal capping expressed in CHO. The depiction shows the knockout screen of glycosyltransferase genes involved in N-glycosylation in CHO using human EPO as recombinant expressed reporter glycoprotein. (A) The common tetraantennary N-glycan with poly-LacNAc on the β6-antenna and capping by sialic acids is shown, the knockout genes are boxed, and genes not expressed in the CHO cells are annotated. Note that human ST6Gal-I (ST6GAL1) has been introduced by ZFN-mediated knock-in. Designations for monosaccharides according to the Consortium for Functional Glycomics (CFG) are indicated. (B) Schematic depiction of the actual nuclease targeted regions relative to the predicted general domain structure of type II glycosyltransferase proteins (upper panel) and the targeted exon for each gene numbering the respective genes from first coding exon (lower panel). The exon structure depiction only includes the first targeted exons and does not include all exons for all genes.

*a total of 208 hGTfs are reduced to 200 plus Dpagt1 (a non GTf gene) resulting in total 201 genes included in the RNA_seq data comparison
**the expression levels are not directly comparable that the CHO-GS data is FRKP and for the CHO-K1 data (Xu et al. 2011) depth of reads are takes as a measure for expression, na denoted genes not analyzed due to missing annotations
[1]the Ugt1a and Ugt2a/b genes are very heterogeneous among primates and rodents, and generally encodes the rodent genomes larger and more heterogeneous set of glucuronyl-transferase genes
[2]the Ugt1a1-10 represent one locus with 9 genes, these have been combine into on gene in the RNA_seq data analysis
[3]Dgagt1 is not included in the list of human GTfs
[4]na—not analyzed To explore the functions of individual glycosyltransferase genes putatively involved in N-glycosylation, the present invention employed a ZFN-mediated KO screen in a CHO-GS cell line (Sigma), and also in other cell lines. The present invention designed a KO screen to dissect in vivo functions of all genes encoding isoenzymes with potential to regulate N-glycosylation branching, elongation, and terminal capping expressed in CHO (FIG. 14).

Figure 15:
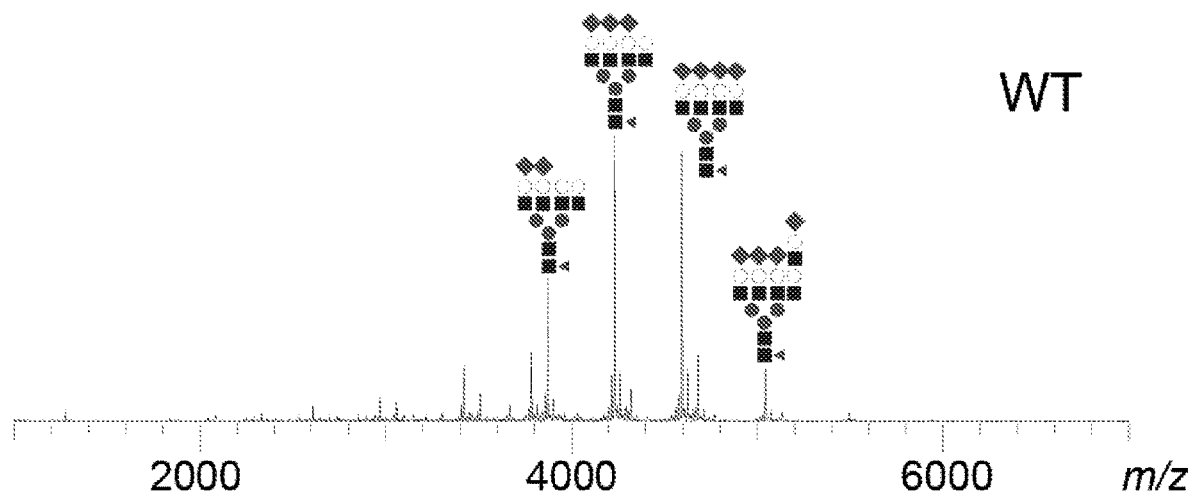
FIG. 15 Glycoprofiling of EPO expressed in CHO WT cells. MALDI-TOF spectra of PNGase F released permethylated N-glycans with predicted structures for the four major species.

The present invention probed the effects of the knockout screen on N-glycosylation capacity by recombinant expression of human erythropoietin (EPO) in CHO mutant cell lines and analysis of glycosylation of purified EPO by release of N-glycans and profiling using MALDI-TOF. EPO was used as reporter for the N-glycosylation capacity because this is one of the best characterized N-glycoproteins produced in CHO having three N-glycans with mainly tetraantennary structure, low level of poly-LacNAc, and α2,3 sialic acid capping (FIG. 15) (Sasaki, Ochi et al. 1988). EPO expressed in the unmodified CHO-GS production line grown in suspension in protein-free medium was glycosylated essentially identical to past reports of EPO produced in CHO-K1 (FIG. 15). Moreover, the glycosylation profile was essentially identical to therapeutic products of EPO produced in CHO and claimed for in drug filings (Sasaki, Bothner et al. 1987).

Figure 5A:
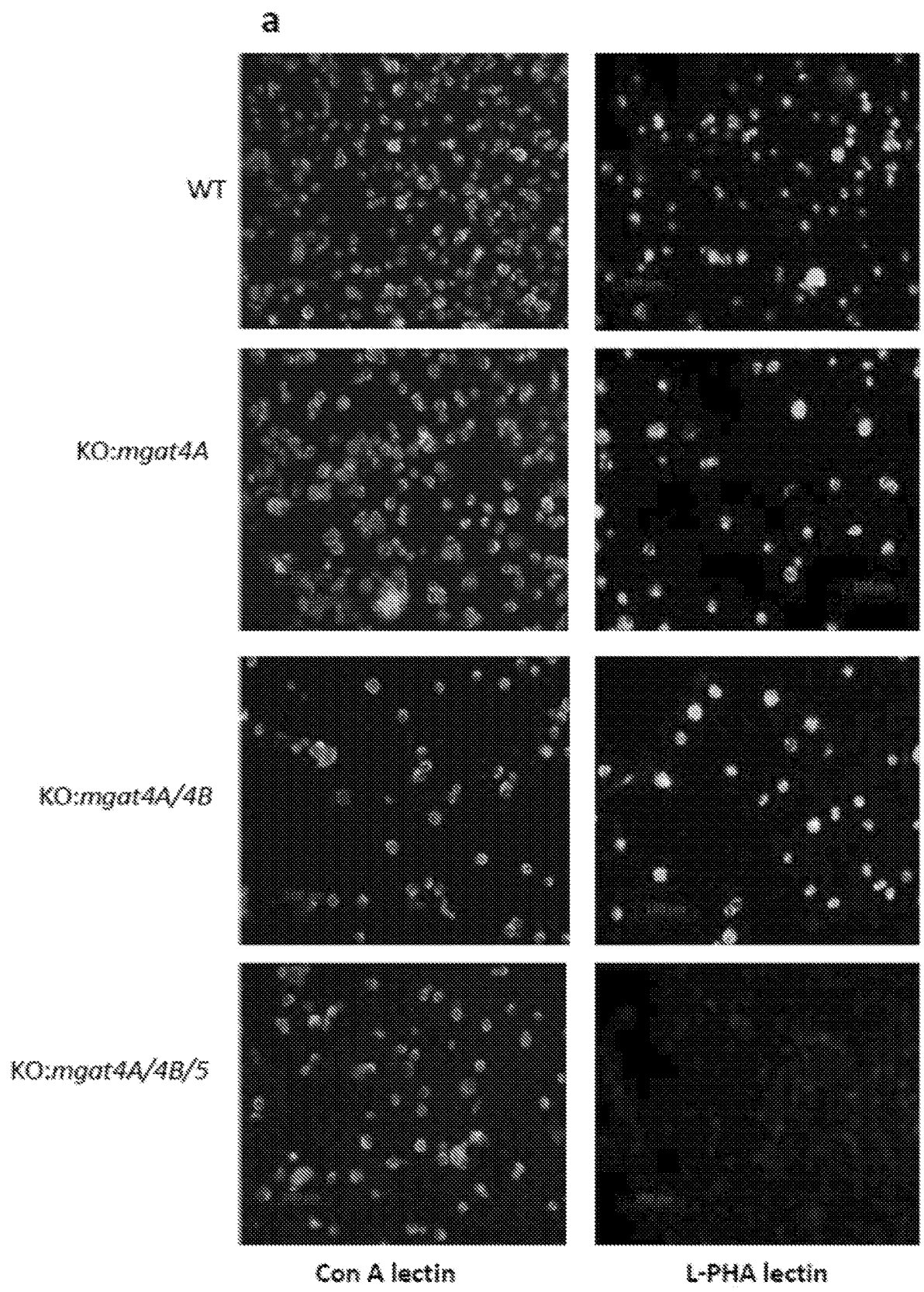
FIG. 5 shows Immunocytology of CHO knockout clones with mutations related to N-glycan branching and poly-LacNAc biosynthesis. (a) The L-PHA lectin was used to specifically probe 86 branching of N-glycans and only KO of mgat5 produced (mgat4A/4b/5) altered L-PHA labeling, while the control lectin ConA binding all types of N-glycans was unaffected. This confirms that MGAT4A and 4B forms the β4 branch, while MGAT5 forms the β6 branch, and hence supports the interpretation of the mass spec data presented in FIG. 1c regarding branch assignments. (b) A similar strategy was used to probe for poly-LacNAc with the LEL, where only KO of B3gnt2 resulted in loss of labeling. This data also support the interpretation of the mass spec data presented in FIG. 2 regarding assignment of LacNAc's to biantennary structures.
Figure 21B:
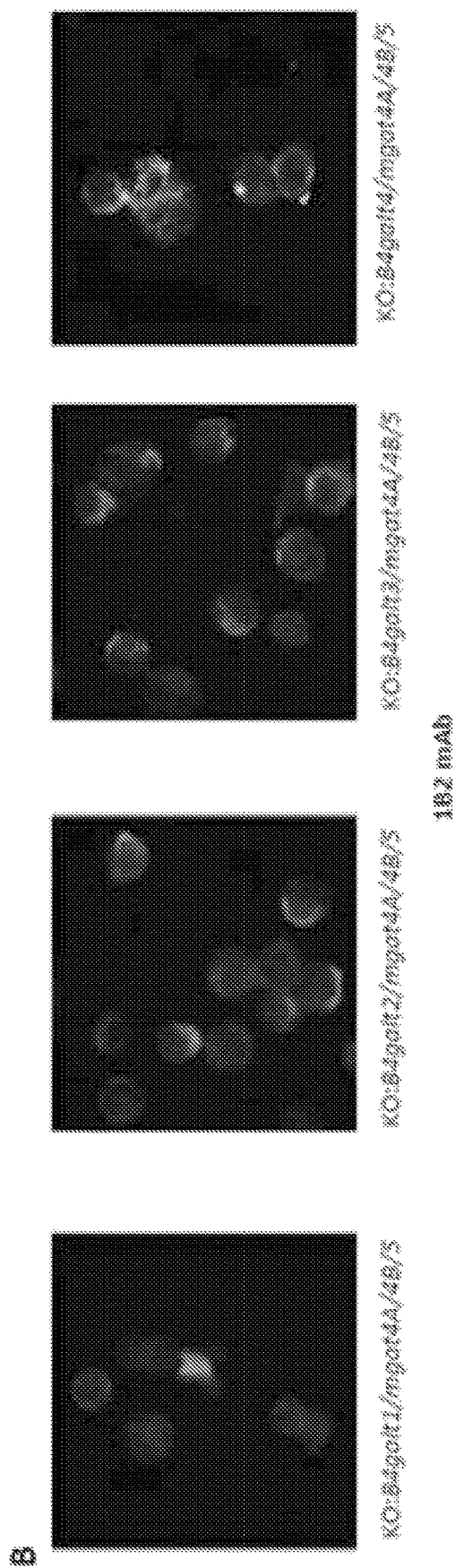
Figure 22:
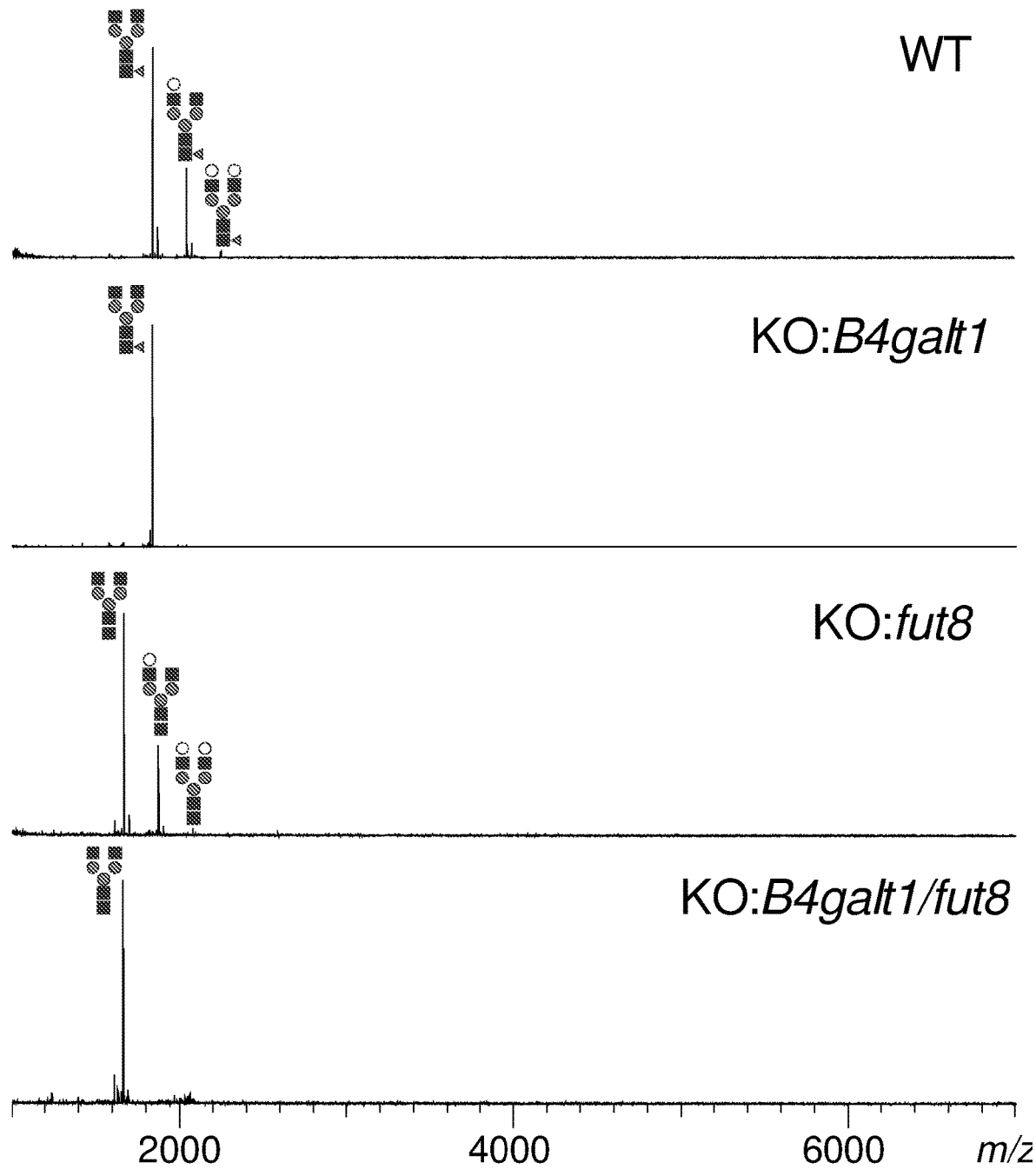
FIG. 22 Recombinant expression of a therapeutic IgG in CHO with KO of B4galt1 resulted in homogenous biantennary N-glycans without galactosylation. Glycoprofiling of IgG produced in CHO WT and B4galt1 KO showing essentially complete loss of the incomplete galactosylation and sialylation characteristic for the conserved N-glycan at Asn297. KO of B4galt1 in combination with fut8 resulted in N-glycans without galactosylation and fucose.

The present invention used ZFNs, TALENs and CRISPR/Cas9 to target and knockout 19 glycosyltransferase genes (FIG. 14A) involved in N-glycan branching (Mgat1/2/3/4A/4B/4C/5/5B) (FIG. 5, FIG. 21B), galactosylation (B4galt1/2/3/4 (FIG. 17), poly-LacNAc elongation (B3gnt1/2/8) (FIG. 18), terminal capping by sialylation (st3gal3/4/6) (FIG. 19), and core fucosylation (fut8) (FIG. 22).

Figure 16A:
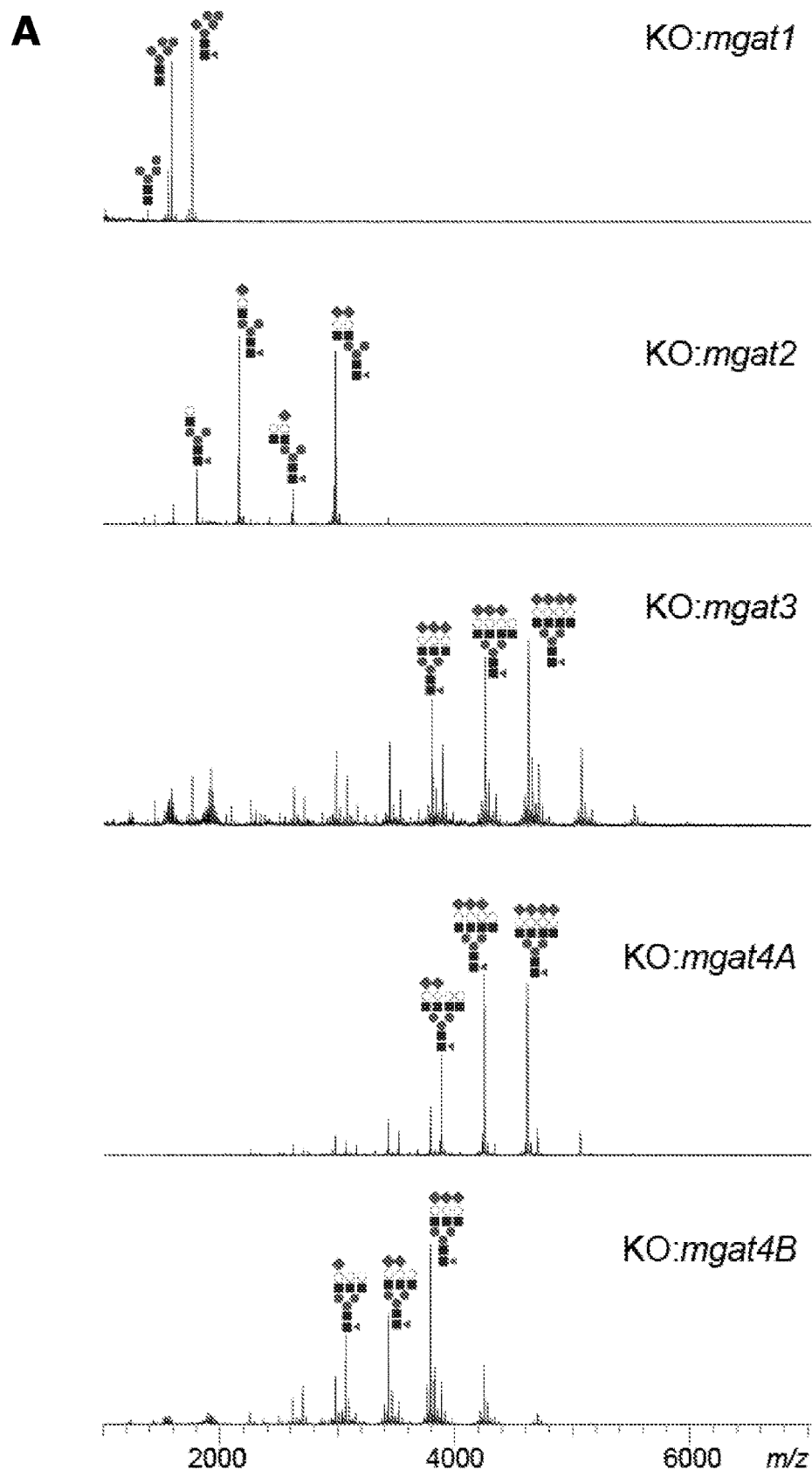
FIG. 16 Glycoprofiling of EPO expressed in CHO cells with KO of genes involved in complex type N-glycan biosynthesis and antennary formation, showing that double KO of mgat4B/5 (B) and triple KO of mgat4A/4B/5 (B) results in homogeneous biantennary N-glycans with a minor amount of poly-LacNAc. Since single KO of mgat4A (A) had minor effects compared to WT it is likely that minor amounts of triantennary structures are present in the double mgat4B/5 KO.
Figure 16B:
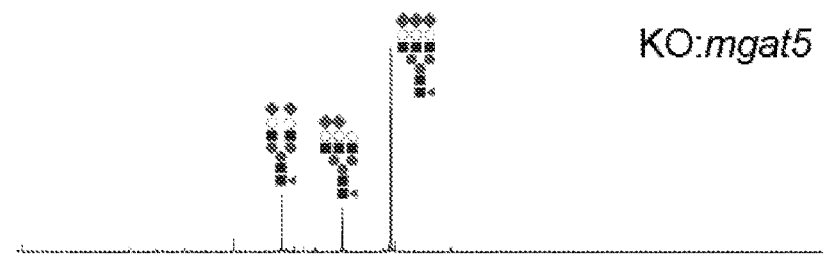
Figure 16B:
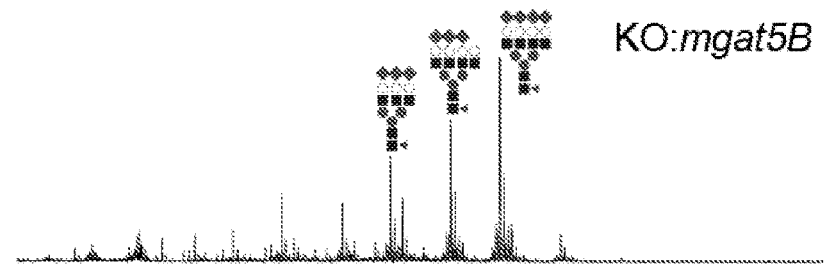
Figure 16B:
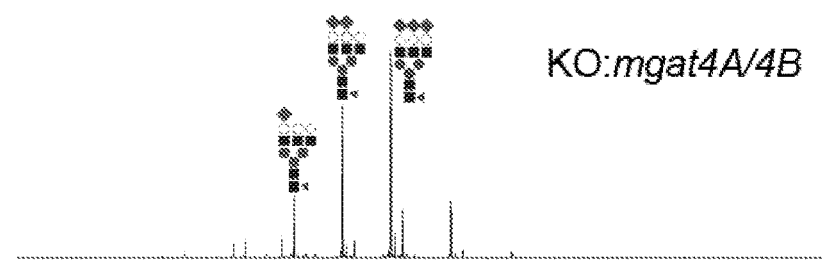
Figure 16B:
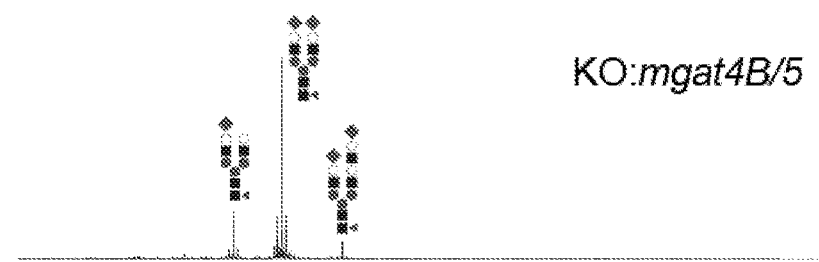
Figure 16B:
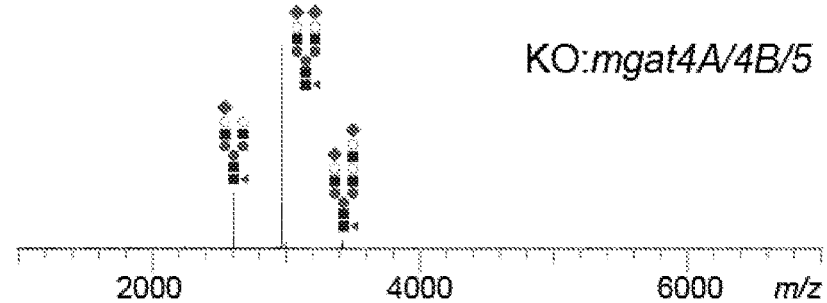

N-glycan antennary status—The biosynthetic control of the N-glycan antennary status was explored first. MGAT1 and 2 each control formation of one of the two β2 branches in biantennary N-glycans, while potential partial functional redundancy is predicted for tri- and tetraantennary branch formation by MGAT4A/4B/4C (β4-branch) and MGAT5/5B (β6-branch), respectively. Only MGAT4B and 5 were found to be substantially expressed in CHO as evaluated by RNAseq results (TABLE 3), however, surprisingly, targeting the Mgat4a gene had a clear effect although minor, and only targeting both Mgat4a/4b completely eliminated β4-branched tetraantennary N-glycans (FIG. 16A-B).

Figure 20:
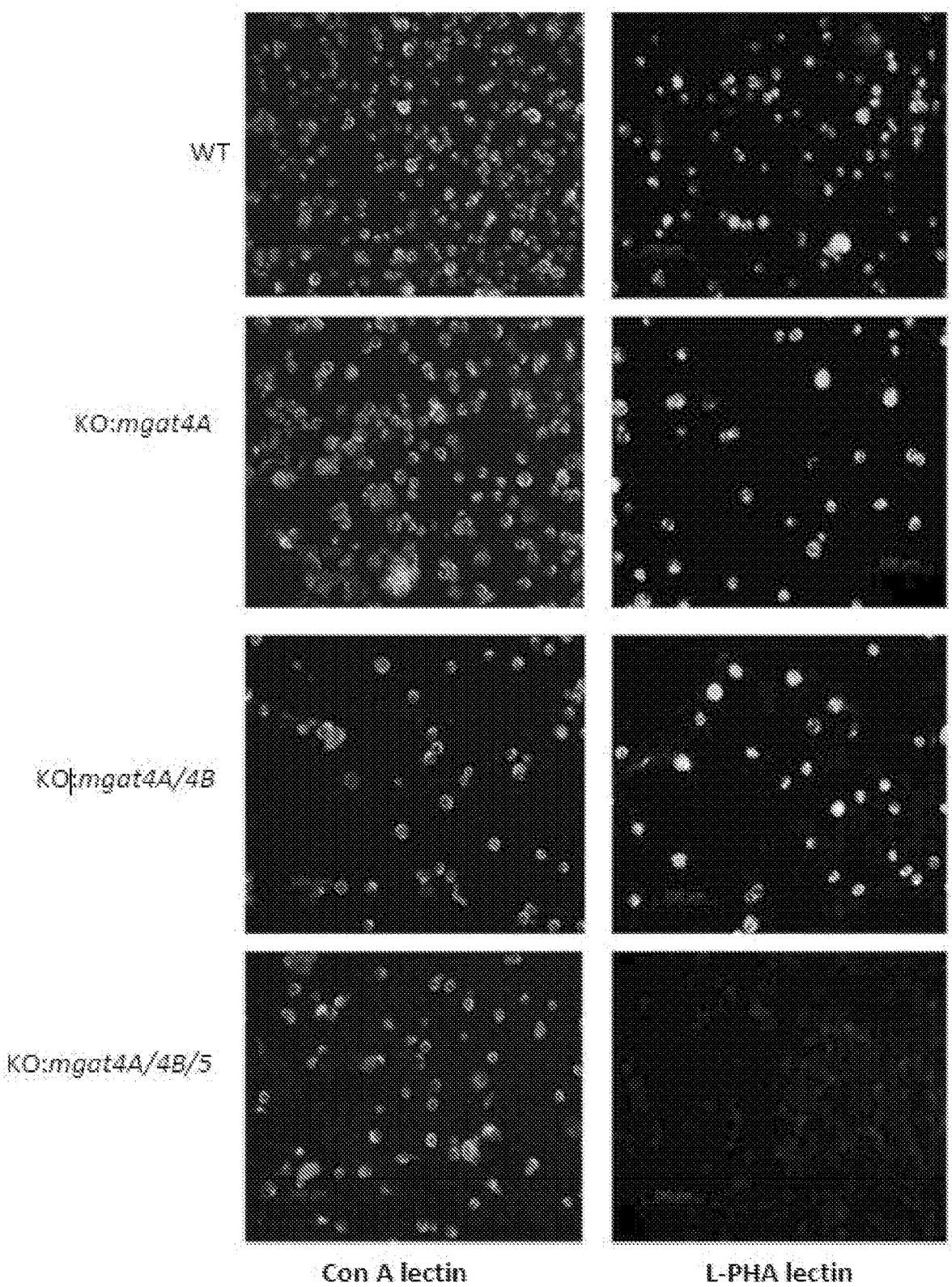
FIG. 20 Immunoflourescense cytology with ConA and L-PHA lectin staining showing loss of L-PHA with knockout of mgat5.

Targeting Mgat5 in contrast eliminated L-PHA lectin labeling of cells (FIG. 20) and β6-branched tetraantennary structures (FIG. 5), which is in agreement with studies of the Lec4 mutant (Patnaik and Stanley 2006; North, Huang et al. 2010). Moreover, stacking KO of Mgat4a/4b/5 produced almost homogenous biantennary N-glycans with a minor amount of poly-LacNAc (FIG. 16B), which is also found as a minor component in wildtype (WT) cells (North, Huang et al. 2010).

Figure 10:
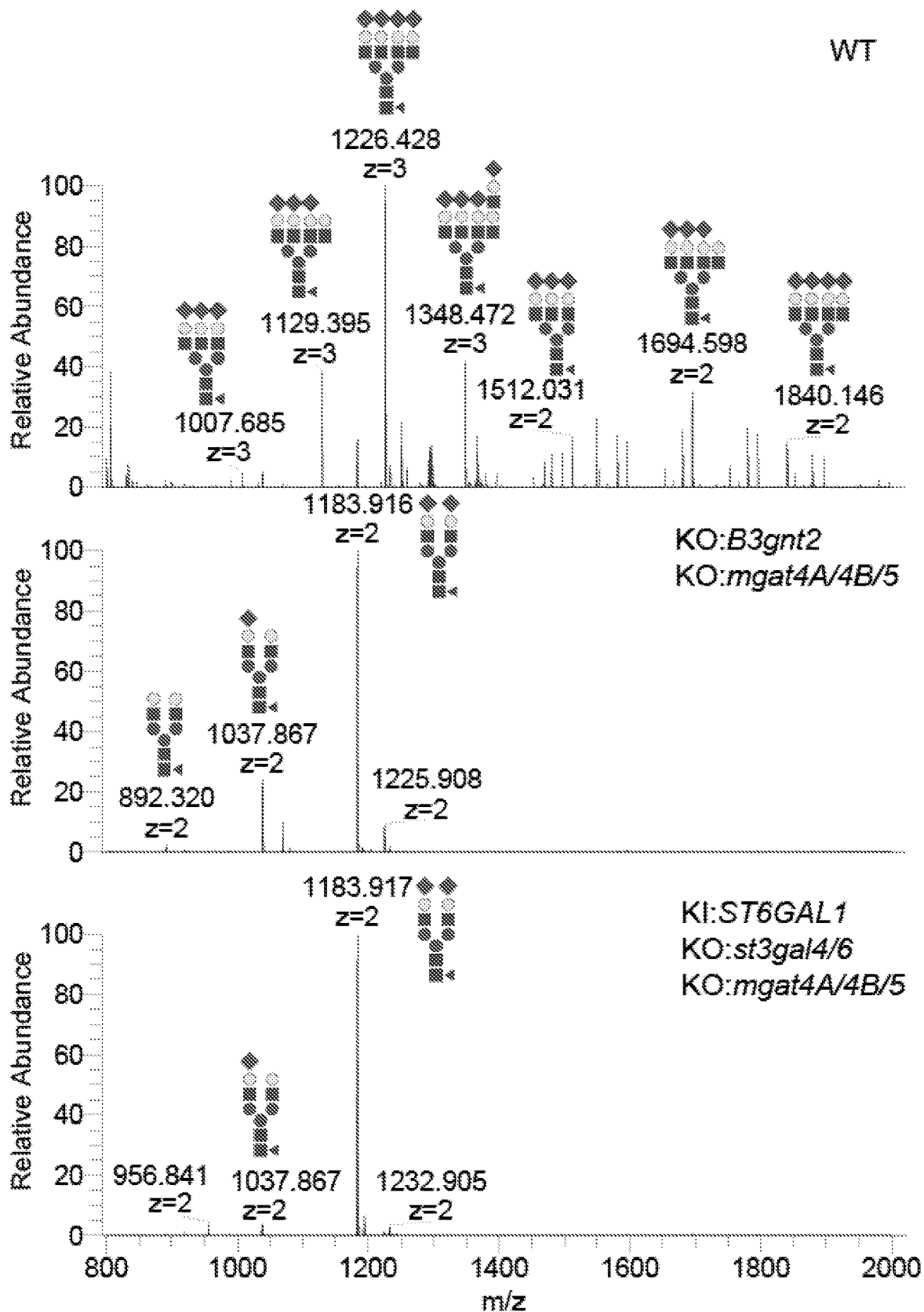
FIG. 10 shows glycoprofiling of EPO produced in CHO-GS WT, B3gnt2/mgat4A/4B/5, and st3gal4/6/mgat4A/413/5 KO with KI of ST6Gal-I, showing complete loss of poly-LacNAc on biantennary N-glycans, and complete de novo capping by α2,6 sialic acid on biantennary N-glycans without poly-LacNAc. Negative ion ESI-MS glycoprofilling was used to validate MALDI-TOF based glycan profiling data.
Figure 11A:
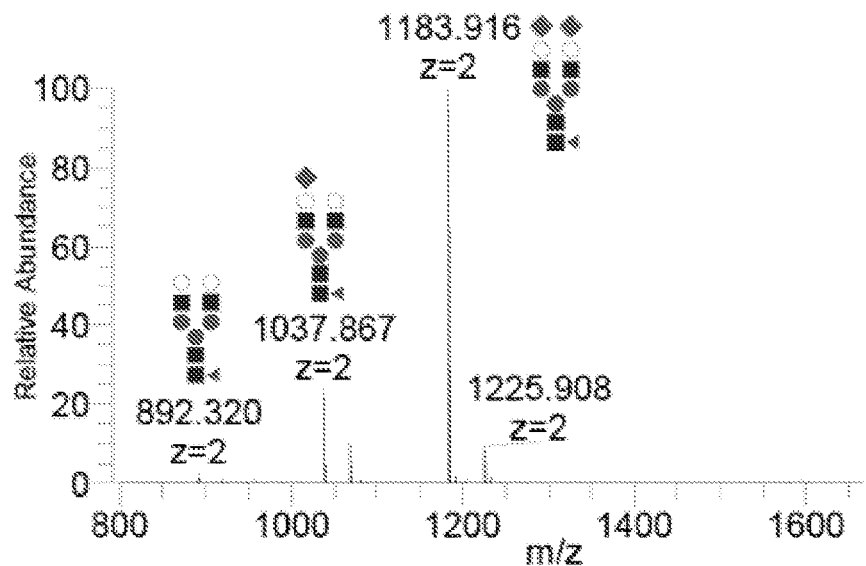
FIG. 11 shows negative ion ESI-MS/MS of the precoursor ions as m/z 1183.92 (sialyllated biantennary N-glycan with core fucose) from EPO produced in CHO with (A) mgat4A/4B/5 KO and with (B) both mgat4A/4B/5 and st3gal4/6 KO and KI of ST6Gal-I. The presence of the diagnostic fragment ions at m/z 306.12 indicates α2,6 terminal sialylation.
Figure 11A:
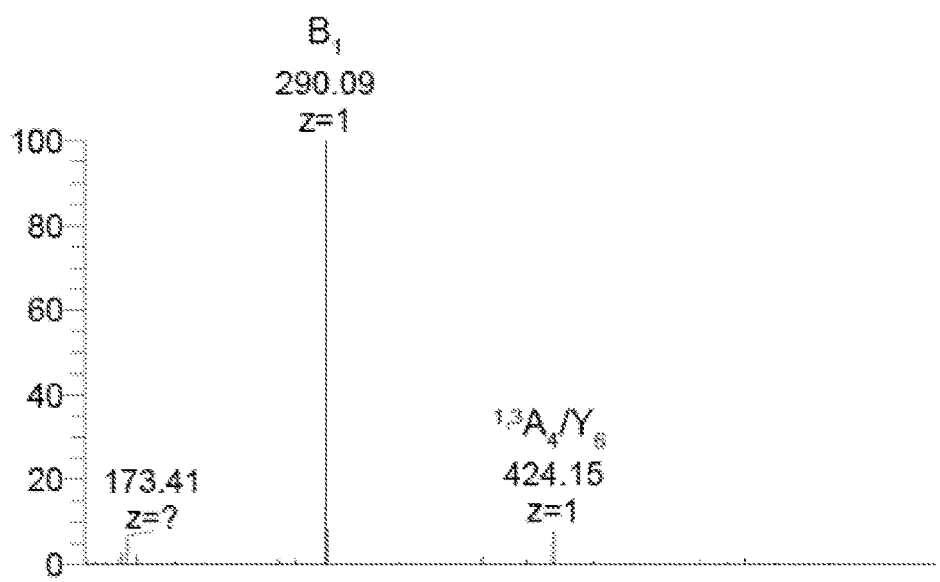
Figure 11B:
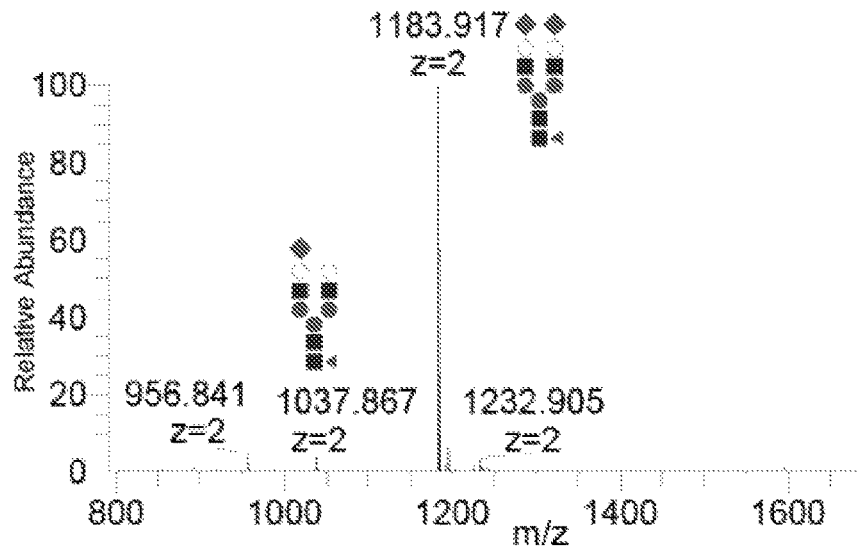
Figure 11B:
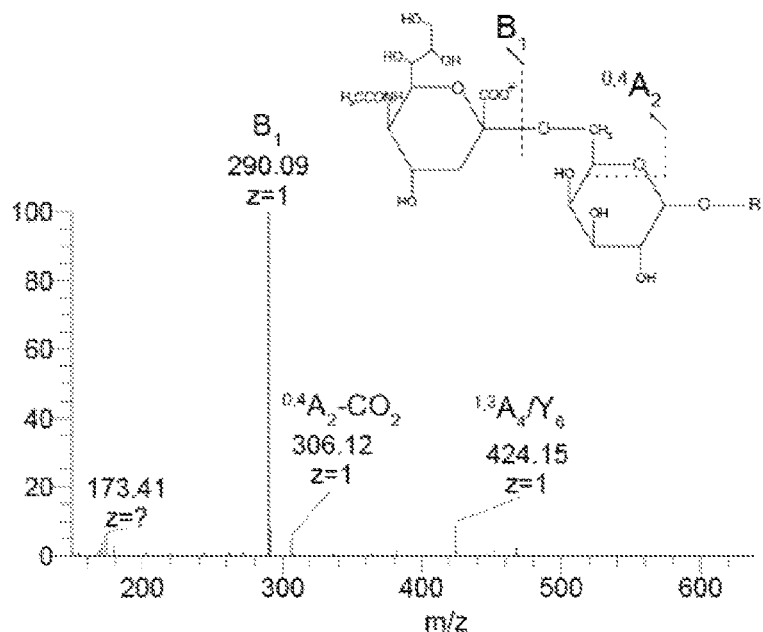
Figure 12A:
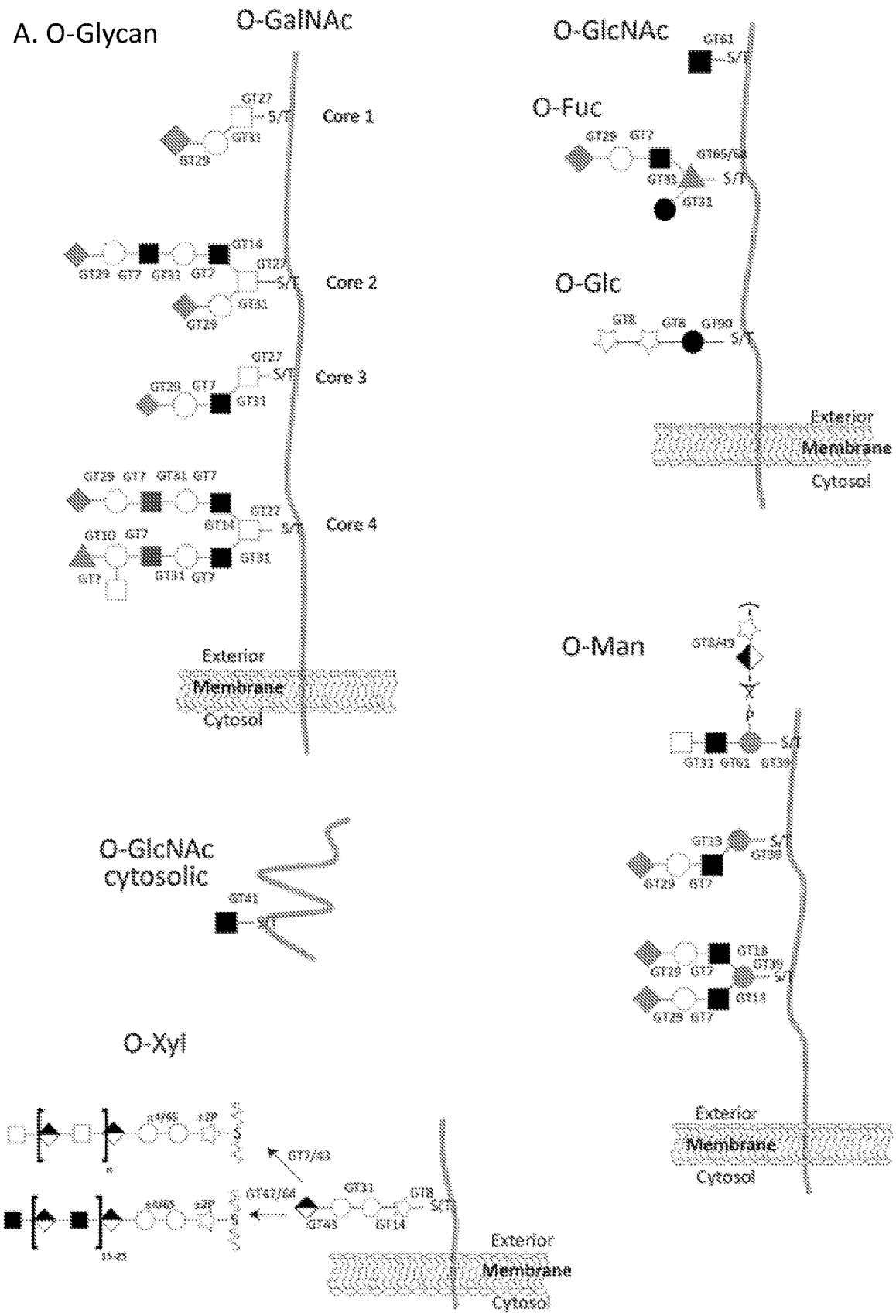
FIG. 12. A graphic depiction of the human CAZy GT families involved in the biosynthesis of the major mammalian glycoconjugates and their different glycosylaton pathways. The common mammalian glycan structures are depicted for (A) O-glycans including O-GalNAc, O-GlcNAc, O-Fuc, O-Glc, O-Man, O-Xyl; (B) N-glycans; (C) GPI-anchors; (D) C-glycans; (E) glycospingolipids; (F) hyaloronan and (G) hydroxy-lysine. Designations for monosaccharides according to the Consortium for Functional Glycomics are indicated.
Figure 17:
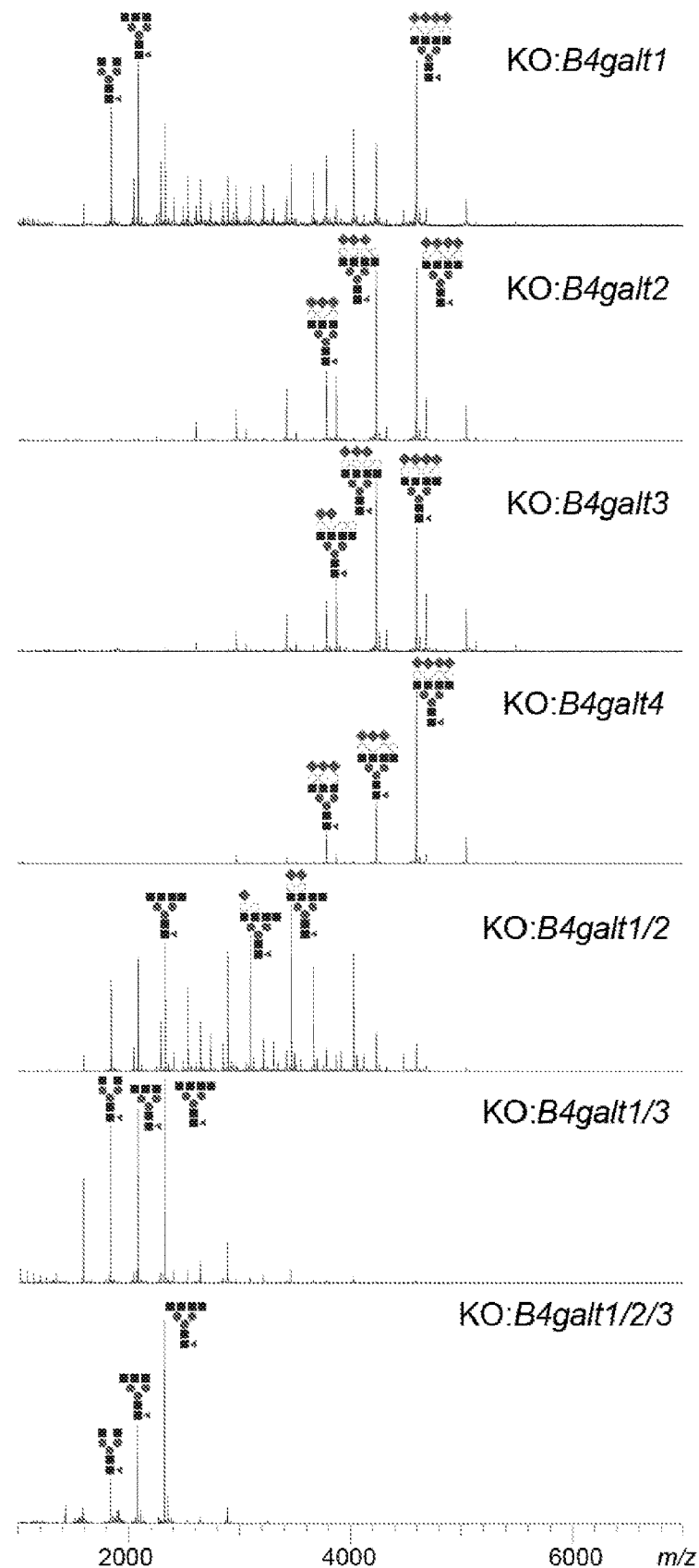
FIG. 17 Glycoprofiling with KO of B4galt1/2/3/4 genes involved in LacNAc biosynthesis, showing that only B4galt1 KO alone produced substantial albeit partial loss of galactosylation, while only stacked KO of B4galt1/3 resulted in near complete loss of galactosylation, while stacked KO of B4galt1/3 resulted in near complete loss of galactosylation. Stacked KO of B4galt1/2/3 resulted in essentially complete loss of galactosylation.

Control of LacNAc—CHO cells express all seven known β4galactosyltransferases (TABLE 3), and our understanding of the in vivo functions of these isoenzymes is poor. Only B4galt1-4 are expected to serve functions in N-glycosylation and they have been suggested to have preferences for different N-glycan branches. The current invention first screened individual KO of B4galt1-4 in CHO-GS WT, and confirmed that B4galt1 appeared to have the major role in LacNAc formation using EPO as reporter molecule (FIG. 17). Thus, the invention could only assess contributions of the other isoforms in stacked combinations with KO of B4galt1. Probing stacked combinations by immunocytology with an antibody to LacNAc show surprisingly that only stacked KO of B4galt1/3, and not B4galt1/2/4, appeared to abolish galactosylation (FIG. 10). In agreement with this the invention found that EPO expressed in B4galt1/3 but not B4galt1/2 stacked KO clones had substantial reduction (>90%) in galactosylation (FIG. 17).

Figure 21A:
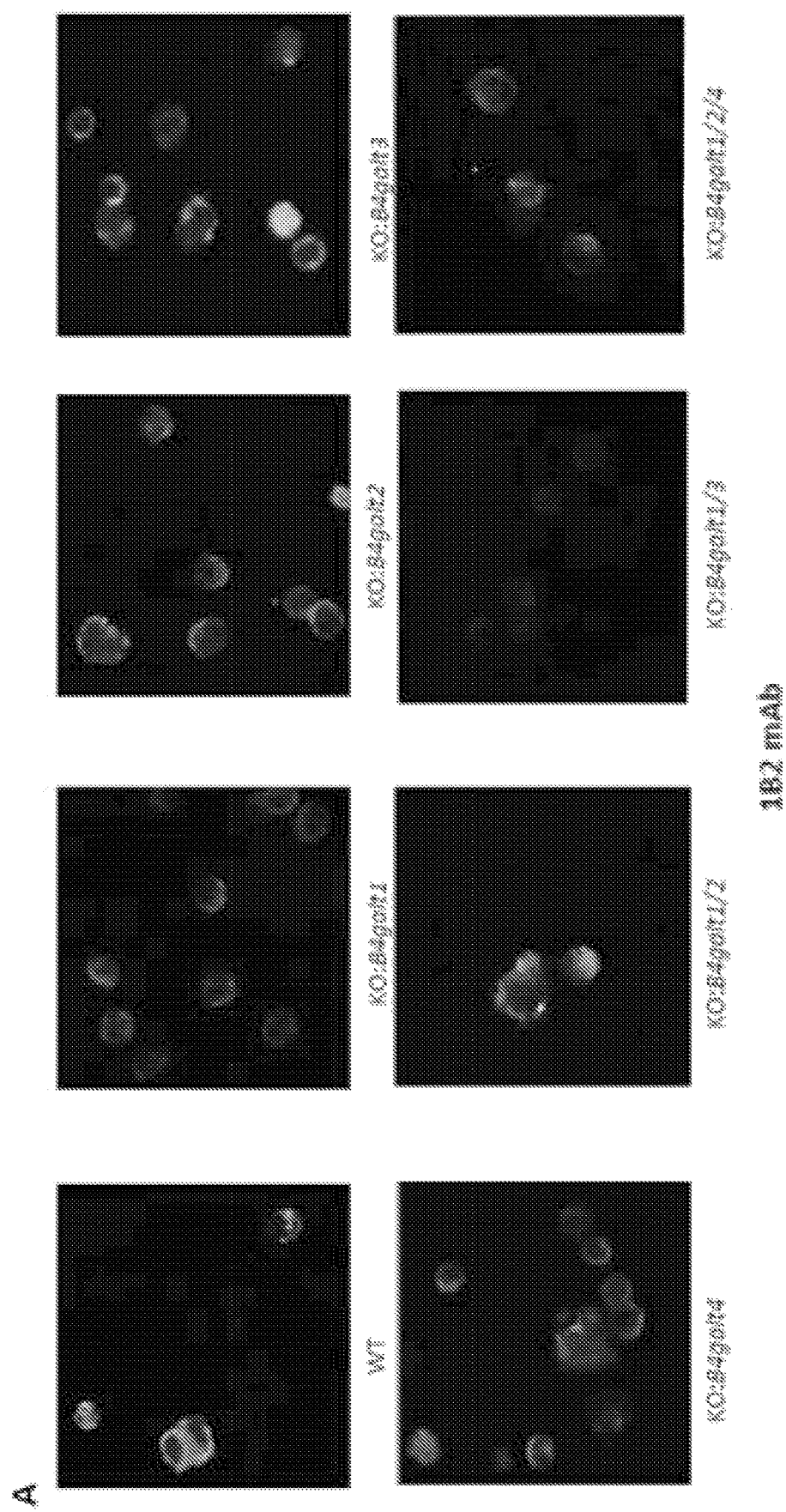
FIG. 21 Immunoflourescense cytology with a monoclonal antibody (clone 1B2) to LacNAc. Panel (A) shows surprisingly that only stacked KO of B4galt1/3, and not B4galt1/2/4, abolished galactosylation. Panel (B) shows that KO of B4galt1 in CHO-GS with KO of mgat4A/4B/5 eliminated immunoreactivity for LacNAc while KO of B4galt2, 3, and 4 in the same CHO-GS had no substantial effects.

The invention further tested stacked KO of individual B4galt's in CHO-GS Mgat4a/4b/5 KO cell lines with homogeneous biantennary N-glycans, and found that KO of B4galt1 eliminated immunoreactivity for LacNAc while KO of B4galt2, 3, and 4 had no substantial effects (FIG. 21A-B). This suggested that the B4galt1 encoded galactosyltransferase isoform is the major or only isoenzyme capable of transferring Gal to biantennary N-glycans, while the other isoforms also function with tri- and tetraantennary N-glycans. To further test this the invention included a human therapeutic IgG as a recombinant expressed reporter molecule (FIG. 22). Human IgGs most often only has one N-glycan in the conserved region at Asn297, and this site is generally only glycosylated with biantennary N-glycans with variable and heterogeneous degrees of galactosylation and sialylation. Some IgG molecules have additional N-glycan sites in the variable regions and these are usually glycosylated with more complex tri and tetraantennary N-glycans structures with efficient galactosylation and capping by sialic acids. Importantly, recombinant expression of an IgG in CHO-GS with KO of B4galt1 resulted in homogenous biantennary N-glycans without galactosylation (FIG. 22). Since CHO only produces IgG with biantennary structures normally, it follows that only knockout of B4galt1 is required to achieve this. This demonstrates that the inherent heterogeneity found in N-glycosylation on therapeutic monoclonal antibodies can be eliminated by use of this modified CHO cell line.

Since CHO produce a high degree of α6Fuc on N-glycans and elimination of this glycosylation can be achieved by knockout of FUT8, it is clear that the combinations of knockout of Mgat4a/4b/5, B4galt1, and Fut8 as well as stacked KO of B4galt1 and Fut8, will generate CHO clones producing homogenous N-glycans without α6Fuc. Such production cell lines will be important for producing therapeutic IgG antibodies with enhanced ADCC.

Figure 18:
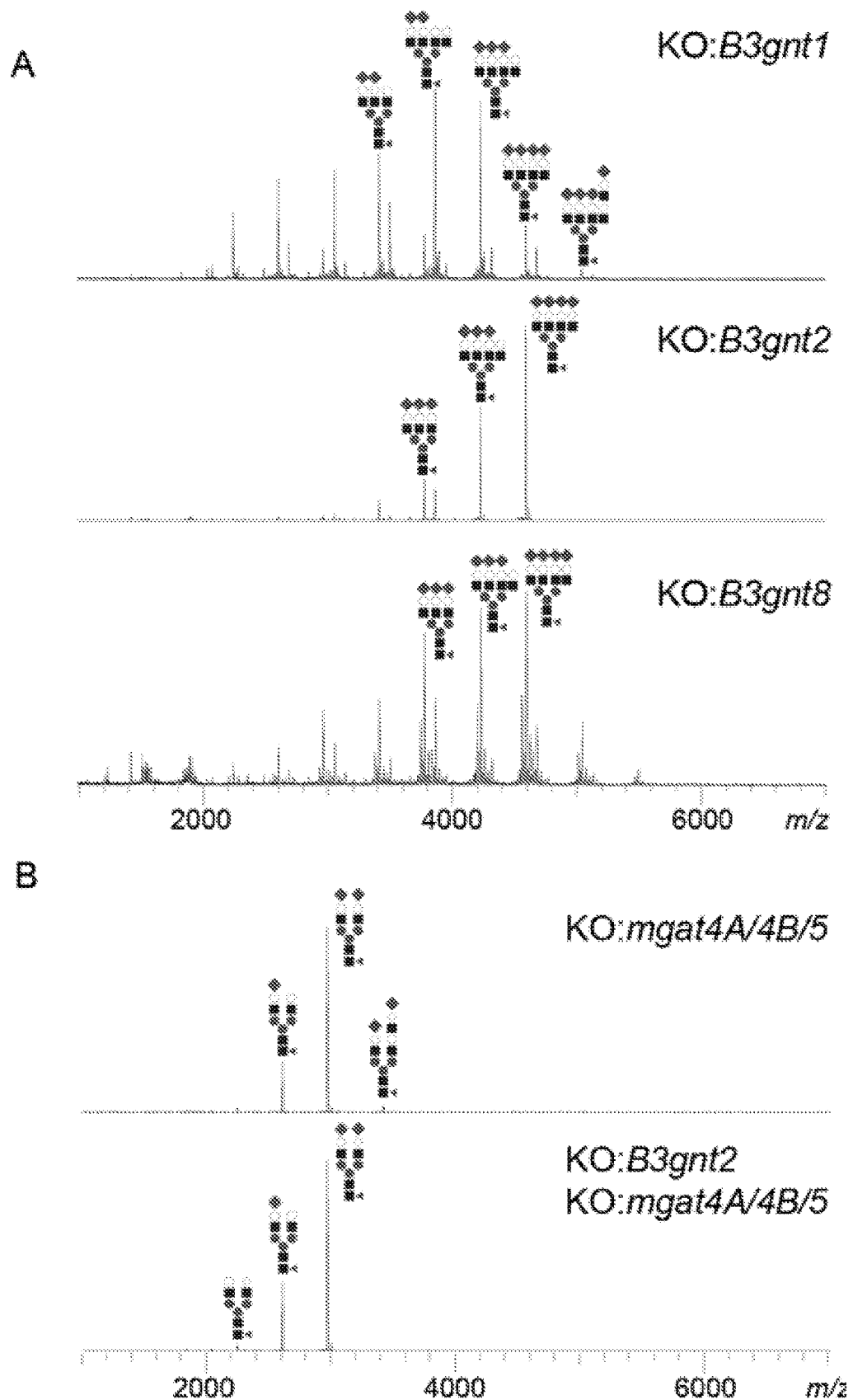
FIG. 18 Glycoprofiling with KO of three β3GlcNAc-transferase genes showing that KO of B3gnt2 results in complete loss of poly-LacNAc, whereas KO of B3gnt1 and B3gnt1 had no effects. Lower PANEL shows that KO of B3gnt2 in combination with mgat4A/4B/5 results in complete loss of poly-LacNAc on biantennary structures.
Figure 23:
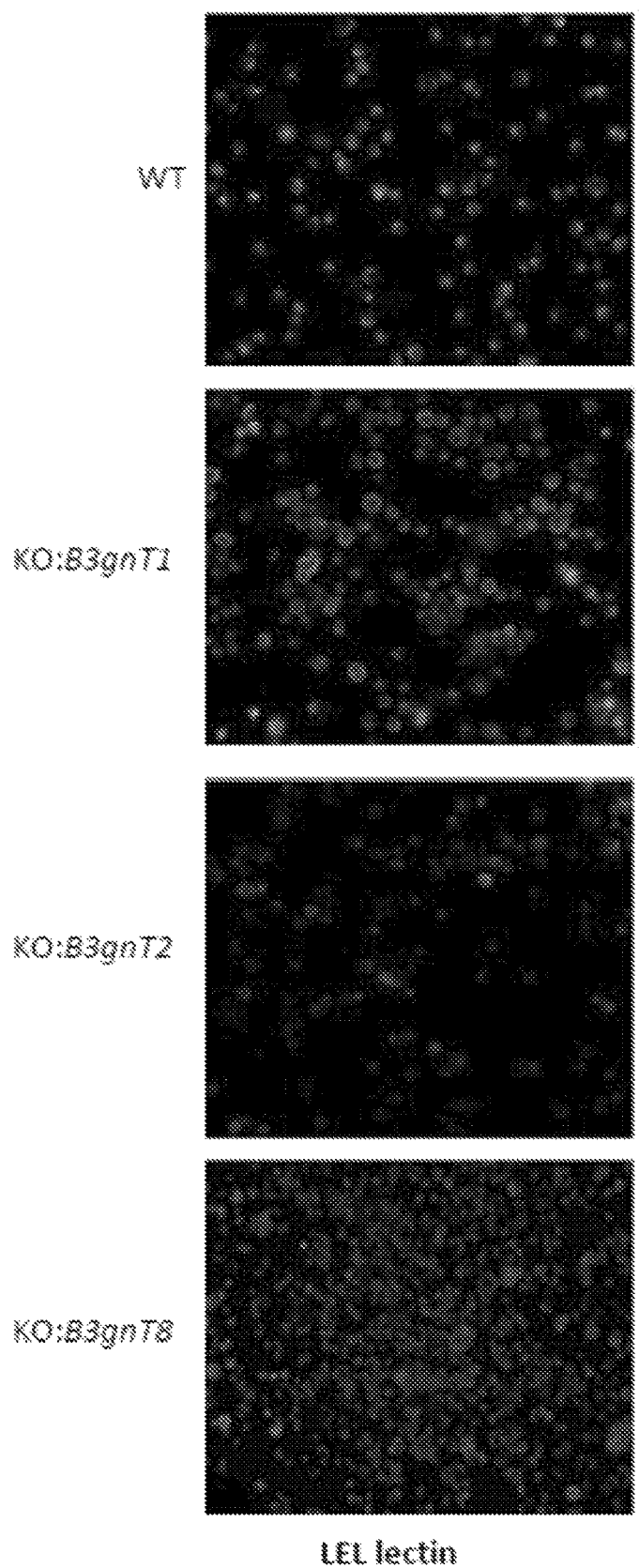
FIG. 23 Immunoflourescence cytology with LEL lectin shows that B3gnt2 is the key gene controlling the LacNAc initiation in CHO cells.

Control of poly-LacNAc—Poly-LacNAc on N-glycans has consistently been found to be incomplete and heterogeneous (Fukuda, Sasaki et al. 1989; Takeuchi, Inoue et al. 1989; North, Huang et al. 2010). CHO cells generally produce low amounts of poly-LacNAc on N-glycans and mainly on tetraantennary structures on the β6-branch controlled by MGAT5 (North, Huang et al. 2010). Biosynthesis of poly-LacNAc on N-glycans is poorly understood and three genes, B3gnt1, B3gnt2 and B3gnt8, are candidates (Narimatsu 2006). Using single gene KO of B3gnt1, B3gnt2, and B3gnt8 with LEL lectin immunocytology the current invention identified B3gnt2 as the key gene controlling the LacNAc initiation in CHO cells (FIG. 23), and EPO expressed in CHO with KO of B3gnt2 but not B3gnt1 were devoid of poly-LacNAc (FIG. 18). Moreover, KO of B3gnt2 in CHO with additional KO of Mgat4a/4b/5 resulted in EPO with homogenous biantennary N-glycans without poly-LacNAc (FIG. 18). It was surprising that B3GNT1 did not play a role as the gene was originally identified by expression cloning as the poly-LacNAc synthase (Sasaki, Kurata-Miura et al. 1997), although this gene was later shown to also function in O-mannosylation (Bao, Kobayashi et al. 2009). Surprisingly, KO of B3gnt8 did not weaken the LEL Lectin immunocytology. B3gnt8 was previously shown to form heterodimer in vitro with B3gnt2 and activate the enzyme activity of B3gnt2.

Figure 19:
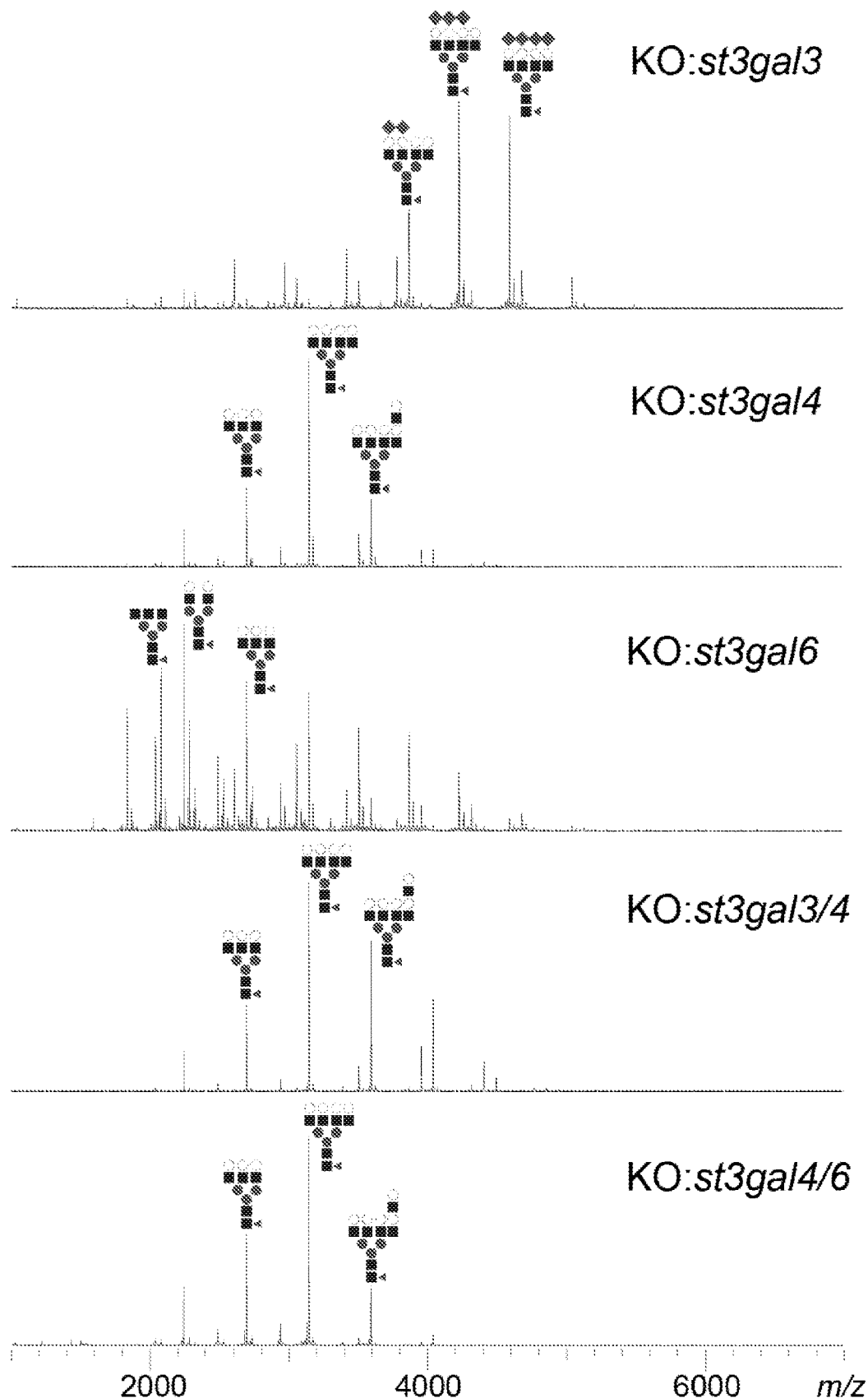
FIG. 19 Glycoprofiling with KO of three α2,3sialyltransferase genes with claimed roles in N-glycosylation, showing that only the double KO of st3gal4/6 resulted in complete loss of sialic acid capping.
Figure 24:
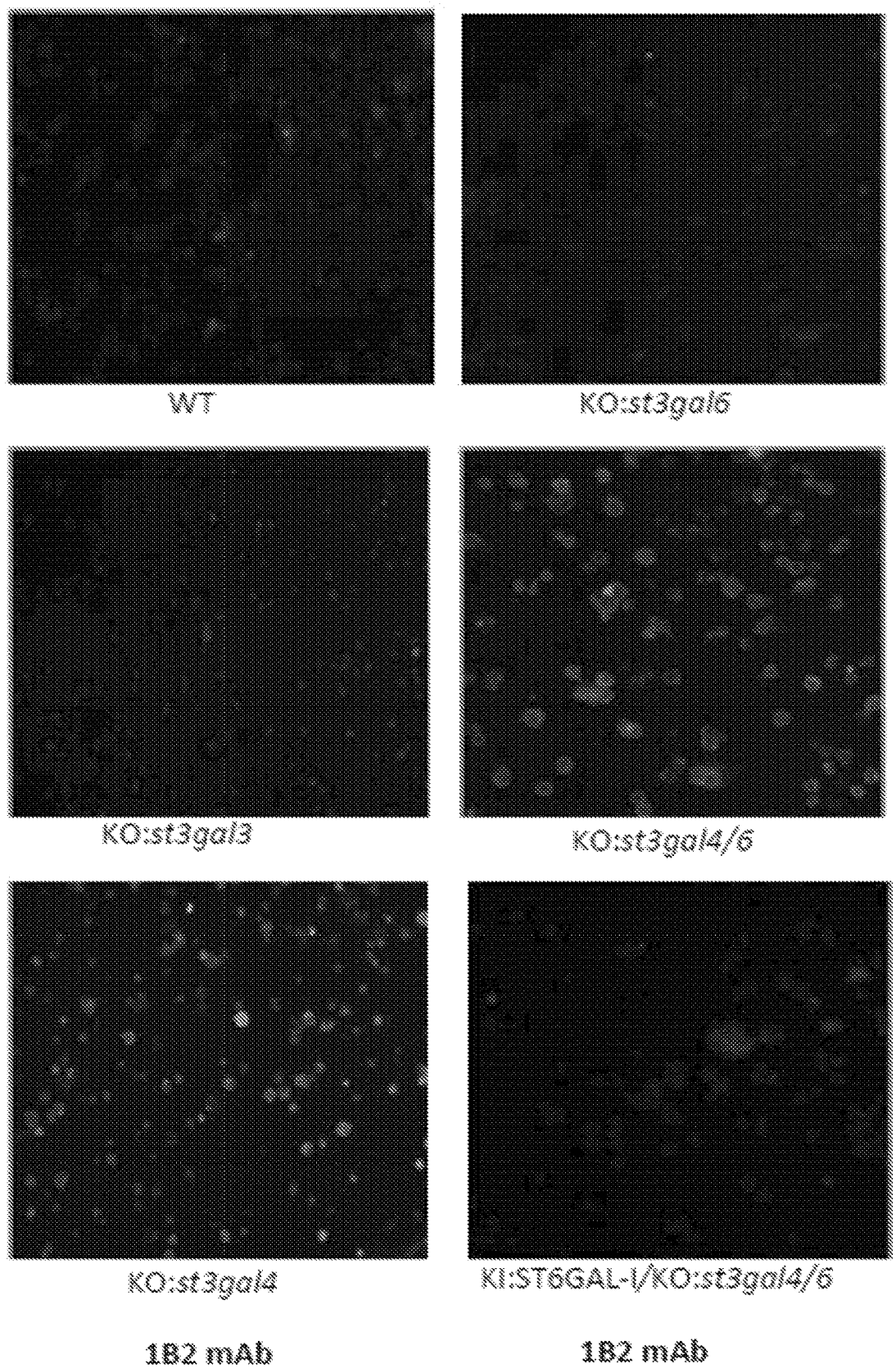
FIG. 24 Immunoflourescence cytology with monoclonal antibody to LacNAc (1B2). Knockout of St3gal3, St3gal4, and St3gal6 individually using immunocytology to evaluate exposure of LacNAc shows that only KO of St3gal4 produced substantial exposure of LacNAc.

Control of sialylation—CHO produce exclusively α2,3 linked NeuAc capping of N-glycans (Watson, Bhide et al. 1994). A few reports have suggested the presence of minor amounts of α2,6NeuAc as well as NeuGc, and genes for synthesis of both the α2,6linkage and CMP-NeuGc are found in CHO but these are not normally expressed (TABLE 3). Nevertheless, either or both genes may be inactivated by the current invention and in previous reports (US patent US20130004992). All six known st3gal1-6 sialyltransferases are expressed in CHO cells (TABLE 3) and the roles of each of these in sialylation of N-glycans are poorly understood (Tsuji, Datta et al. 1996). The sialyltransferase genes st3gal3, st3gal4, and st3gal6 were first targeted individually using immunocytology to evaluate exposure of LacNAc, and it was found that only KO of st3gal4 produced substantial exposure of LacNAc (FIG. 24). Analysis of EPO expressed in single and stacked KO clones showed that loss of st3gal4 and 6 produced substantial exposure. In CHO WT KO of st3gal4/6 resulted in EPO with heterogeneous tetraantennary N-glycans without sialylation (FIG. 19).

Figure 25A:
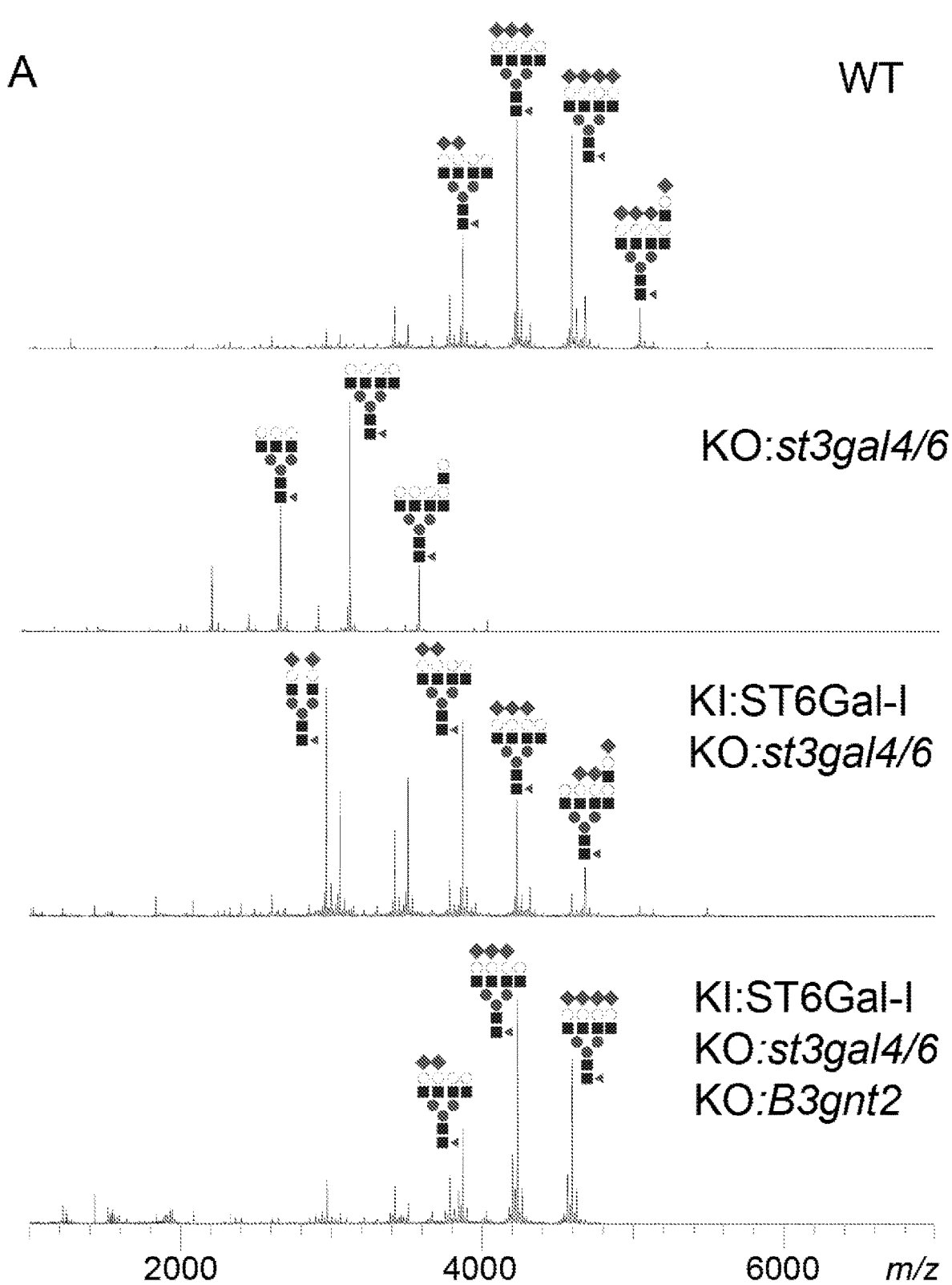
FIG. 25 Glycoprofiling of EPO expressed in CHO with KO of mgat4a/4b/5 and ZFN-mediated knockin of human ST6GAL1. Panel A shows profiling of EPO with homogenous α2,6NeuAc capping of the complete range of N-glycan antennary structures. Also shown is KI of ST6GAL1 in CHO with KO of mgat4a/4b/5/B3gnt2, which produced more homogeneous tetraantennary structures. Panel B shows profiling with additional KO of mgat4a/4b/5 where EPO is produced with homogenous biantennary N-glycans capped by α2,6NeuAc. Also shown are KI of human ST3Gal-4 in combination with KO of st3gal4/6/mgat4a/4b/5/63gnt2 where EPO is produced with homogeneous biantennary N-glycans without poly-LacNAc and capped by α2,3NeuAc.
Figure 25B:
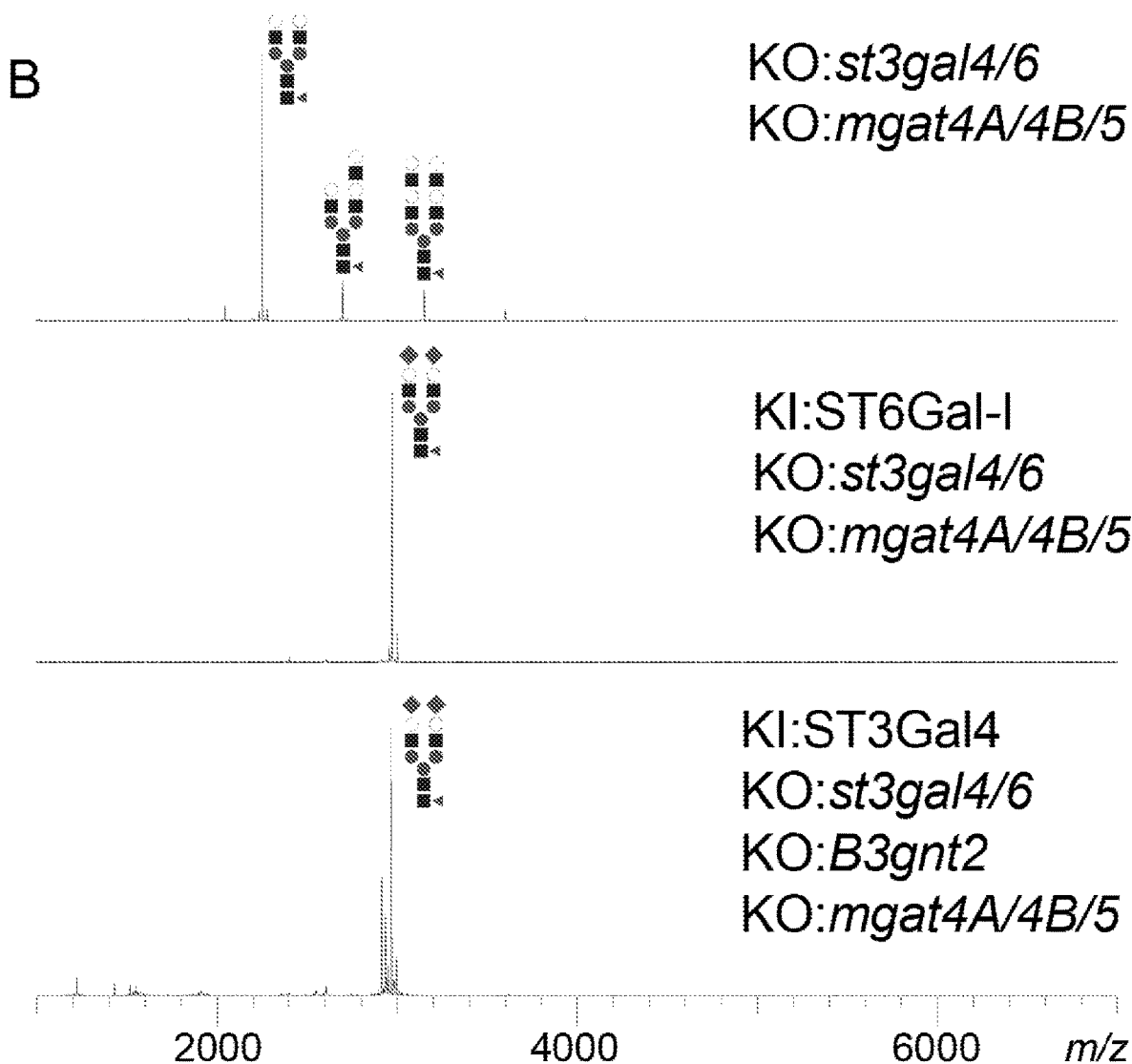
Figure 26A:
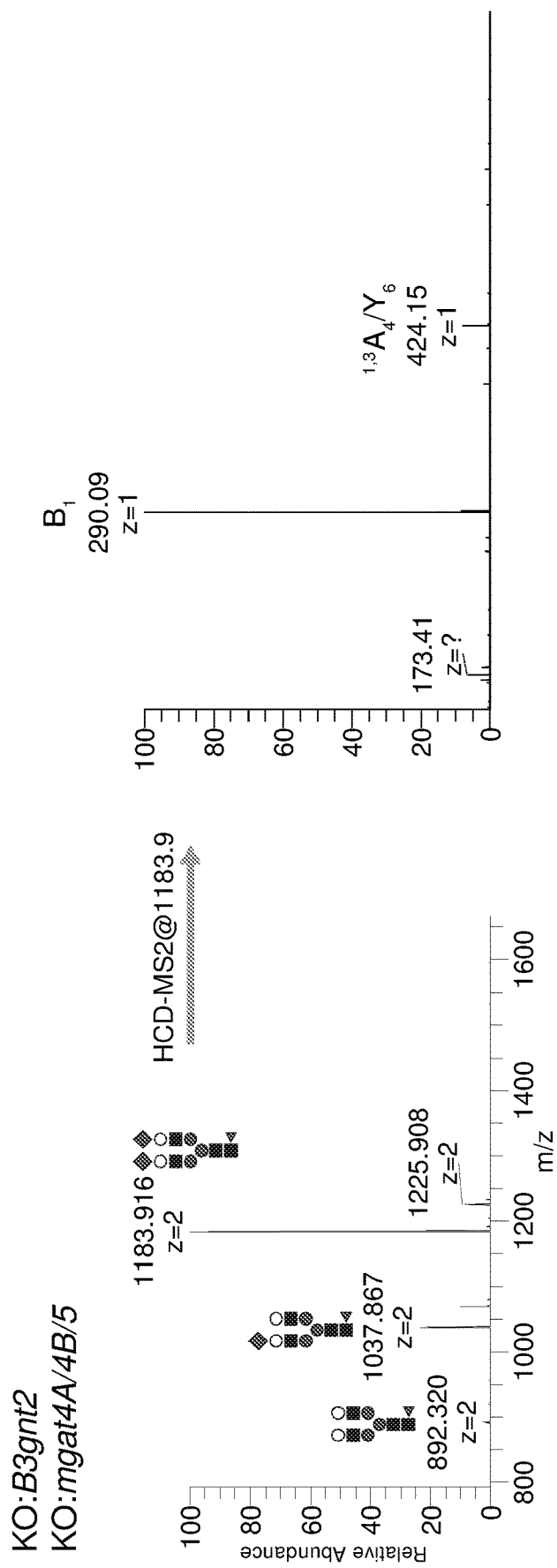
FIG. 26 Negative ion ESI-MS/MS of the precursor ions at m/z 1183.92 (sialylated biantennary N-glycan with core fucose) from EPO produced in CHO with (A) Mgat4a/4b/5 KO and with (B) both Mgat4a/4b/5 and st3gal4/6 KO and KI of ST6GAL1. The presence of the diagnostic fragment ions at m/z 306.12 demonstrates the presence of α2,6 terminal sialylation.
Figure 26B:
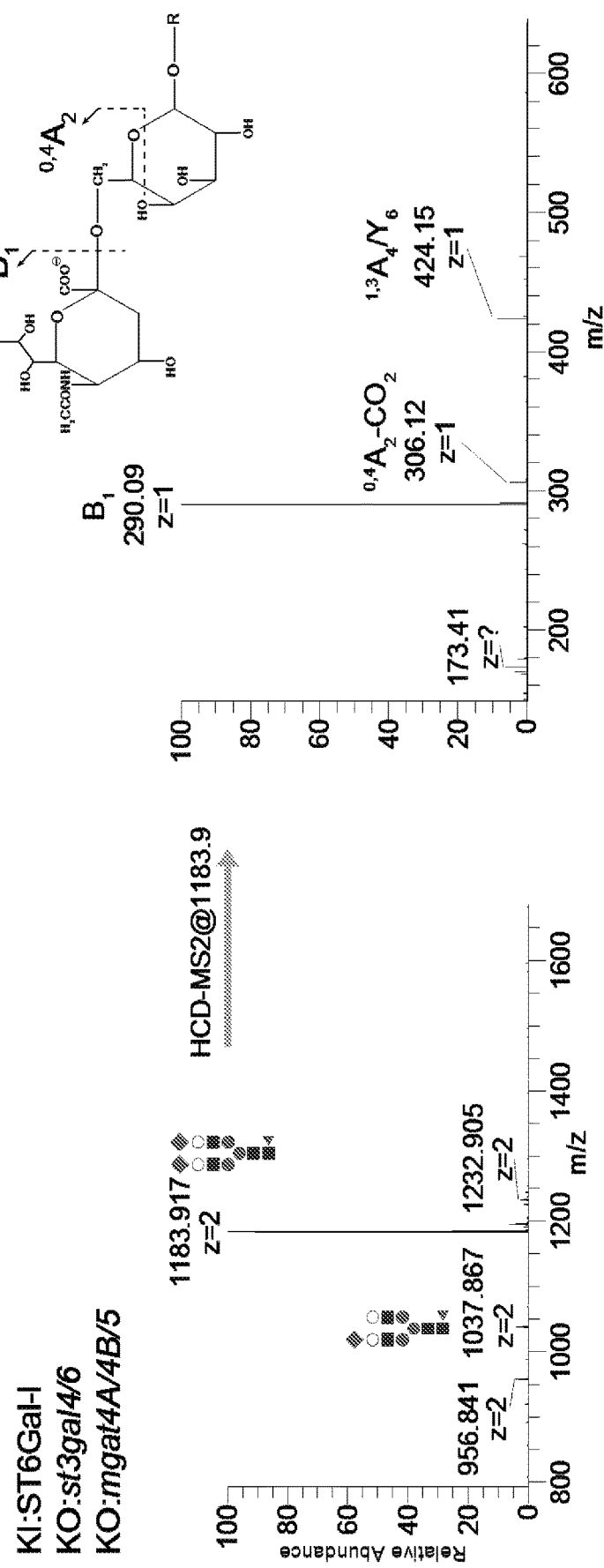
Figure 27:
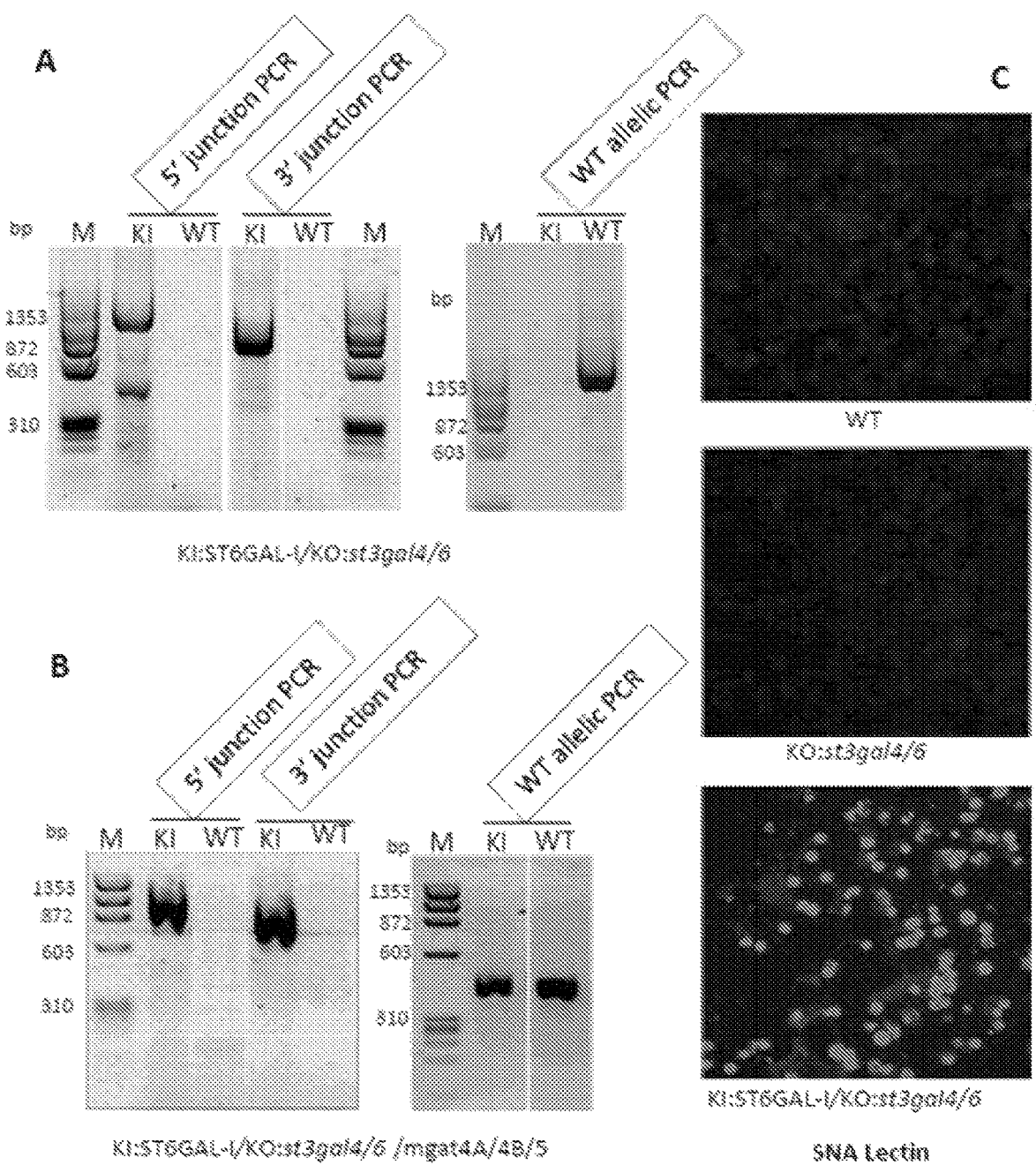
FIG. 27 Analysis of targeted KI of ST6GAL1 by junction PCR. Panel A shows that a modified ObLiGaRe targeted KI strategy utilizing two inverted ZFN binding sites flanking the ST6GAL1 full open reading frame in donor plasmid was used. 5 'and 3' junction PCR confirmed targeted integration into the Safeharbor #1 site in the CHO clone with st3gal4/6 KO. (b) 5 'and 3' junction PCR confirmed targeted integration in the CHO clone with st3gal4/6/mgat4a/4b/5 KO. The status of allelic copy number of integration was determined by WT allelic PCR. The presence of desired band in WT allelic PCR indicates the presence of Safeharbor #1 site without the integration of targeted KI of gene of interest on at least one of the allele. The results showed biallelic integration of ST6Gal-I at Safeharbor #1 site in the CHO st3gal4/6 KO clone and monoallelic integration in the mgat4a/4b/5/St3gal4/6 KO clone. The ObLiGaRe KI strategy was highly efficient with approximately 30-50% single cloned cells expressing ST6GAL1 as evaluated by antibody and lectin immunocytology.

Using the current invention it was shown KO of St3gal4/6 in combination with Mgat4a/4b/5 interestingly produced biantennary N-glycans without sialylation but increase in poly-LacNAc (FIG. 25). Thus, CHO with st3gal4/6 KO can produce EPO with uncapped LacNAc termini and this opens for the first time for de novo engineering of recombinant glycoproteins with α2,6NeuAc capping without competition by endogenous α2,3sialylation (El Mai, Donadio-Andrei et al. 2013).

Figure 32:
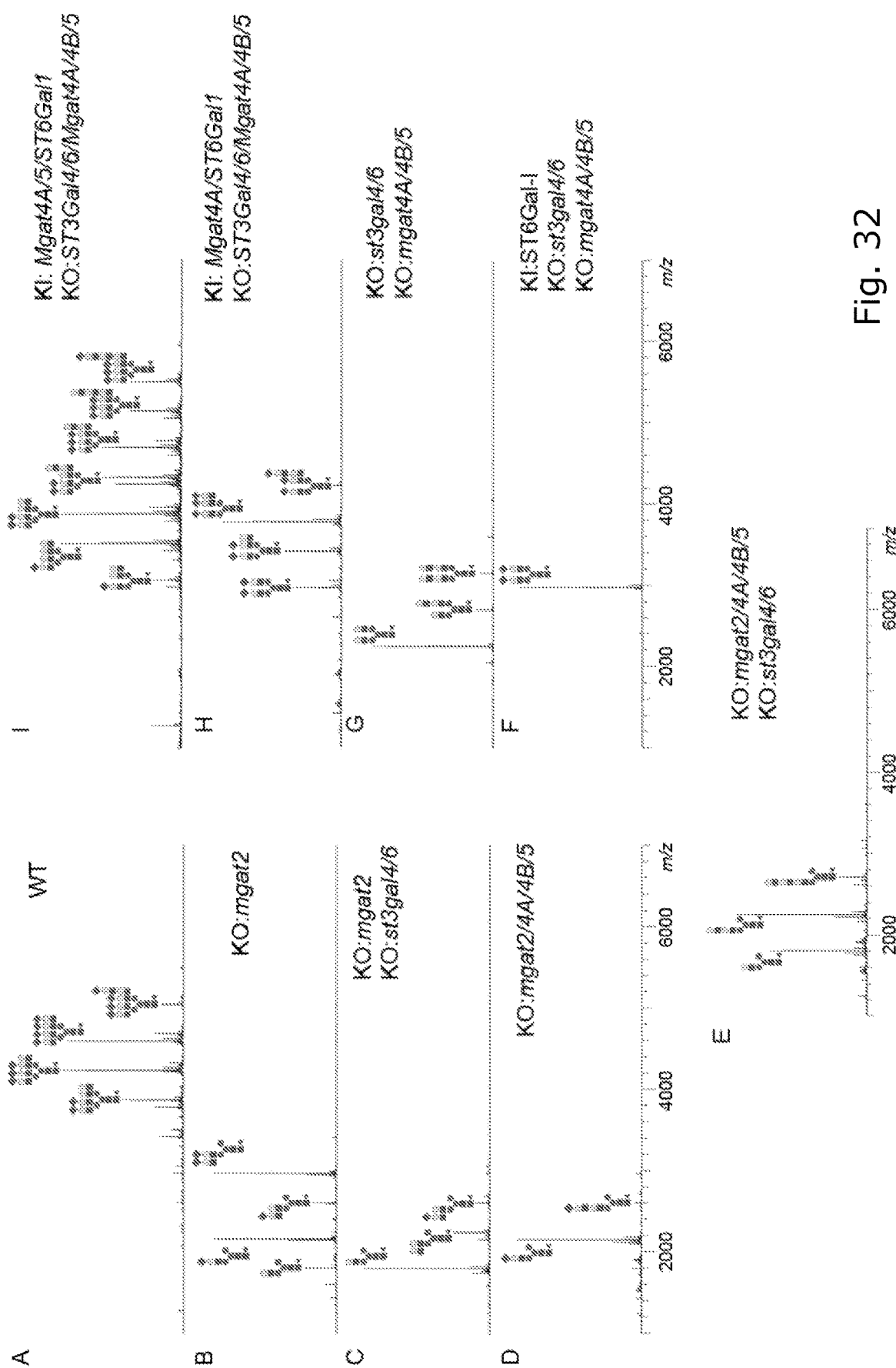
FIG. 32 Glycoprofiling of EPO expressed in CHO with KO of mgat2 showing loss of tetra and triantennary N-glycan structures and appearance of mono and biantennary N-glycans with galactose and NeuAc capping (PANEL B), and without sialic acid capping with KO of st3gal4/6 (PANEL C). Further KO of mgat4A/4B/5 resulted in monoantennary structures with minor amounts of poly-LacNAc (PANELS D and E). Reintroduction of human mgat4A and mgat5 in combination with ST6Gal-I resulted in loss of monoantennary N-glycans and restoration of tri and tetraantennary structures (PANELS H and I).

Monoantennary N-glycans—Using the current invention we also probed the effect of mgat2 KO alone and in combination with Mgat4a/4b/5 and st3gal4/6 (FIG. 32). KO of mgat2 alone produced a mixture of mono and biantennary N-glycan structures, and in further combination with Mgat4a/4b/5 homogeneous monoantennary N-glycans. To confirm that the monoantennary N-glycan was linked β1-2 to the α1-3Man branch controlled by mgat1, we reintroduced by knockin human MGAT4A as well as MGAT4A and 5 in combination together with ST6Gal-I, which resulted in tri and tetraantennary N-glycans, respectively (FIG. 32).

Reconstruction of Homogeneous Glycosylation

The present invention further provides strategies to develop mammalian cell lines with defined and/or more homogenous glycosylation capacities that serves as template for de novo engineering of desirable glycosylation capacities by introduction of one or more glycosyltransferases using site-directed gene insertions and/or classical random transfection of cDNA and/or genomic constructs. The strategy involves inactivating glycosyltransferase genes to obtain a homogenous glycosylation capacity in a particular desirable type of glycosylation, for example using the deconstruction matrix developed herein for N-glycosylation, and for example but not limited to inactivation of the St3gal4 and 6 sialyltransferase genes in a cell and obtaining a cell without sialic acid capping of N-glycans. In such a cell the de novo introduction of one or more new glycosylation capacities that utilize the more homogenous truncated glycan product obtained by one or more glycosyltransferase gene inactivation events, will provide for non-competitive glycosylation and more homogeneous glycosylation by the de novo introduced glycosyltransferases. For example but not limited to introduction of a α2,6sialyltransferase such as ST6GAL1 into a mammalian cell with inactivated St3gal4 and St3gal6 sialyltransferase genes. The general principle of the strategy is to simplify glycosylation of a particular pathway, e.g. N-glycosylation, to a point with reasonable homogeneous glycan structures being produced in the mammalian cell in which one or more glycosyltransferase gene inactivation events has been introduced in a deconstruction process as provided in the present invention for N-glycosylation. Taking such mammalian cell with deconstructed and simplified glycosylation capacity, and introduce de novo desirable glycosylation capacities that build on the glycan structures produced by the deconstruction.

Reconstruction of N-Glycan Sialylation by Targeted Knockin—De Novo Design of α2,6NeuAc Capping Most glycoproteins in circulation in man are capped with α2,6NeuAc (El Mai, Donadio-Andrei et al. 2013), while essentially all recombinant therapeutics are produced with α2,3NeuAc in CHO, HEK293 and other current production cell lines. It is therefore clearly desirable to obtain mammalian cell lines like CHO with capacity for production of more human-like glycoproteins with homogeneous α2,6NeuAc capping. A number of research groups have approached this and attempted to produce stable CHO cells capable of producing homogenous N-glycans with α2,6NeuAc capping without success (El Mai, Donadio-Andrei et al. 2013).

To demonstrate the perspectives for reconstruction and de novo glycoengineering enabled by our KO deconstruction screen, CHO clones capable of producing homogenous α2,6NeuAc capping were generated (FIG. 25). To circumvent past problems with random plasmid integration (El Mai, Donadio-Andrei et al. 2013), ZFN targeted knockin (KI) of ST6GAL1 with a modified ObLiGaRe strategy into a SafeHarbor integration site was used (Maresca, Lin et al. 2013). This strategy also does not involve or need antibiotic selection or maintenance for cloning and stability, which is important for potential in production of recombinant therapeutics for clinical use. Human ST6GAL1 introduced in CHO with KO of St3gal4/6 produced the complete range of N-glycan antennary structures with normal degree of NeuAc capping (FIG. 25), and when introduced in CHO with additional KO of Mgat4a/4b/5, EPO was produced with homogenous biantennary N-glycans capped by α2,6NeuAc (FIG. 25). That the introduced sialylation was indeed α2,6-linked NeuAc and not α2,3-linked was confirmed by negative ion ESI-MS/MS as described in FIG. 15.

Surprisingly, de novo introduction of ST6Gal-I abrogated the minor amounts of poly-LacNAc formed on biantennary structures in CHO with KO of Mgat4a/4b/5 (FIG. 25). Knockout of B3gnt2 was required to eliminate poly-LacNAc in CHO WT and in CHO with KO of Mgat4a/4b/5 (FIG. 18). This example clearly demonstrates the intricate interplay between glycosyltransferases using the same acceptor substrate, and how different glycosylation reactions may out compete each other in unpredictable ways. Thus, it is possible to introduce capacity for α2,6NeuAc sialylation without competing α2,3sialylation, and to reconstruct a CHO cell capable of producing sialylated N-glycoproteins with homogeneous α2,6NeuAc capping either with the normal repertoire of N-glycan branching or with homogeneous biantennary N-glycans.

Construction of Monoantennary N-Glycans Suitable for Homogeneous Enzymatic Glycomodification Enzymatic glycopegylation and other modifications of proteins is a well-established method for site-specific attachments of poly-ethylene glycol (PEG) chains or other compounds to prolong half-life of drugs (DeFrees, Wang et al. 2006). Site-specific glycomodification of N-glycans using an α2,3-sialyltransferase to introduce the modification through a modified CMP-NeuAc substrate relies on i) a purified recombinant expressed glycoprotein with one or more N-glycans; ii) removal of sialic acids capping the N-glycans on the glycoprotein using a recombinant neuraminidase; and iii) transfer of the modified sialic acid to exposed galactose residues on the N-glycans using a recombinant sialyltransferase and the modified donor substrate. N-glycans on recombinant glycoproteins have varying degree of bi, tri and tetra antennary structures and desialylation of recombinant glycoproteins expose multiple galactose residues from each antennary structure, which results in substantial heterogeneity in the enzymatic glycomodification process. To overcome the desialylation step we produced a number of CHO engineering designs that produce N-glycans without sialic acid capping (FIGS. 19, 25, and 32), and these would enable direct enzymatic glycomodification without pretreatment with neuraminidase to remove sialic acids. To overcome the heterogeneity induced by multiple exposed galactose acceptor sites for enzymatic transfer on each multiantennary N-glycan we targeted mgat2 to block formation of biantennary structures, but KO of mgat2 alone did not as originally expected generate homogeneous monoantennary structures (FIG. 32). Instead about 50% was still biantennary, but combined with KO of mgat4A/4B/5 rather homogeneous monoantennary structures were obtained. The only detectable heterogeneity was associated with poly-LacNAc, which does not provide exposure of multiple galactose residues (FIG. 18).

Figure 35:
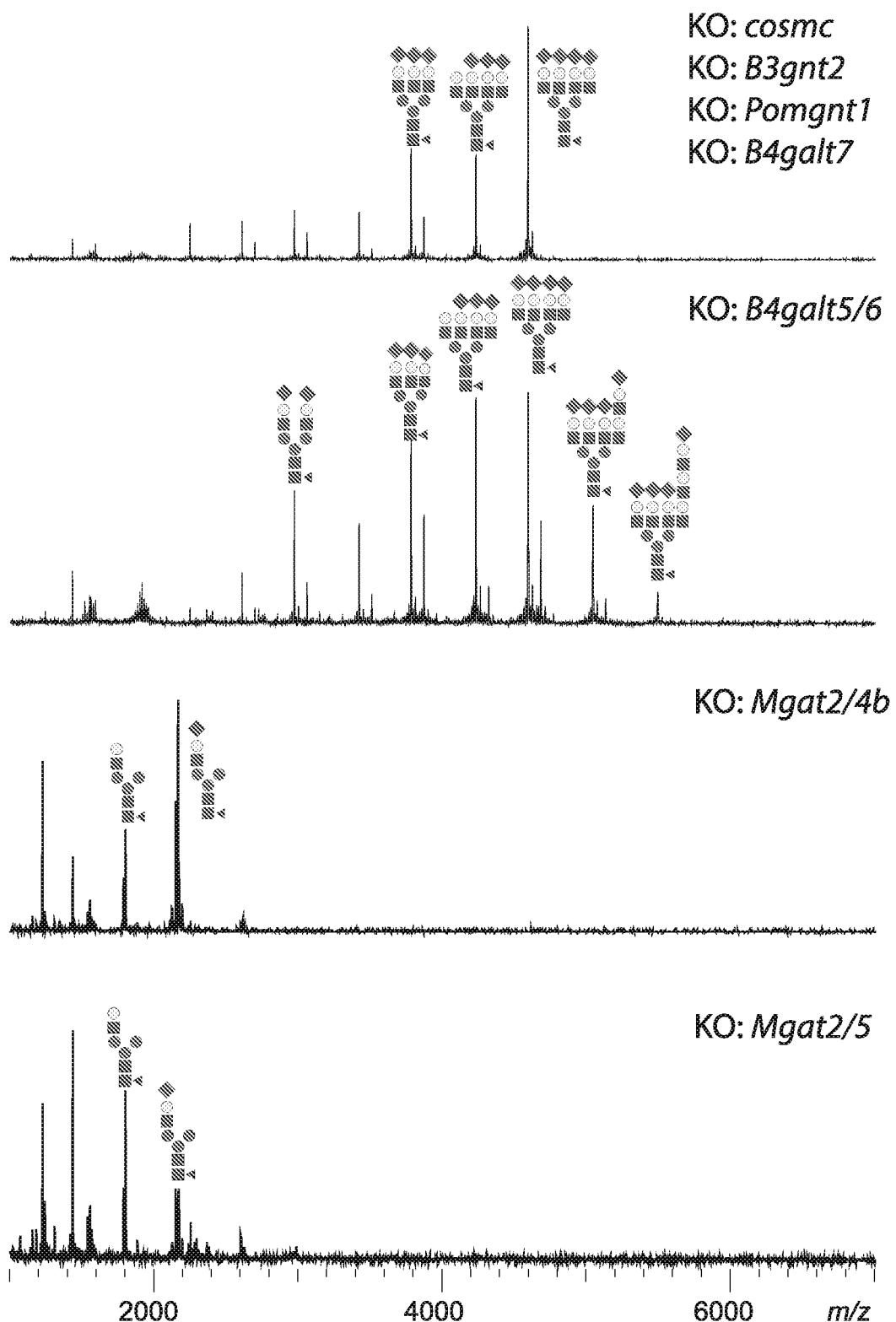

Rather homogeneous mono-antennary structure may also be accomplished by the following double KO's: KO of Mgat2/4B or KO of Mgat2/5. (FIG. 35).

Figure 36:
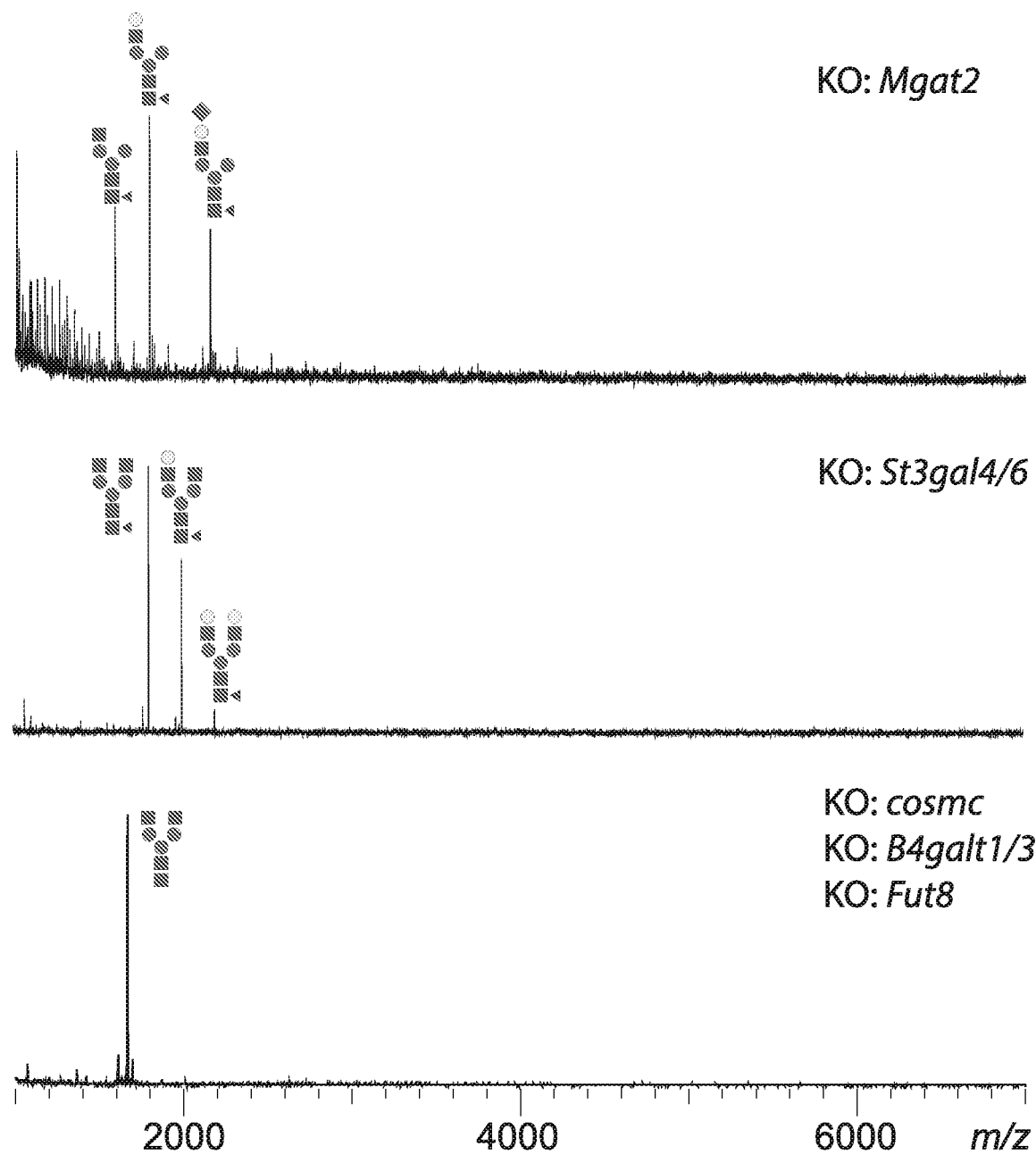
FIG. 36 Glycoprofiling of IgG expressed in CHO cells with KO of Mgat2 (top), double KO of St3Gal4/6 (middle) or KO of B4galt1/3 stacked onto Cosmc/Fut8 (lower panel). The Mgat2 KO results in homogeneous mono antennary structure and higher degree of sialylation than wt IgG (compare with FIG. 22). St3gal4/6 KO gives higher galactosylation (compare with FIG. 22). Double KO of B4galt1 and B4galt3 show more homogenous N-glycans without galactose than obtained with single ko of B4galt1 (compare with FIG. 22, lower panel).

For IgG antibody a homogeneous mono antennary structure and higher degree of sialylation may be obtained by KO of Mgat2 (FIG. 36).

Knockout of Unnecessary Glycosylation Pathways

Figure 29:
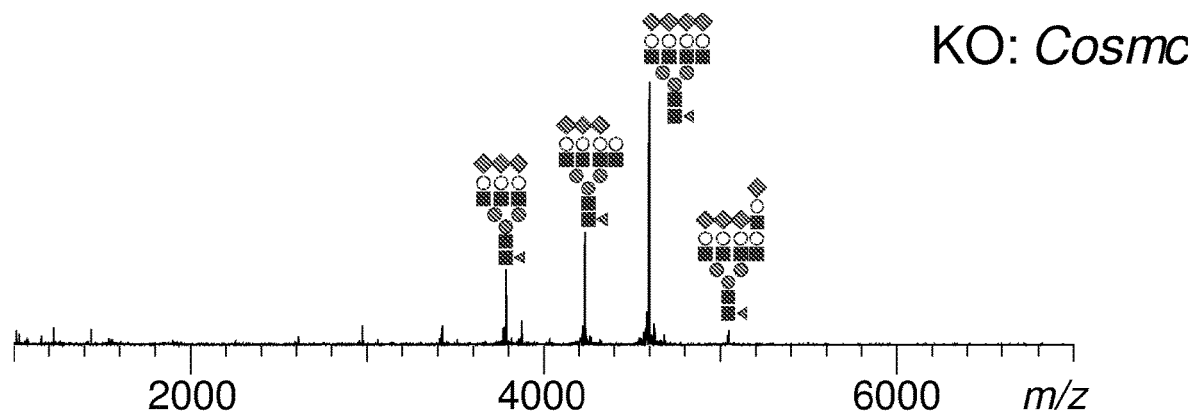
FIG. 29 Glycoprofiling of EPO expressed in CHO with KO of Cosmc to eliminate O-GalNAc elongation with Gal and NeuAc showing improved capacity for sialic acid capping of N-glycans at all three N-glycosites present in EPO, when compared to WT as shown in FIG. 15.

The methods of the invention allowed investigating if inactivation of different O-glycosylation pathways would affect cell viability and glycosylation efficiencies of non-targeted glycosylation pathways. We first abrogated the Core1 elongation pathway of O-GalNAc glycosylation as described previously (Yang, Halim et al. 2014) by inactivation of the Cosmc chaperone for the core1 synthase, C1GalT1, which leads to CHO cells capable of producing EPO with truncated O-GalNAc glycosylation limited to a single GalNAc residue without sialylation at the single O-glycosite. CHO WT produces O-glycans with both α2,3 and α2,6 sialic acid capping and O-GalNAc glycosylation is one of the most abundant type of protein glycosylation in a cell, and hence demanding on the sugar nucleotide pool. In line with this we found that EPO produced in CHO with inactivation of Cosmc and O-glycan elongation, produced EPO with improved sialic acid capping of N-glycans at all three N-glycosites present in EPO (FIG. 29)

Figure 30:
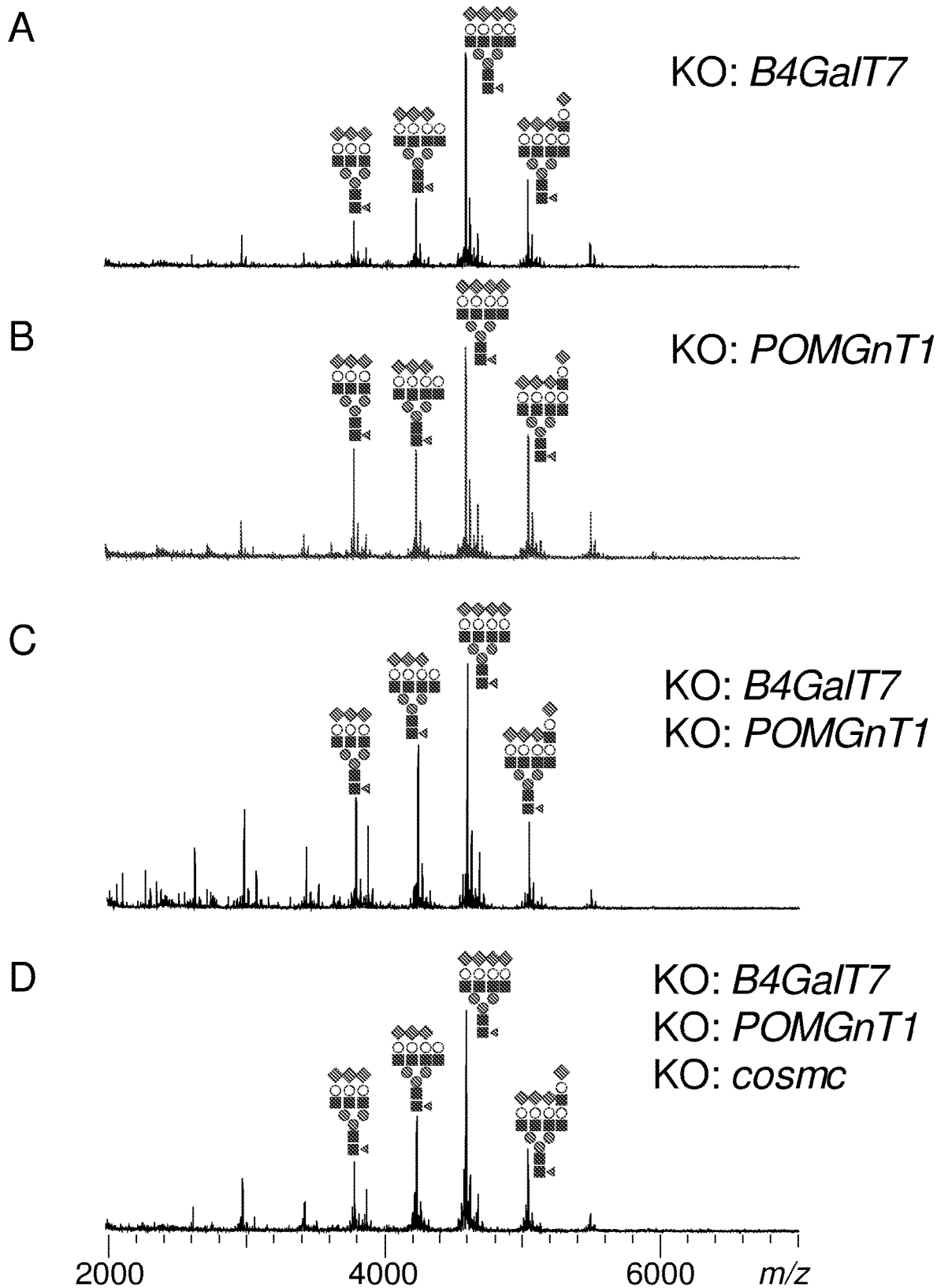
FIG. 30 Glycoprofiling of EPO expressed in CHO with KO of B4galT7 to eliminate O-Xyl elongation with Gal (PANEL A) and Pomgnt1 to eliminate O-Man elongation with Gal and NeuAc (PANEL B) showing enhanced capacity for sialic acid capping of N-glycans at all three N-glycosites present in EPO. PANEL C illustrates glycoprofiling of EPO expressed in double KO of B4galt7 and pomgnt1, and Panel D illustrates glycoprofiling of EPO expressed in triple KO of B4galt7, pomgnt1, and cosmc showing the same improved capacity for sialic acid capping of N-glycans in EPO.
Figure 31:
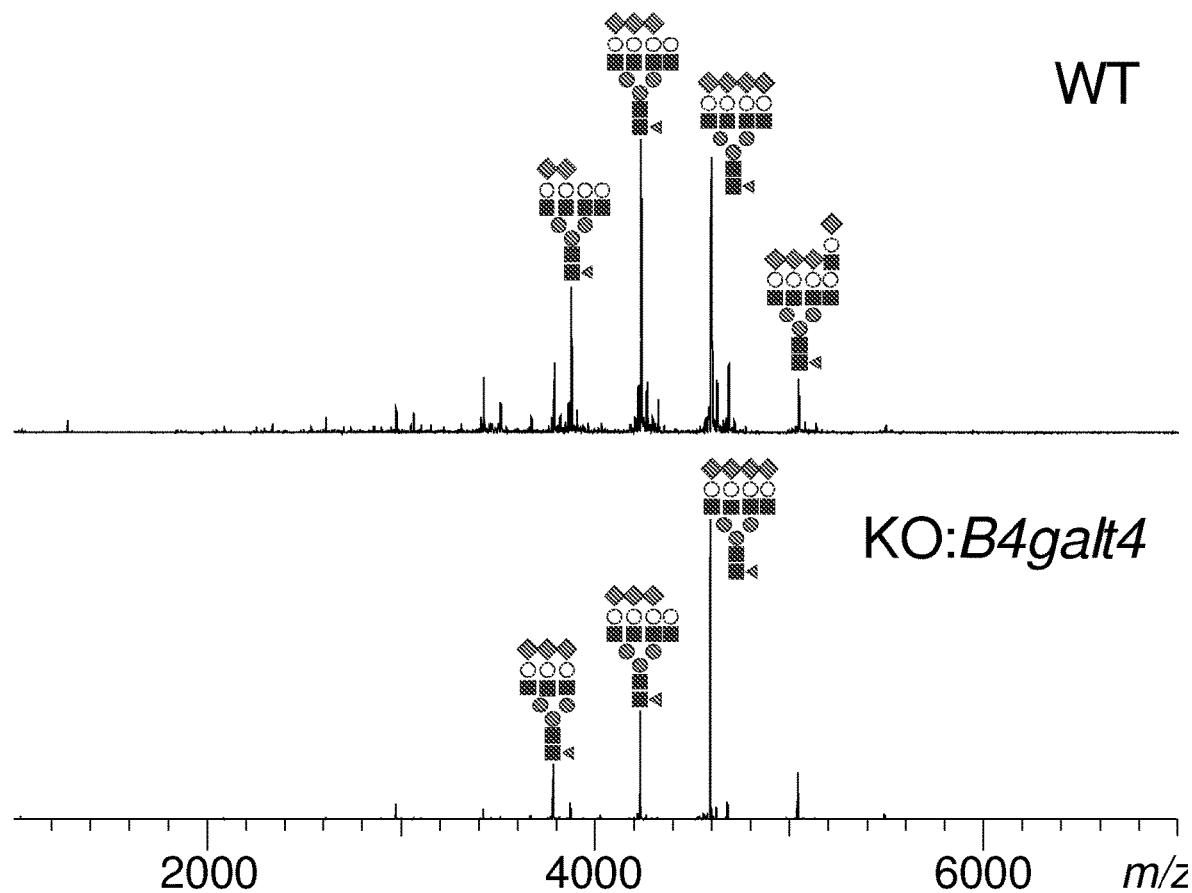
FIG. 31 Glycoprofiling of EPO expressed in CHO with KO of B4galT4 to eliminate a galactosyltransferase paralog not utilized for N-glycans and this glycosylation pathway showing improved capacity for sialic acid capping of N-glycans at all three N-glycosites present in EPO.

Applying methods of current invention the elongation pathway of O-Man glycosylation was targeted by inactivation of Pomgnt1, which encodes the β2GlcNAc-transferase synthesizing the major elongation pathway of O-Man glycans (ref PNAS). Proteins like dystroglycan expressed in mammalian cells, including CHO (Yang, Halim et al. 2014), have dense coverage of the O-Man tetrasaccharide (NeuAcα2,3Galβ1,4GlcNAcβ1,2Manα). When EPO was expressed in a CHO cell with inactivation of Pomgnt1 the degree of galactose, polyLacNac and sialic acid capping was enhanced (FIG. 30).

The current invention was applied to inactivate the elongation pathway of O-Xyl glycosylation by KO of B4galt7, which encodes the β4Galactosyltransferase synthesizing the second step in the linker region required for proteoglycan biosynthesis (Almeida, Levery et al. 1999). CHO cells produce proteoglycans and have efficient capacities for producing these on e.g. exogenously supplied saccharides. When EPO was expressed in a CHO cell with inactivation of B4galt7 the degree of galactose, poly-LacNac and sialic acid capping was enhanced (FIG. 30)

Current invention was also used to inactivate combinations of two or three genes controlling O-GalNAc, O-Man, and O-Xyl glycosylation pathways. Specifically CHO cells were generated with inactivation of both B4galt7 and Pomgnt1, and with inactivation of B4galt7, Pomgnt1, and Cosmc. When EPO was expressed in such CHO cell lines with inactivation of two or three types of O-glycosylation pathways the degree of galactose and sialic acid capping was enhanced.

Figure 13B:
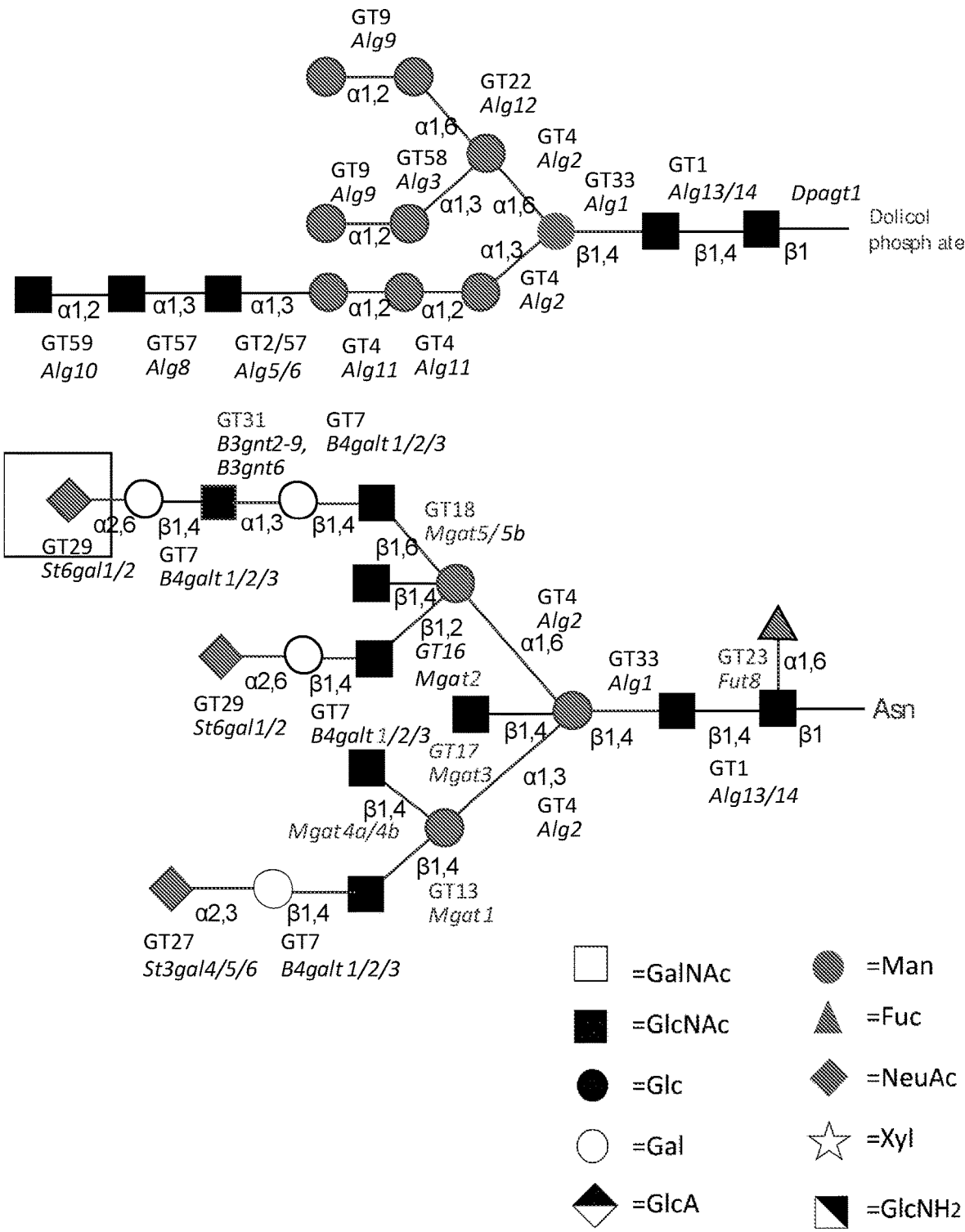
FIG. 13 A graphic representation of the different glycan structures and glycosylation pathways found in CHO cell lines with designations of glycosyltransferase genes expressed in CHO cell lines and their predicted role in biostynthic steps. The genes are assigned to the major confirmed or putative functions in the O-glycosylation (O-GalNAc (A1), O-Man (A2), and O-Fuc, O-Glc, O-GlcNAc, O-Xyl (A3)) and N-glycosylation pathways relevant for recombinant glycoprotein therapeutics today. (A1-4) O-GalNAc glycosylation pathway with extended core 1, core 2, core 3, and core 4 structures; (B) N-glycosylation pathway; (C) glycosphingolipid biosynthetic pathways; (D) C-glycan, and (E) GPI-anchors. The CAZy families of glycosyltransferase (GT genes are notated and GT genes expressed in CHO cell lines are shown. Glycan structures not synthesized in CHO are boxed. Designations for monosaccharides according to the Consortium for Functional Glycomics are indicated.
Figure 13C:
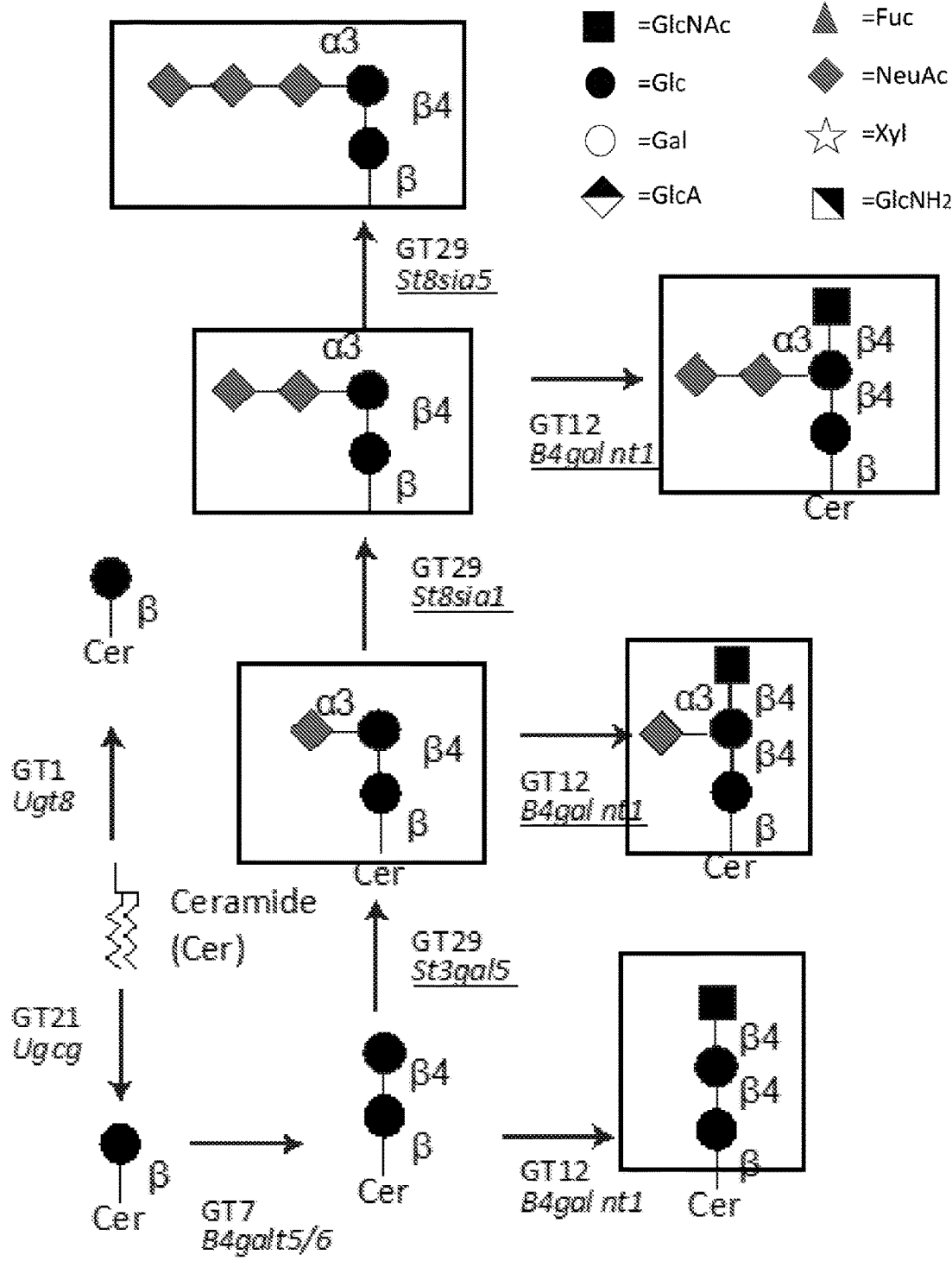

These results clearly demonstrate that the capacity for more homogeneous glycosylation of recombinant expressed proteins in mammalian cells such as CHO can be improved by inactivation of unnecessary glycosylation pathways that utilize the common sugar nucleotide donor pools and other parts of the general cells metabolic and glycosylation capacities. It is known to the skilled in the art that inactivation of other genes listed in TABLES 1 and 2 in the above glycosylation pathways or other glycosylation pathways will have similar effects and may be desirable engineering events alone or in combination with any of the genetic engineering performed herein or conceivable from the glycosylation pathways outlined in FIG. 13.

The general principle for selection of optimal inactivation strategies with the aim to direct use of sugar nucleotides in a mammalian host cell for glycosylation pathways that are relevant for recombinant production of a given glycoprotein, is to block non-relevant glycosylation pathways at an early step in the biosynthetic pathway where a single gene inactivation results in truncated glycan structures preferably without elongation and capping by sialic acid, and/or galactose, and/or GlcNAc. Examples are provided for inactivation of three distinct types of O-glycosylation by targeting the second step in their biosynthesis to avoid and/or limit use of CMP-NeuAc, UDP-Gal and UDP-GlcNAc for elongation of these pathways. It is evident that many other genes listed in Table 2 with assigned biosynthetic steps for the different glycosylation pathways in the mammalian CHO cell, may be targeted by inactivation to achieve the same or similar effects on the use of donor sugar nucleotides with consideration of the effects the inactivation has on the glycosylation pathway and the altered glycan structures.

Knockout of Unnecessary Glycosyltransferases

ER-Golgi resident glycosyltransferases are retained to function in the secretory pathway by a variety of partly known functions including kin-recognition, type and length of transmembrane region, interactions through the stem region (Colley 1997), and through COP-I vesicle retrograde transport presumably dependent on the cytosolic tails and TMs of the glycosyltransferase proteins by e.g. GOLPH3 (Eckert, Reckmann et al. 2014). When glycosyltransferases are not retained in their natural position in the secretory pathway, they may function different and adversely in glycosylation, and when glycosyltransferases loose their retention, e.g. by proteolytic cleavage in the stem region they become secreted and released with little or no influence left on the glycosylation processes in cells. With the many glycosyltransferases expressed in any given mammalian cell, and e.g. at least over 60 in CHO cells (TABLE 3), we hypothesized that there would be common mechanisms of retention of groups and/or classes of enzymes. A group or class of enzymes could be constituted without intention of limitations e.g. enzymes working in the same pathway, and/or in consecutive biosynthetic steps, and/or enzymes retained in the same subcellular topology, and/or enzymes having similar amino acid sequence and/or structural retention signals. The latter could without intention of limitations e.g. be found in homologous isoenzymes given that they have similar sequences, related catalytic properties, and at least in some cases have been shown to have similar subcellular topologies (Rottger, White et al. 1998). One such group of isoenzymes is the β4galactosyltransferases of which especially B4GAL-T1, T2, T3 and T4 have the highest degree of sequence similarity and related functions (Amado, Almeida et al. 1999; Togayachi, Sato et al. 2006). The understanding of the in vivo functions of these four enzymes is poor and all have been shown to produce the Galβ1-4GlcNAc linkage in vitro. As shown herein β4Galt1 and 3 appear to be the main β4galactosyltransferases involved in N-glycosylation, and previous studies have demonstrated that B4GALT4 primarily has roles in glycolipid biosynthesis and/or in sulfated glycans (Schwientek, Almeida et al. 1998). We therefore generated CHO cells with inactivation of B4galt4 in CHO WT as well as combined with inactivation of mgat4a/4b/5. Expression of EPO in CHO cells with inactivation of B4galt4 alone resulted in increased tetraantennary N-glycans with more complete sialic acid capping (FIG. 17). KO of B3gnt2 resulted in EPO glycostructures without poly LacNac (FIG. 35) whereas KO of B4galt5/6 gave more polyLacNac (FIG. 35). Along these lines IgG produced in CHO cells in which St3gal4/6 has been knocked out have higher galactosylation (FIG. 36). These results clearly demonstrate that the capacity for more homogeneous glycosylation of recombinant expressed proteins in mammalian cells such as CHO can be improved by inactivation of unnecessary glycosyltransferases that may compete for mechanisms directing ER-Golgi residence and/or utilize the common sugar nucleotide donor pools and other parts of the general metabolic and glycosylation capacities in a mammalian cell.

These results clearly demonstrate that the capacity for more homogeneous glycosylation of recombinant expressed proteins in mammalian cells such as CHO can be improved by inactivation of unnecessary glycosylation pathways that utilize the common sugar nucleotide donor pools and other parts of the general cells metabolic and glycosylation capacities. It is known to the skilled in the art that inactivation of other genes listed in TABLES 1 and 2 in the above glycosylation pathways or other glycosylation pathways will have similar effects and may be desirable engineering events alone or in combination with any of the genetic engineering performed herein or conceivable from the glycosylation pathways outlined in FIG. 13.

Knockout of Posttranslational N-Glycosylation Capacity

The oligosaccharyltransferase complex initiating N-glycosylation of proteins consists of eight proteins of which one subunit involves two paralogous genes, STT3A and STT3B. Studies have suggested that an oligosaccharyltransferase complex containing the STT3A subunit primarily function in co-translational N-glycosylation, while an oligosaccharyltransferase complex containing the STT3B subunit primarily function in post-translational N-glycosylation. We hypothesized that the fidelity and stoichiometry of co-translational N-glycosylation naturally is better than that of post-translational N-glycosylation. Many recombinantly expressed glycoproteins have N-glycosites that are poorly utilized resulting in incomplete N-glycan occupancy (stoichiometry) and/or N-glycan processing (structure). We therefore next generated CHO cells with inactivation of Stt3b as well as CHO cells with combined inactivation of the Mgat4A/4B/5 genes. These CHO cells have improved capacity for producing homogenous glycoproteins with higher degree of N-glycan stoichiometry and/or glycan structures when proteins with naturally poorly utilized N-glycosites are expressed.

Knockout Targeting Strategy

It is clear to the known in the art that inactivation of a glycosyltransferase gene can have a multitude of outcomes and effects on the transcript and/or protein product translated from this. Targeted inactivation experiments performed herein involved PCR and sequencing of the introduced alterations in the genes as well as RNAseq analysis of clones to determine whether a transcript was formed and if potential novel splice variations introduced new protein structures. Moreover, methods for determining presence of protein from such transcripts are available and include mass spectrometry and SDS-PAGE Western blot analysis with relevant antibodies detecting the most N-terminal region of the protein products.

Figure 14B:
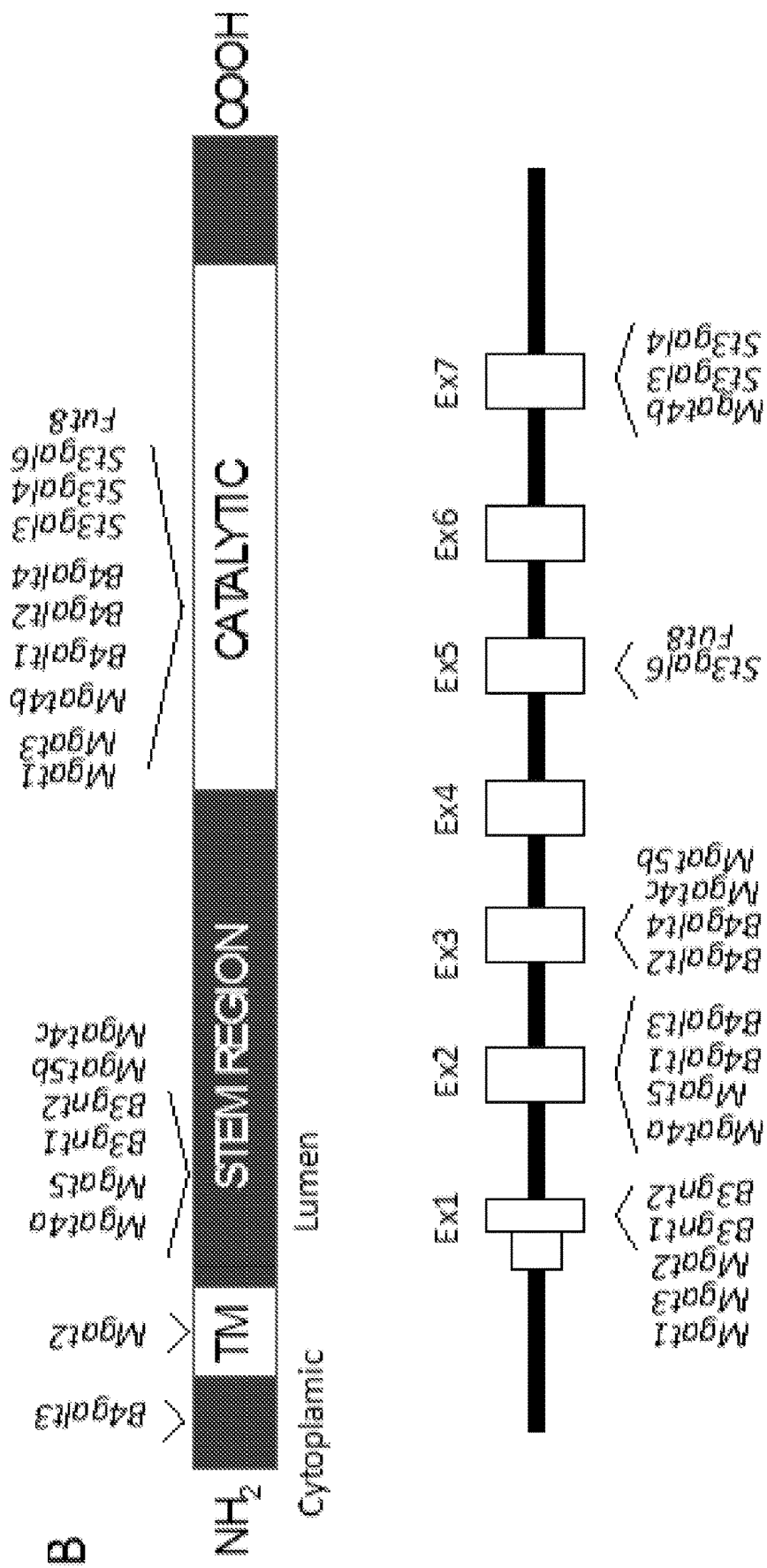

The targeting constructs were generally designed to target the first 1/3 of the open reading frame (ORF) of the coding regions but other regions were targeted as well FIG. 14B. For most clones selected, out of frame mutations (Indels) that introduced stop or non-sense codons within the same exon were selected. This would be expected to produce truncated proteins if any protein at all and without the catalytic domain and hence enzymatic activity. The majority of KO clones exhibited insertions and/or deletions (indels) in the range of ±20 bps, and most targeted genes were present with two alleles, while some (mgat4B and mgat5) were present with 1 or 3 alleles, respectively (TABLE 4). In a few cases larger deletions were found and these disrupted one or more exons and exon/intron boundaries also resulting in truncated proteins.

Most ER-Golgi glycosyltransferases share the common type 2 transmembrane structure with a short cytosolic tail that may direct retrograde trafficking and residence time, a non-cleaved signal peptide containing a hydrophobic transmembrane α-helix domain for retention in the ER-Golgi membrane, a variable length stem or stalk region believed to displace the catalytic domain into the lumen of the ER-Golgi, and a C-terminal catalytic domain required for enzymatic function (Colley 1997). Only polypeptide GalNAc-transferases have an additional C-terminal lectin domain (Bennett, Mandel et al. 2012). The genomic organization of glycosyltransferase genes varies substantially with some genes having a single coding exon and others more than 10-15 coding exons, although few glycosyltransferase genes produce different splice variants encoding different protein products.

Inactivation of glycosyltransferase genes in the early coding regions may thus have a multitude of effects on transcript and protein products if these are made: i) one or more transcripts may be unstable and rapidly degraded resulting in little or no transcript and/or protein; ii) one or more transcripts may be stable but not or only poorly translated resulting in little or no protein translation; iii) one or more transcripts may be stable and translated resulting in protein translation; iv) one or more transcripts may result in protein translation but protein products are degraded due to e.g. truncations and/or misfolding; v) one or more transcripts may result in protein translation and stable protein products that are truncated and enzymatically inactive; and vi) one or more transcripts may result in protein translation and stable protein products that are truncated but have enzymatic activity.

It is evident for the skilled in the art that gene inactivation that lead to protein products with enzymatic activity is undesirable, and these event are easily screened for by the methods used in the present invention, e.g. but not limited to lectin/antibody labeling and glycoprofiling of proteins expressed in mutant cell lines.

However, it is desirable to eliminate potential truncated protein products that may be expressed from mutated transcripts as these may have undesirable affects on glycosylation capacity. Thus, truncated protein products from type 2 glycosyltransferase genes containing part of or entire part of the cytosolic, and/or the transmembrane retention signal, and/or the stem region, and/or part of the catalytic domain may exert a number of effects on glycosylation in cells. For example, the cytosolic tail may compete for COP-I retrograde trafficking of Golgi resident proteins (Eckert, Reckmann et al. 2014), the transmembrane domain may compete for localization in ER-Golgi and potential normal associations and/or aggregations of proteins, and the stem region as well as part of an inactive catalytic domain may have similar roles or part of roles in normal associations and/or aggregations of proteins in ER-Golgi. Such functions and other unknown ones may affect specific glycosylation pathways that the enzymes are involved in, specific functions of isoenzymes, or more generally glycosylation capacities of a cell. While these functions and effects are unknown and unpredictable today, it is an inherent part of the present invention that selection of mammalian cell clones with inactivated glycosyltransferase genes includes selection of editing events that do not produce truncated protein products.

Figure 28:
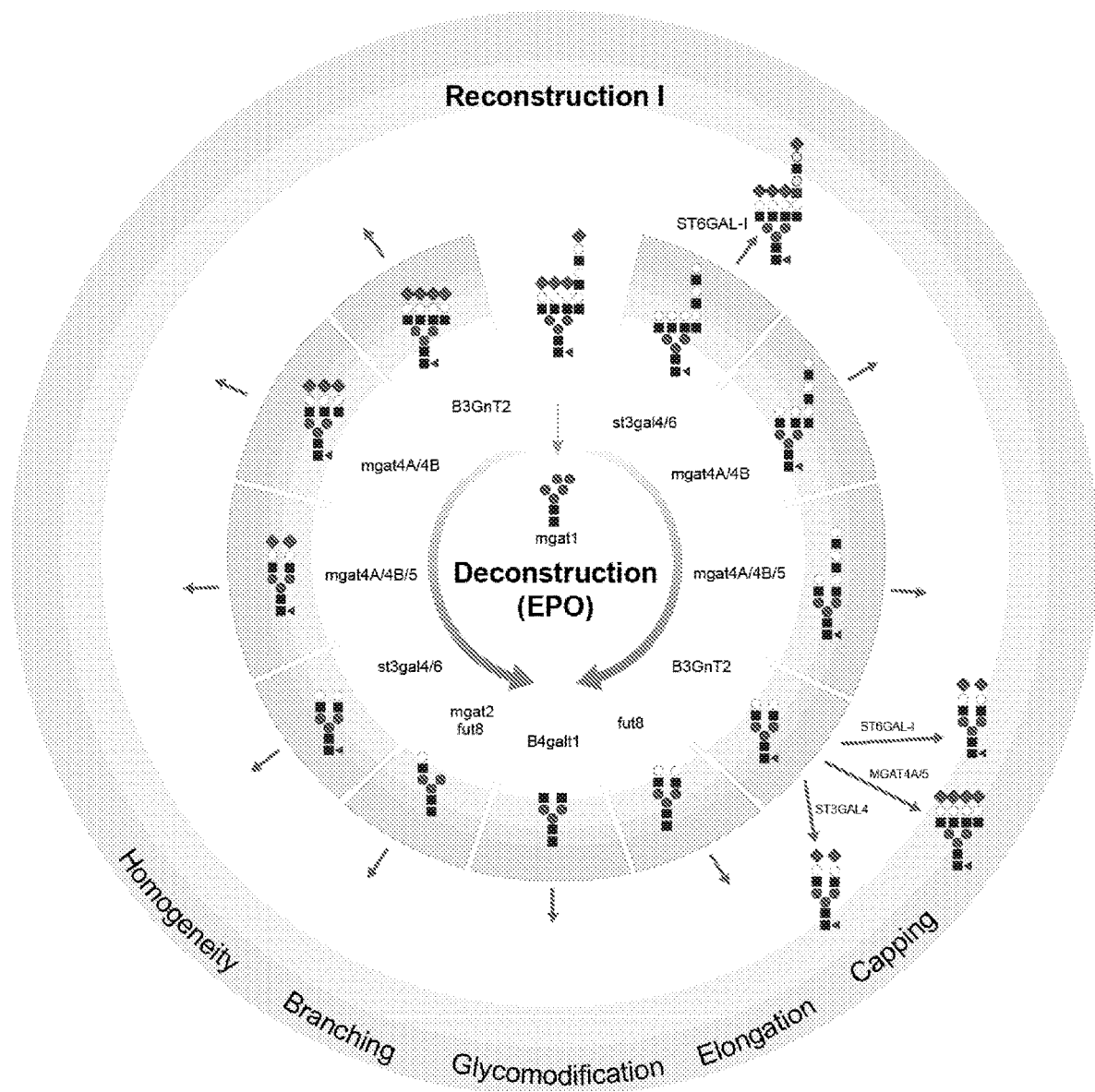
FIG. 28 Graphic depiction of the genetic deconstruction of N-glycosylation in CHO established using EPO as N-glycoprotein reporter. Several KO CHO lines have potential for production of glycoprotein therapeutics with more homogenous glycosylation (e.g. biantennary α2,3-sialylated N-glycans for EPO, and biantennary non-galactosylated/sialylated with and without core Fuc for IgG. Examples of reconstruction based on KI are shown producing homogenous α2,6-sialylation after KO of α2,3-sialylation capacities with either WT N-glycan branching heterogeneity or homogenous biantennary structure, homogeneous α2,3-sialylation after KO of endogenous sialylation, and homogeneous tetranatennary structures with α2,6-sialylation after KO of endogeneous branching and sialylation capacities. Reconstruction may address homogeneity as shown, but also branching, poly-LacNAc elongation, and any type of capping as indicated.

It is evident that the KO deconstruction screen performed identifies the key glycogenes that control decisive steps in N-glycosylation of proteins in CHO and provides a design matrix for genetic deconstruction of N-glycosylation capacity to desirable homogeneous structures that can serve as starting points for resconstruction of improved, novel and/or more homogenous glycosylation capacities by stable introduction of one or more glycosyltransferase genes. FIG. 28 provides general examples of N-glycan scaffolds that can be produced by the deconstruction design matrix, which serves as platforms for reconstruction of desirable more homogenous glycosylation capacities. The value of this strategy of combined deconstruction and reconstruction is clearly exemplified here by the design of CHO cells with capacity for production of EPO with homogeneous biantennary N-glycans with α2,3 and for the first time homogenous α2,6-sialic acid capped N-glycans. These CHO lines complement and clearly extend the milestone efforts performed previously to establish glycoengineered yeast with capacity for production of EPO with homogenous biantennary N-glycans as well as the tour-de-force chemical synthesis of EPO with biantennary N-glycans (Hamilton, Davidson et al. 2006; Wang, Dong et al. 2013). More specifically, the produced CHO lines enable production of EPO and other glycoproteins in a proven mammalian host cell with well-established protein folding and processing capabilities and decades long safety profile for human therapeutics.

It is further evident from the KO deconstruction screen performed here that the CHO cell has remarkable plasticity and tolerance for glycoengineering. The glycosylation capacities achieved by KO's in CHO were found to be stable and consistent in production of recombinant glycoproteins, and it is expected that these CHO engineered CHO lines will perform similar to CHO WT in bioprocessing. Furthermore, the reconstruction of glycosylation capacities by KI exemplified by introduction of ST6Gal-1 without competing α2,3sialyltransferases demonstrates that stable and consistent glycoengineering can be achieved by the deconstruction and reconstruction strategy invented here, and this should be applicable to other desirable glycosylation capacities. This includes rebuilding endogenous glycosylation capacities of CHO WT, which are inconsistent and heterogenous such as for example N-glycan multi-antennary branch formation (tri and tetra antennary) and poly-LacNAc chains. Other examples include improving capacity for capping N-glycans on IgG. Furthermore, the engineering design matrix is expected to be transferable to any CHO host line as well as established production lines. Moreover, the engineering design matrix is expected to be transferable to any mammalian cell line with due expansion depending on existence of more complex glycosylation capacities. The panel of CHO cells generated here will enable dissection and de novo reconstruction design of N-glycosylation for any protein therapeutics. Moreover, this panel of CHO cells can be used to produce therapeutic glycoproteins with an array of different glycoforms, which for the first time will enable experimental evaluation of the biological properties of defined glycoforms and make rational selection of optimal designs. The panel of CHO cells produced here enables direct testing of the functional effects of specific N-glycan structures on any therapeutic glycoprotein, which will provide guidance for the optimal design of a glycoprotein drug. Thus, using the panel of CHO cells the effect of N-glycan branching, poly-LacNAc extension, and type of sialylation can be addressed in a systematic fashion. These effects for example include protein secretion, stability, yield, circulatory half-life in blood, biodistribution, bioactivity, and general pharmacokinetic properties of relevance for therapeutic drugs. The CHO panel will also enable e.g. design of de novo glycoprotein therapeutics, where introduction of N-glycans are used to enhance circulatory half-life without interfering with biological activity. In this instance the effect of position, size and structure of N-glycans introduced can be mapped in detail in order to design new glycoprotein biologics with optimal pharmacokinetic properties. The present invention thus provides a new era for the biggest producer of glycoprotein therapeutics, the CHO cell.

An object of the present invention relates to a cell comprising one or more glycosyltransferase genes that have been inactivated.

In one embodiment the cell has new and/or more homogeneous stable glycosylation capacities.

In another embodiment of the present invention the cell comprises two or more glycosyltransferase genes that have been inactivated.

In another embodiment of the present invention the cell comprises one or more glycosyltransferase genes that have been introduced stably by site-specific gene or non-site-specific knockin and with new and/or more homogeneous glycosylation capacities.

Another object of the present invention relates to a cell comprising one or more glycosyltransferase genes that have been introduced stably by site-specific gene or non-site-specific knockin. The cell may have new and/or more homogeneous glycosylation capacities.

In one embodiment of the present invention the cell comprises two or more glycosyltransferase that have been introduced stably by site-specific or non-site-specific gene knockin.

An embodiment of the present invention relates to a cell comprising one or more glycosyltransferase genes introduced stably by site-specific or non-site-specific gene knockin, and furthermore comprising one or more endogenous glycosyltransferase genes that have been inactivated by knockout, and with improved and/or novel and/or more homogeneous glycosylation capacities.

A further aspect of the present invention relates to a cell comprising two or more glycosyltransferase genes encoding isoenzymes with partial overlapping glycosylation functions in the same biosynthetic pathway and/or same biosynthetic step inactivated, and for which inactivation of two or more of these genes is required for loss of said glycosylation functions in the cell.

In one embodiment of the present invention the cell comprises one or more glycosyltransferase genes inactivated to block and truncate one or more glycosylation pathways.

In another embodiment of the present invention, the cell comprises two or more glycosyltransferase genes inactivated to block and truncate one or more glycosylation pathways.

In one embodiment of the present invention the cell comprises targeted inactivation of one or more glycosyltransferase genes for which no transcripts are detectable.

A further aspect of the present invention relates to a cell comprising targeted inactivation of one or more glycosyltransferase genes for which no protein products are detectable.

Another aspect of the present invention relates to a cell comprising targeted inactivation of one or more glycosyltransferase genes for which no protein products with intact cytosolic and/or transmembrane region is detectable.

In another embodiment of the present invention is the glycosyltransferase any one or more of the genes listed in Table 1, 2 or 3.

In a further embodiment of the present invention is the glycosyltransferase that is inactivated a glycosyltransferase gene that is not involved in the biosynthesis of the glycans on a particular glycoprotein produced recombinantly in said cell.

In one embodiment of the present invention are the glycosyltransferases that are inactivated working in the same glycosylation pathway.

In another embodiment of the present invention are the glycosyltransferases that are inactivated working in the same glycosylation step.

In yet another embodiment of the present invention are the glycosyltransferases that are inactivated working in consecutive biosynthetic steps.

In one embodiment of the present invention are the glycosyltransferases that are inactivated retained in the same subcellular topology.

In another embodiment of the present invention are the glycosyltransferases that are inactivated having similar amino acid sequence.

In a further embodiment of the present invention are the glycosyltransferases that are inactivated belonging to the CAZy family.

In yet another embodiment of the present invention are the glycosyltransferases that are inactivated belonging to same subfamily of isoenzymes in a CAZy family.

In one embodiment of the present invention are the glycosyltransferases that are inactivated having similar structural retention signals (transmembrane sequence and length).

In another embodiment of the present invention are the glycosyltransferase genes functioning in the same glycosylation pathway inactivated, and wherein they are not involved in the same glycosylation step.

In a further embodiment of the present invention are the glycosyltransferase genes functioning in the same glycosylation pathway inactivated, and wherein they are involved in the same glycosylation step.

In a further embodiment of the present invention has FUT8 been knocked out.

In one embodiment of the present invention the cell or cell line is a mammalian cell or cell line, or an insect cell or cell line.

In another embodiment of the present invention the cell is derived from Chinese hamster ovary or from human kidney.

In a further embodiment of the present invention the cell is selected from the group consisting of CHO, NS0, SP2/0, YB2/0, CHO-K1, CHO-DXB11, CHO-DG44, CHO-S, HEK293, HUVEC, HKB, PER-C6, NS0, or derivatives of any of these cells.

In one embodiment of the present invention is the cell a CHO cell.

In another embodiment of the present invention encodes the cell furthermore an exogenous protein of interest.

In yet another embodiment of the present invention is the protein of interest an antibody, an antibody fragment, or a polypeptide.

In a further embodiment of the present invention is the antibody is an IgG antibody.

In one embodiment of the present invention is the polypeptide EPO, a protein involved in hemostasis, including a coagulation factor.

In one embodiment of the present invention is the glycosylation made more homogenous.

In another embodiment of the present invention is the glycosylation non-sialylated.

In yet another embodiment of the present invention is the glycosylation non-galactosylated.

In one embodiment of the present invention comprises the glycosylation biantennary N-glycans.

In another embodiment of the present invention does the glycosylation not comprise poly-LacNAc.

In yet another embodiment of the present invention is the glycosylation any combination without fucose.

In one embodiment of the present invention has B4galt1 been knocked out allowing generation of more homogeneous N-glycans without galactose.

In another embodiment of the present invention has B4galt1 and fut8 been knocked out allowing generation of more homogeneous N-glycans without galactose and fucose.

In yet another embodiment of the present invention has B4galt1 and B4galt3 been knocked out resulting in more homogeneous N-glycans without galactose than obtained with single ko of B4galt1 or B4galt3 (FIG. 36).

In one embodiment of the present invention, the cell has knockout of one or more of the glycosyl transferase genes selected from the group consisting of mgat1, mgat2, mgat4A, mgat4B, mgat4C, mgat5 and mgat5B.

In another embodiment of the present invention, the cell has knockout of one or more of the glycosyltransferase genes selected from the group consisting of mgat4A, mgat4B, and mgat4C.

In a further embodiment of the present invention, the cell has knockout of mgat4A, mgat4B, and mgat4C.

In another embodiment of the present invention, the cell has knockout of mgat5 and/or mgat5B.

In yet another embodiment of the present invention, the cell has knockout of mgat5 and mgat5B.

In one embodiment of the present invention, the cell has knockout of one or more of the galatosylation genes selected from the group consisting of B4gal1, B4gal2, B4gal3 and B4 gal.

In another embodiment of the present invention, B4gal1 or B4gal3, or B4gal1 and B4gal3 has been knocked out.

In a further embodiment of the present invention, the cell has knockout of one or more of the poly-LacNAc elongation genes selected from the group consisting of B3gnt1, B3gnt2 and B3gnt8.

In yet another embodiment of the present invention, B3gnt2 has been knocked out.

In one embodiment of the present invention, B3gnt2, mgat4A, mgat4B and mgat5 have been knocked out.

In another embodiment of the present invention, the cell has knockout of one or more of the sialyltransferase genes selected from the group consisting of ST3gal3, ST3gal4 and ST3gal6.

In yet another embodiment of the present invention, ST3gal3, ST3gal4 and ST3gal6 have been knocked out.

In a further embodiment of the present invention, ST3gal4 and ST3gal6 have been knocked out.

In one embodiment of the present invention, ST3gal4, ST3gal6, mgat4A, mgat4B and mgat5 have been knocked out.

In another embodiment of the present invention, ST6gal1 has been knocked in and ST3gal4 and ST3gal6 have been knocked out.

In yet another embodiment of the present invention, ST6gal1 has been knocked in and ST3gal4, ST3gal6, mgat4A, mgat4B and mgat5 have been knocked out.

In one embodiment of the present invention, mgat2, ST3gal4, and ST3gal6 have been knocked out.

In another embodiment of the present invention, mgat2, mgat4A, mgat4B and mgat5 have been knocked out.

In yet another embodiment of the present invention, mgat2, ST3gal4, ST3gal6, mgat4A, mgat4B, and mgat5 have been knocked out.

In a further embodiment of the present invention has mgat2 been knocked out with and without knockout of mgat4A and/or mgat4B and/or mgat5 allowing production of N-glycans with monoantennary structure.

In yet another embodiment of the present invention has mgat2 been knocked out with and without knockout of mgat4A and/or mgat4B and/or mgat5 in combination with knockout of sialyltransferases allowing production of N-glycans with monoantennary structure and without sialic acid capping.

In one embodiment of the present invention has mgat2 been knocked out with and without knockout of mgat4A and/or mgat4B and/or mgat5 in combination with KO of sialyltransferases and B3gnt2 allowing production N-glycans with monoantennary structure and without sialic acid capping and without poly-LacNAc.

One aspect of the present invention relates to a glycoprotein according to the present invention, which is a homogeneous glycoconjugate produced from a glycoprotein having a simplified glycan profile.

An object of the present invention is to provide a cell capable of expressing a gene encoding a polypeptide of interest, wherein the polypeptide of interest is expressed comprising one or more posttranslational modification patterns.

In one embodiment of the present invention is the posttranslational modification pattern a glycosylation.

The optimal glycoform of a glycoprotein may be identified by the following process:

(i) producing a plurality of different glycoforms of said glycoprotein by expressing in cell lines harboring at least one novel glycosylation capacity for example by harboring two or more modifications of GT gene expression levels, and (ii) determination of the activity of the different glyco forms in comparison with a reference glycoprotein in (a) suitable bioassay(s); and (iii) selection of the glycoform with the higher/highest activity and determination of the production cell genotype fingerprint which is correlated with the higher/highest activity level of said glycoprotein.

The above described process allows the identification of the optimal glycoform of a glycoprotein. For those skilled in the art by using the genotype fingerprint identified in (iii) may generate an efficient engineered cell line with the optimal genotype for producing glycoprotein with said glycoform.

Another aspect of the present invention relates to a glycoprotein according to the present invention, which is a homogeneous glycoprotein conjugate comprising a polymer selected from, PEG, HEP, XTEN, PSA, HES.

A further aspect of the present invention relates to a glycoprotein according to the present invention, which is a homogeneous PEGylated protein conjugate produced from a protein variant according to the invention having a simplified glycan profile.

Another aspect of the present invention relates to a glycoprotein according to the present invention, which is a homogeneous PEGylated EPO conjugate produced from an EPO variant having a simplified glycan profile.

One aspect of the present invention relates to a glycoprotein according to the present invention, which is a simplified enzymatic glycoPEGylation process using glycoengineered EPO variants that provides high yield of di- and triPEGylated EPO forms.

Another aspect of the present invention relates to a glycoprotein according to the present invention, which is a protein conjugate according to the invention comprising FII, FV, FVIIa, FVIII, FIX, FX, FXIII, a Fab fragment of an antibody, or a Fc domain of an antibody.

A further aspect of the present invention relates to a glycoprotein according to the present invention, which is a protein-protein conjugate produced from a glycoprotein with a simplified glycan profile.

In one embodiment of the present invention is the glycoprotein according to the present invention a protein-protein conjugate produced from a glycoprotein with a simplified glycan profile comprising a Fab fragment and one of either FII, FV, FVIIa, FVIII, FIX, FX or FXIII.

In another embodiment of the present invention is the glycoprotein according to the present invention a protein-protein conjugate produced from a glycoprotein with a simplified glycan profile comprising a Fc Domain and one of either FII, FV, FVIIa, FVIII, FIX, FX or FXIII.

In a further embodiment of the present invention is the glycoprotein according to the present invention a homogeneous PEGylated EPO conjugate produced from an EPO variant having a simplified glycan profile.

One aspect of the present invention relates to the use of recombinant glycoproteins comprising monoantennary N-glycans for enzymatic modification of polypeptides.

One aspect of the present invention relates to a method for inactivation of one or more glycosyltransferase genes in a mammalian cell, the method comprising the step of inactivation of one or more glycosyltransferase genes in a mammalian cell, and determining that said gene inactivation can not result in protein product with a transmembrane retention signal, and/or stem region, and/or part of a catalytic domain.

Another aspect of the present invention relates to a method for the production of a cell that can generate recombinant glycoproteins that do not carry specific glycans, the method comprising the step of inactivation of one or more glycosyltransferase genes in a cell, wherein the one or more glycosyltransferase genes are involved in the biosynthesis of the specific glycans, and determining that said gene inactivation can not result in protein product with a transmembrane retention signal, and/or stem region, and/or part of a catalytic domain.

A further aspect of the present invention relates to a method for the production of di- and triPEGylated EPO glycoproteins, the method comprising the step of enzymatic glycoPEGylation of glycoengineered polypeptides variants, such as EPO variants.

One aspect of the present invention relates to a method for producing a glycoproteins having modified glycan profile wherein the cell producing the glycoprotein has more than one modification of one or more glycosyltransferase genes.

In one embodiment of the present invention has the cells been modified by glycosyltransferase gene knock-out and/or knock-in of an exogeneous DNA sequence coding for a glycosyltransferase.

In one embodiment of the present invention is Cosmc knocked in or knocked out.

One aspect of the present invention relates to a method for producing a glycoprotein having a simple glycan profile, the method comprising inactivation of one or more glycosyltransferases, and/or knockin of one or more glycosyltransferases, or a combination hereof in a cell, and expression of a protein in said cell.

Another aspect of the present invention relates to a method for generating glycoproteins with improving glycosylation efficiency, the method comprising the step of inactivation of one or more glycosyltransferase genes to block and truncate one or more glycosylation pathways.

A further aspect of the present invention relates to a method for the production of recombinant glycoproteins that do not have specific types of glycosylation, the method comprising the step of inactivating two or more glycosyltransferase genes to block and truncate one or more glycosylation pathways.

One aspect of the present invention relates to a method for the production of recombinant glycoproteins, comprising the step of generating a mammalian cell with specific glycosylation properties.

In one embodiment of the present invention is the specific glycosylation property the capacity for monoantennary N-glycan synthesis.

A further aspect of the present invention relates to a glycoprotein obtainable from a method according to the present invention.

In one embodiment of the present invention has the glycostructure outcome one or more of the following changes selected from the group consisting of simpler glycan structure, more homogeneous product, more sialic acids per molecule, non-sialylated, non-galactosylated, more homogeneous bi-antennary, more homogeneous monoantennary, more homogeneous triantennary, more homogeneous without poly-LacNAc, higher productivity in cell culture, new stable homogeneous glycosylation capacities, more human glycostructure, more homogeneous glycosylation and improved ADCC targeting of IgG, modified fucose level, no fucose, improved substrate for generating glycoconjugates.

In another aspect of the present invention is one or more of the above mentioned genes knocked out using transcription activator-like effector nucleases (TALENs).

TALENs are artificial restriction enzymes generated by fusing a TAL effector DNA binding domain to a DNA cleavage domain.

In yet another aspect of the present invention is one or more of the above mentioned genes knocked out using CRISPRs (clustered regularly interspaced short palindromic repeats).

CRISPRs are DNA loci containing short repetitions of base sequences. Each repetition is followed by short segments of "spacer DNA" from previous exposures to a virus.

CRISPRs are often associated with cas genes that code for proteins related to CRISPRs. The CRISPR/Cas system is a prokaryotic immune system that confers resistance to foreign genetic elements such as plasmids and phages and provides a form of acquired immunity.

CRISPR spacers recognize and cut these exogenous genetic elements in a manner analogous to RNAi in eukaryotic organisms.

The CRISPR/Cas system is used for gene editing (adding, disrupting or changing the sequence of specific genes) and gene regulation in species throughout the tree of life. By delivering the Cas9 protein and appropriate guide RNAs into a cell, the organism's genome can be cut at any desired location.

In a further embodiment of the present invention the mammalian cell does or does not have $\alpha$-1,6-fucosyltransferase activity.

The cell of the present invention may by a cell that does not comprise the gene of interest to be expressed or the cell may comprise the gene of interest to be expressed. The cell that does not comprise the gene of interest to be expressed is usually called "a naked cell".

The host cell of the present invention may be any host, so long as it can express an antibody molecule. Examples include a yeast cell, an animal cell, an insect cell, a plant cell and the like.

In one embodiment of the present invention is the cell selected from the group consisting of CHO, NS0, SP2/0, YB2/0, YB2/3HL.P2.G11.16Ag.20, NSO, SP2/0-Ag14, BHK cell derived from a syrian hamster kidney tissue, antibody-producing hybridoma cell, human leukemia cell line (Namalwa cell), an embryonic stem cell, and fertilized egg cell.

In a preferred embodiment of the present invention is the cell a CHO cell.

The cell can be an isolated cell or in cell culture or a cell line.

The protein of interest can be various types of protein, and in particular proteins that benefit from being expressed as glycoproteins In a preferred embodiment the protein is erythropoietin (EPO).

In another embodiment is the protein α1-antitrypsin.

In one aspect of the present invention is the protein a recombinant blood factor.

In one embodiment of the present invention is the recombinant blood factor selected from the group consisting of one or more of factor VIII, factor IX, factor XIII A-subunit, thrombin, and factor VIIa.

In yet another embodiment of the present invention the protein of interest is a coagulation factor such as coagulation factor II (FII), coagulation factor V (FV), coagulation factor VII (FVIIa), coagulation factor VIII (FVIII), coagulation factor IX (FIX), coagulation factor X (FX), or coagulation factor XIII (FXIII).

In one aspect of the present invention is the protein human growth hormone.

In yet another embodiment of the present invention is the protein of interest an antibody, an antibody fragment, such as a Fab fragment, an Fc domain of an antibody, or a polypeptide.

A further aspect of the present invention relates to a method for producing an enzymatically modified glycoprotein, comprising the step of generating a cell with specific glycosylation properties, and the enzymatically modification of interest.

In one embodiment of the present invention is the enzymatically modification a polymer.

In another embodiment of the present invention is the enzymatically modification a conjugation to another protein.

Another aspect of the present invention relates to a glycoprotein according to the present invention, which is a homogeneous glycoprotein conjugate comprising a polymer.

The glycoprotein can be enzymatically modified with the polymer, and the glycoprotein can be produced by the cell according to the present invention.

In one aspect of the present invention is the protein a recombinant thrombolytic, anticoagulant or another blood-related product.

In one embodiment of the present invention is the recombinant thrombolytic, anticoagulant or another blood-related product selected from the group consisting of one or more of tissue plasminogen activator (tPA), hirudin, antithrombin, plasmin, plasma kallikrein inhibitor, and activated protein C.

In one aspect of the present invention is the protein a recombinant hormone.

In one embodiment of the present invention is the recombinant hormone selected from the group consisting of one or more of insulin, insulin degludec, human growth hormone, somatropin, pegvisomant, follicle-stimulating hormone, follitropin alfa, corifollitropin alfa, follitropin beta, metreleptin, liraglutide, parathyroid hormone, lutropin, teriparatide, nesiritide, and glucagon.

In one aspect of the present invention is the protein a recombinant growth hormone.

In one embodiment of the present invention is the recombinant growth hormone selected from the group consisting of one or more of EPO, filgrastim, sargramostim, mecaserim, and palifermin.

In one aspect of the present invention is the protein a Recombinant interferon, interleukin or tumor necrosis factor.

In one embodiment of the present invention is the Recombinant interferon, interleukin or tumor necrosis factor selected from the group consisting of one or more of interferon alfa, PEGinterferon alfa, PEGinterferon alfa-2a, PEGinterferon alfa, interferon beta-1b, algulcosidase alfa, and laronidase.

In one aspect of the present invention is the protein an antigen or vaccine component.

In one aspect of the present invention is the protein of the present invention relevant for a disease or disorder selected from the group consisting of one or more of Hemophilia A, Hemophilia B, Acute myocardial infarction, heparinassociated thrombocytopenia, venous thrombosis, Symptomatic vitreomacular adhesion/vitreomacular traction, Acute angioedema, Hereditary antithrombin deficiency, Hereditary angioedema, sepsis, diabetes, diabetes mellitus, Growth failure/growth hormone deficiency, infertility/subfertility, Type 2 diabetes, Osteoporosis, Hypoglycemia, Paget's disease, cancer, Anemia, Neutropenia, Hepatitis C, and Hyperuricemia, Rheumatoid arthritis, hepatitis A and B, Arthritis, colitis, Crohn's, psoriasis, ankylosing spondylitis, Ulcerative colitis.

In one embodiment of the present invention the protein is an antibody.

In a preferred embodiment of the present invention is the antibody an IgG antibody.

In the present invention, the antibody molecule includes any molecule, so long as it comprises the Fc region of an antibody. Examples include an antibody, an antibody fragment, a fusion protein comprising an Fc region, and the like.

The antibody is a protein which is produced in the living body by immune reaction as a result of exogenous antigen stimulation and has an activity to specifically bind to the antigen. Examples of the antibody include an antibody secreted by a hybridoma cell prepared from a spleen cell of an animal immunized with an antigen; an antibody prepared by a genetic recombination technique, namely an antibody obtained by introducing an antibody gene-inserted antibody expression vector into a host cell; and the like. Specific examples include an antibody produced by a hybridoma, a humanized antibody, a human antibody and the like.

A hybridoma is a cell which is obtained by cell fusion between a B cell obtained by immunizing a mammal other than human with an antigen and a myeloma cell derived from mouse or the like and can produce a monoclonal antibody having the desired antigen specificity.

Examples of the humanized antibody include a human chimeric antibody, a human CDR-grafted antibody and the like.

A human chimeric antibody is an antibody which comprises an antibody heavy chain variable region (hereinafter referred to as "HV" or "VH", the heavy chain being "H chain") and an antibody light chain variable region (hereinafter referred to as "LV" or "VL", the light chain being "L chain"), both of an animal other than human, a human antibody heavy chain constant region (hereinafter also referred to as "CH") and a human antibody light chain constant region (hereinafter also referred to as "CL"). As the animal other than human, any animal such as mouse, rat, hamster, rabbit or the like can be used, so long as a hybridoma can be prepared therefrom.

The human chimeric antibody can be produced by obtaining cDNA's encoding VH and VL from a monoclonal antibody-producing hybridoma, inserting them into an expression vector for host cell having genes encoding human antibody CH and human antibody CL to thereby construct a human chimeric antibody expression vector, and then introducing the vector into a host cell to express the antibody.

As the CH of human chimeric antibody, any CH can be used, so long as it belongs to human immunoglobulin (hereinafter referred to as "hIg") can be used. But those belonging to the hIgG class are preferable and any one of the subclasses belonging to the hIgG class, such as hIgG1, hIgG2, hIgG3 and hIgG4, can be used. Also, as the CL of human chimeric antibody, any CL can be used, so long as it belongs to the hIg class, and those belonging to the κ class or λ class can also be used.

A human CDR-grafted antibody is an antibody in which amino acid sequences of CDR's of VH and VL of an antibody derived from an animal other than human are grafted into appropriate positions of VH and VL of a human antibody.

The human CDR-grafted antibody can be produced by constructing cDNA's encoding V regions in which CDR's of VH and VL of an antibody derived from an animal other than human are grafted into CDR's of VH and VL of a human antibody, inserting them into an expression vector for host cell having genes encoding human antibody CH and human antibody CL to thereby construct a human CDR-grafted antibody expression vector, and then introducing the expression vector into a host cell to express the human CDR-grafted antibody.

As the CH of human CDR-grafted antibody, any CH can be used, so long as it belongs to the hIg, but those of the hIgG class are preferable and any one of the subclasses belonging to the hIgG class, such as hIgG1, hIgG2, hIgG3 and hIgG4, can be used. Also, as the CL of human CDR-grafted antibody, any CL can be used, so long as it belongs to the hIg class, and those belonging to the κ class or λ class can also be used.

A human antibody is originally an antibody naturally existing in the human body, but it also includes antibodies obtained from a human antibody phage library, a human antibody-producing transgenic animal and a human antibody-producing transgenic plant, which are prepared based on the recent advance in genetic engineering, cell engineering and developmental engineering techniques.

Regarding the antibody existing in the human body, a lymphocyte capable of producing the antibody can be cultured by isolating a human peripheral blood lymphocyte, immortalizing it by its infection with EB virus or the like and then cloning it, and the antibody can be purified from the culture.

The human antibody phage library is a library in which antibody fragments such as Fab, single chain antibody and the like are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the marker. The antibody fragment can be converted further into a human antibody molecule comprising two full B chains and two full L chains by genetic engineering techniques.

A human antibody-producing transgenic non-human animal is an animal in which a human antibody gene is introduced into cells. Specifically, a human antibody-producing transgenic animal can be prepared by introducing a human antibody gene into ES cell of a mouse, transplanting the ES cell into an early stage embryo of other mouse and then developing it. By introducing a human chimeric antibody gene into a fertilized egg and developing it, the transgenic animal can be also prepared. Regarding the preparation method of a human antibody from the human antibody-producing transgenic animal, the human antibody can be produced and accumulated in a culture by obtaining a human antibody-producing hybridoma by a hybridoma preparation method usually carried out in mammals other than human and then culturing it.

Examples of the transgenic non-human animal include cattle, sheep, goat, pig, horse, mouse, rat, fowl, monkey, rabbit and the like.

Another aspect of the present invention relates to a method for producing an antibody composition, which comprises culturing the mammalian cell according to the present invention in a medium to produce and accumulate an antibody composition in the culture; and recovering the antibody composition from the culture Also, in the present invention, it is preferable that the antibody is an antibody which recognizes a tumor-related antigen, an antibody which recognizes an allergy- or inflammation-related antigen, an antibody which recognizes circulatory organ disease-related antigen, an antibody which recognizes an autoimmune disease-related antigen or an antibody which recognizes a viral or bacterial infection-related antigen, and a human antibody which belongs to the IgG class is preferable.

An antibody fragment is a fragment which comprises the Fc region of an antibody. Examples of the antibody fragment include an H chain monomer, an H chain dimer and the like.

A fusion protein comprising an Fc region is a composition in which an antibody comprising the Fc region of an antibody or the antibody fragment is fused with a protein such as an enzyme, a cytokine or the like.

One embodiment of the present invention relates to a composition comprising the antibody of the present invention, also referred to as antibody composition.

In one embodiment of the present invention shows the antibody or antibody composition high ADCC activity.

In the present invention, the ADCC activity is a cytotoxic activity in which an antibody bound to a cell surface antigen on a tumor cell in the living body activate an effector cell through an Fc receptor existing on the antibody Fc region and effector cell surface and thereby obstruct the tumor cell and the like.

The antibody composition of the present invention has potent antibody-dependent cell-mediated cytotoxic activity (ADCC). An antibody having potent antibody-dependent cell-mediated cytotoxic activity is useful for preventing and treating various diseases including cancers, inflammatory diseases, immune diseases such as autoimmune diseases, allergies and the like, circulatory organ diseases and viral or bacterial infections.

In the case of cancers, namely malignant tumors, cancer cells grow. General anti-tumor agents inhibit the growth of cancer cells. In contrast, an antibody having potent antibody-dependent cell-mediated cytotoxic activity can treat cancers by injuring cancer cells through its cell killing effect, and therefore, it is more effective as a therapeutic agent than the general anti-tumor agents.

In immune diseases such as inflammatory diseases, autoimmune diseases, allergies and the like, in vivo reactions of the diseases are induced by the release of a mediator molecule by immunocytes, so that the allergy reaction can be inhibited by eliminating immunocytes using an antibody having potent antibody-dependent cell-mediated cytotoxic activity.

Examples of the circulatory organ diseases include arteriosclerosis and the like. The arteriosclerosis is treated using balloon catheter at present, but circulatory organ diseases can be prevented and treated by inhibiting growth of arterial cells in restricture after treatment using an antibody having potent antibody-dependent cell-mediated cytotoxic activity.

Various diseases including viral and bacterial infections can be prevented and treated by inhibiting proliferation of cells infected with a virus or bacterium using an antibody having potent antibody-dependent cell-mediated cytotoxic activity.

The glycoproteins of the present invention may there for be use to treat immune diseases, cancer viral or barterial infections or other diseases or disorders mentioned above.

The medicament comprising the glycoprotein composition of the present invention can be administered as a therapeutic agent alone, but generally, it is preferable to provide it as a pharmaceutical formulation produced by an appropriate method well known in the technical field of manufacturing pharmacy, by mixing it with at least one pharmaceutically acceptable carrier.

It is desirable to select a route of administration which is most effective in treatment. Examples include oral administration and parenteral administration, such as buccal, tracheal, rectal, subcutaneous, intramuscular, intravenous or the like. In an antibody preparation, intravenous administration is preferable.

The dosage form includes sprays, capsules, tablets, granules, syrups, emulsions, suppositories, injections, ointments, tapes and the like.

Examples of the pharmaceutical preparation suitable for oral administration include emulsions, syrups, capsules, tablets, powders, granules and the like.

Liquid preparations, such as emulsions and syrups, can be produced using, as additives, water; saccharides, such as sucrose, sorbitol, fructose, etc.; glycols, such as polyethylene glycol, propylene glycol, etc.; oils, such as sesame oil, olive oil, soybean oil, etc.; antiseptics, such as p-hydroxybenzoic acid esters, etc.; flavors, such as strawberry flavor, peppermint, etc.; and the like.

Capsules, tablets, powders, granules and the like can be produced using, as additive, fillers, such as lactose, glucose, sucrose, mannitol, etc.; disintegrating agents, such as starch, sodium alginate, etc.; lubricants, such as magnesium stearate, talc, etc.; binders, such as polyvinyl alcohol, hydroxypropylcellulose, gelatin, etc.; surfactants, such as fatty acid ester, etc.; plasticizers, such as glycerine, etc.; and the like.

Examples of the pharmaceutical preparation suitable for parenteral administration include injections, suppositories, sprays and the like.

Injections may be prepared using a carrier, such as a salt solution, a glucose solution, a mixture of both thereof or the like. Also, powdered injections can be prepared by freeze-drying the antibody composition in the usual way and adding sodium chloride thereto.

Suppositories may be prepared using a carrier such as cacao butter, hydrogenated fat, carboxylic acid or the like.

Also, sprays may be prepared using the antibody composition as such or using a carrier which does not stimulate the buccal or airway mucous membrane of the patient and can facilitate absorption of the antibody composition by dispersing it as fine particles.

Examples of the carrier include lactose, glycerol and the like. Depending on the properties of the antibody composition and the carrier, it is possible to produce pharmaceutical preparations such as aerosols, dry powders and the like. In addition, the components exemplified as additives for oral preparations can also be added to the parenteral preparations.

Although the clinical dose or the frequency of administration varies depending on the objective therapeutic effect, administration method, treating period, age, body weight and the like, it is usually 10 µg/kg to 20 mg/kg per day and per adult.

It should be noted that embodiments and features described in the context of one of the aspects of the present invention also apply to the other aspects of the invention.

Definitions

General Glycobiology

Basic glycobiology principles and definitions are described in Varki et al. Essentials of Glycobiology, 2nd edition, 2009.

"N-glycosylation" refers to the attachment of the sugar molecule oligosaccharide known as glycan to a nitrogen atom residue of a protein "O-glycosylation" refers to the attachment of a sugar molecule to an oxygen atom in an amino acid residue in a protein.

"Galactosylation" means enzymatic addition of a galactose residue to lipids, carbohydrates or proteins.

"Sialylation" is the enzymatic addition of a neuraminic acid residue.

"Neuraminic acid" is a 9-carbon monosaccharide, a derivative of a ketononose.

"Monoantennary" N-linked glycan is a engineered N-glycan consist of the N-glycan core (Manα1-6(Manα1-3) Manβ1-4GlcNAcβ1-4GlcNAcβ1-Asn-X-Ser/Thr) that elongated with a single GlcNAc residue linked to C-2 and of the mannose α1-3. The single GlcNAc residue can be further elongated for example with Gal or Gal and NeuAc residues.

"Biantennary" N-linked glycan is the simplest of the complex N-linked glycans consist of the N-glycan core (Manα1-6(Manα1-3)Manβ1-4GlcNAcβ1-4GlcNAcβ1-Asn-X-Ser/Thr) elongated with two GlcNAc residues linked to C-2 and of the mannose α1-3 and the mannose α1-6. This core structure can then be elongated or modified by various glycan structures.

"Triantennary" N-linked glycans are formed when an additional GlcNAc residue is added to either the C-4 of the core mannose α1-3 or the C-6 of the core mannose α1-6 of the bi-antennary core structure. This structure can then be elongated or modified by various glycan structures.

"Tetratantennary" N-linked glycans are formed when two additional GlcNAc residues are added to either the C-4 of the core mannose α1-3 or the C-6 of the core mannose α1-6 of the bi-antennary core structure. This core structure can then be elongated or modified by various glycan structures.

"Poly-LacNAc" poly-N-acetyllactosamine ([Galβ1-4GlcNAc]n; n≥2.)

"Glycoprofiling" means characterization of glycan structures resident on a biological molecule or cell.

"Glycosylation pathway" refers to assembly of monosaccharides into a group of related complex carbohydrate structures by the stepwise action of enzymes, known as glycosyltransferases. Glycosylation pathways in mammalian cells are classified as N-linked protein glycosylation, different O-linked protein glycosylation (O-GalNAc, O-GlcNAc, O-Fuc, O-Glc, O-Xyl, O-Gal), different series of glycosphingolipids, and GPI-anchors.

"Biosynthetic Step" means the addition of a monosaccharide to a glycan structure.

"Glycosyltransferases" are enzymes that catalyze the formation of the glycosidic linkage to form a glycoside. These enzymes utilize 'activated' sugar phosphates as glycosyl donors, and catalyze glycosyl group transfer to a nucleophilic group, usually an alcohol. The product of glycosyl transfer may be an O-, N-, S-, or C-glycoside; the glycoside may be part of a monosaccharide, oligosaccharide, or polysaccharide.

"Glycosylation capacity" means the ability to produce an amount of a specific glycan structure by a given cell or a given glycosylation process.

"HEP" is an abbreviation for heparosan. Heparosan (HEP) is a natural sugar polymer comprising (-GlcUA-1,4-GlcNAc-1,4-) re-peats. It belongs to the glycosaminoglycan polysaccharide family and is a negatively charged polymer at physiological pH. It can be found in the capsule of certain bacteria's but it is also found in higher vertebrate where it serves as precursor for the natural polymers heparin and heparan sulphate.

"PEG" is an abbreviation for polyethylene glycol. PEG polymers are generally used for increasing the half-life of therapeutic molecule. With their high hydrodynamic volume, PEG polymers increases the effective size of drugs and thus slows their clearance from the bloodstream via kidney filtration or by shielding the protein drug towards clearance receptors and proteolytical degradation.

"XTEN" is well defined peptide sequences based on a limited subset of amino acids, and assembled into longer repeating sequences. XTEN also increases the size of therapeutic molecules and prolongs their presence in the bloodstream. "GlycoPEGylation" is the process of covalently attaching PEG to glycans of a protein of interest.

"Enzymatic GlycoPEGylation" is the process of covalently attaching PEG to glycans of a protein of interest using a glycosyltransferase and suitable PEGylated glycosyl transfer groups, such as PEGylated NeuAc-CMP molecules.

"Glycoconjugate" is a macromolecule that contains monosaccharides covalently linked to proteins or lipids "Simple(r) glycan structure" is a glycan structure containing fewer monosaccharides and/or having lower mass and/or having fewer antennae.

"Human like glycosylation" means having glycan structures resembling those of human cells. Examples including more sialic acids with α2,6 linkage (more α2,6 sialyltransferase enzyme) and/or less sialic acids with α2,3 linkage and/or more N-acetylneuraminic acid (Neu5Ac) and/or less N-glycolylneuraminic acid (Neu5Gc).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

"Deconstruction" means obtaining cells producing a simpler glycan structures by single or stacked knock out of glycosyltransferases. Deconstruction of a glycosylation pathway means KO of glycosyltransferases involved in each step in biosynthesis and identification of glycosyltransferases controlling each biosynthetic step.

"Reconstruction" refers to inserting exogenous gene(s) into cells or activation of endogenous silent gene(s) to obtain more complex glycan structures. Typically target cells are producing simple glycan structures as result of deconstruction.

"Modified glycan profile" refers to change in number, type or position of oligosaccharides in glycans on a given glycoprotein.

More "homogeneous glycosylation" or "homogeneous stable glycosylation capacities" means that the proportion of identical glycan structures observed by glycoprofiling a given protein expressed in one cell is larger than the proportion of identical glycan structures observed by glycoprofiling the same protein expressed in another cell. A more homogeneous glycosylation may be obtained by knock-in and/or knock-out of one or more glycosyltransferase genes in a cell. An example of such a modification could be knock-out of B4galt1 to generate more homogeneous N-glycans without galactose. Additional knock-out of fut8 allows production of more homogeneous N-glycans without galactose and fucose. Overall, this type of knock-in and/or knock-out modifications can result in changes of the glycostructure outcome of the modified cell, such as the non-limiting list of simpler glycan structure, more homogeneous product, more sialic acids per molecule, non-sialylated, non-galactosylated, more homogeneous bi-antennary, more homogeneous monoantennary, more homogeneous triantennary, more homogeneous glycosylation without poly-LacNAc, higher productivity in cell culture, new stable homogeneous glycosylation capacities, more human glycostructure, more homogeneous glycosylation and improved ADCC targeting of IgG, modified fucose level, no fucose, and improved substrate for generating glycoconjugates.

General DNA, mol. biol. Any of various techniques used for separating and recombining segments of DNA or genes, commonly by use of a restriction enzyme to cut a DNA fragment from donor DNA and inserting it into a plasmid or viral DNA. Using these techniques, DNA coding for a protein of interest is recombined/cloned (using PCR and/or restriction enzymes and DNA ligases or ligation independent methods such as USER cloning) into a plasmid (known as an expression vector), which can subsequently be introduced into a cell by transfection using a variety of transfection methods such as calcium phosphate transfection, electroporation, microinjection and liposome transfection. Overview and supplementary information and methods for constructing synthetic DNA sequences, insertion into plasmid vectors and subsequent transfection into cells can be found in Ausubel et al, 2003 and/or Sambrook & Russell, 2001.

"Gene" refers to a DNA region (including exons and introns) encoding a gene product, as well as all DNA regions which regulate the production of the gene product, whether or not such regulatory sequences are adjacent to coding and/or transcribed sequences or situated far away from the gene which function they regulate. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

"Targeted gene modifications", "gene editing" or "genome editing" Gene editing or genome editing refer to a process by which a specific chromosomal sequence is changed. The edited chromosomal sequence may comprise an insertion of at least one nucleotide, a deletion of at least one nucleotide, and/or a substitution of at least one nucleotide. Generally, genome editing inserts, replaces or removes nucleic acids from a genome using artificially engineered nucleases such as Zinc finger nucleases (ZFNs), Transcription Activator-Like Effector Nucleases (TALENs), the CRISPR/Cas system, and engineered meganuclease re-engineered homing endonucleases. Genome editing principles are described in Steentoft et al and gene editing methods are described in references therein and also broadly used and thus known to person skilled in the art.

"Endogenous" sequence/gene/protein refers to a chromosomal sequence or gene or protein that is native to the cell or originating from within the cell or organism analyzed "Exogenous" sequence or gene refers to a chromosomal sequence that is not native to the cell, or a chromosomal sequence whose native chromosomal location is in a different location in a chromosome or originating from outside the cell or organism analyzed "Inactivated chromosomal sequence" refer to genome sequence that has been edited resulting in loss of function of a given gene product. The gene is said to be knocked out.

"Heterologous" refers to an entity that is not native to the cell or species of interest.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide.

The terms "polypeptide" and "protein" are used interchangeably to refer to a polymer of amino acid residues. These terms may also refer to glycosylated variants of the "polypeptide" or "protein", also termed "glycoprotein". "polypeptide", "protein" and "glycoprotein" is used interchangeably throughout this disclosure.

The term "recombination" refers to a process of exchange of genetic information between two polynucleotides. For the purposes of this disclosure, "homologous recombination" refers to the specialized form of such exchange that takes place, for example, during repair of double-strand breaks in cells. This process requires sequence similarity between the two polynucleotides, uses a "donor" or "exchange" molecule to template repair of a "target" molecule (i.e., the one that experienced the double-strand break), and is variously known as "non-crossover gene conversion" or "short tract gene conversion," because it leads to the transfer of genetic information from the donor to the target. Without being bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized homologous recombination often results in an alteration of the sequence of the target molecule such that part or all of the sequence of the donor polynucleotide is incorporated into the target polynucleotide.

As used herein, the terms "target site" or "target sequence" refer to a nucleic acid sequence that defines a portion of a chromosomal sequence to be edited and to which a targeting endonuclease is engineered to recognize, bind, and cleave.

"Targeted integration" is the method by which exogenous nucleic acid elements are specifically integrated into defined loci of the cellular genome. Target specific double stranded breaks are introduced in the genome by genome editing nucleases that allow for integration of exogenously delivered donor nucleic acid element into the double stranded break site. Thereby the exogenously delivered donor nucleic acid element is stably integrated into the defined locus of the cellular genome.

Sequence identity Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

All patent and non-patent references cited in the present application, are hereby incorporated by reference in their entirety.

The invention will now be described in further details in the following non-limiting examples.

EXAMPLES

The purpose of the following examples are given as an illustration of various embodiments of the invention and are thus not meant to limit the present invention in any way. Along with the present examples the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1—Deconstruction of N-glycosylation in CHO Cells

Introductory Paragraph

The Chinese hamster ovary cell (CHO) is the cell factory of choice for recombinant production of biological therapeutics. CHO is capable of handling many posttranslational modifications needed for production of bioactive proteins, and has a generic capacity for glycosylation of proteins compatible with human use. Glycosylation has wide ranges of effects on production, product consistency, solubility, stability, bioactivity, and circulatory half-life of protein therapeutics, and availability of a single generic CHO production platform is a limiting factor for design and development of biologics. This example shows a comprehensive knockout screen of glycosyltransferase genes involved in N-glycosylation in CHO that defines the key enzymes controlling antennary branching, elongation, and sialylation. A panel of stably engineered CHO lines with designer glycosylation capacities such as homogenous biantennary glycans with and without α2,3 and α2,6 sialic acid capping was established. The screen demonstrates great plasticity for CHO glycoengineering and provides clear pathways for custom designs.

Introduction

Glycoprotein biologics is the fastest growing class of therapeutics, and most of these can only be produced recombinantly in mammalian cells with capacity for human-like glycosylation. The Chinese hamster ovary (CHO) cell has gained a leading role as host cell for recombinant production of glycoprotein therapeutics mainly because it produces rather simple N-glycans with branching and capping similar to what is produced in some human cells.

Notably, CHO produce complex-type heterogenous N-glycans with bi-, tri-, and tetraantennary structures with core α 6Fucose (Fuc), a minor amount of poly-N-Acetyllactosamine (poly-LacNAc) mainly on the α1,6 arm of tetraantennary structures, and exclusive capping of LacNAc with α2,3 linked neuraminic acid (NeuAc) (See FIG. 1a). CHO does not generally produce the non-human and in man immunogenic capping structures, such as N-glycolylneuraminic acid (NeuGc) or α3Gal, although the occurrence of these have been reported perhaps as a result of gene induction. N-glycosylation may vary for different proteins as well as for different glycosites in individual proteins, and e.g. IgG antibodies are produced with truncated N-glycan structures at the conserved Asn297 glycosite (biantennary structures with core α6Fuc, limited LacNAc, and NeuAc capping). A major concern with CHO is the substantial heterogeneity in N-glycan processing, which can be difficult to control during bioprocessing and can pose issues for bioactivity as well as biosafety. Thus, a major activity in bioprocessing of therapeutics is devoted to glycan analysis and control of fermentation to achieve consistency.

Substantial efforts in the last two decades have been devoted to genetic glycoengineering of CHO cells with the aims to expand the capacity for glycosylation, reduce heterogeneity, and improve or alter especially sialylation. These studies have essentially all used random integration of cDNAs encoding glycosyltransferases and experienced problems with stability, consistency, and predictability of the introduced glycosylation capacity. The major obstacle has been the need to rely on overexpression of glycosyltransferases and competition with the endogenous expressed enzymes because of lack of simple methods to knock these out in cell lines. Thus, to our knowledge such glycoengineered CHO cells have not reached production of clinical therapeutics. One successful glycoengineering strategy has, however, emerged after the discovery that IgGs without core α 6Fuc on the Asn297 N-glycan exhibits markedly higher Antibody-Dependent Cell Cytotoxicity (ADCC).

Thus, through a tour-de-force using two rounds of homologous recombination both alleles of the fut8 gene encoding the α 6fucosyltransferase controlling core fucosylation was knocked out in CHO, and at least one therapeutic IgG produced in CHO without the fut8 gene is now in clinical use. More recently, the fut8 gene was knocked out using precise gene editing with Zinc finger nuclease (ZFN) gene targeting with a fraction of time and resources spent. The emergence of precise gene editing technologies for knockout (KO) and knockin (KI) have opened up for an entirely different level of speed and ease with which stable genetic manipulation of host cell lines to remove and introduce glycosyltransferase genes can be achieved, and this will undoubtedly impact engineering of mammalian host cell factories for recombinant production of therapeutics.

Figure 4:
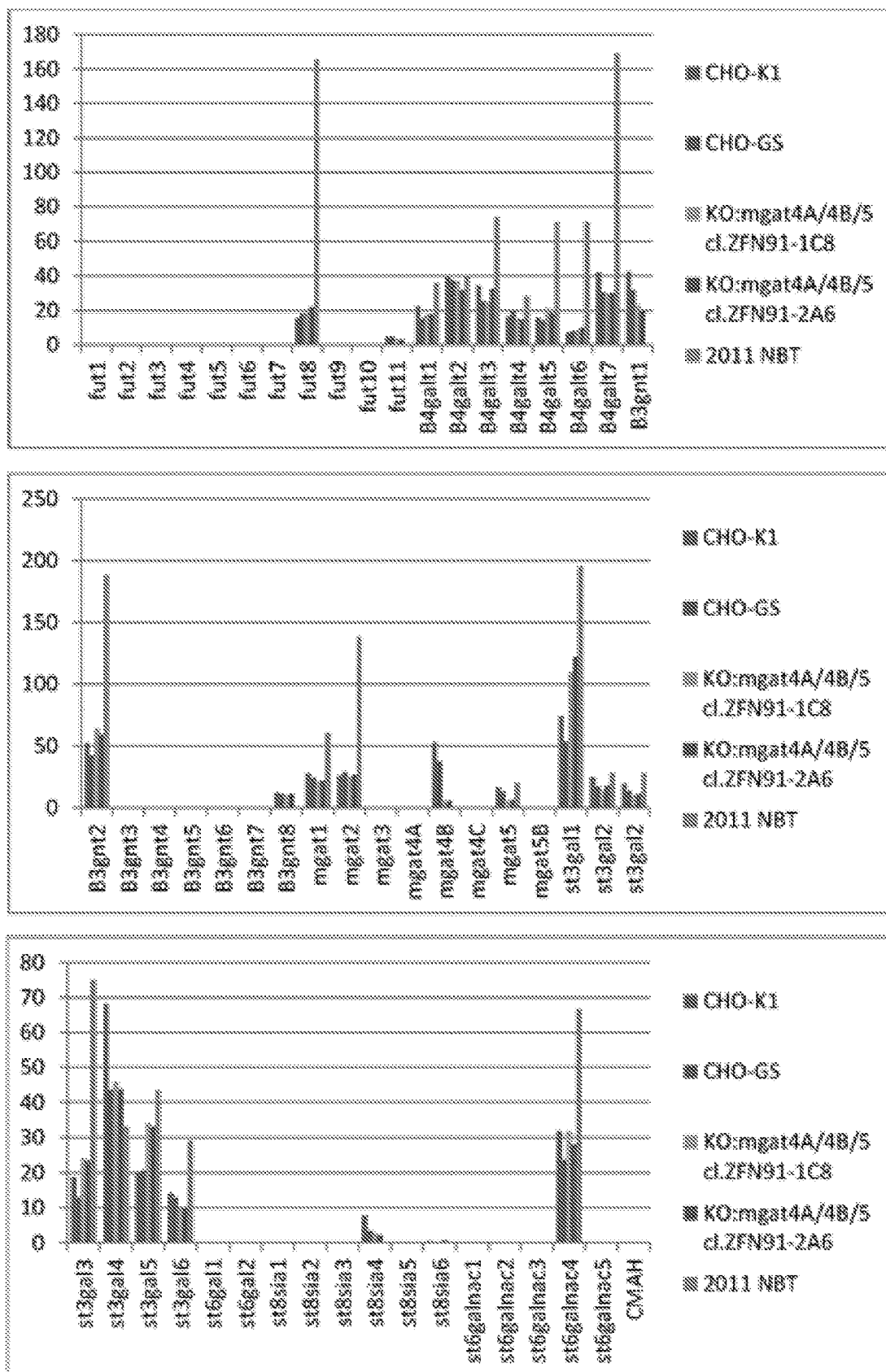
FIG. 4 shows expression profiling of selected glycosyltransferase genes by RNAseq in CHO. RNAseq analysis was performed on two common CHO lines (CHO-K1, CHO-GS) and two independent CHO GS triple mgat4A/4B/5 KO clones (cl #1, cl #2). The reported RNAseq analysis of CHO K1 is included, and this was largely identical to our analyses except that the relative expression levels were higher. Importantly, a few genes including mgat4b reported previously not to be expressed in CHO K1, were found in the present study to be expressed, and mgat4b was found to be essential for the glycoengineering experiments reported here. Another important observation was that the expression profiles of glycogenes in the two triple KO clones analyses were identical to those of the parental CHO lines, providing evidence that the precise gene editing does not alter expression of other glycogenes even for functional compensatory reasons. For more conclusive evaluation of this we clearly need to obtain broader RNAseq data for all mutant clones.

Here, we first employed a ZFN-mediated knockout screen in CHO to explore the potential for engineering N-glycosylation of recombinant glycoproteins. Many steps in the N-glycan biosynthetic pathway are potentially catalyzed by multiple isoenzymes, which leave genetic engineering unpredictable (FIG. 1a). Dissection of the in vivo functions of each of these isoenzymes is required to construct a matrix for design options. The KO screen included all genes encoding isoenzymes with potential to regulate N-glycosylation branching, elongation, and terminal capping expressed in CHO. The expression of the relevant genes in CHO GS was assessed by quantitative next generation RNA sequencing (RNAseq) (FIG. 4). The strategy has only been made possible with the recent sequencing of the CHO genome and analysis of the CHO-K1 transcriptome. We targeted individual genes and most relevant stacked combinations.

Figure 1D:
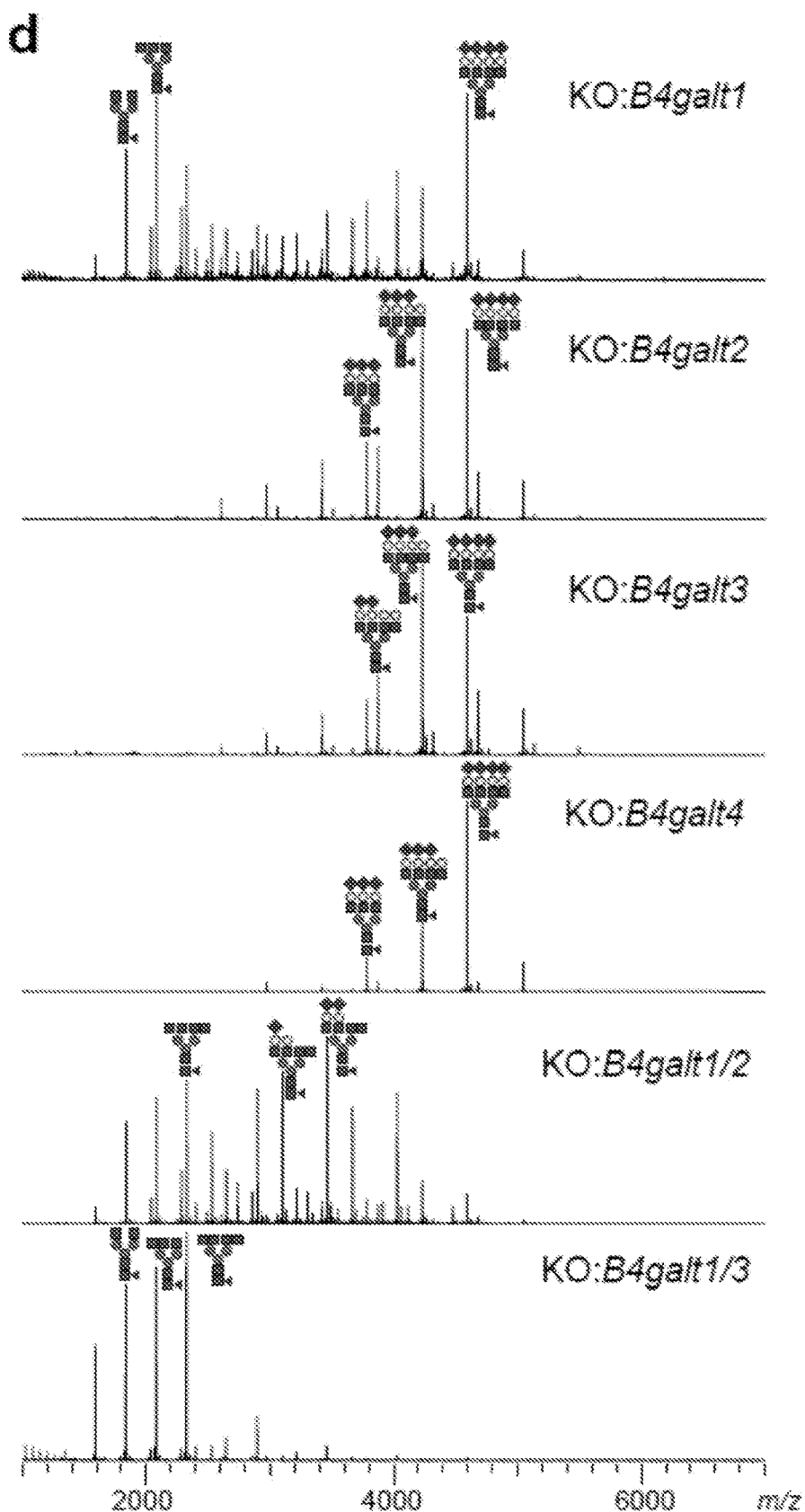
Figure 1E:
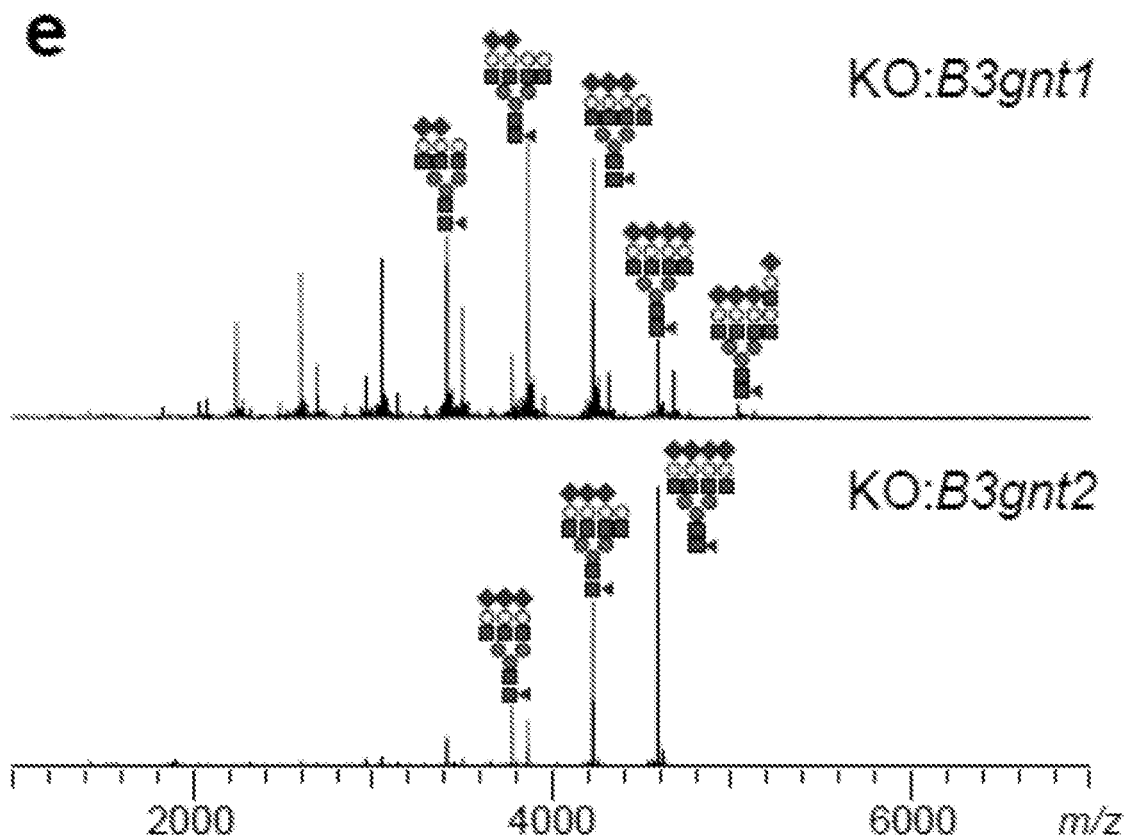
Figure 1F:
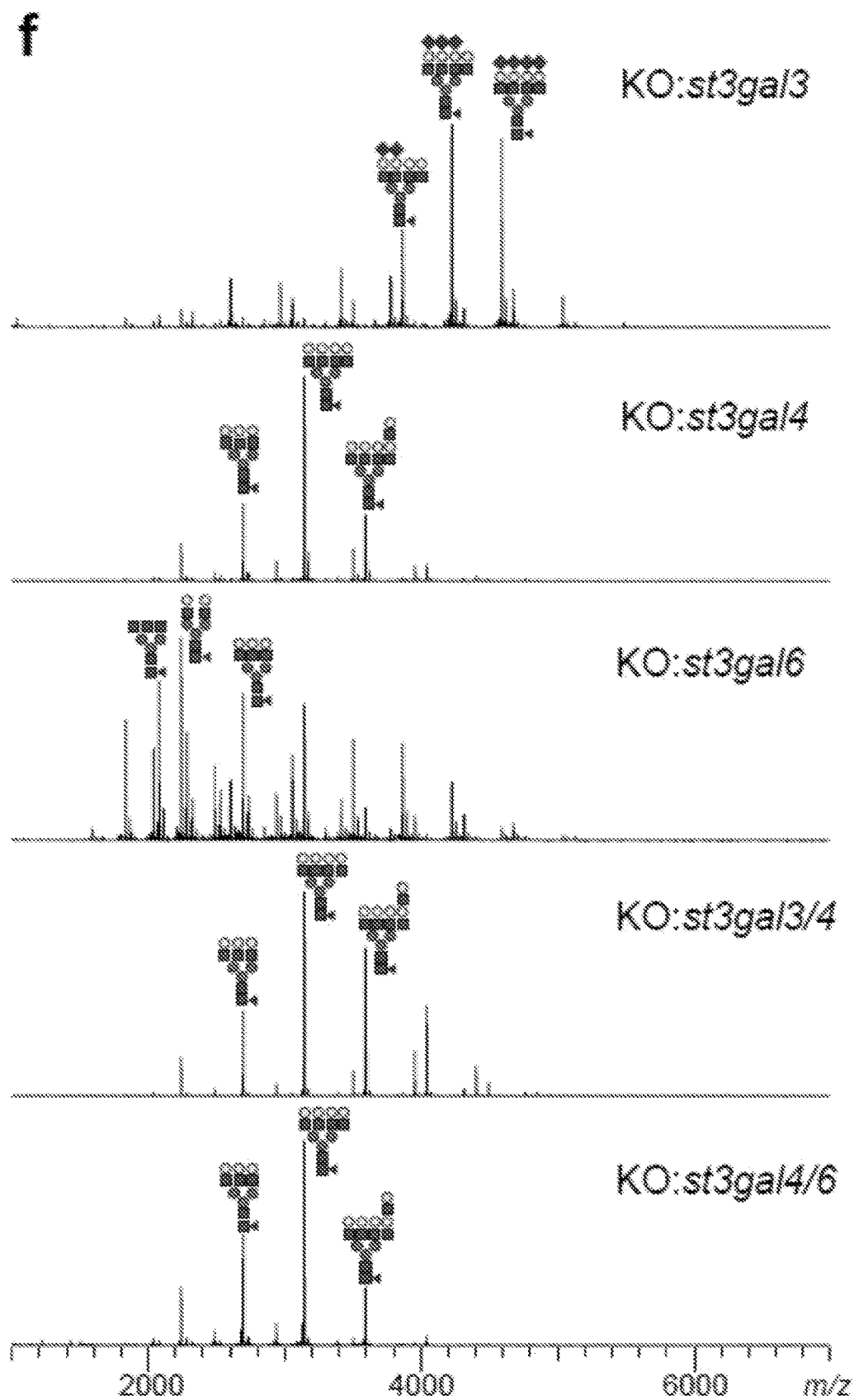

We used a total of 15 ZFNs targeting glycosyltransferase genes (FIG. 1a) involved in antennary branching (mgat4A/4B/4C/5/5B) (FIG. 1c), galactosylation (B4galt1/2/3/4 (FIG. 1d), poly-LacNAc elongation (B3gnt1/2/8) (FIG. 1e), and terminal capping by sialylation (st3gal3/4/6) (FIG. 1f). We utilized recently developed methods for enriching KO clones by FACS (GFP/Crimson tagged ZFNs) and high throughput screening by an amplicon labelling strategy (IDAA). The majority of KO clones exhibited insertions and/or deletions (indels) in the range of ±20 bps, and most targeted genes were present with two alleles, while some (mgat4B and mgat5) were present with 1 or 3 alleles, respectively. To monitor effects of the glycogene KO screen we used stable recombinant expression of human erythropoietin (EPO), since this protein has three N-glycans with mainly tetraantennary structures, low level of poly-LacNAc, and α2,3 sialic acid capping (FIG. 1b), and is one of the best characterized N-glycoproteins produced in CHO. The engineering was performed in the CHO-GS production line (Sigma) grown in suspension in protein-free medium, and EPO expressed in the wildtype cell was found to be glycosylated similar to what has been reported in the past with other CHO lines (FIG. 1b).

No apparent consistent morphology or growth phenotypic characteristics were noted apart from subtle clone variations. On average 5-50 clones for each were screened by ELISA and clones with the highest expression were selected. The final purification yields ranging from 0.2 mgs/L to 6.2 mgs/L, but this variation is mainly if not fully ascribable to chance and the limited number of clones screened for each KO clone. The selected CHO WT clone produced final yields of 0.9 mgs/L, while e.g. the KO clone mgat4A/4B/5/B3gnt2 with four deleted genes produced 3.4 mgs/L.

Control of N-Glycan Antennary Status

MGAT1 and 2 each control formation of one of the two β2 branches in biantennary N-glycans, while potential partial functional redundancy is predicted for tri- and tetraantennary branch formation by MGAT4A/4B/4C (β4 branch) and MGAT5/5B (β6 branch), respectively. Only mgat4B and 5 appear to be expressed in CHO (FIG. 4). Targeting mgat4A had minor effect while targeting both mgat4A/4B almost eliminated β4-branched tetraantennary N-glycans (FIG. 1c). Targeting mgat5 in contrast completely eliminated β6-branched tetraantennary structures (FIG. 1c) as well as L-PHA lectin labeling of cells (FIG. 5), which is in agreement with previous studies of lectin-resistant CHO mutants lacking mgat5. Stacking KO of mgat4A/4B and 5 produced homogenous biantennary N-glycans on EPO (FIG. 1c). A minor amount of poly-LacNAc on the biantennary N-glycans was, however, still found, and this is also found as a minor component in wildtype cells.

Control of LacNAc

Figure 3:
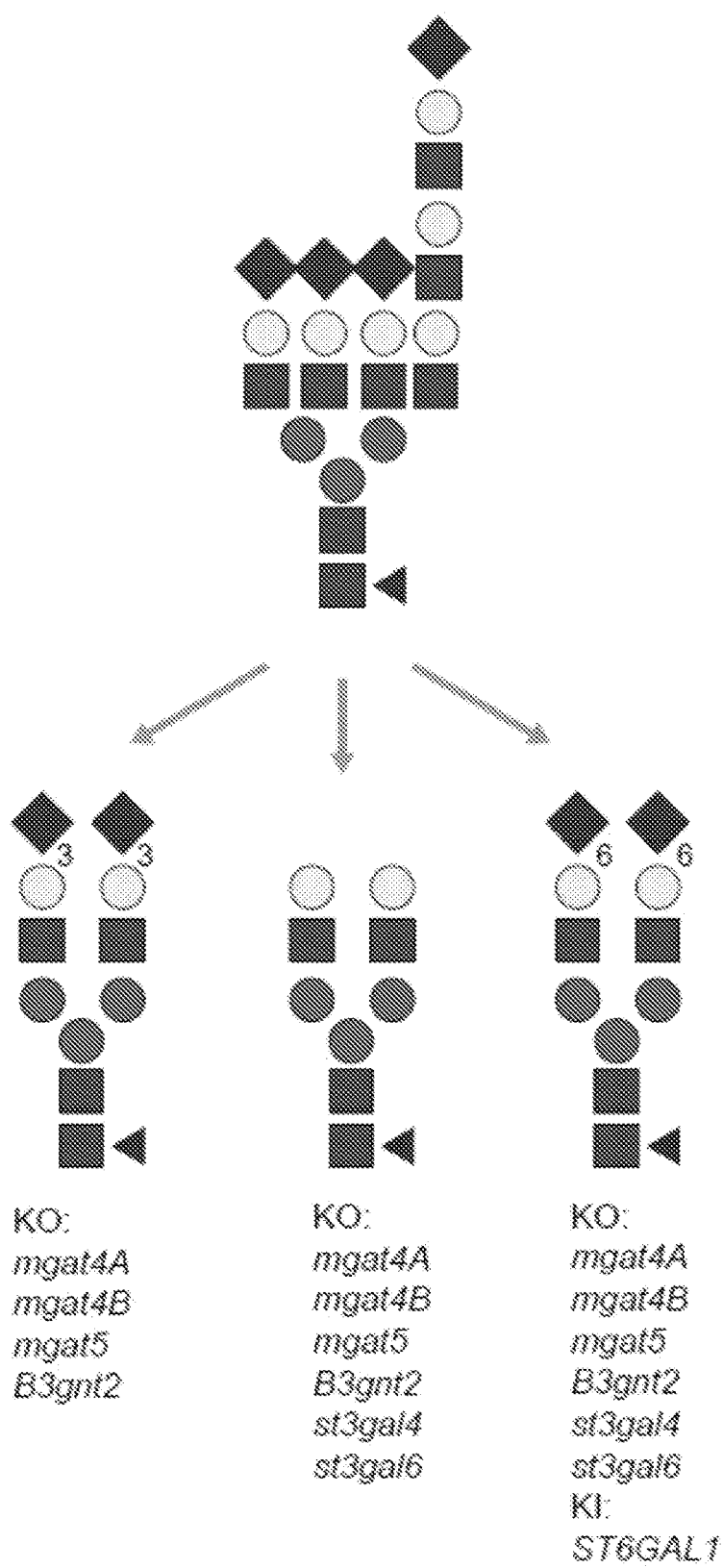
FIG. 3 shows graphic depiction of the design matrix for genetic engineering of CHO N-glycosylation capacity to produce homogeneous biantennary N-glycans with α2,3NeuAc capping, without sialylation, and with α2,3NeuAc capping on EPO. Additional KO of fut8 would result in loss of core fucosylation.

CHO express all seven known β4galactosyltransferases and our understanding of the in vivo functions of these isoenzymes is poor, but only B4Gal-T1-4 are expected to serve functions in N-glycosylation. We first screened individual KO clones for B4galt1-4, and found that B4Gal-T1 appeared to have the major role (FIG. 1d). Thus, contributions of the other isoforms could only be assessed in stacked combinations with KO of B4galt1. We probed stacked combinations by immunocytology with an antibody to LacNAc showing that only stacked KO of B4galt1/3, but not B4galt1/2/4, appeared to abolish galactosylation (Supplementary FIG. 3). In agreement with this we found that EPO expressed in B4galt1/3 but not B4galt1/2 stacked KO clones had substantial reduction (>90%) in of galactosylation on N-glycans (FIG. 1d). However, complete loss of galactosylation capacity on EPO may require KO of three or more genes.

Control of poly-LacNAc

Figure 5B:
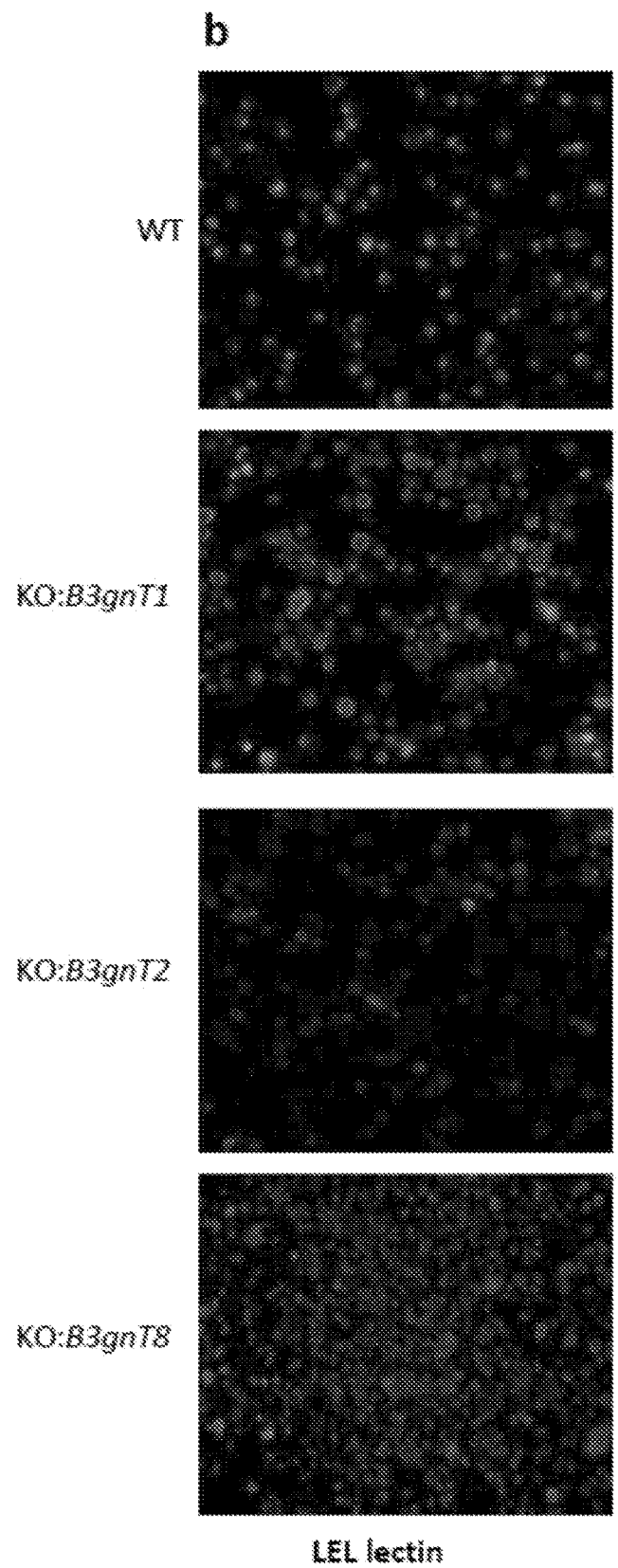
Figure 6A:
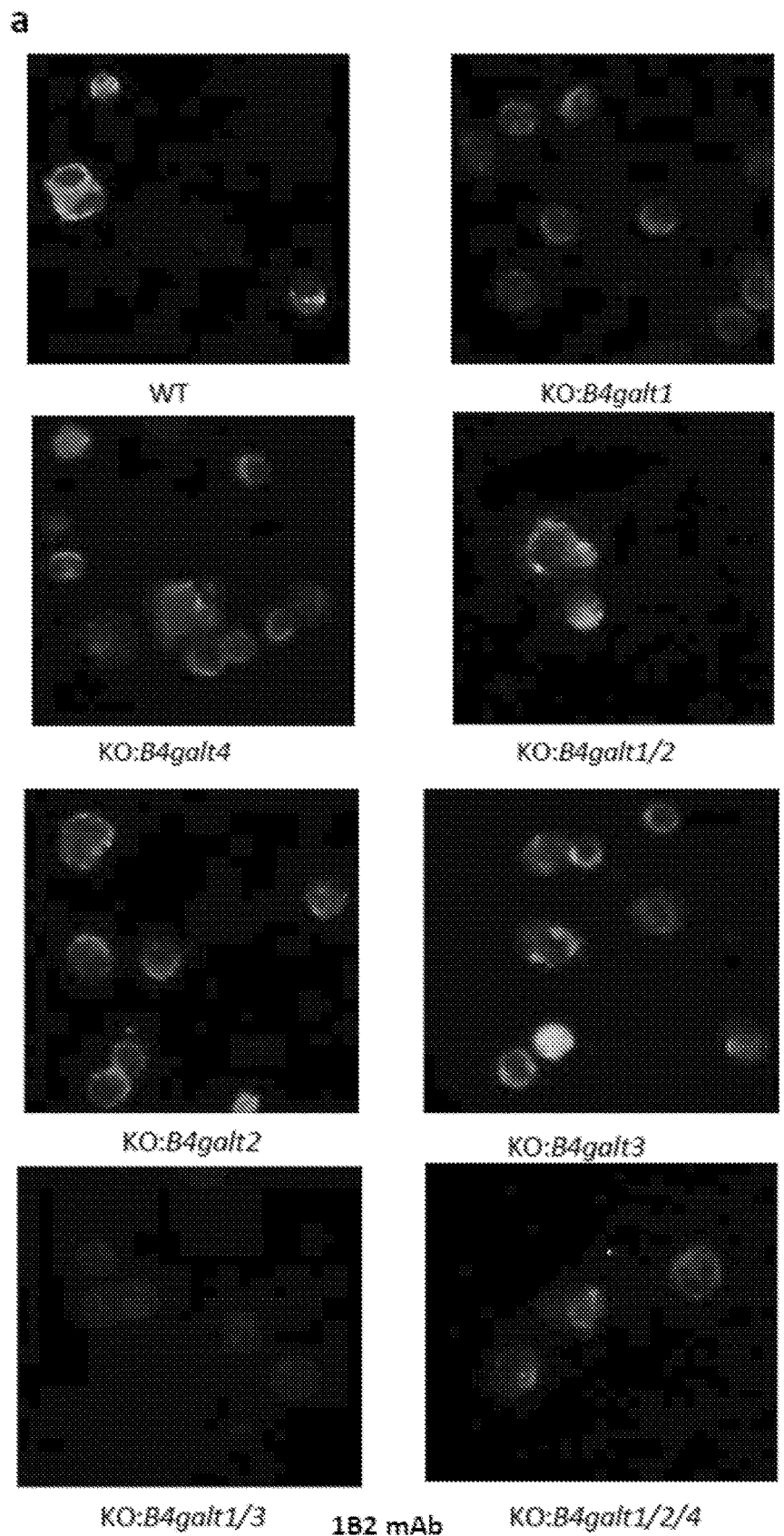
FIG. 6 shows immunocytology of CHO knockout clones with mutations related to LacNAc formation. (a) The MAb 1B2 was used to label presence of LacNAc after removal of sialic acids by neuraminidase pretreatment. Analysis of KO of B4galt1-4 in CHO GS WT with heterogeneous branching showed that KO of B4galt1 reduced labeling, while only stacked KO of B4galt1/3 completely abolished labeling. (b) The same analysis of KO of B4galt1-4 in CHO GS engineered with homogenous biantennary N-glycans (KO of mgat4A/4B/5) showed that KO of B4galt1 alone essentially abolished MAb 1B2 labeling, indicating that β4Gal-T1 is the main enzyme responsible for galactosylation of biantennary N-glycans. This finding is expected to have implications for recombinant production of therapeutic IgGs in CHO, since these proteins in general are produced with biantennary N-glycans with limited galactosylation.
Figure 6B:
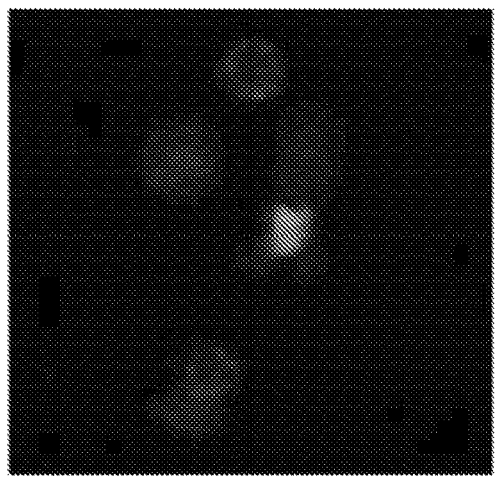
Figure 6B:
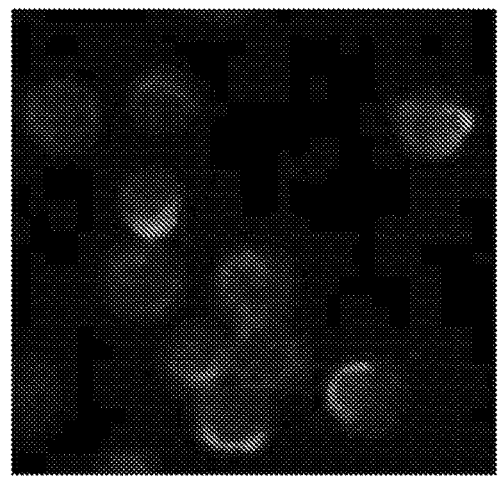
Figure 6B:
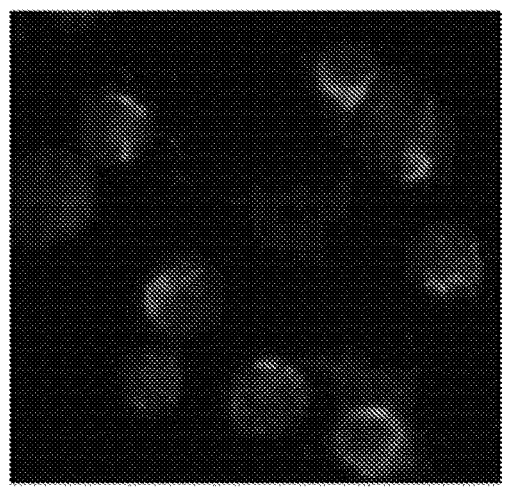
Figure 6B:
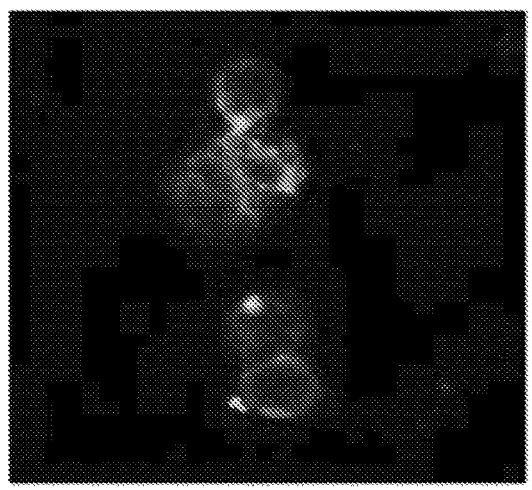
Figure 7A:
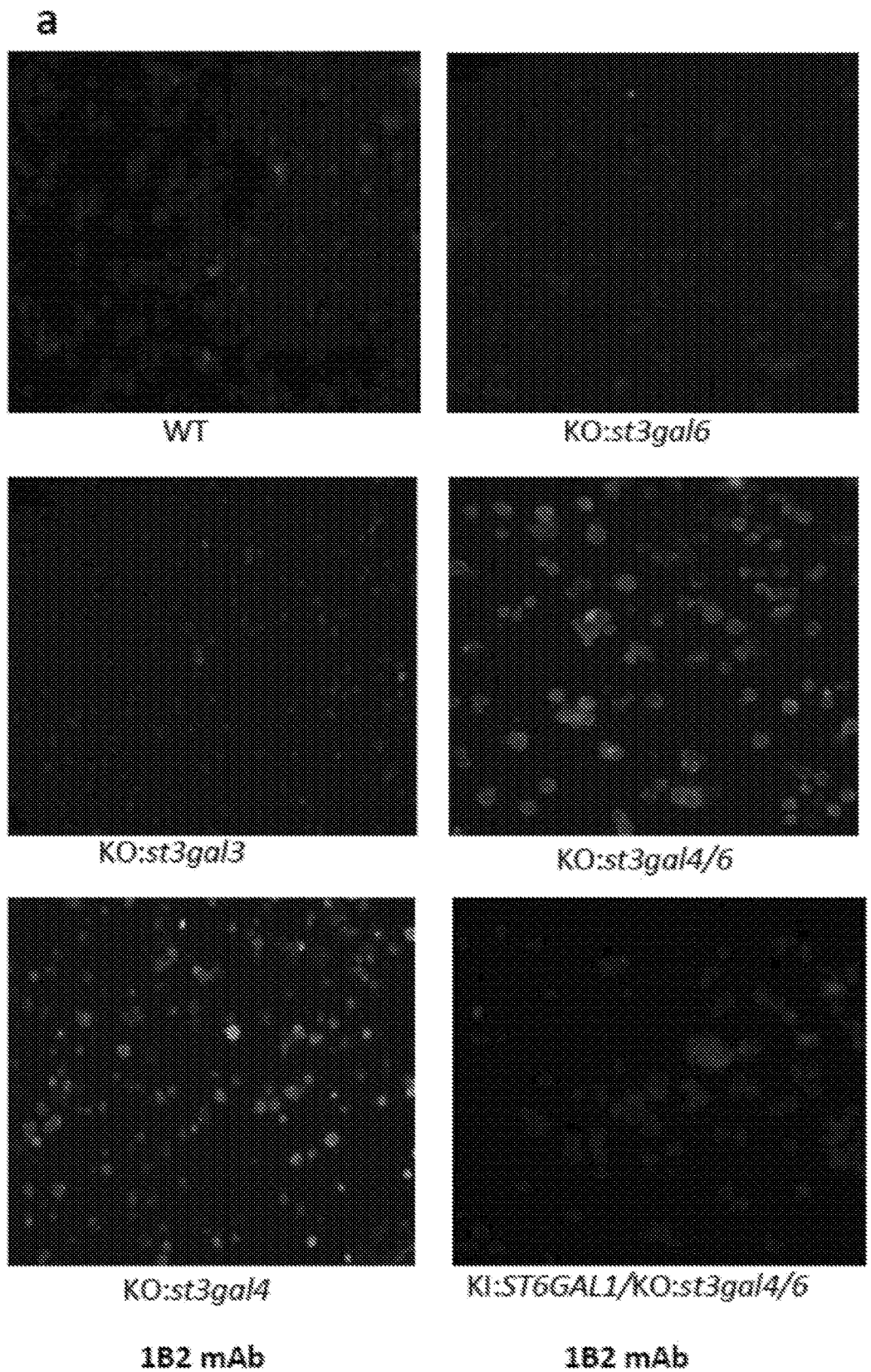
FIG. 7 shows immunocytology of CHO knockout and knockin clones related to sialylation. (a) The MAb 1B2 was used to label exposure of LacNAc as a result of loss of sialylation capacity, and this demonstrated that KO of st3gal3 and st3gal6 did not affect labeling substantially, while KO of st3galt4 and stacked KO of st3galt4/6 resulted in strong labeling. This suggests that the ST3Gal-IV enzyme is the main sialyltransferase responsible for α2,3sialylation of N-glycans. Furthermore, de novo introduction of human ST6Gal-1 in the stacked st3galt4/6 KO clone completely abolished MAb 1B2 labeling demonstrating efficient sialylation by this enzyme. (b) To confirm the de novo introduction of human ST6Gal-1 resulted in α2,6sialylation we used the lectin SNA, which did not label CHO WT cells as expected and only labeled after introduction of ST6GAL1. This result supports the mass spec interpretations presented in FIG. 2.
Figure 7B:
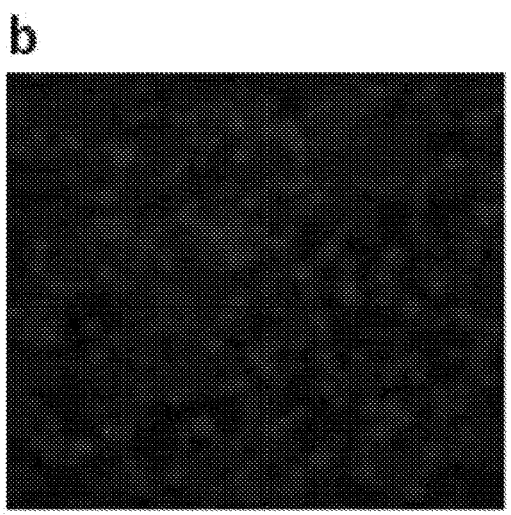
Figure 7B:
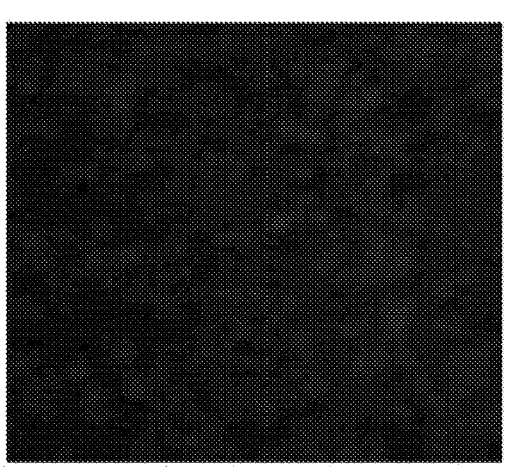
Figure 7B:
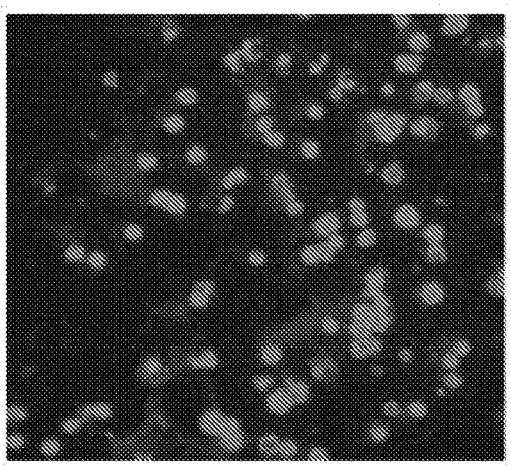
Figure 8:
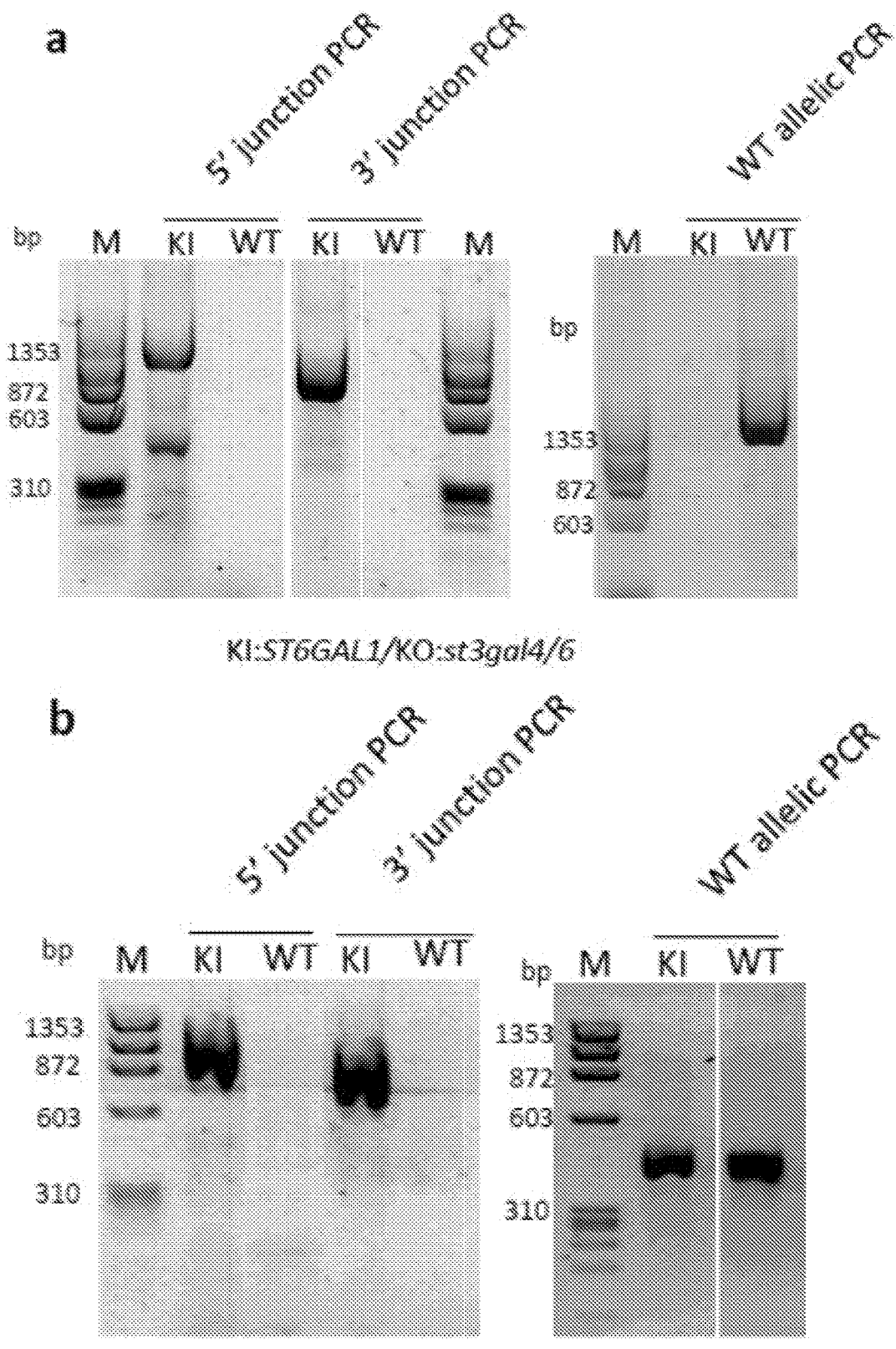
FIG. 8 shows analysis of targeted knockin of ST6GAL1 by junction PCR. (a) We used a modified Obligare targeted KI strategy utilizing two inverted ZFN binding sites flanking the ST6GAL1 gene in donor plasmid. 5 'and 3' junction PCR confirmed targeted integration into the Safeharbor #1 site in the CHO clone with st3gal4/6 KO. (b) 5 'and 3' junction PCR confirmed targeted integration in the CHO clone with st3gal4/6/mgat4A/413/5 KO. The status of allelic copy number of integration was determined by WT allelic PCR. The presence of desired band in WT allelic PCR indicates the presence of Safeharbor #1 site without the integration of targeted KI of gene of interest on at least one of the allele. The results showed biallelic integration of st6gal1 to Safeharbor #1 site in st3gal4/6 KO and monoallelic integration to mgat4A/413/5/st3gal4/6 KO, respectively.
Figure 9:
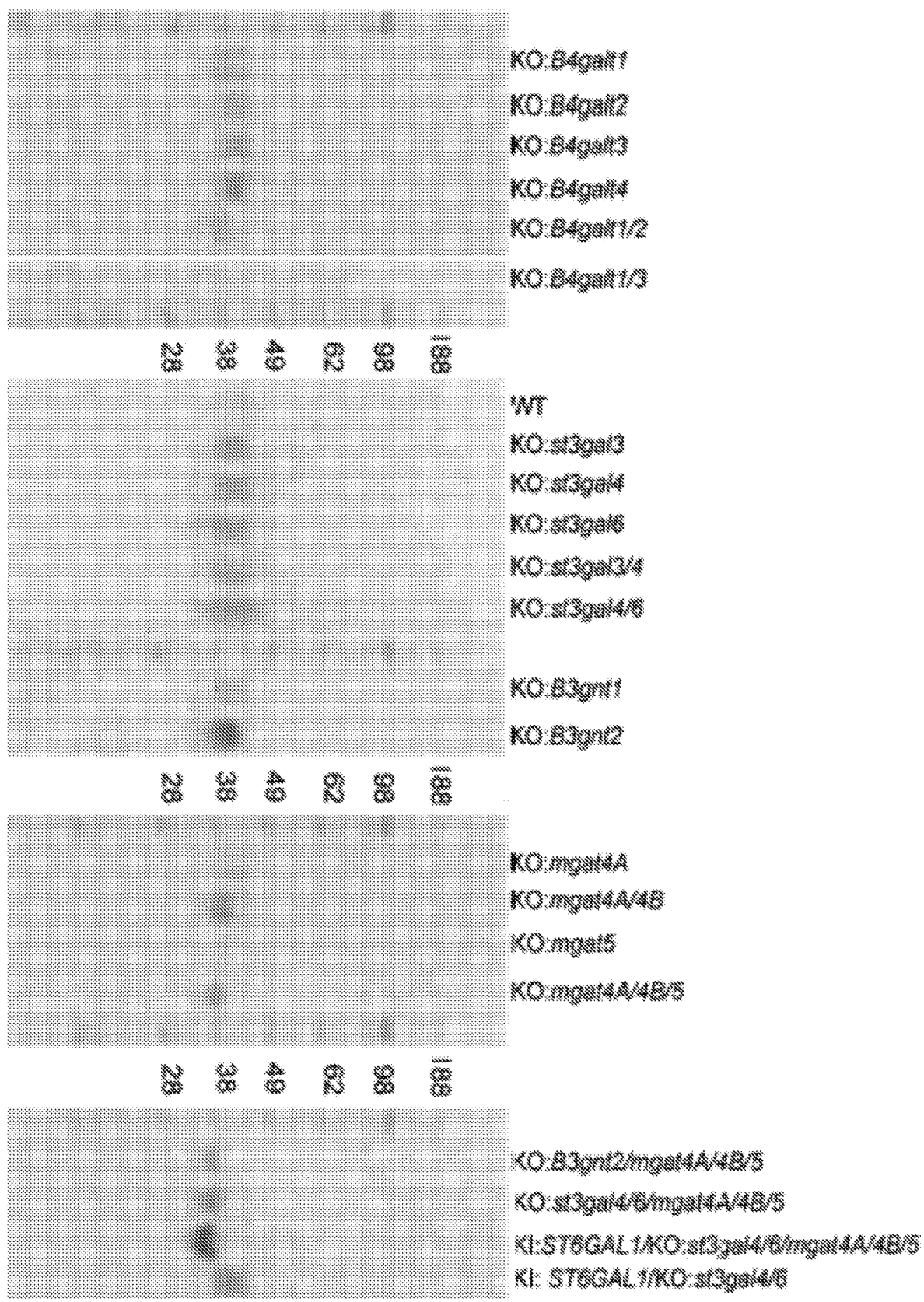
FIG. 9 shows SDS-PAGE Coomassie analysis of purified recombinant EPO expressed in CHO clones. Approximately 1 µg of purified EPO based on OD was loaded.

While poly-LacNAc on N-glycans can confer superior circulatory half-life properties to e.g. EPO, this modification is always incomplete and one of the most heterogeneous and difficult to control for product consistency. CHO cells generally produce low amounts of poly-LacNAc on N-glycans and mainly on tetraantennary structures on the β6arm controlled by MGAT5. Biosynthesis of poly-LacNAc on N-glycans is poorly understood and three genes may be involved, B3gnt1, B3gnt2, and B3gnt8. We screened single gene KO of B3gnt1, B3gnt2, and B3gnt8 with lectin immunocytology using the LEL lectin that recognize poly-LacNAc, and identified B3gnt2 as the key gene controlling the LacNAc initiation in CHO cells (FIG. 5B). In agreement with this, EPO expressed in CHO clones with KO of B3gnt2 and not B3gnt1, resulted in elimination of the minor fraction of poly-LacNAc on EPO (FIG. 1e).

Control of Sialylation

CHO produce almost exclusively α2,3 linked NeuAc capping of N-glycans. All six known ST3Gal transferases are expressed in CHO cells (FIG. 4) and the roles of each of these in sialylation of N-glycans are poorly understood, but candidates are mainly the ST3Gal-III, ST3Gal-IV, and ST3Gal-VI isoforms. We first targeted these three genes individually using immunocytology to evaluate exposure of LacNAc and found that only KO of st3gal4 produced substantial effects (FIG. 7). Analysis of EPO expressed in single and stacked KO clones, showed that loss of st3gal4 and 6 both produced substantial effects, while we found two patterns in clones with KO of st3gal4/6. In WT background KO of st3gal4/6 produced EPO with heterogeneous tetraantennary N-glycans without trace of sialylation (FIG. 1f). KO of st3gal4/6 in combination with mgat4A/413/5 produced biantennary N-glycans without sialylation but increase in poly-LacNAc (FIG. 2b), or in one clone no increase in poly-LacNAc but minor amounts of a mono-sialylated biantennary N-glycan. It is thus possible that targeting of st3gal3/4/6 may be required for complete lack of sialic acid. Regardless, CHO clones without st3gal4 and 6 produced EPO with uncapped LacNAc termini and this opens for de novo engineering of recombinant glycoproteins with α2,6NeuAc capping.

Custom Glycoengineering of CHO to Produce α2,6NeuAc Capped N-Glycans

Figure 2:
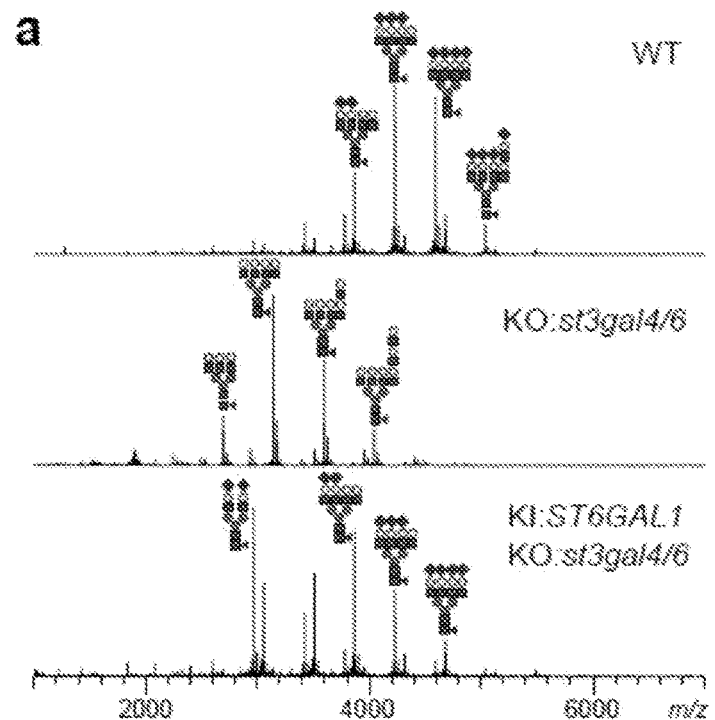
FIG. 2 shows De novo design of sialylation capacity in CHO GS by ZFN targeted knockin. (a) Glycoprofiling of EPO expressed in WT, double st3gal4/6 KO, and st3gal4/6 KO with ST6GAL1 KI, showing that the range of tetraantannary N-glycan structures produced in WT CHO regain sialylation to same degree after KI of ST6GAL1. (b) Glycoprofiling of EPO with triple mgat4A/4B/5 and B3gnt2 KO, showing complete loss of poly-LacNAc on biantennary N-glycans. Glycoprofiling of mgat4A/4B/5 and st3gal4/6 KO without and with KI of ST6GAL1, showing complete loss of sialic acid capping on biantennary N-glycans and complete de novo capping by α2,6 sialic acid on biantennary N-glycans, respectively.
Figure 2:
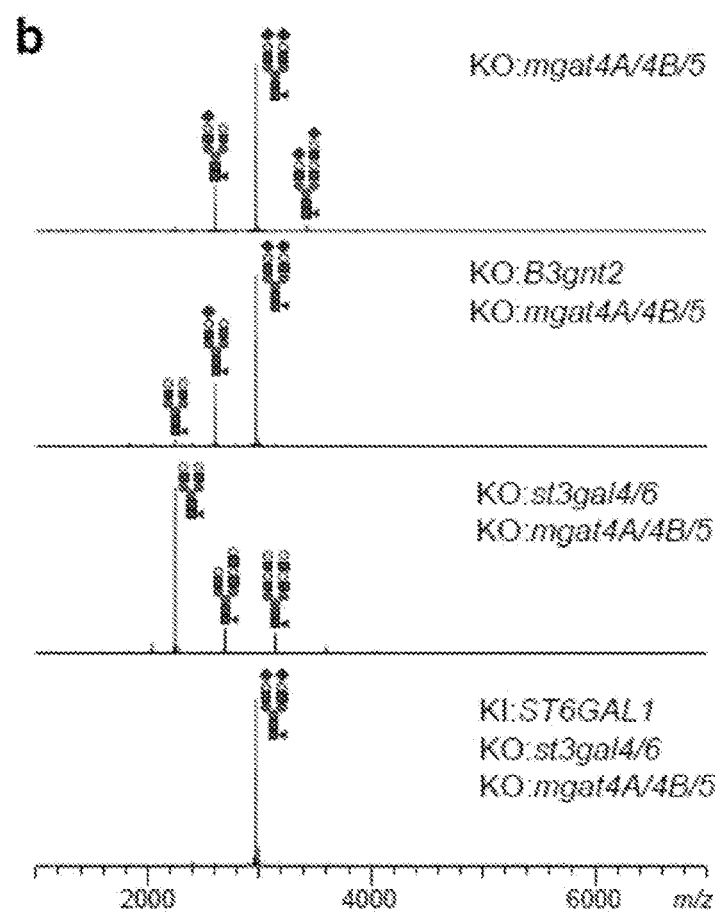

Most glycoproteins in circulation are capped with α2,6NeuAc, while essentially all recombinant therapeutics are produced with α2,3NeuAc. It has been of longstanding interest to produce CHO cells capable of producing homogenous N-glycans with α2,6NeuAc capping. To demonstrate the perspectives for de novo glycoengineering provided by our KO screen, we generated CHO clones capable of producing homogenous α2,6NeuAc capping (FIG. 2). To circumvent past problems with random plasmid integration, we used ZFN targeted knockin (KI) of ST6Gal-I with a modified Obligare strategy into a SafeHarbor integration site. Human ST6GAL1 introduced in CHO with KO of st3gal4/6 produced the complete range of N-glycan antennary structures with normal degree of NeuAc capping (FIG. 2a), and when introduced in CHO with additional KO of mgat4A/4B/5 EPO was produced with homogenous biantennary N-glycans capped by α2,6NeuAc (FIG. 2b). Interestingly, de novo introduction of ST6GAL1 also abrogated the minor amounts of poly-LacNAc formed on biantennary structures when sialylation was eliminated (FIG. 2b), demonstrating that KO of B3gnt2 as well was unnecessary. Thus, we could introduce capacity for α2,6NeuAc sialylation and produce a CHO cell capable of producing N-glycoproteins with homogenous α2,6NeuAc capping. The Obligare KI strategy was highly efficient with approximately 30-50% single cloned cells expressing ST6Gal-I as evaluated by antibody and lectin immunocytology (FIG. 7), while relying on ZFN-mediated homologous recombination did not produce successful targeted integration in CHO cells. The ST6GAL1

KI clones were stable for over 20 passages as evaluated by immunocytology with SNA lectin and 1B2 MAb (not shown).

In summary, the KO screen performed identifies the key glycogenes controlling decisive steps in N-glycosylation of proteins in CHO (FIG. 3), and demonstrates remarkable plasticity in tolerance for glycoengineering without evidence of unexpected compensatory changes in glycosylation. We provide design strategies for generation of CHO host cells with homogeneous biantennary N-glycans with and without sialylation that will serve as platforms for de novo build up of desired glycosylation capacities. The matrix provides general guidance for custom design of the N-glycosylation capacity of CHO, which likely can be used for any CHO host line and even established production lines. We demonstrate the feasibility of de novo engineering of homogenous glycosylation capacities by introducing α2,6sialylation in CHO by a precise KI strategy in CHO lines with KO of endogenous α2,3sialyltransferase genes. The panel of CHO cells generated will enable dissection and de novo design of N-glycosylation for any protein therapeutics, and production of a diverse array of glycoforms of therapeutic proteins will enable simple evaluation and selection of optimal design. The advent of precise gene engineering clearly holds promise for a new era for the biggest producer of glycoprotein therapeutics today, the CHO cell.

Methods

ZFN targeting of glycogenes in CHO cells. All gene targeting was performed in the CHOZN GS-/- (Glutamine Synthase) clone produced by ZFN KO and provided by Sigma-Aldrich, St. Louis, Mo., or in CHO-K1 obtained from ATCC. All CHO media, supplements and other reagents used were obtained from Sigma-Aldrich unless otherwise specified. CHO GS cells were maintained as suspension cultures in EX-CELL CHO CD Fusion serum-free media, supplemented with 4 mM L-glutamine. Cells were seeded at $0.5 \times 10^6$ cells/mL in T25 flask (NUNC, Denmark) one day prior to transfection. $2 \times 10^6$ cells and 2 μg endotoxin free plasmid DNA of each ZFN (Sigma, USA) were used for transfection. Each ZFN were tagged with GFP and Crimson by a 2A linker. Transfections were conducted by electroporation using Amaxa kit V and program U24 with Amaxa Nucleofector 2B (Lonza, Switzerland). Electroporated cells were subsequently placed in 3 mL growth media in a 6-well plate. Cells were moved to 30° C. for a 24 h cold shock. 72 h post nucleofection the 10-15% highest labelled cell pool for both GFP and Crimson were enriched by FACS. Cells were single cell FACS sorted again one week later to obtain single clones in round bottom 96 well plates. KO clones were identified by insertion deletion analysis (IDAA) as recently described, as well as when possible by immunocytology with appropriate lectins and monoclonal antibodies. Selected clones were further verified by TOPO for in detail characterization of mutations introduced. The strategy enabled fast screening and selection of KO clones with frameshift mutations, and on average we selected 2-5 clones from each targeting event. RNAseq analysis of CHO clones was performed by BGI.

Recombinant expression of human EPO in CHO cells. An expression construct containing the entire coding sequence of human EPO cloned into pcDNA3.1/myc-His (C-terminal tags) was synthesised by Genewiz, USA. EPO is a 166 amino acid protein with N-glycans at Asn24, Asn38, and Asn83. CHO cells were co-transfected with EPO and GFP plasmids, followed by a FACS to enrich clones expressing GFP. Stable transfectants were selected in 0.4 mg/ml Zeocin (Invitrogen), Positive stable clones were screened by direct enzyme-linked immunosorbent assays (ELISA) using monoclonal anti-His antibody(C-Term)-HRP antibody (Invitrogen). His-tagged recombinant human EPO was purified by nickel affinity purification (Invitrogen, US). Media was mixed 3:1 (v/v) in 4× binding buffer (200 mM Tris, pH8.0, 1.2 M NaCl) and applied to 0.3 ml packed NiNTA agarose (Invitrogen), pre-equilibrated in binding buffer (50 mM Tris, pH 8.0, 300 mM NaCl). The column was washed with binding buffer and then bound protein was eluted with binding buffer with additional 250 mM imidazole. Fractions containing EPO were determined by SDS-PAGE and further purified on a reverse-phase HPLC purification with a Jupiter C4 column (5 μm, 300 Å, column 250×4.6 mm) (Phenomenex), using 0.1% trifluoroacetic acid (TFA) and a gradient of 10-100% acetonitrile. Purity was evaluated by Coomassie staining of SDS-PAGE gels and proteins quantified by BCA Protein Assay Kit (Thermo Scientific).

N-glycan profiling of recombinant EPO in CHO clones. Approximately 25 μg purified EPO was digested by 2 U PNGase F (Roche Diagnostics, Mannheim, Germany) in 50 mM ammonium bicarbonate at 37° C. for overnight. Released N-glycans were separated from rhEPO using in-house packed Stagetips (Empore disk-C18, 3M) and incubated in 100 mM ammonium acetate, pH 5.0 for 60 min at 22° C. The N-glycans were dried in glass vials and permethylated as described previously. Permethylated N-glycans were extracted with chloroform and desalted by washing the organic phase repeatedly with deionized water. The organic phase was evaporated over a stream of nitrogen gas and the permethylated N-glycans were dissolved in 20 μL 50% methanol. Finally, 1 μL sample was co-crystalized with 1 μL matrix composed of 2,5-dihydroxybenzoic acid (10 mg/ml) in 70% (v/v) acetonitrile, 0.1% (v/v) trifluoroacetic acid and 2.5 mM sodium acetate. Permethylated N-glycans were analyzed by positive mode MALDI-TOF (Autoflex Speed, BrukerDaltronics, Bremen) operated in the reflector mode with data acquisition in the m/z 1000-7000 mass range.

Example 2

Determining the Glycosyltransferase Repertoire Expressed in a Mammalian CHO Cell Line.

CHO-K1 was obtained from ATCC and CHO-GS (CHOZN GS$^{-/-}$ (Glutamine Synthase) clone produced by ZFN KO) was obtained from Sigma-Aldrich, St. Louis, Mo. All CHO media, supplements and other reagents used were obtained from Sigma-Aldrich unless otherwise specified. CHO-GS ells were maintained as suspension cultures in EX-CELL CHO CD Fusion serum and animal component free media, supplemented with 4 mM L-glutamine. CHO cells were seeded at $0.25 \times 10^6$ cells/ml in 6 well plate and harvested at exponential phase 48 h post inoculation for total RNA extraction with RNeasy mini kit (Qiagen). RNA intergrity and quality were checked by 2100-Bioanalyser (Agilent Technologies). Library construction and next generation sequencing was performed using Illumina HiSeq 2000 System (Illumina, USA) under standard conditions as recommended by the RNASeq service provider. The aligned data was used to calculate the distribution of reads on CHO reference genes and coverage analysis was performed. Only alignment results that passed QC were used for downstream gene expression analysis.

RNAseq analysis was performed on two common CHO lines (CHO-K1, CHO-GS) and two independent CHO-GS triple mgat4a/4b/5 KO clones (ZFN91-1C8, ZFN91-2A6) (TABLE 3). The reported RNAseq analysis of CHO-K1 was included for reference, and this was largely similar to our analyses except that the relative expression levels were higher. Importantly, a few genes including e.g. galnt1 and mgat4b, which was reported not to be expressed in CHO-K1 previously (Xu, Nagarajan et al. 2011), were found to be expressed. Moreover, in the case of mgat4b this gene was found to be essential for the glycoengineering experiments carried out here.

An important observation of the analysis of CHO transcriptomes was that the expression profiles of glycogenes in the two triple KO clones analyses were identical to those of the parental CHO lines, demonstrating that the targeted ko gene editing performed in the CHO cell lines did not alter expression of other glycosyltransferase genes.

Example 3

Gene Inactivation of Glycosyltransferase Genes in the N-Glycosylation Pathway (Deconstruction).

All the glycosyltransferase gene targeted inactivation were performed in CHO-GS and/or in CHO-K1 and cells were grown as described in Example 2. Cells were seeded at $0.5 \times 10^6$ cells/mL in T25 flask (NUNC, Denmark) one day prior to transfection. $2 \times 10^6$ cells and 2 µg endotoxin free plasmid DNA of each ZFN (Sigma, USA) were used for transfection. Each ZFN was tagged with GFP and Crimson by a 2A linker (Duda, Lonowski et al. 2014). Transfections were conducted by electroporation using Amaxa kit V and program U24 with Amaxa Nucleofector 2B (Lonza, Switzerland). Electroporated cells were subsequently plated in 3 mL growth media in a 6-well plate. Cells were moved to 30° C. for a 24 h cold shock. 72 h post nucleofection the 10-15% highest labeled cell pool for both GFP and Crimson were enriched by FACS. We utilized recent developed methods for enriching KO clones by FACS (GFP/Crimson tagged ZFNs) (Duda, Lonowski et al. 2014) and high throughput screening by an amplicon labeling strategy (IDAA) (Zhang, Steentoft et al. submitted). Cells were single cell FACS sorted one week later to obtain single clones in round bottom 96 well plates. KO clones were identified by IDAA, and when possible also by immunocytology with appropriate lectins and monoclonal antibodies. Selected clones were further verified by TOPO cloning of PCR products (Invitrogen, US) for in detail Sanger sequencing characterization of mutations introduced in individual TOPO clones. The strategy enabled fast screening and selection of KO clones with appropriate inactivation mutations as outlined herein, and on average we selected 2-5 clones from each targeting event.

The majority of KO clones exhibited out of frame causing insertions and/or deletions (indels) in the range of ±20 bps, and most targeted genes were present with two alleles, while some (mgat4B and mgat5) were present with 1 or 3 alleles, respectively (TABLE 4).

TABLE 4 lists all individual and stacked glycosyltransferase gene inactivation events and the order (ancestry line) of stacking of glycosyltransferase gene inactivation in cells to produce a deconstruction matrix of the N-glycosylation pathway.

Example 4

Gene Insertion of Glycosyltransferase Genes in the N-Glycosylation Pathway (Reconstruction).

Target specific integration (knockin/KI) was directed towards the CHO Safe Harbor #1 locus (S. Bahr et al., *BMC Proceedings* 2013, 7(Suppl 6):P3.doi:10.1186/1753-6561-7-S6-P3). A modified ObLiGaRe strategy (33) was used where two inverted ZFN binding sites flank the donor plasmid gene of interest to be knocked in. Firstly a shuttle vector designated ObLiGaRe-2X-Ins was synthesized (TABLE 5). ObLiGaRe-2X-Ins was designed in such a way, that any cDNA sequence encoding protein of interest can be inserted into a multiple cloning site where transcription is driven by CMV IE promotor and a BgH terminator. In order to minimize epigenetic silencing, two insulator elements flanking the transcription unit were inserted. In addition an AAVS1 "landing pad" was included at the 3' end of ObLiGaRe-2X-Ins just upstream of the 3' inverted ZFN binding site. A full ST6GAL1 open reading frame was inserted directionally into ObLiGaRe-2X-Ins generating ObLiGaRe-2X-Ins-ST6GAL1 (TABLE 5). Transfection and sorting of clones were performed as described in EXAMPLES 2 and 3. Clones were initially screened by positive SNA lectin staining and selected clones further analyzed by 5' and 3' junction PCR to confirm correct targeted integration event into Safe-harbor #1 site in the CHO st3gal4/6 KO clones. The allelic copy number of integration was determined by WT allelic PCR. Subsequently, full human MGAT4A open reading frame was inserted directionally into 2nd allele of Safe Harbor #1 in ST6GAL1 KI clone, followed by inserting full human MGAT5 to AAVS1 "landing pad", which was included at the 3' end of ObLiGaRe-2X-Ins just upstream of the 3' inverted ZFN binding site (TABLE 5).

Example 5

Recombinant Production of Human EPO and IgG in Gene Edited Mammalian CHO Cells.

Expression constructs containing the entire coding sequence of human EPO and a therapeutic IgG cloned into pcDNA3.1/myc-His (C-terminal tags) and pBUDCE4.1 (Invitrogen), respectively, were synthesized by Genewiz, USA. EPO is a 166 amino acid protein with N-glycans at Asn24, Asn38, and Asn83, and IgG has a single N-glycan at Asn297, respectively. Wt or KO CHO cells were transfected with EPO or IgG and maintained at 37° C. as suspension cultures in EX-CELL CHO CD Fusion serum-free media, supplemented with 4 mM L-glutamine and 400 ug/ml Zeocin in 5% $CO_2$ incubator. Clones were scaled up and grown in T75 flasks at a seeding density of $0.5 \times 10^6$ cells/ml, and harvested 72 h or 96 h later. Cell viability was higher than 90% in all reporter expressing clones and viable cell density are between $2-3 \times 10^6$ cells/ml upon harvest. Cells were removed by centrifugation at 300 g for 5 min, and the supernatant were stored at −80° C. His-tagged recombinant human EPO was purified by nickel affinity purification (Invitrogen, US). Media was mixed 3:1 (v/v) in 4× binding buffer (200 mM Tris, pH 8.0, 1.2 M NaCl) and applied to 0.3 ml packed NiNTA agarose (Invitrogen), pre-equilibrated in binding buffer (50 mM Tris, pH 8.0, 300 mM NaCl). The column was washed with binding buffer and then bound protein was eluted with binding buffer with additional 250 mM imidazole. Fractions containing EPO were determined by SDS-PAGE and further purified on a reverse-phase HPLC purification with a Jupiter C4 column (5 µm, 300 Å, column 250×4.6 mm) (Phenomenex), using 0.1% trifluoroacetic acid (TFA) and a gradient of 10-100% acetonitrile. IgG was purified by HiTrap™ Protein G HP (GE Healthcare, US) pre-equilibrated/washed in PBS and eluted with 0.1 M Glycine (pH 2.7). Purity of protein was evaluated by Coomassie staining of SDS-PAGE gels, and proteins were quantified by BCA Protein Assay Kit (Thermo Scientific, Rockford, US).

Example 6

N-Glycan Profiling of Purified EPO and IgG.

Approximately 25 µg purified EPO was digested with 2 U PNGase F (Roche Diagnostics, Mannheim, Germany) in 50 mM ammonium bicarbonate at 37° C. for overnight. For IgG, 35 µg samples were initially digested (overnight, 37° C.) with trypsin in 50 mM ammonium bicarbonate, and then heated at 95° C. for 15 min and cooled to RT before PNGase F digestion as above. Released N-glycans were separated from intact EPO or IgG tryptic digest using in-house packed Stagetips (Empore disk-C18, 3M) and incubated in 100 mM ammonium acetate, pH 5.0 for 60 min at 22° C. The N-glycans were split in three equal aliquots. One-third was dried in glass vials and permethylated as described previously (Ciucanu and Costello 2003) and the remainder was saved for the native N-glycan analysis. Permethylated N-glycans were extracted with chloroform and desalted by washing the organic phase repeatedly with deionized water. The organic phase was evaporated over a stream of nitrogen gas and the permethylated N-glycans were dissolved in 20 µL 50% (v/v) methanol. Finally, 1 µL sample was co-crystalized with 1 µL matrix composed of 2,5-dihydroxy-benzoic acid (10 mg/ml) in 70% (v/v) acetonitrile, 0.1% (v/v) trifluoroacetic acid and 2.5 mM sodium acetate. Permethylated N-glycans were analyzed by positive mode MALDI-TOF (Autoflex Speed, BrukerDaltronics, Bremen) operated in the reflector mode with data acquisition (2000 shots/spot) in the m/z 1000-7000 mass range. Glycan compositional analysis of all spectra was performed by the SysBioWare platform and is presented in Supplementary Table 4 (Vakhrushev, Dadimov et al. 2009). Released native N-glycans were reconstituted in MeOH/$H_2O$ (1/1; v/v, containing 50 mM Ammonium bicarbonate) at the concentration of 0.5 pmol/µl and analyzed on an OrbiTrap Fusion MS (Thermo San Hose, USA). Samples were directly infused via EASY-Spray and analysed by negative ion mode. Flow rate was set to 500 nl/min, spray voltage 1,900-2,100 V, and ion transfer tube temperature 275° C. Precursor ions were selected (isolation width, m/z 3) and subjected to HCD fragmentation at 35% normalized collision energy (default charge state, z=2). All spectra were recorded at resolution 120,000.

Example 7

Inactivation of Glycosyltransferase Genes by Tandem Single Stranded Oligo Deoxy Nucleotide (ssODN)/ZFN Precise Multi Exon Gene Editing.

In this example, gene inactivation is performed by eliminating exons encoding the N-terminal cytoplasmic tail, transmembrane region, and parts of the stem region of the targeted glycosyltransferase gene. The target region deletion is mediated by use of the tandem single stranded oligo deoxy nucleotide (ssODN)/ZFN approach (Duda, Lonowski et al. 2014). The ZFN target site is selected in or as close as possible around the sequence coding for the transmembrane region of the glycosyltransferase. As an example CHO mgat4a is targeted using CHO mgat4a ComposR ZFN's (Sigma) and an ssODN possessing 60 bp homology arm sequences flanking the 5' UTR region including translational start site and 3' flanking mgat4a exon2 ZFN target site (mgata ssODN: gagagagattggtcttgcttgtcatcaccaacgtatgaacc-agtgtgatggtgaaatgagtcGCCGTGCAGGAGCAGCAACTA-ACGGAAGTAACACTGCATTGACTACATTTTCAGGT-AC) (5' UTR region shown in lower case, partial ZFN cut site in lower case italics and 3' flanking exons 2 ZFN binding site in upper case), thus removing the exon 1-2 encoding cytoplasmic tail, transmembrane domain and stem of mgat4a. Gene inactivation is performed in CHO-GS as described in Example 2 including mgata ssODN. Transfections were conducted by electroporation using Amaxa kit V and program U24 with Amaxa Nucleofector 2B (Lonza, Switzerland). Electroporated cells were subsequently placed in 3 mL growth media in a 6-well plate. Cells were moved to 30° C. for a 24 h cold shock. 72 h post nucleofection the 10-15% highest labeled cell pool for both GFP and Crimson were enriched by FACS. Cells were single cell FACS sorted again one week later to obtain single clones in round bottom 96 well plates. Enrichment of KO clones was performed by FACS (GFP/Crimson tagged ZFNs). Clones are analyzed by PCR using primers Mgataex1F (5'-TATCCACTGTGTTGCTTGCTG-3')/Mgataex2R (5'-Actgctcttccagaggtcctg d-3'), only detecting correctly target deleted clones. Mono/bi-allelic targeting was determined by PCR wt allele presence detection using primers Mgataex2F (5'-gaacgccttcgaatagctgaacatagg-3')/Mgataex2R. Genetic PCR results are validated by Southern blot analysis using an intron2 specific probe detecting correct removal of 37 KBp intron1 target region carrying diagnostic KpnI sites.

Example 8

Inactivation of Glycosyltransferase Genes by Multi-Exon Dual CRISPR/Cas9 Gene Editing.

Gene inactivation is ensured by removal of exons encoding the cytoplasmic tail/transmembrane and parts of the stem encoded sequences of the desired gene needed to be inactivated. Target region deletion is mediated by use of a pairs of CRISPR/Cas9-gRNAs targeting the flanking regions encoding Mgat4a signal sequence, transmembrane anchoring and stem-regions. CHO Mgat4a is targeted using CHO Mgat4a CRISPR/Cas9 gRNA's Mgat4aEx1gRNA (5'-GGTATACCACATGGCAAAATGGG-3') specific for exon1 and Mgat4aEx2gRNA (5'-GTC-CAACAGTTTCGCCGTGCAGG-3') specific for exon2. Both gRNA's were cloned into the BbsI (NEB, USA) gRNA target site of px458 (Addgene, USA) encoding GFP tagged S. pyogenes Cas9 and U6 promoter driven gRNA casette, generating px458-CRISPR-Mgat4aex1gRNA and px458-CRISPR-Mgat4aex2gRNA. Precise gene editing by nucleofection using 2 ug of these CRISPR/Cas9-Mgat4a editing tools and target selection validation was performed in CHO-GS cells as described in Examples 3 and 7.

Example 9

Enzymatic GlycoPEGylation of Glycoproteins Monoantennary N-Glycans.

KO of mgat2 in combination with mgat4a/4b/5 in CHO cells resulted in homogeneous monoantennary N-glycans when EPO was expressed (FIG. 32).

Figure 33:
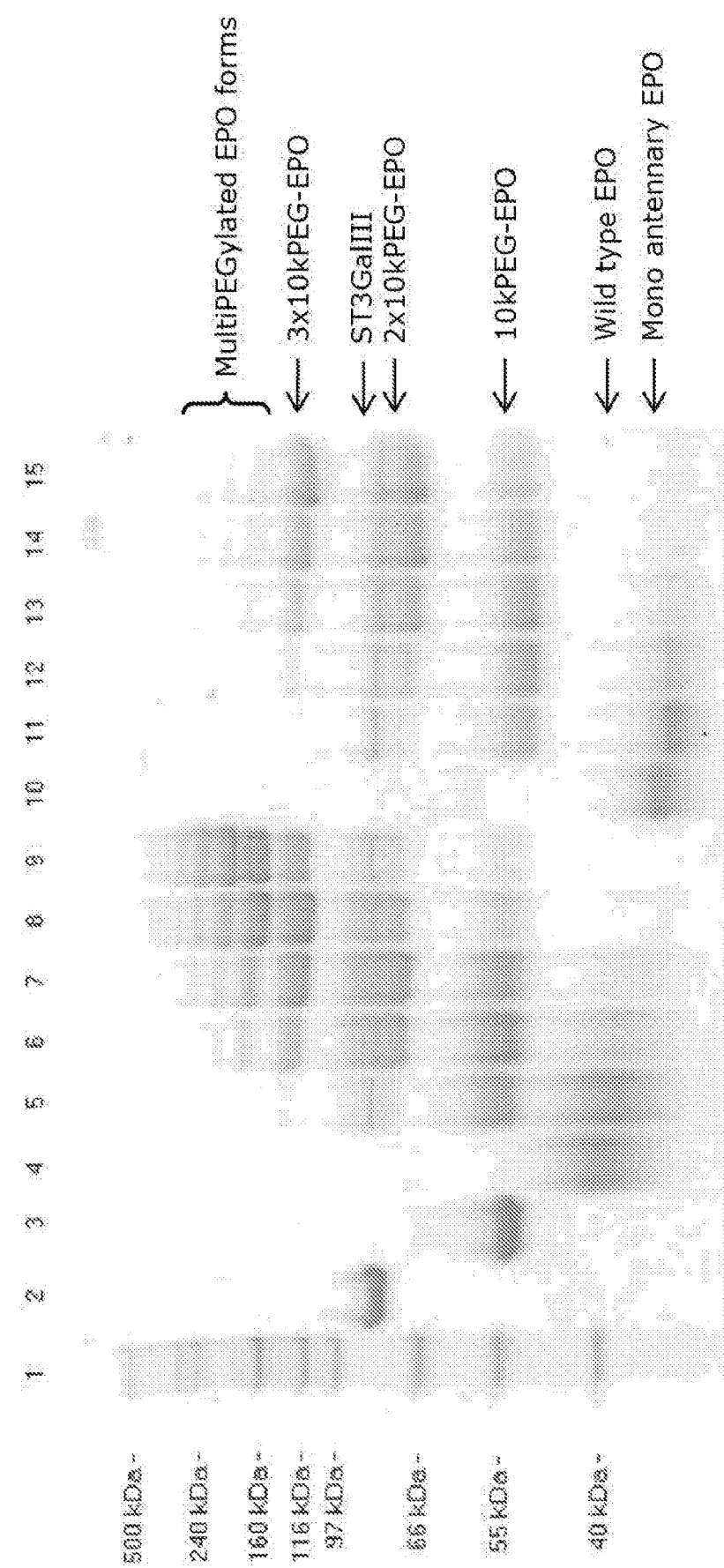
FIG. 33 SDS-PAGE gel analysis of glycoPEGylation reactions of recombinant wildtype EPO-Myc-His6 and recombinant EPO-Myc-His6 with monoantennary N-glycans. Lanes contained: (1) HiMark Standard, (2) ST3Gal3, (3) Sialidase, (4) wt hEPO, wt EPO-Myc-His6 glycoPEGylated with ST3Gal-III and (5) 1×, (6) 5×, (7) 10×, (8) 25×, (9) 50×10 kDa-PSC reagent respectively, (10) EPO-Myc-His6 glycosylation variant and EPO-Myc-His6 glycosylation variant glycoPEGylated with ST3Gal-III and (11) 1×, (12) 5×, (13) 10×, (14) 25×, (15) 50×10 kDa-PSC reagent. Bands above approximately 160 kD indicates GlycoPegylation with more than two PEG chains at one or more N-glycans.
Figure 34:
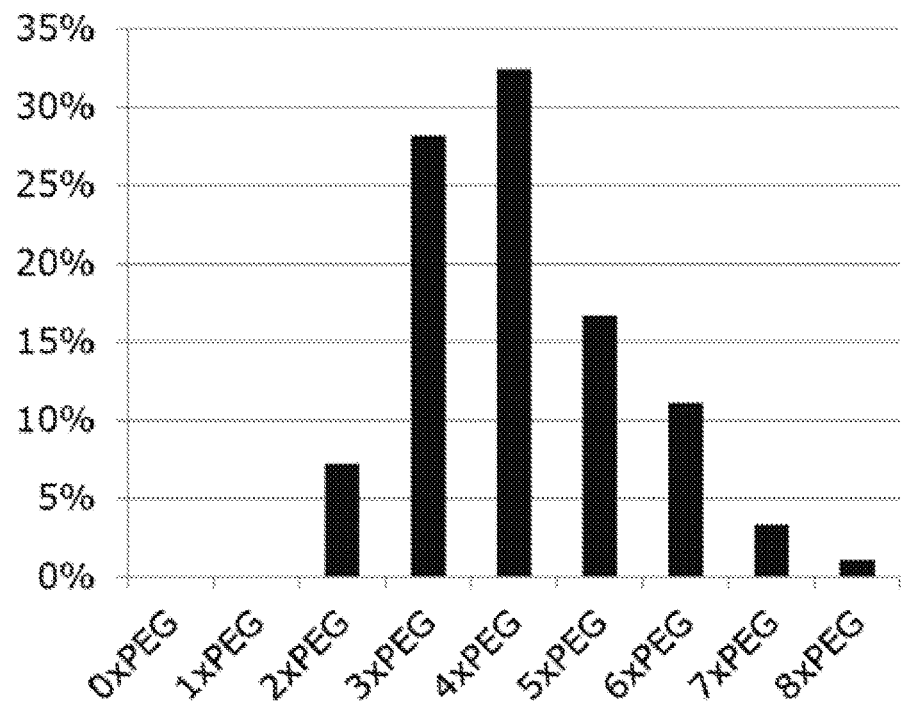
FIG. 34 Quantification of number of attached PEG chains by densitometry of SDS-PAGE gels. (PANEL A) Product profile of enzymatic 10 kDa-GlycoPEGylation reaction with EPO-Myc-His6 produced in ordinary CHO cell lines. (PANEL B) Product profile of enzymatic 10 kDa-GlycoPEGylation reaction with EPO-Myc-His6 produced in Mgat2/4a/4b/5 KO CHO cell lines. Profiles A and B were obtained by densitometry measurements on lane 9 and lane 15 in FIG. 33, respectively FIG. 35 Glycoprofiling of EPO expressed in CHO cells with KO of B3gnt2 stacked with KO of Cosmc/Pomgnt1/B4galt7 (this latter triple KO is seen in FIG. 30D) (top panel), double KO of B4galt5 and B4galt6 (second panel), double KO's of Mgat2 and Mgat4B (third panel) and double KO of Mgat2 and Mgat5 (lower panel). Compared to background (see FIG. 30D) KO of B3gnt2 abolishes poly-LacNac. KO of B4galt5 and B4galt6 gives more LacNac when comparing with wt EPO (FIG. 31). The two last panels with double KO's of Mgat2/4b or Mgat2/5 both show that monoantennary can be obtained with double KO's so KO of four genes Mgat2/4A/4B/5 is not needed (compare with FIG. 32D).
Figure 34:
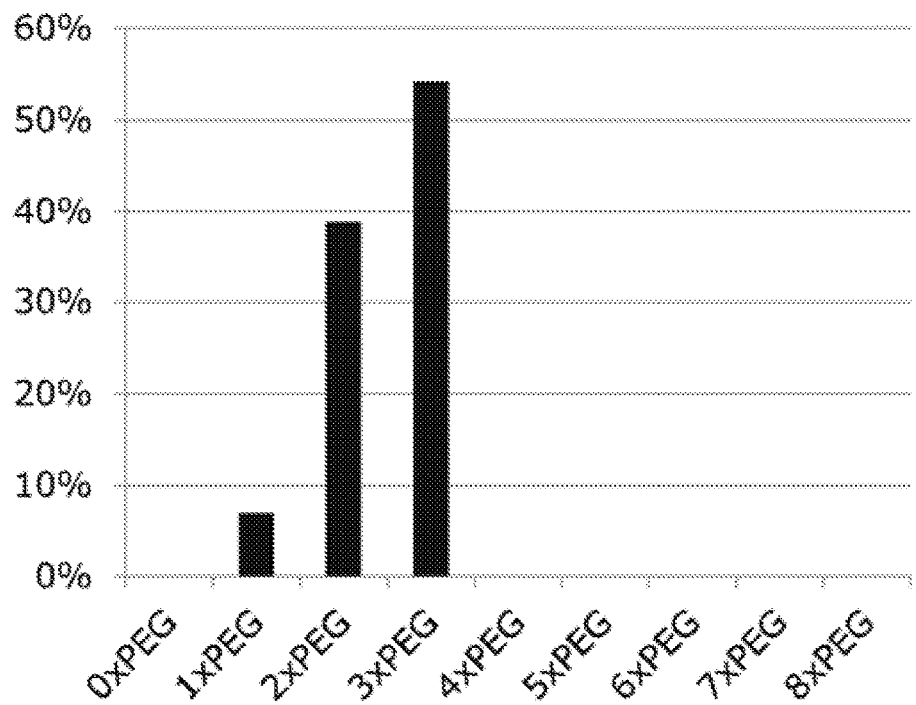

Reintroduction of human MGAT4A as well as MGAT4A and 5 in combination by knockin resulted in tri and tetraantennary N-glycans, respectively (FIG. 32), demonstrating that the monoantennary N-glycan obtained is linked β1-2 to the α1-3Man branch controlled by mgat1. Enzymatic glycopegylation or transfer of other compounds by sialyltransferases and CMP-(PEG)NeuAc or relevant modified donor was tested using EPO as an example (FIGS. 33-34).

Material and Methods Glycovariants of EPO-Myc-His6 were produced in CHO with KO mgat2/4a/4b/5 and purified on a nickel-NTA column and buffer exchanged into 100 mM Tris, 150 mM NaCl, 0.005% NaN3, pH 7.2 buffer as described in Example 4. Wild type EPO-Myc-His6 with normal glycosylation profile was produced in non modified CHO cells and in similar way purified on a nickel-NTA column before buffer exchanged into 100 mM Tris, 150 mM NaCl, 0.005% NaN3, pH 7.2 buffer. Protein concentrations were determined by NanoDrop Lite Spectrophotometer (Thermo Scientific™). Sialyltransferase (ST3Gal-III; 1.35 U/ml) in 20 mM HEPES, 120 mM NaCl, 50% glycerol, pH 7.0 was obtained from FujiFilm Diosynth Biotechnologies, Japan. Sialidase (*Artherobacter urifaciens*) was produced at Novo Nordisk A/S and used as a 200 U/ml solution in 20 mM HEPES, 120 mM NaCl, 50% glycerol, pH 7.0. Support bound neuraminidase (*Clostridium perfringens*) on agarose was obtained from Sigma (Cat. # N5254-10UN). The resin was washed extensively in MilliQ water before use. 10 k-PSC (cytidine-5'-monophosphoryl-[5-(N-10 kDa-methoxypolyoxyethylene-oxycarboxamido)glycylamido-3, 5-dideoxy-D-glycero-n-galacto-2-nonulopyranosuronate], Lot: 3605-A-R0-01-61-1) was obtained from Albany Molecular Research, Inc, Albany, N.Y. 12203, US. 10 k-PSC was produced as described in WO03031464. The tris-buffer used in examples below contained 50 mM tris-HCl, 150 mM NaCl, pH 7.6.

SDS-PAGE gel electrophoresis was performed on NuPage precast gels (NuPage 7 Tris-Acetate Gel, 15 wells, Invitrogen cat. No. EA03555BOX) using NuPage Tris-Acetate SDS Running buffer (Invitrogen cat. No. # LA0041). Samples (0.15 mg/ml) were added NuPage Sample Reducing Agent (Invitrogen cat. No. NP0004) and LDS sample buffer (Invitrogen cat. No. NP0008) and heated to 70° C. for 10 min before gel loading. HiMark HMW (Invitrogen cat. No. LC6060) was used as standard. Electrophoresis was performed at 150 V, 120 mA & 25 W for 60 min. Gels were stained with SimplyBlue SafeStain (Invitrogen cat. No. LC5688) according to Invitrogen protocols. Coomasie stained gels were analysed by densitometry using GelQuant software and methods described previously (Rehbein and Schwalbe 2015) (FIG. 34).

HPLC analysis of GlycoPEGylated EPO-Myc-His6 conjugates of the invention was performed as follows. Samples were analysed in non-reduced form. A Zorbax 300SB-C3 column (4.6×50 mm; 3.5 um Agilent, Cat. No.: 865973-909) was used. Column was operated at 30° C. 2.5 ug sample was injected, and column eluted with a water (A)—acetonitrile (B) solvent system containing 0.1% trifluoroacetic acid. The gradient program was as follows: 0 min (25% B); 4 min (25% B); 14 min (46% B); 35 min (52% B); 40 min (90% B); 40.1 min (25% B).

Enzymatic glycoPEGylation of EPO-Myc-His6 variants was performed by either an one-pot method using sialidase in combination with ST3Gal-III, or by a sequential method where the EPO-Myc-His6 variant was first reacted with agarose-neuraminidase gel for 3 h at 25° C., then after transferring the supernatant to a fresh vial reacted with the ST3Gal-III and PSC reagent. The one-pot method relies on the fact that *Artherobacter urifaciens* sialidase is unable to desialylate PEGylated sialosides. Use of recombinant glycoproteins with monoantennary N-glycans without sialic acid capping as invented eliminates the need for prior desialylation.

GlycoPEGylation of recombinant human erythropoietin—Recombinant wildtype EPO-Myc-His6 produced in CHO cell lines was dissolved in 100 mM Tris, 150 mM NaCl, 0.005% NaN3 (pH 7.2) to a concentration of 1.17 mg/ml. 10 k-PSC reagent (2.0 mg) was dissolved in 100 ul 50 mM Tris-HCl, 150 mM NaCl (pH 7.6) to a concentration of 20 mg/ml. ST3Gal-III and AUS were both dissolved in 20 mM HEPES, 120 mM NaCl, 50% glycerol, pH 7.0 to a volumetric concentration of 1.35 U/ml and 200 U/ml respectively. Reagents were mixed according to scheme below:

|  | Unit | Exp. 1 | Exp. 2 | Exp. 3 | Exp. 4 | Exp. 5 |
|---|---|---|---|---|---|---|
| wtEPO | ug | 10 | 10 | 10 | 10 | 10 |
| 10k-PSC | eq | 1 | 5 | 10 | 25 | 50 |
| ST3Gal3 | mU/ug wtEPO | 0.196 | 0.196 | 0.196 | 0.196 | 0.196 |
| Sialidase | U/ml | 5 | 5 | 5 | 5 | 5 |
| Tris buffer | ul | 9.0 | 8.4 | 7.6 | 5.3 | 1.3 |
| Final volume | ul | 28.45 | 28.45 | 28.45 | 28.45 | 28.45 |
| Final [wtEPO] | mg/ml | 0.35 | 0.35 | 0.35 | 0.35 | 0.35 |

Reactions were incubated for 18 h at 32° C. Samples were then analysed by HPLC and SDS-PAGE (FIG. 33, lanes 5-9).

GlycoPEGylation of erythropoietin produced in CHO cells with KO of mgat2/4A/4B/5—Recombinant wtEPO-Myc-His6 glycosylation variant produced in Mgat2/4a/4b/5 knock-out CHO cell line was dissolved in 100 mM Tris, 150 mM NaCl, pH 7.2 to a concentration of 0.585 mg/ml. 10 k-PSC reagent (2.0 mg) was dissolved in 100 ul 50 mM Tris-HCl, 150 mM NaCl, pH 7.6 to a concentration of 20 mg/ml. ST3GalIII and AUS were both dissolved in 20 mM HEPES, 120 mM NaCl, 50% glycerol, pH 7.0 to a volumetric concentration of 1.35 U/ml and 200 U/ml respectively. Reagents were mixed according to scheme below:

|  | Unit | Exp. 1 | Exp. 2 | Exp. 3 | Exp. 4 | Exp. 5 |
|---|---|---|---|---|---|---|
| EPO-Myc-His6 | ug | 10 | 10 | 10 | 10 | 10 |
| 10k-PSC | eq | 1 | 5 | 10 | 25 | 50 |
| ST3Gal3 | mU/ug EPO | 0.196 | 0.196 | 0.196 | 0.196 | 0.196 |
| Sialidase | U/ml | 5 | 5 | 5 | 5 | 5 |
| Tris buffer | ul | 9.0 | 8.4 | 7.6 | 5.3 | 1.3 |
| Final volume | ul | 28.45 | 28.45 | 28.45 | 28.45 | 28.45 |
| Final [EPO] | mg/ml | 0.35 | 0.35 | 0.35 | 0.35 | 0.35 |

Reactions were incubated for 18 h at 32° C. Samples were then analysed by HPLC and SDS-PAGE (FIG. 22, lanes 11-15).

Two step glycoPEGylation reaction of recombinant human erythropoietin—EPO-Myc-His6 (272 ug) in 100 mM Tris, 150 mM NaCl, 0.005% NaN3, pH 7.2 (0.214 mg/ml) was treated with prewashed immobilized sialidase (150 ul suspension, 150 mU) for 3 h at room temperature. Resin was then removed by filtration. The filtrate was analysed by LC-MS to confirm formation of asialo EPO-Myc-His6 in monoantennary N-glycan form (calculated mass 25,464.97 Da, analysis 25,465.30 Da).

| Calc. average mass | Found | Assignment |
|---|---|---|
| 26921.23 Da | 26921.53 Da | Penta sialylated EPO-myc-His6 containing 3 mono antennary N-glycanes and one O-glycan |
| 26629.98 Da | 26630.34 Da | Tetra sialylated EPO-myc-His6 containing 3 mono antennary N-glycanes and one O-glycan |
| 26338.72 Da | 26339.16 Da | Tri sialylated EPO-myc-His6 containing 3 mono antennary N-glycanes and one O-glycan |
| 25464.97 Da | 25465.30 Da | Desialylated (neuraminidase treated) EPO-myc-His6 containing 3 mono antennary N-glycanes and one O-glycan |

The filtrate was then added 10 k-PSC reagent dissolved in 100 ul 50 mM Tris-HCl, 150 mM NaCl, pH 7.6. ST3Gal-III and AUS were both dissolved in 20 mM HEPES, 120 mM NaCl, 50% glycerol, pH 7.0 to a volumetric concentration of 1.35 U/ml and 200 U/ml respectively. Reagents were mixed according to scheme below:

| | Unit | Exp. 1 | Exp. 2 | Exp. 3 | Exp. 4 | Exp. 5 |
|---|---|---|---|---|---|---|
| asialo EPO-Myc-His6 | ug | 20 | 20 | 20 | 20 | 20 |
| 10k-PSC | eq | 1 | 3 | 5 | 10 | 20 |
| St3Gal3 | mU/ug EPO | 0.196 | 0.196 | 0.196 | 0.196 | 0.196 |
| Tris buffer | ul | 14.0 | 12.5 | 11.0 | 7.4 | 0 |
| Final volume | ul | 117.6 | 117.6 | 117.6 | 117.6 | 117.6 |
| Final EPO | mg/ml | 0.17 | 0.17 | 0.17 | 0.17 | 0.17 |

Reactions were incubated for 20 h at 32° C. Samples were then analysed by HPLC and SDS-PAGE.

Further Tables

TABLE 4

ZFN design and sequence analysis of CHO glycoengineered clones.

| Clone | Inser & Del | Alignment$^\alpha$ |
|---|---|---|

KO:mgat4A

| Clone | Inser & Del | Alignment |
|---|---|---|
| mgat4A-WT | ZFN | TTCTGAGTTGAA<u>TGCCATTGTCCAACA</u>gtt------------- tc<u>GCCGTGCAGGAG</u>CAGCAACTAACGGAAG |
| mgat4A-alle1 | −5 bp | TTCTGAGTTGAATGCCATTGTCCAACAg------------------ CCGTGCAGGAGCAGCAACTAACGGAAG |
| mgat4A-alle2 | +13 bp | TTCTGAGTTGAATGCCATTGTCCAACAgttGAATTCTAGATGAtcGCCGTGC AGGAGCAGCAACTAACGGAAG |

KO:mgat4A/4B

| Clone | Inser & Del | Alignment |
|---|---|---|
| mgat4A-WT | ZFN | TTCTGAGTTGAA<u>TGCCATTGTCCAACA</u>gtt------------- tc<u>GCCGTGCAGGAG</u>CAGCAACTAACGGAAG |
| mgat4A-alle1 | −5 bp | TTCTGAGTTGAATGCCATTGTCCAACAg------------------ CCGTGCAGGAGCAGCAACTAACGGAAG |
| mgat4A-alle2 | +13 bp | TTCTGAGTTGAATGCCATTGTCCAACAgttGAATTCTAGATGAtcGCCGTGC AGGAGCAGCAACTAACGGAAG |
| mgat4B-WT | ZFN | <u>GCCCTCCAGCAGCCCTCT</u>gagga<u>CTGGATGATCCTGGAGTT</u> |
| mgat4B-alle1 | −7 bp | GCCCTCCAGCAGCCCTCTg-------GATGATCCTGGAGTT |

KO:mgat5

| Clone | Inser & Del | Alignment |
|---|---|---|
| mgat5-WT | ZFN | GGGGGATGATGCTTCTGCACTTCACCATCCAg-------------- cagcg<u>GACTCAGCCTGAGAGCAGCTCCATGTT</u> |
| mgat5-alle1 | +14 bp | GGGGGATGATGCTTCTGCACTTCACCATCCAgcaTGAATTCTAGATGAgcgG ACTCAGCCTGAGAGCAGCTCCATGTT |
| mgat5-alle2 | −1 bp | GGGGGATGATGCTTCTGCACTTCACCATCCAg--------------- agcgGACTCAGCCTGAGAGCAGCTCCATGTT |
| mgat5-alle3 | +61 bp | GGGGGATGATGCTTCTGCACTTCACCATCCAgcag-----(+61 bp)-- cgGACTCAGCCTGAGAGCAGCTCCATGTT |

KO:mgat4A/4B/5

| Clone | Inser & Del | Alignment |
|---|---|---|
| mgat4A-WT | ZFN | TTCTGAGTTGAA<u>TGCCATTGTCCAACA</u>gtt------------- tc<u>GCCGTGCAGGAG</u>CAGCAACTAACGGAAG |
| mgat4A-alle1 | −5 bp | TTCTGAGTTGAATGCCATTGTCCAACAg------------------ CCGTGCAGGAGCAGCAACTAACGGAAG |
| mgat4A-alle2 | +13 bp | TTCTGAGTTGAATGCCATTGTCCAACAgttGAATTCTAGATGAtcGCCGTGC AGGAGCAGCAACTAACGGAAG |
| mgat4B-WT | ZFN | <u>GCCCTCCAGCAGCCCTCT</u>gagga<u>CTGGATGATCCTGGAGTT</u> |
| mgat4B-alle1 | −7 bp | GCCCTCCAGCAGCCCTCTg-------GATGATCCTGGAGTT GGGGGATGATGCTTCTGCACTTCACCATCCAg---- |
| mgat5-WT | ZFN | cagcg<u>GACTCAGCCTGAGAGCAGCTCCATGTT</u> |
| mgat5-alle1 | +4 bp | GGGGGATGATGCTTCTGCACTTCACCATCCAgcagcCAGCgGACTCAGCCTG AGAGCAGCTCCATGTT |
| mgat5-alle2 | −4 bp | GGGGGATGATGCTTCTGCACTTCACCATCCAg-------- gGACTCAGCCTGAGAGCAGCTCCATGTT |
| mgat5-alle3 | −16 bp | GGGGGATGATGCTTCTGCACTTC-------------------- CTCAGCCTGAGAGCAGCTCCATGTT |

KO:B3gnt1

| Clone | Inser & Del | Alignment |
|---|---|---|
| B3gnt1-WT | ZFN | <u>TGCAGCTGCTCTACCTGTC</u>----------gctgc<u>TCTCCGGACTGCACG</u> |
| B3gnt1-alle1 | +11 bp | TGCAGCTGCTCTACCTGTCgcagcTGCTCTACCTGTCTCTCCGGACTGCACG |
| B3gnt1-alle2 | −5 bp | TGCAGCTGCTCTACCTGTC----------------TCTCCGGACTGCACG |

TABLE 4 -continued

ZFN design and sequence analysis of CHO glycoengineered clones.

| Clone | Inser & Del | Alignment<sup>α</sup> |
|---|---|---|

KO:B3gnt2

| Clone | Inser & Del | Alignment |
|---|---|---|
| B3gnt2-WT | ZFN | TTCAGCCCTTCCcgggcGTACTGGAACAGAGAGCA |
| B3gnt2-alle1 | -1 bp | TTCAGCCCTTCC-gggcGTACTGGAACAGAGAGCA |
| B3gnt2-alle2 | -4 bp | TTCAGCCCTTCCcg----TACTGGAACAGAGAGCA |

KO:B4galt1

| Clone | Inser & Del | Alignment |
|---|---|---|
| B4galt1-WT | ZFN | TGCATCCGGTCCTACAGCgccagc----AACTGGACTATGGTA |
| B4galt1-alle1 | +4 bp | TGCATCCGGTCCTACAGCgccagcCAGCAACTGGACTATGGTA |

KO:B4galt2

| Clone | Inser & Del | Alignment |
|---|---|---|
| B4galt2-WT | ZFN | CAGCCCCGCCACTTTgcc-----------atcGCCATGGACAAGTTTGGCT |
| B4galt2-alle1 | +73 bp | CAGCCCCGCCACTTTgcc--(+73 bp)--atcGCCATGGACAAGTTTGGCT |

KO:B4galt3

| Clone | Inser & Del | Alignment |
|---|---|---|
| B4galt3-WT | ZFN | CTAGCCCTCAAGTCAGGAtgt-----tgCGGAGGCTGCTGGAGAGG |
| B4galt3-alle1 | +5 bp | CTAGCCCTCAAGTCAGGAtgtCGTGTtgCGGAGGCTGCTGGAGAGG |
| B4galt3-alle2 | +2 bp | CTAGCCCTCAAGTCAGGAtgt---tgCCCGGAGGCTGCTGGAGAGG |

KO:B4galt4

| Clone | Inser & Del | Alignment |
|---|---|---|
| B4galt4-WT | ZFN | AACTGGGACTGCTTTat----attcCACGATGTGGACCTGGTG |
| B4galt4-alle1 | +1 bp | AACTGGGACTGCTTTat---TattcCACGATGTGGACCTGGTG |
| B4galt4-alle2 | +4 bp | AACTGGGACTGCTTTatattTATTcCACGATGTGGACCTGGTG |

KO:B4galt1/2

| Clone | Inser & Del | Alignment |
|---|---|---|
| B4galt1-WT | ZFN | TGCATCCGGTCCTACAGCgccagc----AACTGGACTATGGTA |
| B4galt1-alle1 | +4 bp | TGCATCCGGTCCTACAGCgccagcCAGCAACTGGACTATGGTA |
| B4galt2-WT | ZFN | CAGCCCCGCCACTTTgccatcGCCATGGACAAGTTTGGCT |
| B4galt2-alle1 | -8 bp | CAGCCCCGCCAC--------cGCCATGGACAAGTTTGGCT |
| B4galt2-alle2 | -14 bp | CAGCCC--------------cGCCATGGACAAGTTTGGCT |

KO:st3Gal3

| Clone | Inser & Del | Alignment |
|---|---|---|
| st3Gal3-WT | ZFN | CTCTCTCTTTGTCCTTGCtggcttCAAATGGCAGGACTTCAAG |
| st3Gal3-alle1 | -5 bp | CTCTCTCTTTGTCCTTGCt-----CAAATGGCAGGACTTCAAG |
| st3Gal3-alle2 | -1 bp | CTCTCTCTTTGTCCTTGCtggct-CAAATGGCAGGACTTCAAG |

KO:st3Gal4

| Clone | Inser & Del | Alignment |
|---|---|---|
| st3Gal4-WT | ZFN | GGCAGCCTCCAGTGTCGTCgttgt----gTTGTGGTGGGGAATGGGC |
| st3Gal4-alle1 | +4 bp | GGCAGCCTCCAGTGTCGTCgttgtTTGTgTTGTGGTGGGGAATGGGC |
| st3Gal4-alle2 | -4 bp | GGCAGCCTCCAGTGTCGTCg--------gTTGTGGTGGGGAATGGGC |

TABLE 4 -continued

ZFN design and sequence analysis of CHO glycoengineered clones.

| Clone | Inser & Del | Alignment[a] |
|---|---|---|
| KO:st3Gal6 | | |
| st3Gal6-WT | ZFN | CGGTACCTCTGATTTTGCTttgccCTATGGGACAAGGCC |
| st3Gal6-alle1 | -4 bp | CGGTACCTCTGATTTTGCTt----CTATGGGACAAGGCC |
| st3Gal6-alle2 | -22 bp | CGGTACCTCTGA---------------------AGGCC |
| KO:st3Gal3/4 | | |
| st3Gal3-WT | ZFN | CTCTCTCTTTGTCCTTGCtggcttCAAATGGCAGGACTTCAAG |
| st3Gal3-alle1 | -5 bp | CTCTCTCTTTGTCCTTGCt-----CAAATGGCAGGACTTCAAG |
| st3Gal3-alle2 | -1 bp | CTCTCTCTTTGTCCTTGCtggct-CAAATGGCAGGACTTCAAG |
| st3Gal4-WT | ZFN | GGCAGCCTCCAGTGTCGTCgttgt-----gTTGTGGTGGGGAATGGGC |
| st3Gal4-alle1 | -4 bp | GGCAGCCTCCAGTGTCGTCg---------gTTGTGGTGGGGAATGGGC |
| st3Gal4-alle2 | +5 bp | GGCAGCCTCCAGTGTCGTCgACACGttgtTTGTGGTGGGGAATGGGC |
| KO:st3Gal4/6 | | |
| st3Gal4-WT | ZFN | GGCAGCCTCCAGTGTCGTCgttgt----gTTGTGGTGGGGAATGGGC |
| st3Gal4-alle1 | +4 bp | GGCAGCCTCCAGTGTCGTCgttgtTTGTgTTGTGGTGGGGAATGGGC |
| st3Gal4-alle2 | -4 bp | GGCAGCCTCCAGTGTCGTCg--------gTTGTGGTGGGGAATGGGC |
| st3Gal6-WT | ZFN | CGGTACCTCTGATTTTGCT-ttgccCTATGGGACAAGGCC |
| st3Gal6-alle1 | +1 bp | CGGTACCTCTGATTTTGCTTttgccCTATGGGACAAGGCC |
| st3Gal6-alle2 | -7 bp | CGGTACCTCTGATTTTG--------CTATGGGACAAGGCC |
| KO:B3gnt2/mgat4A/4B/5 | | |
| mgat4A-WT | ZFN | TTCTGAGTTGAATGCCATTGTCCAACAgtt-------------tcGCCGTGCAGGAGCAGCAACTAACGGAAG |
| mgat4A-alle1 | -5 bp | TTCTGAGTTGAATGCCATTGTCCAACAg------------------CCGTGCAGGAGCAGCAACTAACGGAAG |
| mgat4A-alle2 | +13 bp | TTCTGAGTTGAATGCCATTGTCCAACAgttGAATTCTAGATGAtcGCCGTGCAGGAGCAGCAACTAACGGAAG |
| mgat4B-WT | ZFN | GCCCTCCAGCAGCCCTCTgaggaCTGGATGATCCTGGAGTT |
| mgat4B-alle1 | -7 bp | GCCCTCCAGCAGCCCTCTg-------GATGATCCTGGAGTT |
| mgat5-WT | ZFN | GGGGGATGATGCTTCTGCACTTCACCATCCAg----cagcgGACTCAGCCTGAGAGCAGCTCCATGTT |
| mgat5-alle1 | +4 bp | GGGGGATGATGCTTCTGCACTTCACCATCCAgcagcCAGCgGACTCAGCCTGAGAGCAGCTCCATGTT |
| mgat5-alle2 | -4 bp | GGGGGATGATGCTTCTGCACTTCACCATCCAg--------gGACTCAGCCTGAGAGCAGCTCCATGTT |
| mgat5-alle3 | -16 bp | GGGGGATGATGCTTCTGCACTTC--------------------CTCAGCCTGAGAGCAGCTCCATGTT |
| B3gnt2-WT | ZFN | TTCAGCCCTTCC--cgggcGTACTGGAACAGAGAGCA |
| B3gnt2-alle1 | +2 bp | TTCAGCCCTTCCCCcgggcGTACTGGAACAGAGAGCA |
| B3gnt2-alle2 | +1 bp | TTCAGCCCTTCCC-cgggcGTACTGGAACAGAGAGCA |
| KO:st3Gal4/6/mgat4A/4B/5 | | |
| mgat4A-WT | ZFN | TTCTGAGTTGAATGCCATTGTCCAACAgtt-------------tcGCCGTGCAGGAGCAGCAACTAACGGAAG |
| mgat4A-alle1 | -5 bp | TTCTGAGTTGAATGCCATTGTCCAACAg------------------CCGTGCAGGAGCAGCAACTAACGGAAG |
| mgat4A-alle2 | +13 bp | TTCTGAGTTGAATGCCATTGTCCAACAgttGAATTCTAGATGAtcGCCGTGCAGGAGCAGCAACTAACGGAAG |

TABLE 4 -continued

ZFN design and sequence analysis of CHO glycoengineered clones.

| Clone | Inser & Del | Alignment[a] |
|---|---|---|
| mgat4B-WT | ZFN | GCCCTCCAGCAGCCCTCTgaggaCTGGATGATCCTGGAGTT |
| mgat4B-alle1 | -7 bp | GCCCTCCAGCAGCCCTCTg-------GATGATCCTGGAGTT |
| mgat5-WT | ZFN | GGGGGATGATGCTTCTGCACTTCACCATCCAg----cagcgGACTCAGCCTGAGAGCAGCTCCATGTT |
| mgat5-alle1 | +4 bp | GGGGGATGATGCTTCTGCACTTCACCATCCAgcagcCAGCgGACTCAGCCTGAGAGCAGCTCCATGTT |
| mgat5-alle2 | -4 bp | GGGGGATGATGCTTCTGCACTTCACCATCCAg--------gGACTCAGCCTGAGAGCAGCTCCATGTT |
| mgat5-alle3 | -16 bp | GGGGGATGATGCTTCTGCACTTC--------------------CTCAGCCTGAGAGCAGCTCCATGTT |
| st3Gal4-WT | ZFN | GGCAGCCTCCAGTGTCGTCgttgt----gTTGTGGTGGGGAATGGGC |
| st3Gal4-alle1 | -5 bp | GGCAGCCTCCAGTGTCGTCgttgt---------gGTGGGGAATGGGC |
| st3Gal4-alle2 | +4 bp | GGCAGCCTCCAGTGTCGTCgTTGTttgtgTTGTGGTGGGGAATGGGC |
| st3Gal6-WT | ZFN | CGGTACCTCTGATTTTGCTttgccCTATGGGACAAGGCC |
| st3Gal6-alle1 | -4 bp | CGGTACCTCTGATTTTGCTt----CTATGGGACAAGGCC |
| st3Gal6-alle2 | -2 bp | CGGTACCTCTGATTTTGCTttg--CTATGGGACAAGGCC |

KI:ST6GAL1/KO:st3gal4/6

| Clone | Inser & Del | Alignment[a] |
|---|---|---|
| st3Gal4-WT | ZFN | GGCAGCCTCCAGTGTCGTCgttgt----gTTGTGGTGGGGAATGGGC |
| st3Gal4-alle1 | +4 bp | GGCAGCCTCCAGTGTCGTCgttgtTTGTgTTGTGGTGGGGAATGGGC |
| st3Gal4-alle2 | -4 bp | GGCAGCCTCCAGTGTCGTCg--------gTTGTGGTGGGGAATGGGC |
| st3Gal6-WT | ZFN | CGGTACCTCTGATTTTGCT-ttgccCTATGGGACAAGGCC |
| st3Gal6-alle1 | +1 bp | CGGTACCTCTGATTTTGCTTttgccCTATGGGACAAGGCC |
| st3Gal6-alle2 | -7 bp | CGGTACCTCTGATTTTG--------CTATGGGACAAGGCC |

KI:ST6GAL1/KO:st3gal4/6/mgat4A/4B/5

| Clone | Inser & Del | Alignment[a] |
|---|---|---|
| mgat4A-WT | ZFN | TTCTGAGTTGAATGCCATTGTCCAACAgtt-------------tcGCCGTGCAGGAGCAGCAACTAACGGAAG |
| mgat4A-alle1 | -5 bp | TTCTGAGTTGAATGCCATTGTCCAACAg------------------CCGTGCAGGAGCAGCAACTAACGGAAG |
| mgat4A-alle2 | +13 bp | TTCTGAGTTGAATGCCATTGTCCAACAgttgAATTCTAGATGAtcGCCGTGCAGGAGCAGCAACTAACGGAAG |
| mgat4B-WT | ZFN | GCCCTCCAGCAGCCCTCTgaggaCTGGATGATCCTGGAGTT |
| mgat4B-alle1 | -7 bp | GCCCTCCAGCAGCCCTCTg-------GATGATCCTGGAGTT |
| mgat5-WT | ZFN | GGGGGATGATGCTTCTGCACTTCACCATCCAg----cagcgGACTCAGCCTGAGAGCAGCTCCATGTT |
| mgat5-alle1 | +4 bp | GGGGGATGATGCTTCTGCACTTCACCATCCAgcagcCAGCgGACTCAGCCTGAGAGCAGCTCCATGTT |
| mgat5-alle2 | -4 bp | GGGGGATGATGCTTCTGCACTTCACCATCCAg--------gGACTCAGCCTGAGAGCAGCTCCATGTT |
| mgat5-alle3 | -16 bp | GGGGGATGATGCTTCTGCACTTC--------------------CTCAGCCTGAGAGCAGCTCCATGTT |
| st3Gal4-WT | ZFN | GGCAGCCTCCAGTGTCGTCgttgt----gTTGTGGTGGGGAATGGGC |
| st3Gal4-alle1 | -5 bp | GGCAGCCTCCAGTGTCGTCgttgt---------gGTGGGGAATGGGC |
| st3Gal4-alle2 | +4 bp | GGCAGCCTCCAGTGTCGTCgTTGTttgtgTTGTGGTGGGGAATGGGC |
| st3Gal6-WT | ZFN | CGGTACCTCTGATTTTGCTttgccCTATGGGACAAGGCC |
| st3Gal6-alle1 | -4 bp | CGGTACCTCTGATTTTGCTt----CTATGGGACAAGGCC |
| st3Gal6-alle2 | -2 bp | CGGTACCTCTGATTTTGCTttg--CTATGGGACAAGGCC |

TABLE 4 -continued

ZFN design and sequence analysis of CHO glycoengineered clones.

| Clone | Inser & Del | Alignment[α] |
|---|---|---|
| KO:mgat2 | | |
| mgat2-WT | TALEN | TCCTTTGTCGCCCATTGCTgctccagaggacgaagCCGCAGGCGGCCACCACGA |
| mgat2-alle1 | -4 bp | TCCTTTGTCGCCCATTGCTgctcc----gacgaagccgcaggcggccaccacga |
| KO:mgat2/stgal4/6 | | |
| mgat2-WT | TALEN | TCCTTTGTCGCCCATTGCTgctccagaggacgaagCCGCAGGCGGCCACCACGA |
| mgat2-alle1 | -4 bp | TCCTTTGTCGCCCATTGCTgctccag----cgaagCCGCAGGCGGCCACCACGA |
| st3Gal4-WT | ZFN | GGCAGCCTCCAGTGTCGTCgttgt----gTTGTGGTGGGGAATGGGC |
| st3Gal4-alle1 | +4 bp | GGCAGCCTCCAGTGTCGTCgttgtTTGTgTTGTGGTGGGGAATGGGC |
| st3Gal4-alle2 | -4 bp | GGCAGCCTCCAGTGTCGTCg--------gTTGTGGTGGGGAATGGGC |
| st3Gal6-WT | ZFN | CGGTACCTCTGATTTTGCT-ttgccCTATGGGACAAGGCC |
| st3Gal6-alle1 | +1 bp | CGGTACCTCTGATTTTGCTTttgccCTATGGGACAAGGCC |
| st3Gal6-alle2 | -7 bp | CGGTACCTCTGATTTTG--------CTATGGGACAAGGCC |
| KO:mgat2/mgat4A/4B/5 | | |
| mgat2-WT | TALEN | TCCTTTGTCGCCCATTGCTgctccagaggacgaagCCGCAGGCGGCCACCACGA |
| mgat2-alle1 | -4 bp | TCCTTTGTCGCCCATTGCTgctccag----cgaagCCGCAGGCGGCCACCACGA |
| mgat4A-WT | ZFN | TTCTGAGTTGAATGCCATTGTCCAACAgtt-------------tcGCCGTGCAGGAGCAGCAACTAACGGAAG |
| mgat4A-alle1 | -5 bp | TTCTGAGTTGAATGCCATTGTCCAACAg------------------CCGTGCAGGAGCAGCAACTAACGGAAG |
| mgat4A-alle2 | +13 bp | TTCTGAGTTGAATGCCATTGTCCAACAgttGAATTCTAGATGAtcGCCGTGCAGGAGCAGCAACTAACGGAAG |
| mgat4B-WT | ZFN | GCCCTCCAGCAGCCCTCTgaggaCTGGATGATCCTGGAGTT |
| mgat4B-alle1 | -7 bp | GCCCTCCAGCAGCCCTCTg-------GATGATCCTGGAGTT |
| mgat5-WT | ZFN | GGGGGATGATGCTTCTGCACTTCACCATCCAg----cagcgGACTCAGCCTGAGAGCAGCTCCATGTT |
| mgat5-alle1 | +4 bp | GGGGGATGATGCTTCTGCACTTCACCATCCAgcagcCAGCgGACTCAGCCTGAGAGCAGCTCCATGTT |
| mgat5-alle2 | -4 bp | GGGGGATGATGCTTCTGCACTTCACCATCCAg--------gGACTCAGCCTGAGAGCAGCTCCATGTT |
| mgat5-alle3 | -16 bp | GGGGGATGATGCTTCTGCACTTC--------------------CTCAGCCTGAGAGCAGCTCCATGTT |
| KO:mgat2/st3gal4/6/mgat4A/4B/5 | | |
| mgat2-WT | TALEN | TCCTTTGTCGCCCATTGCTgctccagaggacgaagCCGCAGGCGGCCACCACGA |
| mgat2-alle1 | -5 bp | TCCTTTGTCGCCCATTGCTgctcca-----cgaaGCCGCAGGCGGCCACCACGA |
| mgat4A-WT | ZFN | TTCTGAGTTGAATGCCATTGTCCAACAgtt-------------tcGCCGTGCAGGAGCAGCAACTAACGGAAG |
| mgat4A-alle1 | -5 bp | TTCTGAGTTGAATGCCATTGTCCAACAg------------------CCGTGCAGGAGCAGCAACTAACGGAAG |
| mgat4A-alle2 | +13 bp | TTCTGAGTTGAATGCCATTGTCCAACAgttGAATTCTAGATGAtcGCCGTGCAGGAGCAGCAACTAACGGAAG |
| mgat4B-WT | ZFN | GCCCTCCAGCAGCCCTCTgaggaCTGGATGATCCTGGAGTT |
| mgat4B-alle1 | -7 bp | GCCCTCCAGCAGCCCTCTg-------GATGATCCTGGAGTT |
| mgat5-WT | ZFN | GGGGGATGATGCTTCTGCACTTCACCATCCAg----cagcgGACTCAGCCTGAGAGCAGCTCCATGTT |
| mgat5-alle1 | +4 bp | GGGGGATGATGCTTCTGCACTTCACCATCCAgcagcCAGCgGACTCAGCCTGAGAGCAGCTCCATGTT |
| mgat5-alle2 | -4 bp | GGGGGATGATGCTTCTGCACTTCACCATCCAg--------gGACTCAGCCTGAGAGCAGCTCCATGTT |

TABLE 4 -continued

ZFN design and sequence analysis of CHO glycoengineered clones.

| Clone | Inser & Del | Alignment<sup>α</sup> |
|---|---|---|
| mgat5-alle3 | -16 bp | GGGGGATGATGCTTCTGCACTTC--------------------CTCAGCCTGAGAGCAGCTCCATGTT |
| st3Gal4-WT | ZFN | GGCAGCCTCCAGTGTCGTCgttgt----gTTGTGGTGGGGAATGGGC |
| st3Gal4-alle1 | -5 bp | GGCAGCCTCCAGTGTCGTCgttgt---------gGTGGGGAATGGGC |
| st3Gal4-alle2 | +4 bp | GGCAGCCTCCAGTGTCGTCgTTGTtttgtGTTGTGGTGGGGAATGGGC |
| st3Gal6-WT | ZFN | CGGTACCTCTGATTTTGCTttgccCTATGGGACAAGGCC |
| st3Gal6-alle1 | -4 bp | CGGTACCTCTGATTTTGCTt----CTATGGGACAAGGCC |
| st3Gal6-alle2 | -2 bp | CGGTACCTCTGATTTTGCTttg--CTATGGGACAAGGCC |

| KO:fut8 | | |
|---|---|---|
| fut8-WT | CRISPR | CAAATACTTGATCCGTCCACAACCT-TGGCTGGAAAGGGAA |
| fut8-alle1 | -1 bp | CAAATACTTGATCCGTCCACAACC--TGGCTGGAAAGGGAA |
| fut8-alle2 | +1 bp | CAAATACTTGATCCGTCCACAACCTTTGGCTGGAAAGGGAA |

| KO:fut8/B4galt1 | | |
|---|---|---|
| fut8-WT | CRISPR | CAAATACTTGATCCGTCCACAACCT-TGGCTGGAAAGGGAA |
| fut8-alle1 | -4 bp | CAAATACTTGATCCGTCCACAA-----GGCTGGAAAGGGAA |
| fut8-alle2 | +1 bp | CAAATACTTGATCCGTCCACAACCTTTGGCTGGAAAGGGAA |
| B4galt1-WT | ZFN | TGCATCCGGTCCTACAGCgccagc----AACTGGACTATGGTA |
| B4galt1-alle1 | +4 bp | TGCATCCGGTCCTACAGCgccagcCAGCAACTGGACTATGGTA |

| KO:mgat3 | | |
|---|---|---|
| mgat3-WT | ZFN | TTCCTGGACCACTTCCCAcccggt----------GGCCGGCAGGATGGC |
| mgat3-alle1 | -21 bp | TTCCTGGACCACT-----------------------------ATGGC |
| mgat3-alle2 | +293 bp | TTCCTGGACCACTGATACcc--+293 bp--cggtGGCCGGCAGGATGGC |

| KO:mgat4C | | |
|---|---|---|
| mgat4C-WT | ZFN | ATACTTCAGACTATatgtAATGCTCGAAGATGATGTT |
| mgat4C-alle1 | -13 bp | ATACTTCAGACT-------------CGAAGATGATGTT |
| mgat4C-alle2 | -8 bp | ATACTTCAGACTAT--------GCTCGAAGATGATGTT |

| KO:mgat5B | | |
|---|---|---|
| mgat5B-WT | ZFN | CGTGGCGCCCTCCGCAAGatgagtGACCTGCTGGAGCTG |
| mgat5B-alle1 | -7 bp | CAGCTCCAGCAGGT-------CTTGCGGAGGGCGCCACG |
| mgat5B-alle2 | -5 bp | CAGCTCCAGCAGGT-----ATCTTGCGGAGGGCGCCACG |

| KO:B3gnt8 | | |
|---|---|---|
| B3gnt8-WT | TALEN | TGGTCCAGAGATAGCTAATgaagcttctagggtgGAGAAGCTGGGGCTGCTGA |
| B3gnt8-alle1 | -17 bp | TGGTCCAGAGG-----------------AGGGTGGAGAAGCTGGGGCTGCTGA |

| KO:mgat1 | | |
|---|---|---|
| mgat1-WT | ZEN | AACAAGTTCAAGTTCccagcaGCTGTGGTAGTGGAGGAC |
| mgat1-alle1 | -2 bp | AACAAGTTCAAGTTCc--gcaGCTGTGGTAGTGGAGGAC |

Gene targeting region underlined.

TABLE 5

```
tcgcgcgtttcggtgatgacggtgaaaacctctgacacatgcagctcccggagacggtcacagcttgtctgta
agcggatgccgggagcagacaagcccgtcagggcgcgtcagcgggtgttggcgggtgtcggggctggcttaac
tatgcggcatcagagcagattgtactgagagtgcaccatatgcggtgtgaaataccgcacagatgcgtaagga
gaaaataccgcatcaggcgccattcgccattcaggctgcgcaactgttgggaagggcgatcggtgcgggcctc
ttcgctattacgccagctggcgaaaggggatgtgctgcaaggcgattaagttgggtaacgccagggttttcc
cagtcacgacgttgtaaaacgacggccagtgaattcgagctcggtaccaagcttggttgcatgctgtccggag
tctcagcgttataccagaagtgacctgggtcggggaagactatagtgtcacctaaatctctagagcccttcat
taggcgcgccaatcccattgcaaattctacaaaaggagtgtttcccaactgctctatcaagaggaatgttgca
cactgtgacctgaatgcaaacatcacacgcgccagcagagaggaagaagagaggcttccctgaccgggaatcg
aacccgggccgcggcggtgagagcgccgaatcctaaccactagaccaccagggagcacgcgccaaagctcaat
gagctataattatcccccttggaaaacctacaaaaacagtgtttcaaaactgctctgtgaaaagggaccttgc
tagcacgcggcgccaggcaaaacgtgggcacgctgcgttggccgggaatcgaacccgggtcaactgcttggaa
ggcagctatgctcaccactataccaccaacgcgcacacgcgccagcagattctacgggaagagtgtttcaaaa
ctgctctatcaagagaaatgttccaccttgtgtgtggaatgcagccatcacacgcgtccatgaaagggcttaa
ttaagatatcgtttaaacgtcgacctgcagaggccggcggataactagctgatcgcggaatcctgtccctagg
ccacccactgtggggtgcccttcattaggcgcgccaatcccattgcaaattctacaaaaggagtgtttcccaa
ctgctctatcaagaggaatgttgcacactgtgacctgaatgcaaacatcacacgcgccagcagagaggaagaa
gagaggcttccctgaccgggaatcgaacccgggccgcggcggtgagagcgccgaatcctaaccactagaccac
cagggagcacgcgccaaagctcaatgctataattatcccccttggaaaacctacaaaaacagtgtttcaaaa
ctgctctgtgaaaagggaccttcgctagcacgcggcgccaggcaaaacgtgggcacgctgcgttggccgggaa
tcgaacccgggtcaactgcttggaaggcagctatgctcaccactataccaccaacgcgcacacgcgccagcag
attctacgggaagagtgtttcaaaactgctctatcaagagaaatgttccaccttgtgtgtggaatgcagccat
cacacgcgtccatgaaagggcggttgcatgctgtccggagtctcagcgttataccagaagtgacctgggtcgg
ggaagaaaagcttcatggtcatagctgtttcctgtgtgaaattgttatccgctcacaattccacacaacatac
gagccggaagcataaagtgtaaagcctggggtgcctaatgagtgagctaactcacattaattgcgttgcgctc
actgcccgctttccagtcgggaaacctgtcgtgccagctgcattaatgaatcggccaacgcgcgggagaggc
ggtttgcgtattgggcgctcttccgcttcctcgctcactgactcgctgcgctcggtcgttcggctgcggcgag
cggtatcagctcactcaaaggcggtaatacggttatccacagaatcaggggataacgcaggaaagaacatgtg
agcaaaaggccagcaaaaggccaggaaccgtaaaaaggccgcgttgctggcgtttttccataggctccgcccc
cctgacgagcatcacaaaatcgacgctcaagtcagaggtggcgaaacccgacaggactataaagataccagg
cgtttccccctggaagctccctcgtgcgctctcctgttccgaccctgccgcttaccggatacctgtccgcctt
tctcccttcgggaagcgtggcgctttctcatagctcacgctgtaggtatctcagttcggtgtaggtcgttcgc
tccaagctgggctgtgtgcacgaaccccccgttcagcccgaccgctgcgccttatccggtaactatcgtcttg
agtccaacccggtaagacacgacttatcgccactggcagcagccactggtaacaggattagcagagcgaggta
tgtaggcggtgctacagagttcttgaagtggtggcctaactacggctacactagaagaacagtatttggtatc
tgcgctctgctgaagccagttaccttcggaaaaagagttggtagctcttgatccggcaaacaaaccaccgctg
gtagcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaaaa
aggatcttcacctagatccttttaaattaaaaatgaagttttaaatcaatctaaagtatatatgagtaaactt
ggtctgacagttagaaaaactcatcgagcatcaaatgaaactgcaatttattcatatcaggattatcaatacc
atatttttgaaaaagccgtttctgtaatgaaggagaaaactcaccgaggcagttccataggatggcaagatcc
tggtatcggtctgcgattccgactcgtccaacatcaatacaacctattaatttccctcgtcaaaaataaggt
tatcaagtgagaaatcaccatgagtgacgactgaatccggtgagaatggcaaaagtttatgcatttctttcca
gacttgttcaacaggccagccattacgctcgtcatcaaaatcactcgcatcaaccaaaccgttattcattcgt
gattgcgcctgagcgagacgaaatcgcgatcgctgttaaaaggacaattacaaacaggaatcgaatgcaacc
ggcgcaggaacactgccagcgcatcaacaatattttcacctgaatcaggatattcttctaatacctggaatgc
tgttttcccagggatcgcagtggtgagtaaccatgcatcatcaggagtacggataaaatgcttgatggtcgga
agaggcataaattccgtcagccagtttagtctgaccatctcatctgtaacatcattggcaacgctacctttgc
catgtttcagaaacaactctggcgcatcgggcttcccatacaatcgatagattgtcgcacctgattgcccgac
attatcgcgagcccatttatacccatataaatcagcatccatgttggaatttaatcgcggcctagagcaagac
gtttcccgttgaatatggctcatactcttcctttttcaatattattgaagcatttatcagggttattgtctca
tgagcggatacatatttgaatgtatttagaaaaataaacaaatagggggttccgcgcacatttccccgaaagt
gccacctgacgtctaagaaaccattattatcatgacattaacctataaaaataggcgtatcacgaggccctt
cgtc
```

The invention claimed is:

1. An isolated mammalian cell comprising homogeneous biantennary N-glycans, wherein mgat4A, mgat4B, and mgat5 are inactivated in the cell, thereby generating the homogeneous biantennary N-glycans in the cell.

2. The cell according to claim 1, wherein the genes are inactivated using zinc finger nucleases, TALENs, or CRISPR/Cas9.

3. The cell according to claim 1, wherein mgat4C is additionally inactivated.

4. The cell according to claim 1, wherein mgat5B is additionally inactivated.

5. The cell according to claim 1, wherein FUT8 is additionally inactivated.

6. The cell according to claim 1, wherein B3gnt2 is additionally inactivated.

7. The cell according to claim 1, wherein mgat2 is additionally inactivated.

8. The cell according to claim 1, wherein ST3gal3, ST3gal4, and ST3gal6 are additionally inactivated.

9. The cell according to claim 1, wherein ST6Gal1 is knocked in.

10. The cell according to claim 1, wherein the cell is a CHO, NSO, SP2/0, YB2/0, CHO-K1, CHO-DXB11, CHO-DG44, CHO-S, HEK293, HUVEC, HKB, or PER-C6 cell.

11. The cell according to claim 10, wherein the cell is a CHO cell.

12. The cell according to claim 1, further comprising EPO, an IgG antibody, a protein involved in hemostasis, or a coagulation factor.

* * * * *

SEQUENCE LISTING

<160> NUMBER OF SEQ ID NOS: 60

<210> SEQ ID NO 1
<211> LENGTH: 39
<212> TYPE: DNA
<213> ORGANISM: Artificial Sequence
<220> FEATURE:
<223> OTHER INFORMATION: mgat1-WT

<400> SEQUENCE: 1
aacaagttca agttcccagc agctgtggta gtggaggac        39

<210> SEQ ID NO 2
<211> LENGTH: 37
<212> TYPE: DNA
<213> ORGANISM: Artificial Sequence

```
<220> FEATURE:
<223> OTHER INFORMATION: mgat1-alle1

<400> SEQUENCE: 2
aacaagttca agttccgcag ctgtggtagt ggaggac                    37

<210> SEQ ID NO 3
<211> LENGTH: 54
<212> TYPE: DNA
<213> ORGANISM: Artificial Sequence
<220> FEATURE:
<223> OTHER INFORMATION: mgat2-WT

<400> SEQUENCE: 3
tcctttgtcg cccattgctg ctccagagga cgaagccgca ggcggccacc acga    54

<210> SEQ ID NO 4
<211> LENGTH: 49
<212> TYPE: DNA
<213> ORGANISM: Artificial Sequence
<220> FEATURE:
<223> OTHER INFORMATION: mgat2-alle1

<400> SEQUENCE: 4
tcctttgtcg cccattgctg ctccacgaag ccgcaggcgg ccaccacga         49

<210> SEQ ID NO 5
<211> LENGTH: 39
<212> TYPE: DNA
<213> ORGANISM: Artificial Sequence
<220> FEATURE:
<223> OTHER INFORMATION: mgat3-WT

<400> SEQUENCE: 5
ttcctggacc acttcccacc cggtggccgg caggatggc                   39

<210> SEQ ID NO 6
<211> LENGTH: 18
<212> TYPE: DNA
<213> ORGANISM: Artificial Sequence
<220> FEATURE:
<223> OTHER INFORMATION: mgat3-alle1

<400> SEQUENCE: 6
ttcctggacc actatggc                                          18

<210> SEQ ID NO 7
<211> LENGTH: 20
<212> TYPE: DNA
<213> ORGANISM: Artificial Sequence
<220> FEATURE:
<223> OTHER INFORMATION: mgat3-alle2 (N-terminus)

<400> SEQUENCE: 7
ttcctggacc actgataccc                                        20

<210> SEQ ID NO 8
<211> LENGTH: 19
<212> TYPE: DNA
<213> ORGANISM: Artificial Sequence
<220> FEATURE:
<223> OTHER INFORMATION: mgat3-alle2 (C-terminus)

<400> SEQUENCE: 8
cggtggccgg caggatggc                                         19
```

```
<210> SEQ ID NO 9
<211> LENGTH: 60
<212> TYPE: DNA
<213> ORGANISM: Artificial Sequence
<220> FEATURE:
<223> OTHER INFORMATION: mgat4A-WT

<400> SEQUENCE: 9
ttctgagttg aatgccattg tccaacagtt tcgccgtgca ggagcagcaa ctaacggaag    60

<210> SEQ ID NO 10
<211> LENGTH: 55
<212> TYPE: DNA
<213> ORGANISM: Artificial Sequence
<220> FEATURE:
<223> OTHER INFORMATION: mgat4A-alle1

<400> SEQUENCE: 10
ttctgagttg aatgccattg tccaacagcc gtgcaggagc agcaactaac ggaag          55

<210> SEQ ID NO 11
<211> LENGTH: 73
<212> TYPE: DNA
<213> ORGANISM: Artificial Sequence
<220> FEATURE:
<223> OTHER INFORMATION: mgat4A-alle2

<400> SEQUENCE: 11
ttctgagttg aatgccattg tccaacagtt gaattctaga tgatcgccgt gcaggagcag    60
caactaacgg aag                                                       73

<210> SEQ ID NO 12
<211> LENGTH: 41
<212> TYPE: DNA
<213> ORGANISM: Artificial Sequence
<220> FEATURE:
<223> OTHER INFORMATION: mgat4B-WT

<400> SEQUENCE: 12
gccctccagc agccctctga ggactggatg atcctggagt t                        41

<210> SEQ ID NO 13
<211> LENGTH: 34
<212> TYPE: DNA
<213> ORGANISM: Artificial Sequence
<220> FEATURE:
<223> OTHER INFORMATION: mgat4B-alle1

<400> SEQUENCE: 13
gccctccagc agccctctgg atgatcctgg agtt                                34

<210> SEQ ID NO 14
<211> LENGTH: 38
<212> TYPE: DNA
<213> ORGANISM: Artificial Sequence
<220> FEATURE:
<223> OTHER INFORMATION: mgat4C-WT

<400> SEQUENCE: 14
atacttcaga ctattatgta atgctcgaag atgatgtt                            38

<210> SEQ ID NO 15
<211> LENGTH: 25
<212> TYPE: DNA
<213> ORGANISM: Artificial Sequence
```

```
<220> FEATURE:
<223> OTHER INFORMATION: mgat4C-alle1

<400> SEQUENCE: 15
atacttcaga ctcgaagatg atgtt                                          25

<210> SEQ ID NO 16
<211> LENGTH: 30
<212> TYPE: DNA
<213> ORGANISM: Artificial Sequence
<220> FEATURE:
<223> OTHER INFORMATION: mgat4C-alle2

<400> SEQUENCE: 16
atacttcaga ctatgctcga agatgatgtt                                     30

<210> SEQ ID NO 17
<211> LENGTH: 64
<212> TYPE: DNA
<213> ORGANISM: Artificial Sequence
<220> FEATURE:
<223> OTHER INFORMATION: mgat5-WT

<400> SEQUENCE: 17
gggggatgat gcttctgcac ttcaccatcc agcagcggac tcagcctgag agcagctcca    60
tgtt                                                                 64

<210> SEQ ID NO 18
<211> LENGTH: 78
<212> TYPE: DNA
<213> ORGANISM: Artificial Sequence
<220> FEATURE:
<223> OTHER INFORMATION: mgat5-alle1

<400> SEQUENCE: 18 ggggatgat gcttctgcac ttcaccatcc agcatgaatt ctagatgagc ggactcagcc     60
tgagagcagc tccatgtt                                                  78

<210> SEQ ID NO 19
<211> LENGTH: 63
<212> TYPE: DNA
<213> ORGANISM: Artificial Sequence
<220> FEATURE:
<223> OTHER INFORMATION: mgat5-alle2

<400> SEQUENCE: 19 ggggatgat gcttctgcac ttcaccatcc agagcggact cagcctgaga gcagctccat     60
gtt                                                                  63

<210> SEQ ID NO 20
<211> LENGTH: 35
<212> TYPE: DNA
<213> ORGANISM: Artificial Sequence
<220> FEATURE:
<223> OTHER INFORMATION: mgat5-alle3 (N-terminus)

<400> SEQUENCE: 20 ggggatgat gcttctgcac ttcaccatcc agcag                                35

<210> SEQ ID NO 21
<211> LENGTH: 29
<212> TYPE: DNA
<213> ORGANISM: Artificial Sequence
```

```
<220> FEATURE:
<223> OTHER INFORMATION: mgat5-alle3 (C-terminus)

<400> SEQUENCE: 21
cggactcagc ctgagagcag ctccatgtt                                    29

<210> SEQ ID NO 22
<211> LENGTH: 39
<212> TYPE: DNA
<213> ORGANISM: Artificial Sequence
<220> FEATURE:
<223> OTHER INFORMATION: mgat5B-WT

<400> SEQUENCE: 22
cgtggcgccc tccgcaagat gagtgacctg ctggagctg                         39

<210> SEQ ID NO 23
<211> LENGTH: 32
<212> TYPE: DNA
<213> ORGANISM: Artificial Sequence
<220> FEATURE:
<223> OTHER INFORMATION: mgat5B-alle1

<400> SEQUENCE: 23
cagctccagc aggtcttgcg gagggcgcca cg                                32

<210> SEQ ID NO 24
<211> LENGTH: 34
<212> TYPE: DNA
<213> ORGANISM: Artificial Sequence
<220> FEATURE:
<223> OTHER INFORMATION: mgat5B-alle2

<400> SEQUENCE: 24
cagctccagc aggtatcttg cggagggcgc cacg                              34

<210> SEQ ID NO 25
<211> LENGTH: 39
<212> TYPE: DNA
<213> ORGANISM: Artificial Sequence
<220> FEATURE:
<223> OTHER INFORMATION: B3gnt1-WT

<400> SEQUENCE: 25
tgcagctgct ctacctgtcg ctgctctccg gactgcacg                         39

<210> SEQ ID NO 26
<211> LENGTH: 50
<212> TYPE: DNA
<213> ORGANISM: Artificial Sequence
<220> FEATURE:
<223> OTHER INFORMATION: B3gnt1-alle1

<400> SEQUENCE: 26
tgcagctgct ctacctgtcg cagctgctct acctgtctcc ggactgcacg             50

<210> SEQ ID NO 27
<211> LENGTH: 34
<212> TYPE: DNA
<213> ORGANISM: Artificial Sequence
<220> FEATURE:
<223> OTHER INFORMATION: B3gnt1-alle2

<400> SEQUENCE: 27
tgcagctgct ctacctgtct ctccggactg cacg                              34
```

<210> SEQ ID NO 28
<211> LENGTH: 35
<212> TYPE: DNA
<213> ORGANISM: Artificial Sequence
<220> FEATURE:
<223> OTHER INFORMATION: B3gnt2-WT

<400> SEQUENCE: 28
ttcagccctt cccgggcgta ctggaacaga gagca                              35

<210> SEQ ID NO 29
<211> LENGTH: 34
<212> TYPE: DNA
<213> ORGANISM: Artificial Sequence
<220> FEATURE:
<223> OTHER INFORMATION: B3gnt2-alle1

<400> SEQUENCE: 29
ttcagccctt ccgggcgtac tggaacagag agca                               34

<210> SEQ ID NO 30
<211> LENGTH: 31
<212> TYPE: DNA
<213> ORGANISM: Artificial Sequence
<220> FEATURE:
<223> OTHER INFORMATION: B3gnt2-alle2

<400> SEQUENCE: 30
ttcagccctt cccgtactgg aacagagagc a                                  31

<210> SEQ ID NO 31
<211> LENGTH: 39
<212> TYPE: DNA
<213> ORGANISM: Artificial Sequence
<220> FEATURE:
<223> OTHER INFORMATION: B4galt1-WT

<400> SEQUENCE: 31
tgcatccggt cctacagcgc cagcaactgg actatggta                          39

<210> SEQ ID NO 32
<211> LENGTH: 43
<212> TYPE: DNA
<213> ORGANISM: Artificial Sequence
<220> FEATURE:
<223> OTHER INFORMATION: B4galt1-alle1

<400> SEQUENCE: 32
tgcatccggt cctacagcgc cagccagcaa ctggactatg gta                     43

<210> SEQ ID NO 33
<211> LENGTH: 40
<212> TYPE: DNA
<213> ORGANISM: Artificial Sequence
<220> FEATURE:
<223> OTHER INFORMATION: B4galt2-WT

<400> SEQUENCE: 33
cagccccgcc actttgccat cgccatggac aagtttggct                         40

<210> SEQ ID NO 34
<211> LENGTH: 18
<212> TYPE: DNA
<213> ORGANISM: Artificial Sequence
<220> FEATURE:
<223> OTHER INFORMATION: B4galt2-alle1 (N-terminus)

<400> SEQUENCE: 34
cagccccgcc actttgcc                                                      18

<210> SEQ ID NO 35
<211> LENGTH: 22
<212> TYPE: DNA
<213> ORGANISM: Artificial Sequence
<220> FEATURE:
<223> OTHER INFORMATION: B4galt2-alle1 (C-terminus)

<400> SEQUENCE: 35
atcgccatgg acaagtttgg ct                                                 22

<210> SEQ ID NO 36
<211> LENGTH: 41
<212> TYPE: DNA
<213> ORGANISM: Artificial Sequence
<220> FEATURE:
<223> OTHER INFORMATION: B4galt3-WT

<400> SEQUENCE: 36
ctagccctca agtcaggatg ttgcggaggc tgctggagag g                            41

<210> SEQ ID NO 37
<211> LENGTH: 46
<212> TYPE: DNA
<213> ORGANISM: Artificial Sequence
<220> FEATURE:
<223> OTHER INFORMATION: B4galt3-alle1

<400> SEQUENCE: 37
ctagccctca agtcaggatg tcgtgttgcg gaggctgctg gagagg                       46

<210> SEQ ID NO 38
<211> LENGTH: 43
<212> TYPE: DNA
<213> ORGANISM: Artificial Sequence
<220> FEATURE:
<223> OTHER INFORMATION: B4galt3-alle2

<400> SEQUENCE: 38
ctagccctca agtcaggatg ttgcccggag gctgctggag agg                          43

<210> SEQ ID NO 39
<211> LENGTH: 39
<212> TYPE: DNA
<213> ORGANISM: Artificial Sequence
<220> FEATURE:
<223> OTHER INFORMATION: B4galt4-WT

<400> SEQUENCE: 39
aactgggact gctttatatt ccacgatgtg gacctggtg                               39

<210> SEQ ID NO 40
<211> LENGTH: 40
<212> TYPE: DNA
<213> ORGANISM: Artificial Sequence
<220> FEATURE:
<223> OTHER INFORMATION: B4galt4-alle1

<400> SEQUENCE: 40
aactgggact gctttattat tccacgatgt ggacctggtg                              40

```
<210> SEQ ID NO 41
<211> LENGTH: 43
<212> TYPE: DNA
<213> ORGANISM: Artificial Sequence
<220> FEATURE:
<223> OTHER INFORMATION: B4galt4-alle2

<400> SEQUENCE: 41
aactgggact gctttatatt tattccacga tgtggacctg gtg          43

<210> SEQ ID NO 42
<211> LENGTH: 43
<212> TYPE: DNA
<213> ORGANISM: Artificial Sequence
<220> FEATURE:
<223> OTHER INFORMATION: st3Gal3-WT

<400> SEQUENCE: 42
ctctctcttt gtccttgctg gcttcaaatg gcaggacttc aag          43

<210> SEQ ID NO 43
<211> LENGTH: 38
<212> TYPE: DNA
<213> ORGANISM: Artificial Sequence
<220> FEATURE:
<223> OTHER INFORMATION: st3Gal3-alle1

<400> SEQUENCE: 43
ctctctcttt gtccttgctc aaatggcagg acttcaag                38

<210> SEQ ID NO 44
<211> LENGTH: 42
<212> TYPE: DNA
<213> ORGANISM: Artificial Sequence
<220> FEATURE:
<223> OTHER INFORMATION: st3Gal3-alle2

<400> SEQUENCE: 44
ctctctcttt gtccttgctg gctcaaatgg caggacttca ag           42

<210> SEQ ID NO 45
<211> LENGTH: 43
<212> TYPE: DNA
<213> ORGANISM: Artificial Sequence
<220> FEATURE:
<223> OTHER INFORMATION: st3Gal4-WT

<400> SEQUENCE: 45
ggcagcctcc agtgtcgtcg ttgtgttgtg gtggggaatg ggc          43

<210> SEQ ID NO 46
<211> LENGTH: 47
<212> TYPE: DNA
<213> ORGANISM: Artificial Sequence
<220> FEATURE:
<223> OTHER INFORMATION: st3Gal4-alle1

<400> SEQUENCE: 46
ggcagcctcc agtgtcgtcg ttgtttgtgt tgtggtgggg aatgggc      47

<210> SEQ ID NO 47
<211> LENGTH: 39
<212> TYPE: DNA
<213> ORGANISM: Artificial Sequence
<220> FEATURE:
<223> OTHER INFORMATION: st3Gal4-alle2
```

-continued

```
<400> SEQUENCE: 47
ggcagcctcc agtgtcgtcg gttgtggtgg ggaatgggc                              39

<210> SEQ ID NO 48
<211> LENGTH: 39
<212> TYPE: DNA
<213> ORGANISM: Artificial Sequence
<220> FEATURE:
<223> OTHER INFORMATION: st3Gal6-WT

<400> SEQUENCE: 48
cggtacctct gattttgctt tgccctatgg gacaaggcc                              39

<210> SEQ ID NO 49
<211> LENGTH: 35
<212> TYPE: DNA
<213> ORGANISM: Artificial Sequence
<220> FEATURE:
<223> OTHER INFORMATION: st3Gal6-alle1

<400> SEQUENCE: 49
cggtacctct gattttgctt ctatgggaca aggcc                                  35

<210> SEQ ID NO 50
<211> LENGTH: 17
<212> TYPE: DNA
<213> ORGANISM: Artificial Sequence
<220> FEATURE:
<223> OTHER INFORMATION: st3Gal6-alle2

<400> SEQUENCE: 50
cggtacctct gaaggcc                                                      17

<210> SEQ ID NO 51
<211> LENGTH: 40
<212> TYPE: DNA
<213> ORGANISM: Artificial Sequence
<220> FEATURE:
<223> OTHER INFORMATION: fut8-WT

<400> SEQUENCE: 51
caaatacttg atccgtccac aaccttggct ggaaagggaa                             40

<210> SEQ ID NO 52
<211> LENGTH: 39
<212> TYPE: DNA
<213> ORGANISM: Artificial Sequence
<220> FEATURE:
<223> OTHER INFORMATION: fut8-alle1

<400> SEQUENCE: 52
caaatacttg atccgtccac aacctggctg gaaagggaa                              39

<210> SEQ ID NO 53
<211> LENGTH: 41
<212> TYPE: DNA
<213> ORGANISM: Artificial Sequence
<220> FEATURE:
<223> OTHER INFORMATION: fut8-alle2

<400> SEQUENCE: 53
caaatacttg atccgtccac aacctttggc tggaaaggga a                           41
```

```
<210> SEQ ID NO 54
<211> LENGTH: 120
<212> TYPE: DNA
<213> ORGANISM: Artificial Sequence
<220> FEATURE:
<223> OTHER INFORMATION: ssODN with 60bp homology arm sequences

<400> SEQUENCE: 54
gagagagatt ggtcttgctt gtcatcacca acgtatgaac cagtgtgatg gtgaaatgag      60
tcgccgtgca ggagcagcaa ctaacggaag taacactgca ttgactacat tttcaggtac     120

<210> SEQ ID NO 55
<211> LENGTH: 21
<212> TYPE: DNA
<213> ORGANISM: Artificial Sequence
<220> FEATURE:
<223> OTHER INFORMATION: Mgataex1F

<400> SEQUENCE: 55
tatccactgt gttgcttgct g                                                 21

<210> SEQ ID NO 56
<211> LENGTH: 21
<212> TYPE: DNA
<213> ORGANISM: Artificial Sequence
<220> FEATURE:
<223> OTHER INFORMATION: Mgataex2R

<400> SEQUENCE: 56
actgctcttc cagaggtcct g                                                 21

<210> SEQ ID NO 57
<211> LENGTH: 27
<212> TYPE: DNA
<213> ORGANISM: Artificial Sequence
<220> FEATURE:
<223> OTHER INFORMATION: Mgataex2F

<400> SEQUENCE: 57
gaacgccttc gaatagctga acatagg                                           27

<210> SEQ ID NO 58
<211> LENGTH: 23
<212> TYPE: DNA
<213> ORGANISM: Artificial Sequence
<220> FEATURE:
<223> OTHER INFORMATION: Mgat4aEx1gRNA

<400> SEQUENCE: 58
ggtataccac atggcaaaat ggg                                               23

<210> SEQ ID NO 59
<211> LENGTH: 23
<212> TYPE: DNA
<213> ORGANISM: Artificial Sequence
<220> FEATURE:
<223> OTHER INFORMATION: Mgat4aEx2gRNA

<400> SEQUENCE: 59
gtccaacagt ttcgccgtgc agg                                               23

<210> SEQ ID NO 60
<211> LENGTH: 3873
<212> TYPE: DNA
<213> ORGANISM: Artificial Sequence
```

<220> FEATURE:
<223> OTHER INFORMATION: Shuttle vector

<400> SEQUENCE: 60

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt accaagcttg     420
gttgcatgct gtccggagtc tcagcgttat accagaagtg acctgggtcg gggaagacta     480
tagtgtcacc taaatctcta gagcccttca ttaggcgcgc aatcccattg caaattcta      540
caaaaggagt gtttcccaac tgctctatca agaggaatgt tgcacactgt gacctgaatg     600
caaacatcac acgcgccagc agagaggaag aagagaggct tccctgaccg ggaatcgaac     660
ccgggccgcg gcggtgagag cgccgaatcc taaccactag accaccaggg agcacgcgcc     720
aaagctcaat gagctataat tatccccttg gaaaacctac aaaaacagtg tttcaaaact     780
gctctgtgaa aagggacctt tgctagcacg cggcgccagg caaaacgtgg gcacgctgcg     840
ttggccggga atcgaacccg gtcaactgc ttggaaggca gctatgctca ccactatacc      900
accaacgcgc acacgcgcca gcagattcta cgggaagagt gtttcaaaac tgctctatca     960
agagaaatgt tccaccttgt gtgtggaatg cagccatcac acgcgtccat gaaagggctt    1020
aattaagata tcgtttaaac gtcgacctgc agaggccggc ggataactag ctgatcgcgg    1080
aatcctgtcc ctaggccacc cactgtgggg tgcccttcat taggcgcgcc aatcccattg    1140
caaattctac aaaaggagtg tttcccaact gctctatcaa gaggaatgtt gcacactgtg    1200
acctgaatgc aaacatcaca cgcgccagca gagaggaaga agagaggctt ccctgaccgg    1260
gaatcgaacc cgggccgcgg cggtgagagc gccgaatcct aaccactaga ccaccaggga    1320
gcacgcgcca aagctcaatg agctataatt atccccttgg aaaacctaca aaaacagtgt    1380
ttcaaaactg ctctgtgaaa agggaccttt gctagcacgc ggcgccaggc aaaacgtggg    1440
cacgctgcgt tggccgggaa tcgaacccgg tcaactgct tggaaggcag ctatgctcac     1500
cactatacca ccaacgcgca cacgcgccag cagattctac gggaagagtg tttcaaaact    1560
gctctatcaa gagaaatgtt ccaccttgtg tgtggaatgc agccatcaca cgcgtccatg    1620
aaagggcggt tgcatgctgt ccggagtctc agcgttatac cagaagtgac ctgggtcggg    1680
gaagaaaagc ttcatggtca tagctgtttc ctgtgtgaaa ttgttatccg ctcacaattc    1740
cacacaacat acgagccgga agcataaagt gtaaagcctg gggtgcctaa tgagtgagct    1800
aactcacatt aattgcgttg cgctcactgc ccgctttcca gtcgggaaac tgtcgtgcc     1860
agctgcatta atgaatcggc caacgcgcgg ggagaggcgg tttgcgtatt gggcgctctt    1920
ccgcttcctc gctcactgac tcgctgcgct cggtcgttcg ctgcggcga gcggtatcag     1980
ctcactcaaa ggcggtaata cggttatcca cagaatcagg ggataacgca ggaaagaaca    2040
tgtgagcaaa aggccagcaa aaggccagga accgtaaaaa ggccgcgttg ctggcgtttt    2100
tccataggct ccgcccccct gacgagcatc acaaaaatcg acgctcaagt cagaggtggc    2160
gaaacccgac aggactataa agataccagg cgtttccccc tggaagctcc ctcgtgcgct    2220
```

```
ctcctgttcc gaccctgccg cttaccggat acctgtccgc ctttctccct tcgggaagcg    2280
tggcgctttc tcatagctca cgctgtaggt atctcagttc ggtgtaggtc gttcgctcca    2340
agctgggctg tgtgcacgaa ccccccgttc agcccgaccg ctgcgcctta tccggtaact    2400
atcgtcttga gtccaacccg gtaagacacg acttatcgcc actggcagca gccactggta    2460
acaggattag cagagcgagg tatgtaggcg gtgctacaga gttcttgaag tggtggccta    2520
actacggcta cactagaaga acagtatttg gtatctgcgc tctgctgaag ccagttacct    2580
tcggaaaaag agttggtagc tcttgatccg gcaaacaaac caccgctggt agcggtggtt    2640
tttttgtttg caagcagcag attacgcgca gaaaaaaagg atctcaagaa gatcctttga    2700
tcttttctac ggggtctgac gctcagtgga acgaaaactc acgttaaggg attttggtca    2760
tgagattatc aaaaaggatc ttcacctaga tccttttaaa ttaaaaatga agttttaaat    2820
caatctaaag tatatatgag taaacttggt ctgacagtta gaaaaactca tcgagcatca    2880
aatgaaactg caatttattc atatcaggat tatcaatacc atattttga aaaagccgtt    2940 tctgtaatga aggagaaaac tcaccgaggc agttccatag gatggcaaga tcctggtatc    3000
ggtctgcgat tccgactcgt ccaacatcaa tacaacctat taatttcccc tcgtcaaaaa    3060
taaggttatc aagtgagaaa tcaccatgag tgacgactga atccggtgag aatggcaaaa    3120
gtttatgcat ttctttccag acttgttcaa caggccagcc attacgctcg tcatcaaaat    3180
cactcgcatc aaccaaaccg ttattcattc gtgattgcgc ctgagcgaga cgaaatacgc    3240
gatcgctgtt aaaaggacaa ttacaaacag gaatcgaatg caaccggcgc aggaacactg    3300
ccagcgcatc aacaatattt tcacctgaat caggatattc ttctaatacc tggaatgctg    3360
ttttcccagg gatcgcagtg gtgagtaacc atgcatcatc aggagtacgg ataaaatgct    3420
tgatggtcgg aagaggcata aattccgtca gccagtttag tctgaccatc tcatctgtaa    3480
catcattggc aacgctacct ttgccatgtt tcagaaacaa ctctggcgca tcgggcttcc    3540
catacaatcg atagattgtc gcacctgatt gcccgacatt atcgcgagcc catttatacc    3600
catataaatc agcatccatg ttggaattta atcgcggcct agagcaagac gtttcccgtt    3660
gaatatggct catactcttc cttttttcaat attattgaag catttatcag ggttattgtc    3720
tcatgagcgg atacatattt gaatgtattt agaaaaataa acaaataggg gttccgcgca    3780
catttccccg aaaagtgcca cctgacgtct aagaaaccat tattatcatg acattaacct    3840
ataaaaatag gcgtatcacg aggcccttc gtc                                  3873
```